US012680077B2

(12) United States Patent
Loh et al.

(10) Patent No.: US 12,680,077 B2
(45) Date of Patent: Jul. 14, 2026

(54) GENERATING POPULATIONS OF HUMAN BLOOD AND BLOOD VESSEL PROGENITORS FROM PLURIPOTENT STEM CELLS

(71) Applicant: The Board of Trustees of the Leland Stanford Junior University, Stanford, CA (US)

(72) Inventors: Kyle M. Loh, Piscataway, NJ (US); Lay Teng Ang, Stanford, CA (US); Alana T. Nguyen, Stanford, CA (US); Jonas Fowler, Stanford, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 944 days.

(21) Appl. No.: 17/995,274

(22) PCT Filed: Apr. 6, 2021

(86) PCT No.: PCT/US2021/026024
§ 371 (c)(1),
(2) Date: Apr. 13, 2023

(87) PCT Pub. No.: WO2021/207251
PCT Pub. Date: Oct. 14, 2021

(65) Prior Publication Data
US 2023/0159894 A1      May 25, 2023

Related U.S. Application Data

(60) Provisional application No. 63/005,896, filed on Apr. 6, 2020.

(51) Int. Cl.
*C12N 5/0789* (2010.01)
*C12N 5/071* (2010.01)

(52) U.S. Cl.
CPC ......... *C12N 5/0647* (2013.01); *C12N 5/0691* (2013.01); *C12N 2500/38* (2013.01);
(Continued)

(58) Field of Classification Search
CPC ................................................. C12N 5/0647
See application file for complete search history.

(56) References Cited

U.S. PATENT DOCUMENTS

2003/0166273 A1      9/2003   Kaufman et al.
2018/0030410 A1 *    2/2018   Loh ...................... C12N 5/0657

FOREIGN PATENT DOCUMENTS

WO      WO2013/086029      6/2013
WO      WO2017/078807      5/2017
WO      WO2017/193177      11/2017

OTHER PUBLICATIONS

Loh 2016 Cell, vol. 166, pp. 451 to 467 (Year: 2016).*
(Continued)

*Primary Examiner* — Mark L Shibuya
(74) *Attorney, Agent, or Firm* — Pamela J. Sherwood; Bozicevic, Field & Francis LLP

(57) ABSTRACT

Methods are provided for the efficient differentiation of hPSCs into HSC-like cells and endothelial cells in defined, monolayer conditions solely using extracellular signals to guide differentiation. The instant disclosure also provides methods of screening for cellular responses of the generated hematopoietic stem cells, endothelial cells and derivatives thereof. Treatment methods making use of the generated hematopoietic stem cells and endothelial cells are also
(Continued)

provided. The instant disclosure also provides systems, compositions, and kits for practicing the methods of the disclosure.

9 Claims, 80 Drawing Sheets

(52) U.S. Cl.
CPC .. *C12N 2501/155* (2013.01); *C12N 2501/165* (2013.01); *C12N 2501/235* (2013.01); *C12N 2501/415* (2013.01); *C12N 2506/45* (2013.01); *C12N 2513/00* (2013.01); *C12N 2533/56* (2013.01)

(56) References Cited

OTHER PUBLICATIONS

Sriram, 2015, Stem Cell Research & Therapy, vol. 6:261, pp. 1 to 17 (Year: 2015).*

Sturgeon et al. (2014 ) "Wnt signaling controls the specification of definitive and primitive hematopoiesis from human pluripotent stem cells", *Nature Biotechnology*, 32(6), pp. 554-561.

Sriram et al. (2015) "Efficient differentiation of human embryonic stem cells to arterial and venous endothelial cells under feeder- and serum-free conditions", *Stem Cell Research & Therapy*, 6(1), XP055630854.

Loh et al. (2024) "Building human artery and vein endothelial cells from pluripotent stem cells, and enduring mysteries surrounding arteriovenous development" *Seminars in Cell and Developmental Biology*, 155, pp. 62-75.

Loh et al. (2016) "Mapping the Pairwise Choices Leading from Pluripotency to Human Bone, Heart, and Other Mesoderm Cell Types", *Cell, Elsevier, Amsterdam NL*, 166(2), pp. 451-467.

Teng et al. (2022) "Generating human artery and vein cells from pluripotent stem cells highlights the arterial tropism of Nipah and Hendra viruses", *Cell, Elsevier, Amsterdam NL*, 185(14), p. 2523.

* cited by examiner

A (Cont.)

B

Mid primitive streak induction *in vitro*

Day 1 of differentiation

C

Heterogeneity of lateral mesoderm *in vivo*

*Hand1+ Elf5-* (putative lateral mesoderm)

VEGF induces dorsal lateral mesoderm on day 2 *in vitro*

Day 2 of differentiation (qPCR)

Signals for artery specification for OTL (Artery)

Dorsal lateral mesoderm induction on day 2

B

TGFβ specifies arterial fate, and represses veins, on day 3

C

PI3K inhibition specifies arterial fate, and represses veins, on day 3

Day 3 of differentiation (qPCR)

Day 3 of differentiation (FACS)

D

Efficient generation of SOX17$^+$CD34$^+$ artery cells

Day 3 SOX17⁺CD34⁺ progenitors express arterial, not other markers

FIG. 3 for OTL (Vein)

A

Bifurcation of artery and pre-vein lineages

B   PI3K activation, together with NOTCH and TGFβ repression, specifies "pre-veins" on day 3

Day 3 of differentiation (qPCR)

C

Two-step model for pre-vein and vein formation

D

Temporally dynamic ERK activation, followed by inhibition, specifies veins

Day 4 of differentiation (qPCR)

E

Tracking vein differentiation with *NR2F2-2A-GFP* reporter hESCs

F hESC-derived vein cells express NR2F2

H          FIG. 3 (Cont.)
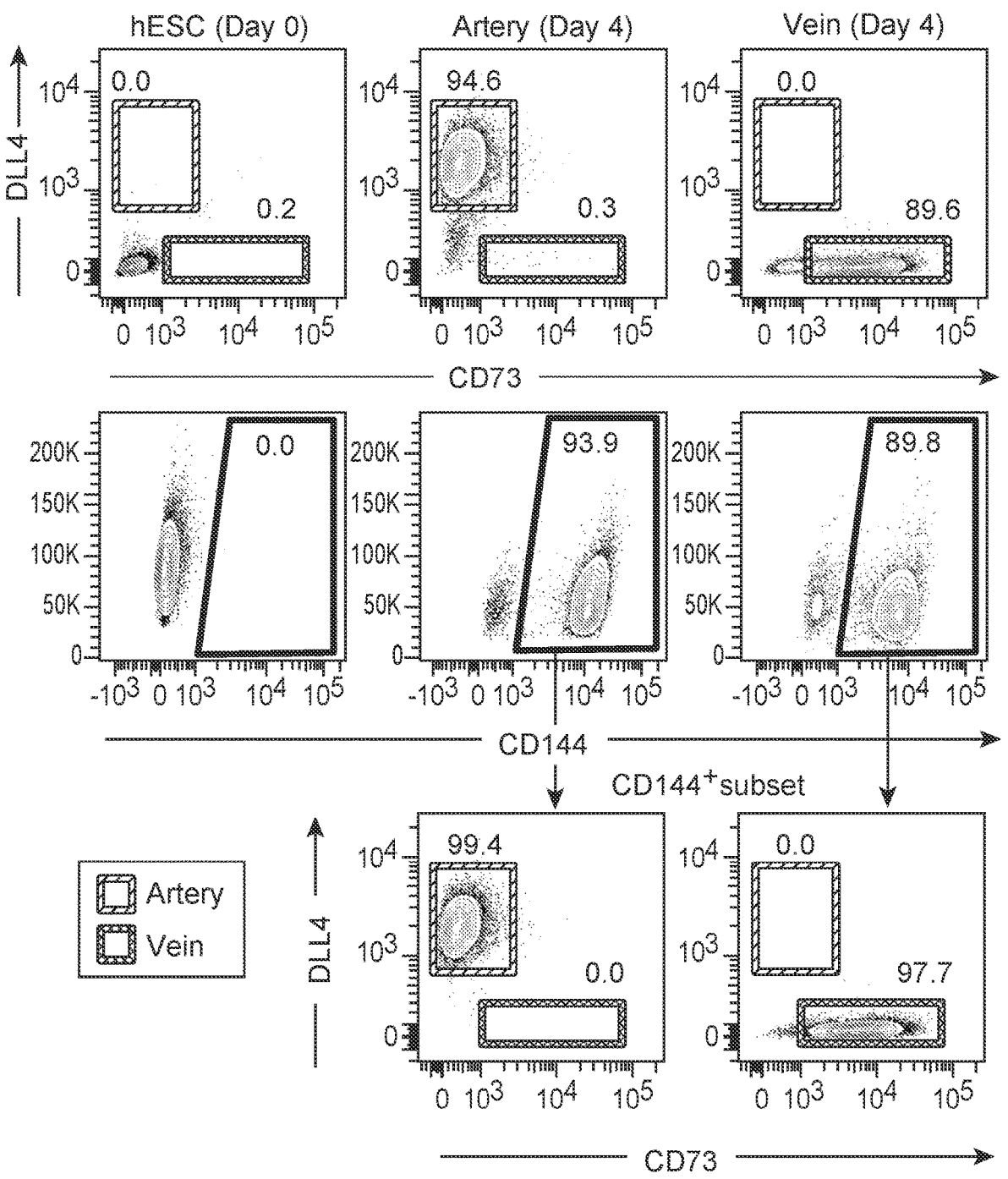
DLL4 and CD73 are mutually-exclusive artery vs. vein surface markers

A

Blood artery and hemogenic endothelium

Chronology of hematopoietic development

C

Efficient generation of hPSC-derived trunk artery cells

D

Arteries bifurcate into hemogenic vs. non-hemogenic endothelium

Day 4 of differentiation (qPCR)

E

Efficient generation of CD144$^+$ RUNX1$^+$ hemogenic endothelium from hPSCs

F

Stepwise upregulation of hemogenic endothelium markers

Trunk artery       Hemogenic endothelium

D3             D6

Early hemogenic endothelium       Late hemogenic endothelium

*RUNX1*                 *MYB*

Late hemogenic endothelium

*GFI1*           *GFI1B*           *PU.1*

FIG. 5

HSPC (Day 9)

Generation of hPSC-derived HSC-like cells in 9 days ii. qPCR

GFI1B

PU.1

CD43

IKZF1

Relative to undifferentiated hPSCs (D0)

A

OSM   LIF
cAMP  TGFβ inh.
IL1β  NOTCH
SR1   UM171

Hemogenic
endothelium
(CD34+ CD144+
CD43- CD45-)
D6

HSC-like
cells
(CD34+ CD144+
CD43+ CD45+)
D9 i. Phase contrast

Day 7     Day 9

A (Cont.)

iii. Flow cytometry

Core blood transcription and chromatin factors expressed by day 9 hPSC-derived HSC-like cells D    Core blood surface markers/homing receptors expressed by day 9 hPSC-derived HSC-like cells

E

Homing receptor expression

F

Day 9 hPSC-derived HSC-like cells do not express HSC signature or *HOXA* genes

A

*In vitro* differentiation and *in vivo* engraftment of hPSC-derived HSPCs

Multilineage hematopoietic differentiation *in vitro*

B

Myeloid-erythroid differentiation *in vitro*

Day 10 of methylcellulose-based differentiation

C

Erythroid and megakaryocyte differentiation *in vitro* i. Day 14 of erythroid differentiation ii. Day 14 of megakaryocyte diff.

i. Day 14 of erythroid differentiation

E hPSC-derived HSC-like cells engraft to some extent
upon intrafemoral transplantation into adult mice i. Neonatal intrahepatic transplant (7 months post-transplant)

E (Cont.)

ii. Adult intrafemoral transplant (5 month post-transplant)

A          for OTL (Dorsal lateral mesoderm)

BMP induces, but WNT and TGFβ represses, dorsal lateral mesoderm on day 2

A (Cont.)

A (Cont.)

PI3K blockade induces dorsal lateral mesoderm on day 2

Day 3 of differentiation (flow cytometry)

FIG. 8 for OTL (Artery 1/3)

BMP specifies heart and blocks artery on day 3

A

B

WNT blockade specifies arterial fate on day 3

Day 3 of differentiation (FACS)

SOX17-mCherry

Day 3 of differentiation (qPCR)

WNT signaling

E
Chronology of artery development

Pluripotency

Primitive streak

Pan-endothelium

Artery-specific markers

Artery-specific markers

Endothelial signaling

E (Cont.)

Dorsal lateral mesoderm

SoxF transcription factors

Human ESC/iPSC (Day 0)

Primitive streak (Day 1)

Dorsal lateral mesoderm (Day 2)

Artery progenitor (Day 3)

Lateral/dorsal lateral mesoderm

Pan-endothelium

A      for OTL (Artery 2/3)

Efficient artery endothelial cell production
across wild-type hESC and hiPSC lines

B (Cont.)

SUN004.1.9 hiPSC

B (Cont.)

B (Cont.)

C

More efficient and rapid artery specification than extant strategies for OTL Artery 3/3 hESC-derived artery endothelial cells can be maintained in culture

B  Expanded hESC-derived artery endothelial cells continue to express artery markers

B (Cont.)

% CD144+ DLL4+

% CD144+CD34+

C    hPSC-derived artery ECs form 3D networks *in vitro*

D hPSC-derived artery ECs sprout in response to chemokines

*In utero* transplantation of hPSC-derived artery ECs

A for OTL (Vein)

WNT converts pre-veins into veins

B

*NR2F2-2A-GFP* targeting strategy in hESCs

C

Successful *NR2F2-2A-GFP* knock-ins

Genomic PCR of clonal hESC lines

D

Comparison of artery and vein cells

**for OTL: Blood Artery (Day 3)
and Hemogenic Endothelium (Day 4-6)**

A

Early RA pathway activation induces *HOXA*

B

Extracellular matrix

Day 3 trunk artery differentiation (% CD34⁺CD144⁺)

C   hPSC-derived trunk artery cells are competent to generate blood progenitors

D    Validation that Super-DLL4 (E12) is a potent NOTCH agonist i. IMCD3 reporter cells ii. hPSC-derived hemogenic endothelium

E

NOTCH agonist promotes hemogenic endothelium & blood specification i. Hemogenic endothelium/blood markers (qPCR)

ii. Blood progenitors (day 7 of differentiation; flow cytometry)

F (Cont.)

High cell density and KOSR promote hemogenic endothelium/blood formation

A

HSPC (Day 9, companion figure)

SR1 and UM171 help induce hPSC-derived HSC-like cells i. qPCR (days 7-9 of differentiation)

ii. Flow cytometry (day 9 of differentiation)

FIG. 13 (Cont.)

Gene expression changes during formation of HSC-like cells

FIG. 13 (Cont.)

C Residual hemogenic endothelium at day 9 of differentiation

Day 9 of hPSC differentiation (flow cytometry)

D Purification of HSPCs from cord blood vs. hPSCs i. Day 9 hPSC-derived HSC-like cells ii. Cultured cord blood HSPCs

E hPSC-derived HSC-like cells express low levels of CXCR4 i. qPCR ii. Day 3 hPSC-derived trunk artery (flow cytometry, positive control)

iii. Day 9 hPSC-derived HSC-like cells (flow cytometry)

F

Medial *HOXA* genes are enriched in CD34$^+$ CD90$^+$ cord blood HSPCs

A

Vein differentiation

Passaging cells at intermediate stage of differentiation enhances purity of vein differentiation

GENERATING POPULATIONS OF HUMAN BLOOD AND BLOOD VESSEL PROGENITORS FROM PLURIPOTENT STEM CELLS

STATEMENT REGARDING FEDERALLY SPONSORED RESEARCH

This invention was made with Government support under OD024558 awarded by the National Institutes of Health. The Government has certain rights in the invention.

BACKGROUND

Myriad diseases are caused by genetic mutations in the blood or immune systems, ranging from leukemia, sickle cell anemia, thalassemia, certain metabolic disorders, inherited immunodeficiency to autoimmune disorders, such as Type 1 Diabetes and multiple sclerosis. These diverse diseases are caused by genetically-mutated blood or immune cells. Therefore such diseases can be prevented or cured by replacing an animal's diseased blood and immune system with a healthy one. Long-term blood and immune system replacement can only be accomplished by transplanting an animal with new blood-forming hematopoietic stem cells (HSCs), whereby they regenerate a new blood and immune system. Clinically, HSC transplantation is used to cure or ameliorate diverse diseases including leukemia, multiple sclerosis, systemic sclerosis, systemic lupus erythematosus and severe combined immunodeficiency in patients. However, there is a dire need for a new source of HSCs. Currently, human HSCs are obtained from patients and cannot be indefinitely expanded in culture; they are thus in limited supply.

The ability to generate limitless amounts of HSCs in vitro from human embryonic or induced pluripotent stem ells (hPSCs) would be a boon for regenerative medicine. First, the ability to regenerate a patient's blood or immune system using hPSC-derived HSCs would potentially prevent or treat many hematologic or immunological disorders. It could also be used to enable patients to recover from sustained chemotherapy or radiation that depleted their blood and immune systems, for instance after cancer therapy or nuclear attack. Second, the hPSCs could be genetically edited to program the resultant hPSC-derived blood and immune systems with desired functionalities; this opens up a new host of possibilities such as built-in resistance against bloodborne pathogens or pre-programmed immune surveillance and attack capabilities. Third, hPSC-derived HSCs might provide a platform for the large-scale in vitro manufacture of blood and immune cell-types (e.g., T cells, red blood cells and platelets) to subserve a variety of applications, including cancer immunotherapy and blood transfusions.

However, it is currently not possible to generate fully-fledged HSCs in vitro from hPSCs. One major roadblock in generating HSCs from hPSCs is that the exact developmental precursor to HSCs in vivo remains equivocal. Multiple cell-types have been proposed as the developmental precursor to HSCs, and no consensus has yet been reached. Uncertainties surrounding the origins of blood progenitors have beleaguered efforts to efficiently differentiate hPSCs into various blood lineages, especially HSCs. Developing methods for efficient production of HSC is therefor of great interest and is addressed herein.

SUMMARY

Methods are provided for efficient differentiation of hPSCs into HSC cells in defined, monolayer conditions solely using extracellular signaling agents, e.g. factors as disclosed herein, to guide differentiation. The methods utilize efficient differentiation of hPSCs in stepwise fashion into mid primitive streak, dorsal lateral mesoderm, artery cells including for example trunk artery cells, hemogenic endothelium and HSC cells, providing a rapid and efficient strategy to generate blood progenitors (including HSC cells) in vitro from hPSCs. The hPSC-derived HSC-like cells express transcription factors and surface markers that mark human HSCs. The hPSC-derived HSC cells are demonstrated to harbor the ability to differentiate into myeloid, erythroid and lymphoid cells, (including T cells) in vitro and also to engraft in vivo. The ability to efficiently and rapidly generate hPSC-derived HSC cells provides a gateway to produce a variety of human blood and immune cell-types including T cells and dendritic cells (for cancer immunotherapy), red blood cells (for transfusions) or megakaryocytes/platelets (for blood clotting).

Artery cells are the upstream developmental precursor to HSCs. hPSC-derived artery cells generated in vitro face a branching lineage choice to remain as arteries (instructed by VEGF and TGFβ) or to convert into hemogenic endothelium (specified by the absence of VEGF and TGFβ together with activation of GP130, NOTCH and PKA signaling). The hemogenic endothelium cells thus derived are endothelial in nature but progressively upregulate a number of hematopoietic transcription factors (first RUNX1, then GFI1 and followed by GFI1B and PU.1), becoming a >80% pure population of CD144$^+$ RUNX1$^+$ hemogenic endothelium cells after in vitro differentiation. Subsequently, following the in vitro differentiation protocol, a substantially pure population of CD34$^+$ CD90$^+$ CD144$^+$ CD45$^+$ HSC cells emerged, where the population may be >60% the desired cell type, greater than 70%, greater than 80% or more.

The differentiation protocol cultures a human pluripotent cell in the presence of a BMP agonist, an FGF agonist, a WNT agonist, and a TGFβ agonist on day 1 to generate a mid-primitive streak cell. The mid-primitive streak cell is cultured in the presence of a WNT inhibitor, BMP agonist, VEGF agonist, PI3K inhibitor, cAMP, RA agent and TGFβ inhibitor on day 2 to generate dorsal lateral mesoderm. The dorsal lateral mesoderm is cultured in the presence of a VEGF agonist, TGFβ agonist, WNT inhibitor, PI3K inhibitor, BMP inhibitor and RA on day 3 to produce a population of artery progenitors. The population of artery progenitors is cultured in the presence of OSM, LIF agonist, cAMP, and TGFβ inhibitor for from about 2 to about 3 days to produce a population of hemogenic endothelium. The hemogenic endothelium is cultured in the presence of OSM, cAMP, IL-1β agonist, SR1, LIF agonist, TGFβ inhibitor and UM171 for a period of from about 2 to about 3 days to generate a populion of hematopoietic stem cells.

In some embodiments, methods are provided for the use of the differentiated cell population in screening for cellular responses and treating a subject for a condition using the produced cell types, and/or terminally differentiated cells and tissues. The instant disclosure also provides systems and kits for producing HSC types and/or screening for cellular responses and/or treating subjects with such HSC.

Aspects of the disclosure relate to producing anterior primitive streak cells through contacting a population of pluripotent progenitor cells with an anterior primitive streak induction composition. As described herein, anterior primitive streak induction compositions may vary and may generally include effective amounts of a TGF-beta pathway activator and/or a Wnt pathway activator and/or a FGF pathway activator and/or a PI3K pathway inhibitor.

Aspects of the disclosure relate to deriving or producing desired a substantially pure population of hematopoietic stem cells through contacting pluripotent cells and/or progenitor cells with one or more induction compositions wherein the contacting is performed for a specified time period sufficient to produce the desired cell type or a desired intermediate. As described herein, time periods produce a desired cell type or a desired intermediate will vary depending on the desired cell type or desired intermediate and/or the induction composition being used. In certain aspects of the disclosure the time period consists essentially 24 hours. In certain aspects of the disclosure the time period consists essentially 24 hours to 72 hours. In certain aspects of the disclosure the time period consists essentially 48 hours. In certain aspects of the disclosure the time period includes at least 72 hours. In certain aspects of the disclosure the time period consists essentially 24 hours to 48 hours.

Aspects of the disclosure relate to producing a substantially pure population of hematopoietic stem cells. As described herein, the level of purity of a particular purified population will vary depending on various factors and may be achieved through use of the cell derivation methods described herein including or excluding the use of one or more binding agents used to isolate particular cell types.

Aspects of the disclosure relate to screening a substantially pure population of hematopoietic stem cells or produced according to the methods described herein for a cellular response. In certain aspects, a method of screening a substantially pure population of hematopoietic stem cells for a cellular response may include contacting a population of substantially pure population of hematopoietic stem cells with a pharmacological agent and evaluating the population of cells for a cellular response induced by the pharmacological agent. In certain aspects, the screening may be in vitro screening and the contacting may be performed in vitro. In certain aspects, the screening may be in vivo screening and the contacting may be performed by administering the pharmacological agent to a host animal that contains the population of cells.

Aspects of the disclosure relate to methods of treating a subject for a condition through the administration of a substantially pure population of hematopoietic stem cells derived or produced according to the methods described herein. In certain aspects, the method of eating a subject for a condition through administration of cells derived according to the methods as described herein may further include co-administration with at least one pro-survival or pro-engraftment factor. In certain aspects, the cells administered to a subject may be genetically modified at least one genetic locus.

Aspects of the disclosure include kits for the production, derivation, purification, and use of a substantially pure population of hematopoietic stem cells that include one or more induction compositions and/or one or more specific binding agents and/or combinations thereof. In certain aspects, such kits may or may not include one or more cell types described herein.

Aspects of the disclosure include systems for the production, derivation, purification, and use of a substantially pure population of hematopoietic stem cells that include one or more components configured to administer one or more induction compositions and/or one or more specific inducing agents and/or one or more specific binding agents and/or combinations thereof. In certain aspects, such systems are configured to administer such compositions and/or agents at specific amounts or for specific periods of time according to the methods described herein.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EMBODIMENTS

Figure 1:
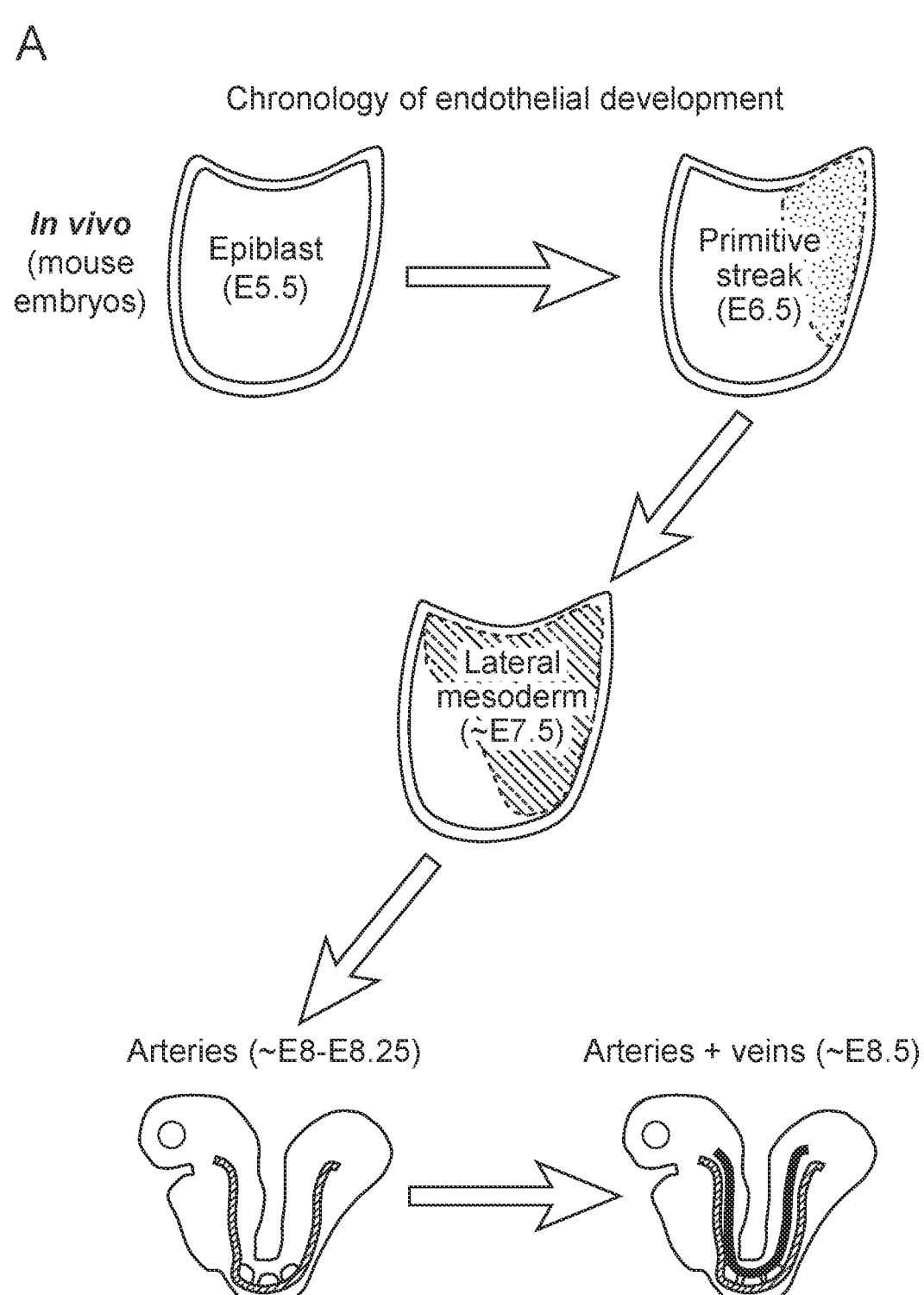
FIG. 1: Efficient generation of human primitive streak and dorsal lateral mesoderm from hPSCs. A) Chronology of artery and vein development in vivo within mouse embryos (top) and in vitro from human pluripotent stem cells (hPSCs; bottom). B) Efficient generation of MIXL1$^+$ mid primitive streak within 24 hours of hPSC differentiation, as assayed by flow cytometry of a MIXL1-GFP reporter hESC line C) In vivo identification of candidate dorsal lateral mesoderm: from a scRNAseq profile of the E7.0 mouse embryo, Hand1$^+$ Elf5$^-$ lateral mesoderm was computationally identified and then sub-clustered; marker genes shown superimposed on t-SNE (top) and in violin plots (below [CPM: counts per million]). D) VEGF treatment induces day 2 dorsal lateral mesoderm; day 1 hPSC-derived primitive streak was treated with BMP4+XAV939 for 24 hours, in the presence or absence of VEGF (10-100 ng/mL) or a VEGFR inhibitor (Axitinib); qPCR was performed on day 2 cell populations E) BMP specifies, whereas TGFβ and WNT repress, day 2 dorsal lateral mesoderm; i) day 1 hPSC-derived primitive streak was treated with VEGF for 24 hours in the presence or absence of BMP4 (10-40 ng/mL) or BMP inhibitors (DMH1 or NOGGIN); ii) day 1 hPSC-derived primitive streak was treated with BMP4+VEGF for 24 hours in the presence or absence of a WNT agonist (CHIR99021, 1-6 µM) or WNT inhibitors (C59 or XAV939); iii) day 1 hPSC-derived primitive streak was treated with BMP4+ VEGF for 24 hours in the presence or absence of a TGFβ agonist (Activin, 5-100 ng/mL) or TGFβ inhibitors (SB505124 or SB431542); qPCR was performed on day 2 cell populations. F) HAND1 and SCL immunostaining of hPSC-derived day 2 dorsal lateral mesoderm (DAPI: nuclear counterstain).
Figure 1:
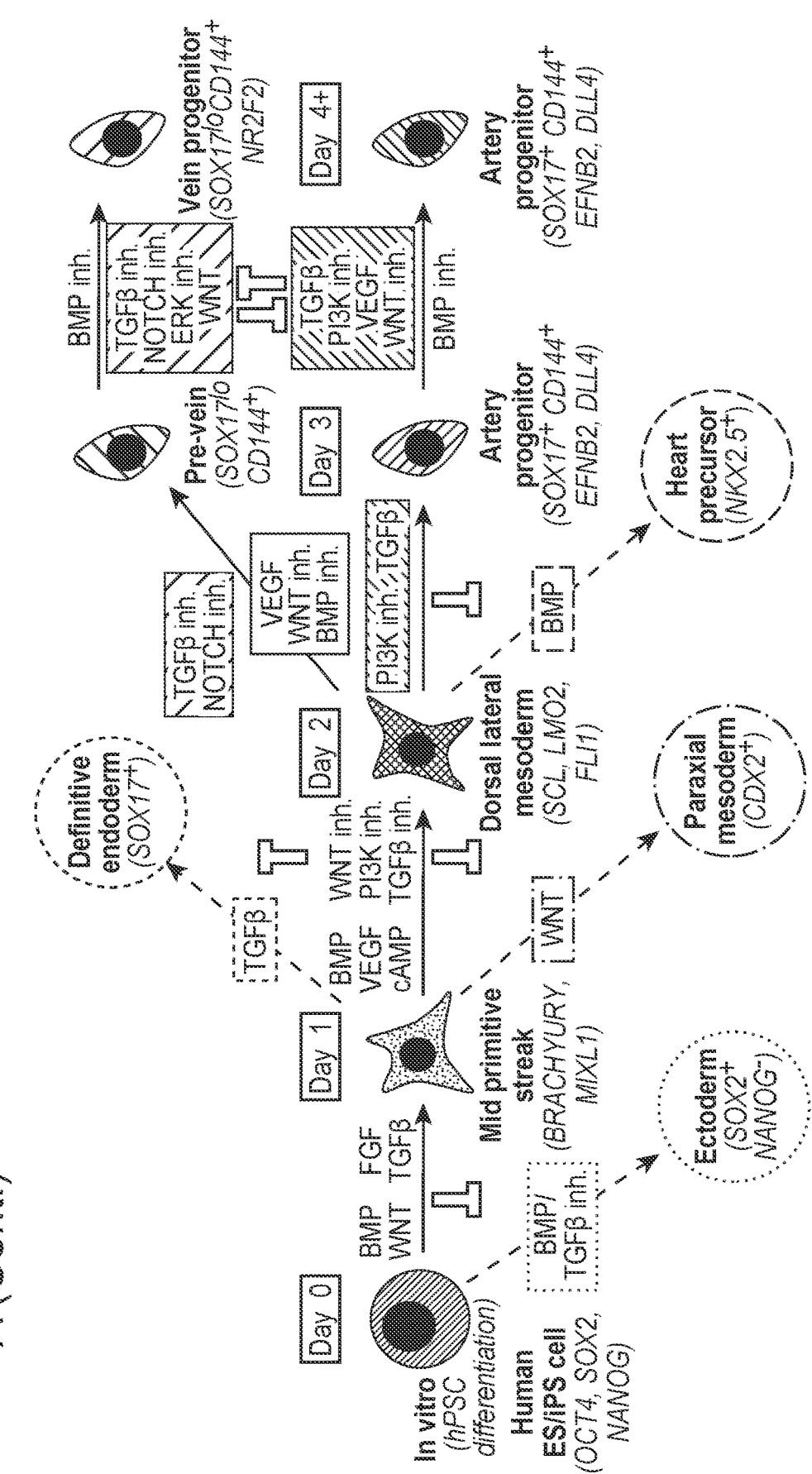
Figure 1:
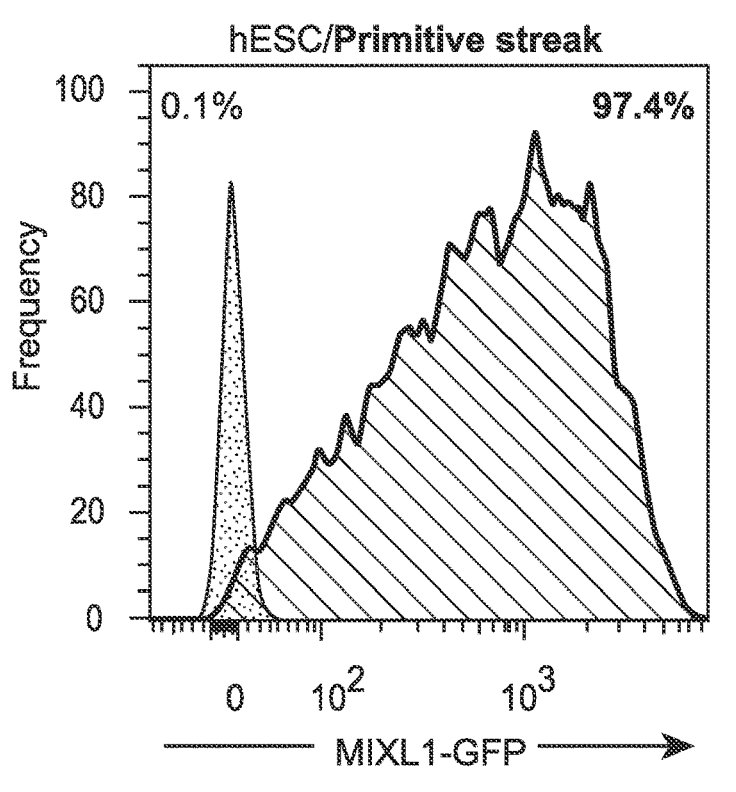
Figure 1:
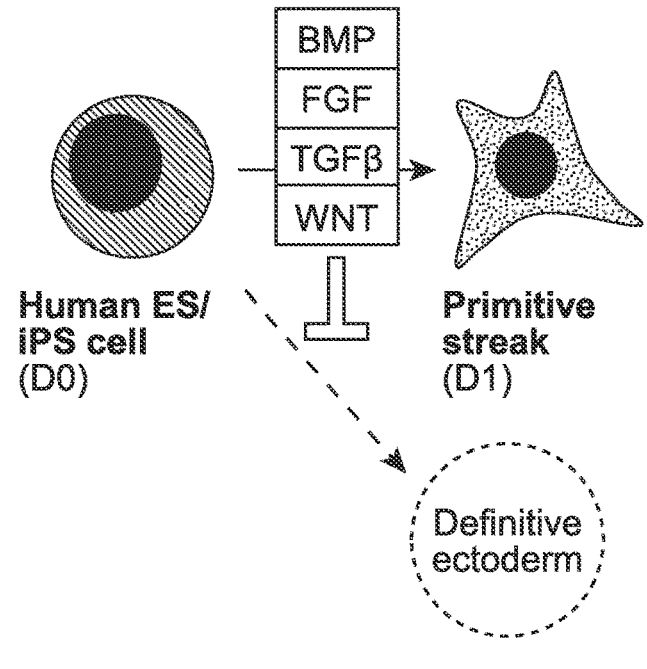
Figure 1:
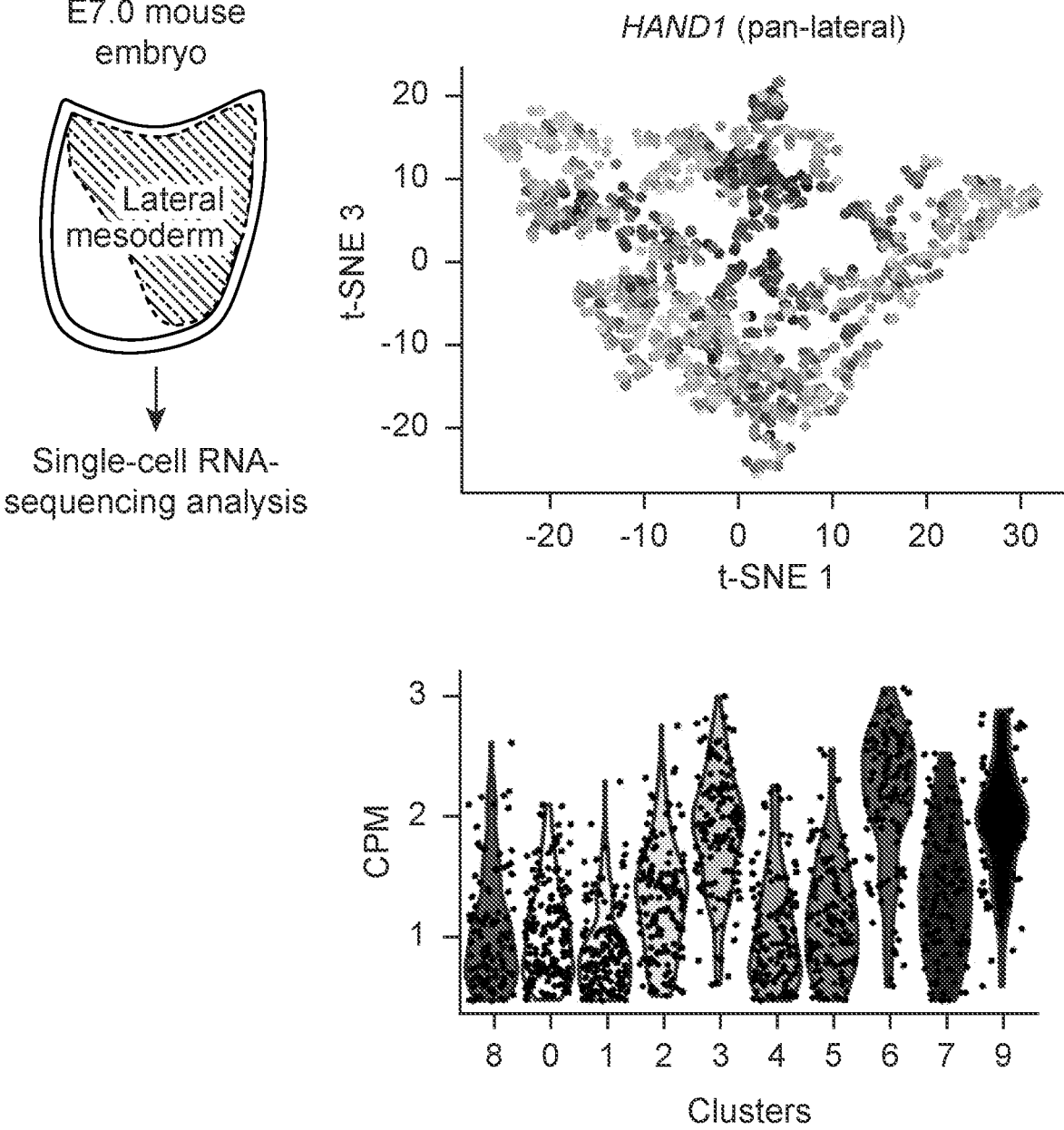
Figure 1:
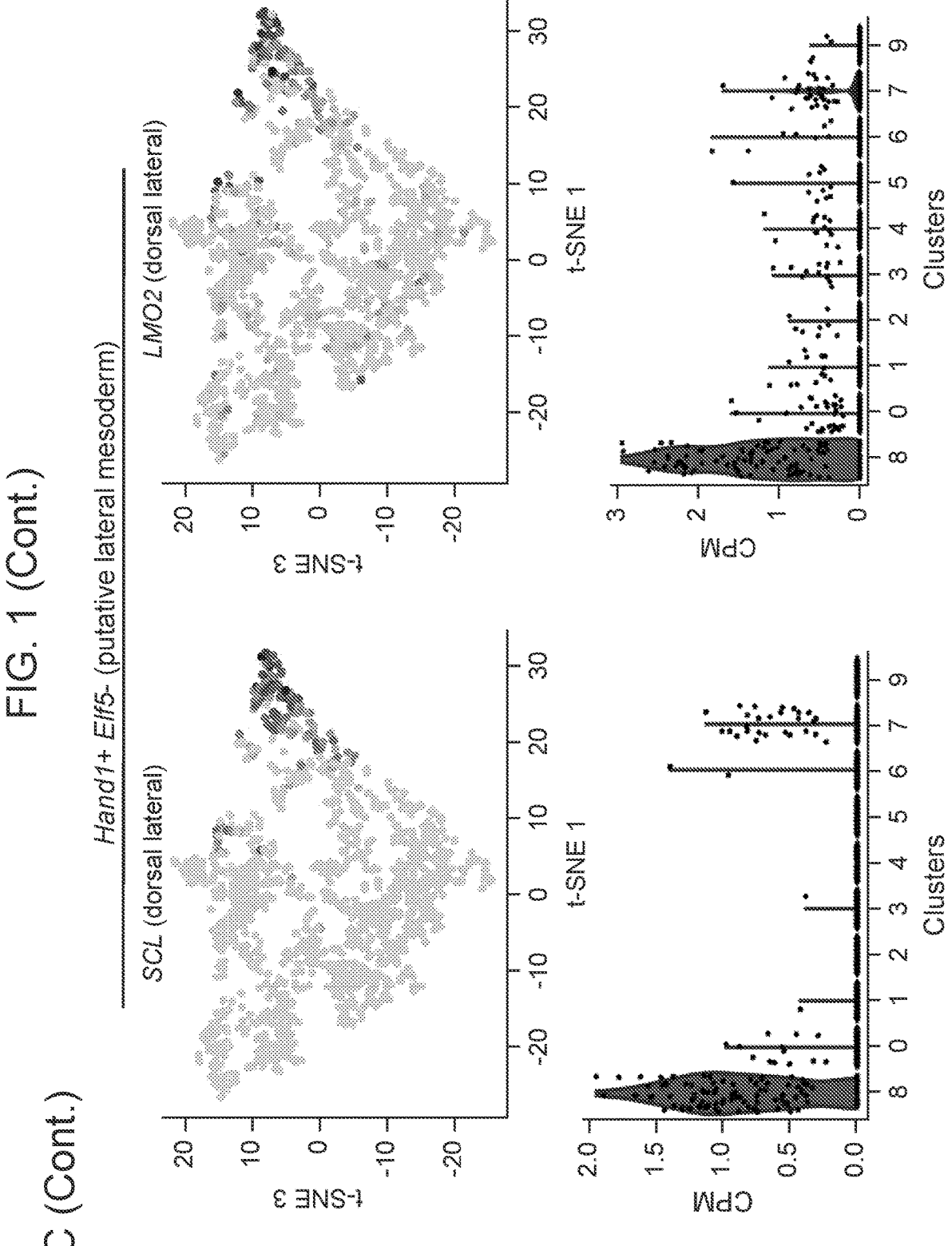
Figure 1:
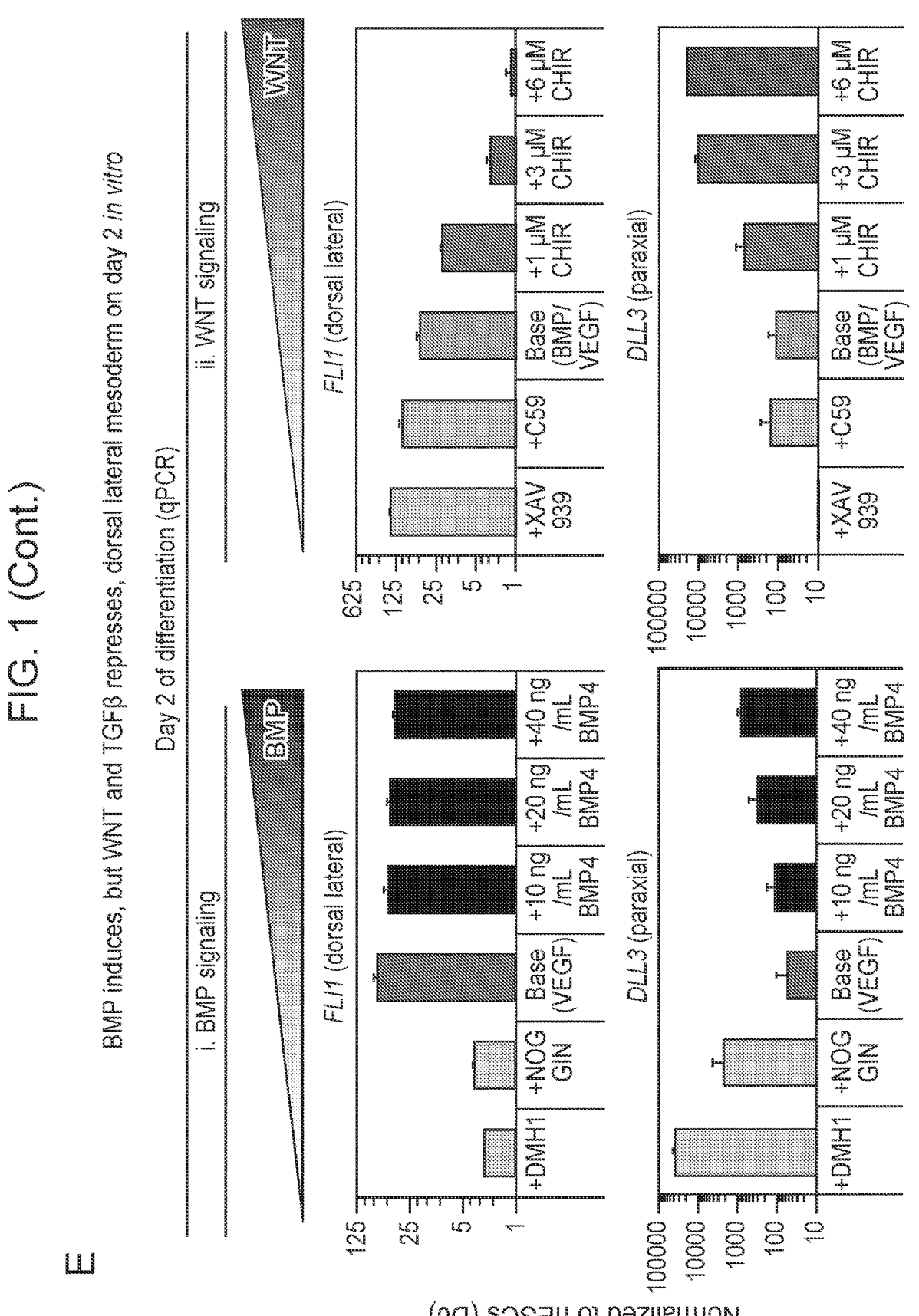

Methods are provided for the generation of substantially purified hematopoietic stem cells. Treatment methods making use of the generated hematopoietic stem cells are also provided. The instant disclosure also provides systems, compositions, and kits for practicing the methods of the disclosure.

Before the present methods and compositions are described, it is to be understood that this invention is not limited to particular method or composition described, and as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The term "treatment" encompasses any treatment of a disease in a mammal, particularly a human, and includes: (a) preventing the disease and/or symptom(s) from occurring in a subject who may be predisposed to the disease or symptom(s) but has not yet been diagnosed as having it; (b) inhibiting the disease and/or symptom(s), i.e., arresting development of a disease and/or the associated symptoms; or (c) relieving the disease and the associated symptom(s), i.e., causing regression of the disease and/or symptom(s).

The terms "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, camels, etc. In some embodiments, the mammal is human.

The terms "pluripotent progenitor cells", "pluripotent progenitors", "pluripotent stem cells", "multipotent progenitor cells" and the like, as used herein refer to cells that are capable of differentiating into two or more different cell types and proliferating. Non limiting examples of pluripotent precursor cells include but are not limited to embryonic stem cells, blastocyst derived stem cells, fetal stem cells, induced pluripotent stem cells. Pluripotent progenitor cells may be acquired from public or commercial sources or may be newly derived. As described herein, in some instances, pluripotent progenitor cells of the subject disclosure are those cells capable of giving rise to hematopoietic stem cells.

The term "lineage bifurcation" and "lineage segregation" are used interchangeably herein and refer to a cell-fate decision where a stem cell and/or progenitor cell has the ability to differentiate into two or more cell-types.

The term "population", e.g., "cell population" or "population of cells", as used herein means a grouping (i.e., a population) of two or more cells that are separated (i.e., isolated) from other cells and/or cell groupings. For example, a 6-well culture dish can contain 6 cell populations, each population residing in an individual well. The cells of a cell population can be, but need not be, clonal derivatives of one another. A cell population can be derived from one individual cell. For example, if individual cells are each placed in a single well of a 6-well culture dish and each cell divides one time, then the dish will contain 6 cell populations. The cells of a cell population can be, but need not be, derived from more than one cell, i.e. non-clonal. The cells from which a non-clonal cell population may be derived may be related or unrelated and include but are not limited to, e.g., cells of a particular tissue, cells of a particular sample, cells of a particular lineage, cells having a particular morphological, physical, behavioral, or other characteristic, etc. A cell population can be any desired size and contain any number of cells greater than one cell. For example, a cell population can be 2 or more, 10 or more, 100 or more, 1,000 or more, 5,000 or more, $10^4$ or more, $10^5$ or more, $10^6$ or more, $10^7$ or more, $10^8$ or more, $10^9$ or more, $10^{10}$ or more, $10^{11}$ or more, $10^{12}$ or more, $10^{13}$ or more, $10^{14}$ or more, $10^{15}$ or more, $10^{16}$ or more, $10^{17}$ or more, $10^{18}$ or more, $10^{19}$ or more, or $10^{20}$ or more cells.

The terms "homogenous population", as it relates to cell populations, refers to a cell population that is essentially pure and does not consist of a significant amount of undesired or contaminating cell types. By significant amount, in this context, is meant an amount of undesired or contaminating cell types that negatively impacts the use of the isolated desired cell population. As such, the actual amount of undesired or contaminating cells that defines a significant amount will vary and depend on the particular type of undesired or contaminating cells and/or the particular use of the desired cell type. For example, in a population of differentiated mesodermal cells used in the treatment of a subject, a significant amount of improperly differentiated contaminating cell types will be small as such cells may a high capacity to negatively impact the use of the generated desired cell population. In comparison, e.g., in a population of differentiated mesodermal cells used in the treatment of a subject, a significant amount of contaminating progenitor cells may be relatively large as such cells may have a low capacity to negatively impact the use of the generated desired cell population. In some instances, a homogenous population may refer to a highly enriched population. Levels of homogeneity will vary, as described, and may, in some instances, be greater than 60% pure, including e.g., more than 65%, more than 70%, more than 75%, more than 80%, more than 85%, more than 90%, more than 95%, more than 96%, more than 97%, more than 98%, more than 99%, more than 99.5%, more than 99.6%, more than 99.7%, more than 99.8%, and more than 99.9%.

The term "heterologous", as it refers to a "heterologous sequence" or "heterologous nucleic acid", means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter.

The term "high cell density", as it relates to cells, means the cell numbers within an area or volume is high. For example, cells are in close contact with one another when cultured in high cell density. In some embodiments high cell density refers to a density of at least about $1.25 \times 10^8$ cells/$cm^2$.

Methods

Aspects of the disclosure include methods for deriving hematopoietic stem cells from pluripotent progenitor cells. What is meant by pluripotent progenitors is described herein. Pluripotent progenitors of the instant disclosure may be acquired from any convenient source, including but not limited to newly derived from a subject of interest or tissue specimen or other cellular sample, obtained from a public repository, obtained from a commercial vendor, and the like. In some instances, pluripotent cells of interest include human cells including but not limited to, e.g., human embryonic stem cells, human induced pluripotent stem cells, human fetal stem cells, and the like.

In some instances, pluripotent progenitor cells of the subject disclosure may be unmodified such that the cells have not been genetically or otherwise modified from their natural state prior to modification according the methods described herein. In other instances, pluripotent progenitor cells of the subject disclosure may be unmodified such that the cells have been genetically or otherwise modified from their natural state prior to modification according the methods described herein. Modification of pluripotent progenitors and derived mesodermal cell type is described in further detail elsewhere herein.

Generation of hematopoietic stem cells from pluripotent progenitors as described herein generally involves one or more lineage restriction events in which cultured pluripotent progenitor cells are subjected to one or more treatments causing the cultured cells or a population thereof to take on the features of one mesodermal cell type or intermediate over another. Such lineage restrictions, in some instances, may be referred to as developmental bifurcations. Multiple lineage restriction events may be required to achieve desired hematopoietic stem cells. In certain instances, lineage restriction events may be performed successively such that a first mesodermal cell type may be achieved by a first linage restriction event and the first cell type may be subjected to a second lineage restriction event to achieve a desired second mesodermal cell type. The number of lineage restriction events required to achieve a particular mesodermal cell type of interest will vary depending on the particular desired mesodermal cell type and the starting progenitor or pluripotent cell type. In some instances, the number of lineage restriction events required to achieve a hematopoietic stem cells may be one or more events, including but not limited to, e.g., 1 lineage restriction event, 2 lineage restriction events, 3 lineage restriction events, 4 lineage restriction events, 5 lineage restriction events, 6 lineage restriction events, etc.

Lineage restriction events as described herein may be induced by induction compositions wherein an induction composition is a composition that contains one or more induction agents useful in guiding cellular development or lineage restricting a cell along a particular lineage. Induction agents include those agents that activate or inhibit particular developmental signaling pathways that drive development. Such signaling pathways that may be activated or inhibited by induction agents include but are not limited to those signaling pathways that upon activation and inhibition generally promote mesodermal differentiation. In some instances, signaling pathways of interest also include those pathways that generally inhibit ectodermal differentiation or those signaling pathways that generally inhibit endodermal differentiation. As will be clear from the instant disclosure, whether activation or inhibition of a particular signaling pathway is necessary to generate a particular mesodermal cell type of interest will depend on a number of factors including but not limited to, e.g., the particular desired mesodermal cell type, the timing of use of the particular inductive agent and/or induction composition, the starting cell type to be induced, etc.

In some embodiments a method is provided for producing a substantially pure population of hematopoietic stem cells (HSC) in defined monolayer conditions in media comprising extracellular signaling agents to guide differentiation, the method comprising: (a) differentiating human pluripotent stem cells into primitive streak cells; (b) differentiating primitive streak cells into dorsal lateral mesoderm; (c) differentiating dorsal lateral mesoderm cells into artery cells, e.g. trunk artery cells; (d) differentiating trunk artery cells into hemogenic endothelium; and (e) differentiating hemogenic endothelium into HSC.

Primitive streak cells can be generated by culturing a human pluripotent cell in media comprising a BMP agonist, an FGF agonist, a WNT agonist, and TGFβ agonist for a period of about 1 day. The factors and relevant concentrations are as defined herein. The population of primitive streak cells can be cultured in media comprising a WNT inhibitor, BMP agonist, VEGF agonist, PI3K inhibitor, cAMP agonist, retinoic acid (RA) agonist, TGFβ inhibitor, and Vitamin C for a period of about 1 day to generate a population of dorsal lateral mesoderm cells. For example, as shown in FIG. 1, VEGF treatment induces day 2 dorsal lateral mesoderm. Day 1 hPSC-derived primitive streak cells are treated with BMP4+XAV939 for 24 hours, in the presence or absence of VEGF (10-100 ng/mL) as a VEGF agonist. BMP specifies, whereas TGFβ and WNT repress, day 2 dorsal lateral mesoderm.

To generate artery progenitor cells, the population of dorsal lateral mesoderm cells is cultured in media comprising a VEGF agonist, TGFβ agonist, WNT inhibitor, PI3K inhibitor, BMP inhibitor, and Vitamin C; optionally in the presence of a retinoic acid (RA) agonist for a period of about 1 day to produce a population of artery progenitor cells.

Figure 2:
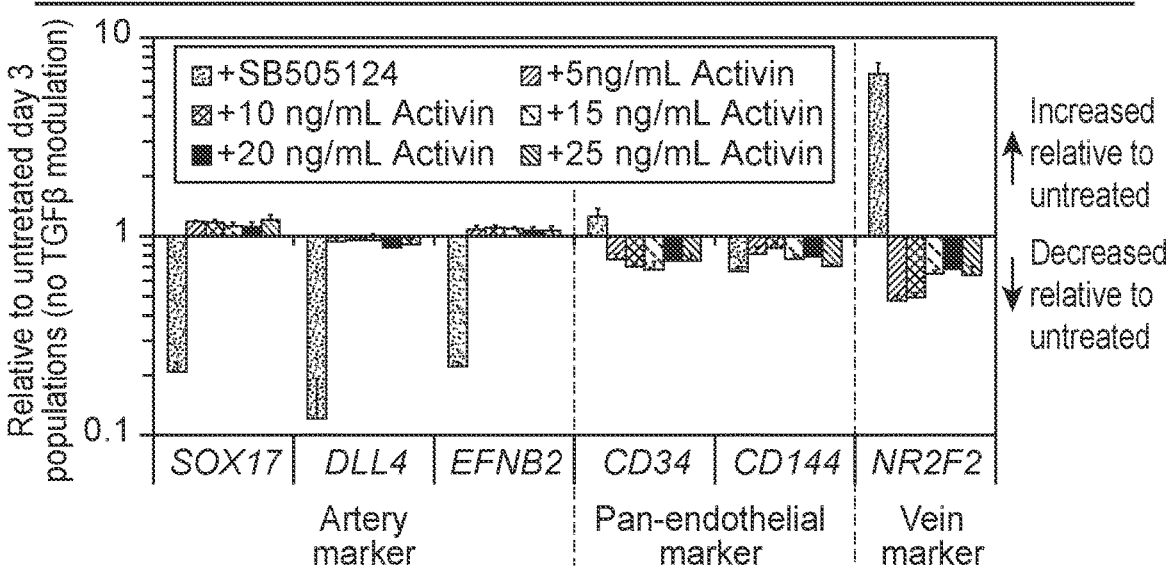
FIG. 2: Efficient generation of human artery endothelial progenitors from hPSCs within 3 days. A) Cartoon of downstream differentiation of day 2 hPSC-derived lateral mesoderm into cardiac progenitors, artery endothelial cells or (pre)-vein endothelial cells. B) TGFβ inhibits day 3 artery formation; day 2 hPSC-derived dorsal lateral mesoderm was further differentiated for 24 hours, in the presence or absence of TGFβ agonist (Activin, 5-25 ng/mL) or TGFβ inhibitor (A-83-01 [1 µM] or SB-505124 [2 µM]); qPCR (top) and flow cytometry (bottom) was performed on day 3 cell populations. C) PI3K inhibits day 3 artery formation; day 2 hPSC-derived dorsal lateral mesoderm was further differentiated for 24 hours, in the presence or absence of PI3K inhibitor (GDC0941, 0.5-2 µM); qPCR (top) and flow cytometry (bottom) was performed on day 3 cell populations. D) Flow cytometry of SOX17-mCherry hPSC-derived day 3 artery endothelial populations reveals highly efficient generation of SOX17$^+$ CD34$^+$ artery progenitors, which co-express CD31 (PECAM1) and CD144 (VE-CADHERIN). E) SOX17 and VE-CADHERIN (CD144) immunostaining of wild-type hPSCs either before or after differentiation into day 3 artery endothelial populations (DAPI: nuclear counterstain). F) qPCR of FACS-purified day 3 SOX17$^+$ CD34$^+$ hPSC-derived artery progenitors (as well as undifferentiated hPSC controls) reveals expression of artery-specific and pan-endothelial markers, while markers of alternate cell fates are minimally expressed; qPCR data are shown relative to the reference gene YWHAZ (100%=same expression as YWHAZ). G) Flow cytometry of H1, H7, H9 and SUN004.1.9 hPSCs differentiated into arteries for 3 days reveals that >94% of cells are CD144⁺ DLL4⁺ arterial cells H) Side-by-side comparison of our artery differentiation system against 4 prevailing methods for endothelial differentiation in the H1 and SUN004.1.9 hPSC lines; flow cytometry to assess the percentage of CD34⁺ CD144⁺ endothelial cells was performed on days 3, 5 and 6 of differentiation.
Figure 2:
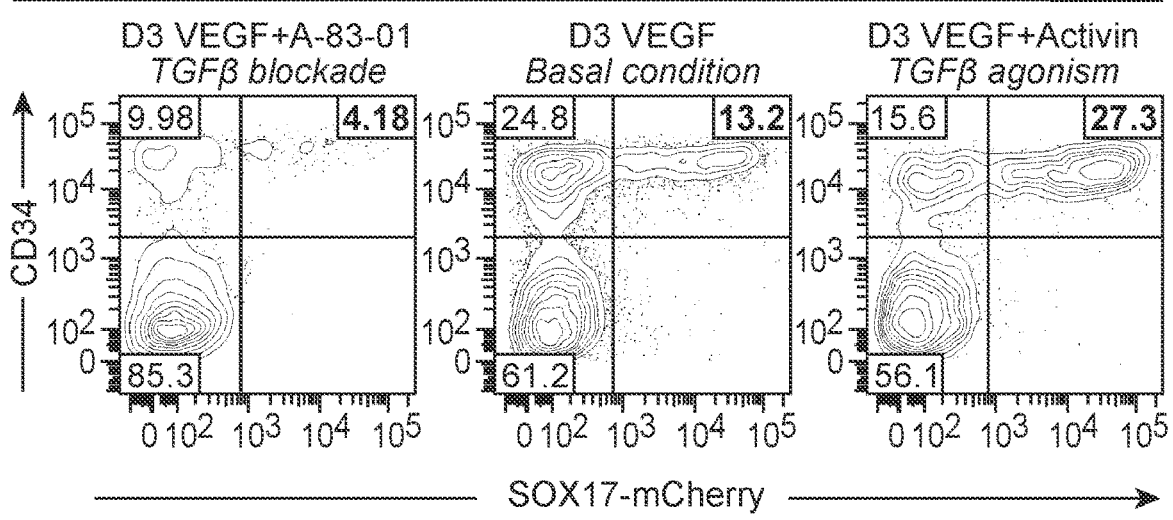
Figure 2:
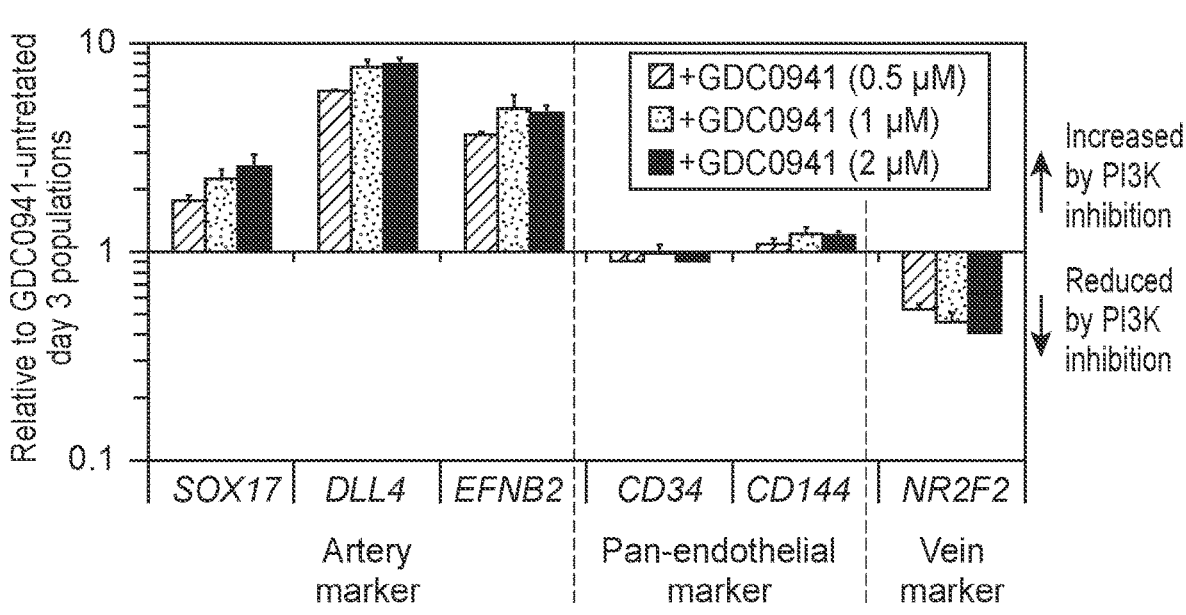
Figure 2:
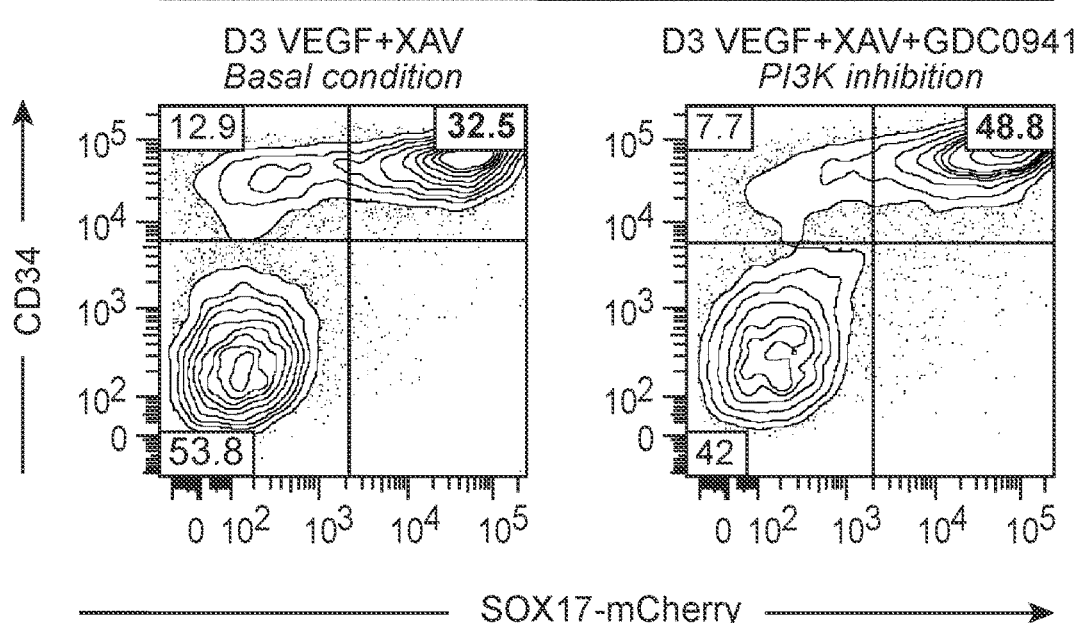
Figure 2:
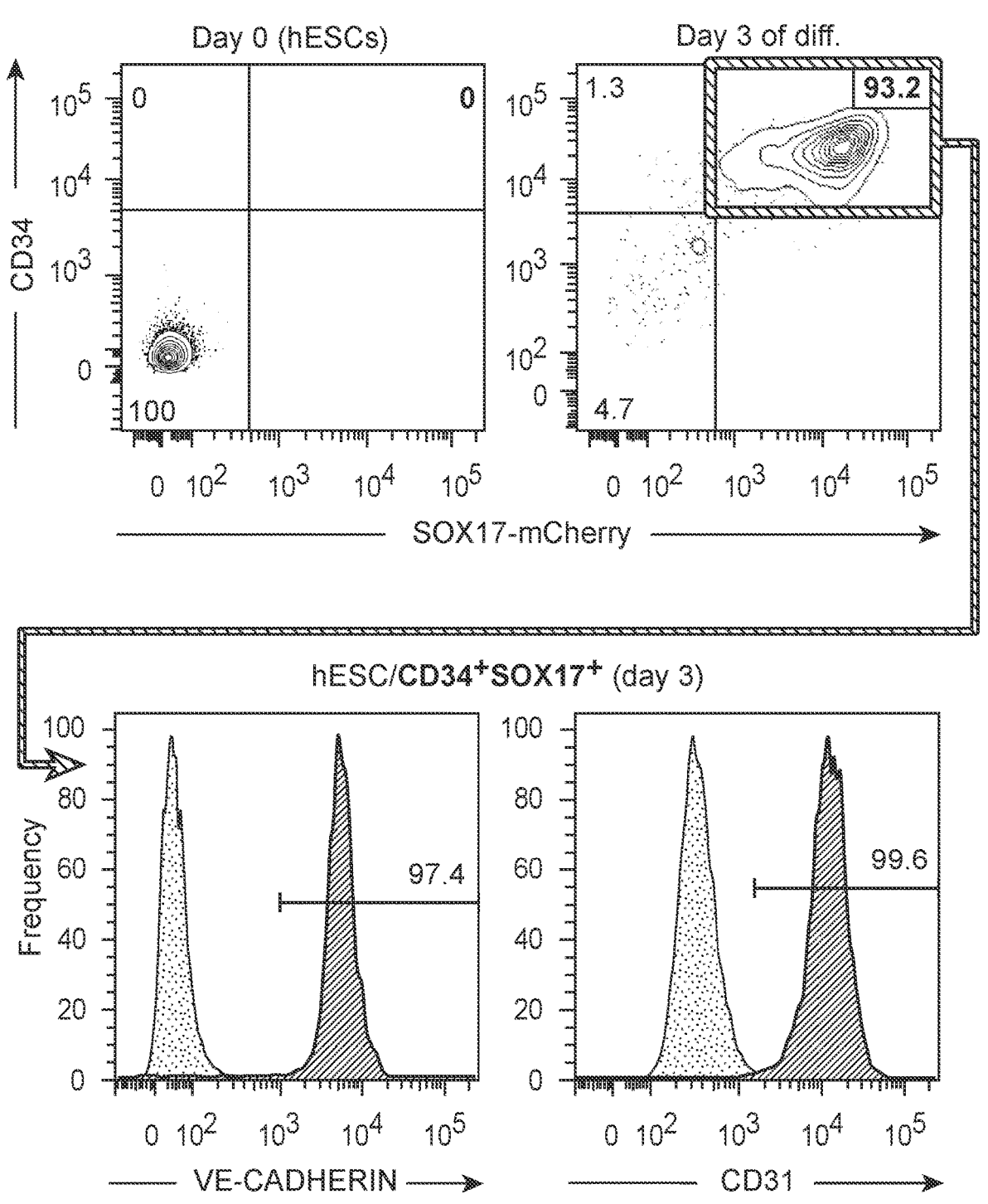
Figure 2:
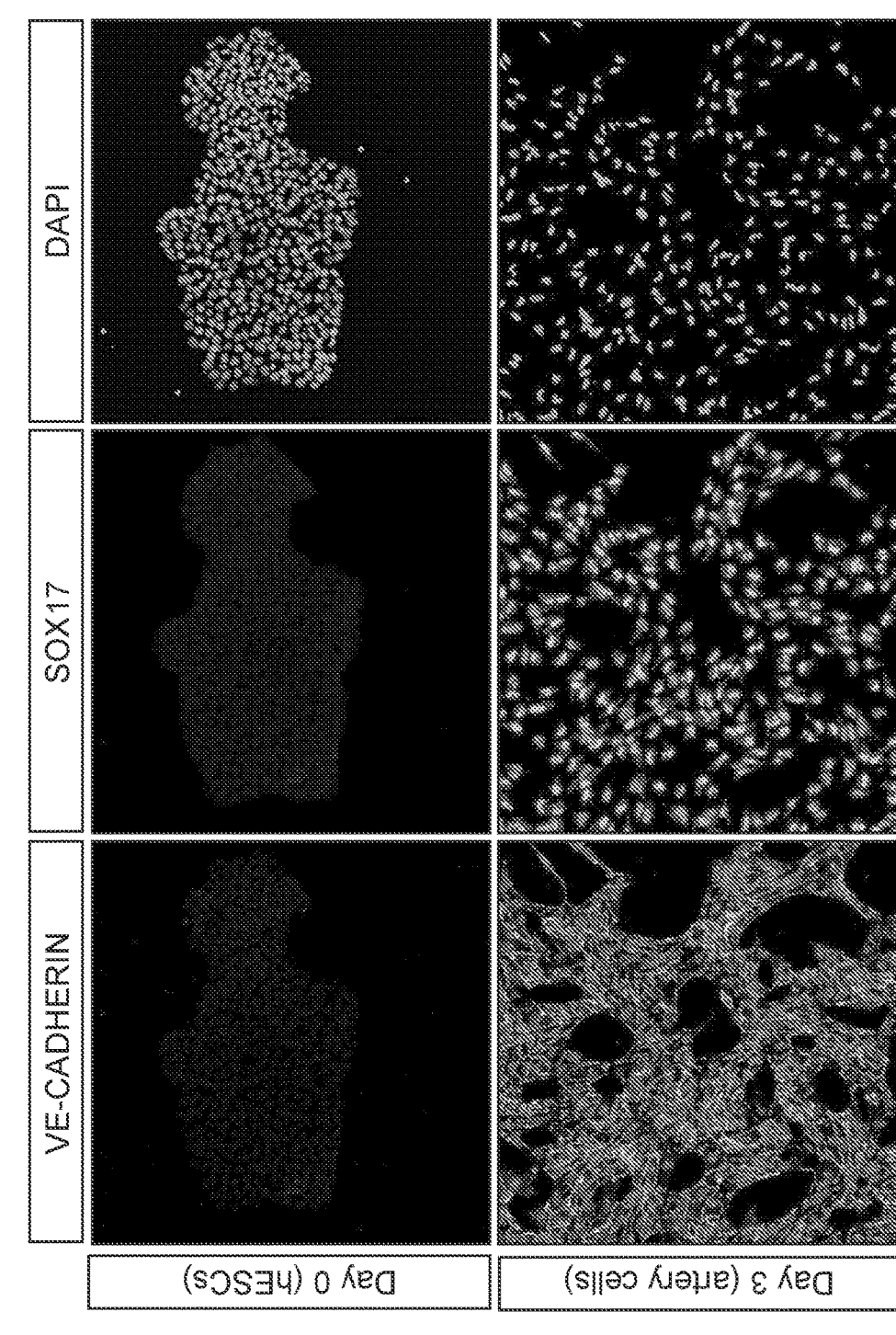
Figure 2:
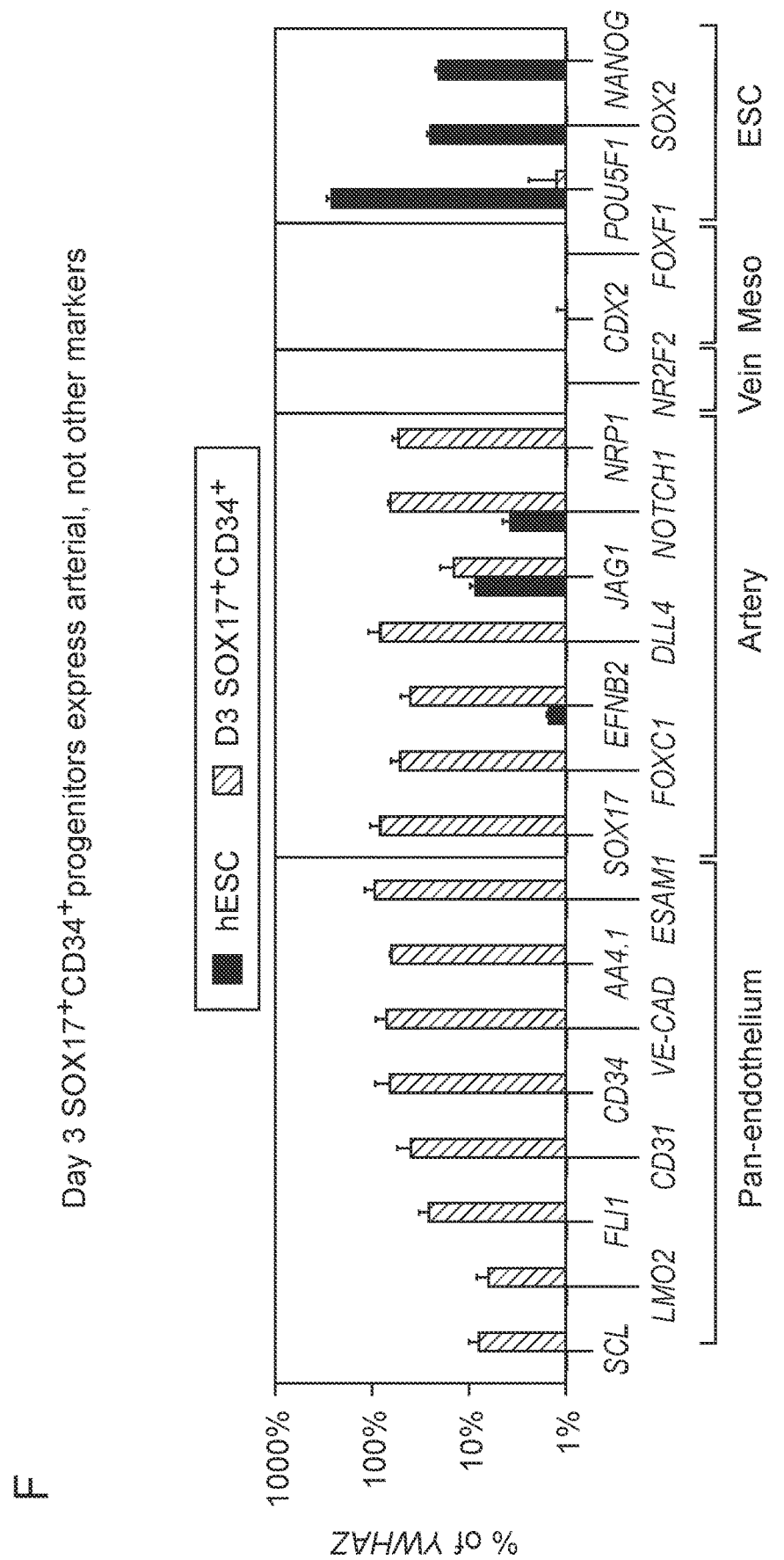
Figure 2:
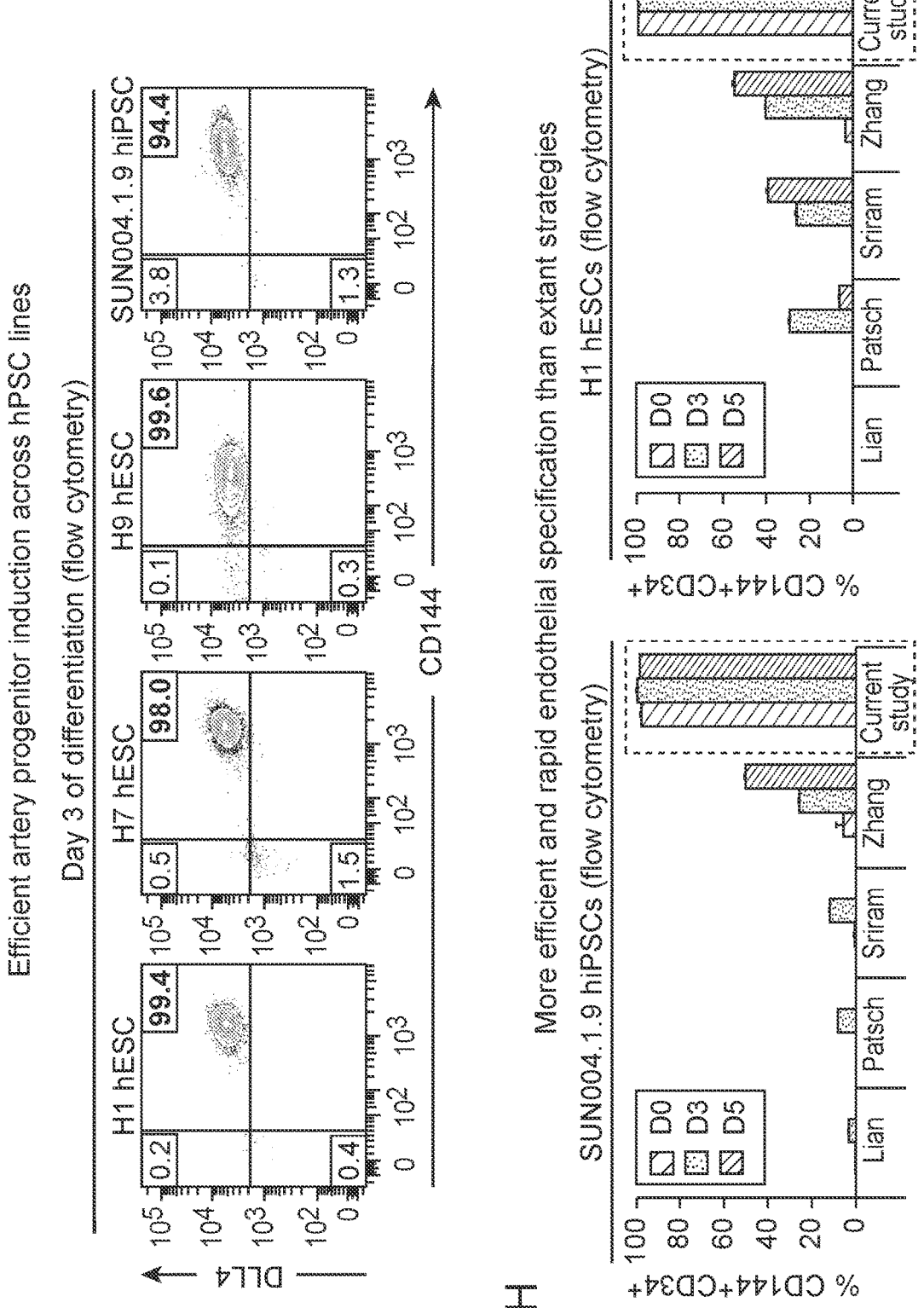

For example as shown in FIG. 2, day 2 hPSC-derived lateral mesoderm can be differentiated into cardiac progenitors, artery endothelial cells or (pre)-vein endothelial cells. The presence of TGFβ inhibits day 3 artery formation, as shown by culture in the presence or absence of TGFβ agonist (Activin, 5-25 ng/mL) or TGFβ inhibitor (A-83-01 [1 μM] or SB-505124 [2 μM]). PI3K inhibits day 3 artery formation; as shown by culture in the presence or absence of PI3K inhibitor (GDC0941, 0.5-2 μM). These methods provide for highly efficient generation of SOX17$^+$ CD34$^+$ artery progenitors, which co-express CD31 (PECAM1) and CD144 (VE-CADHERIN). E) SOX17 and VE-CADHERIN (CD144). In some embodiments, hPSC-derived primitive streak cells are differentiated into artery cells over the course of about hours, in the presence or absence of an RA agonist (TTNPB).

hPSCs differentiated into artery progenitor cells are >94% of CD144$^+$ DLL4$^+$ and can be isolated by contacting the artery progenitor cells with a DLL4 binding agent, for example a DLL4 specific antibody, and isolating the artery progenitor cells by binding of the DLL4 binding agent to the artery progenitor cells and selecting for DLL4 binding cells to produce a purified population of artery progenitor cells.

Figure 4:
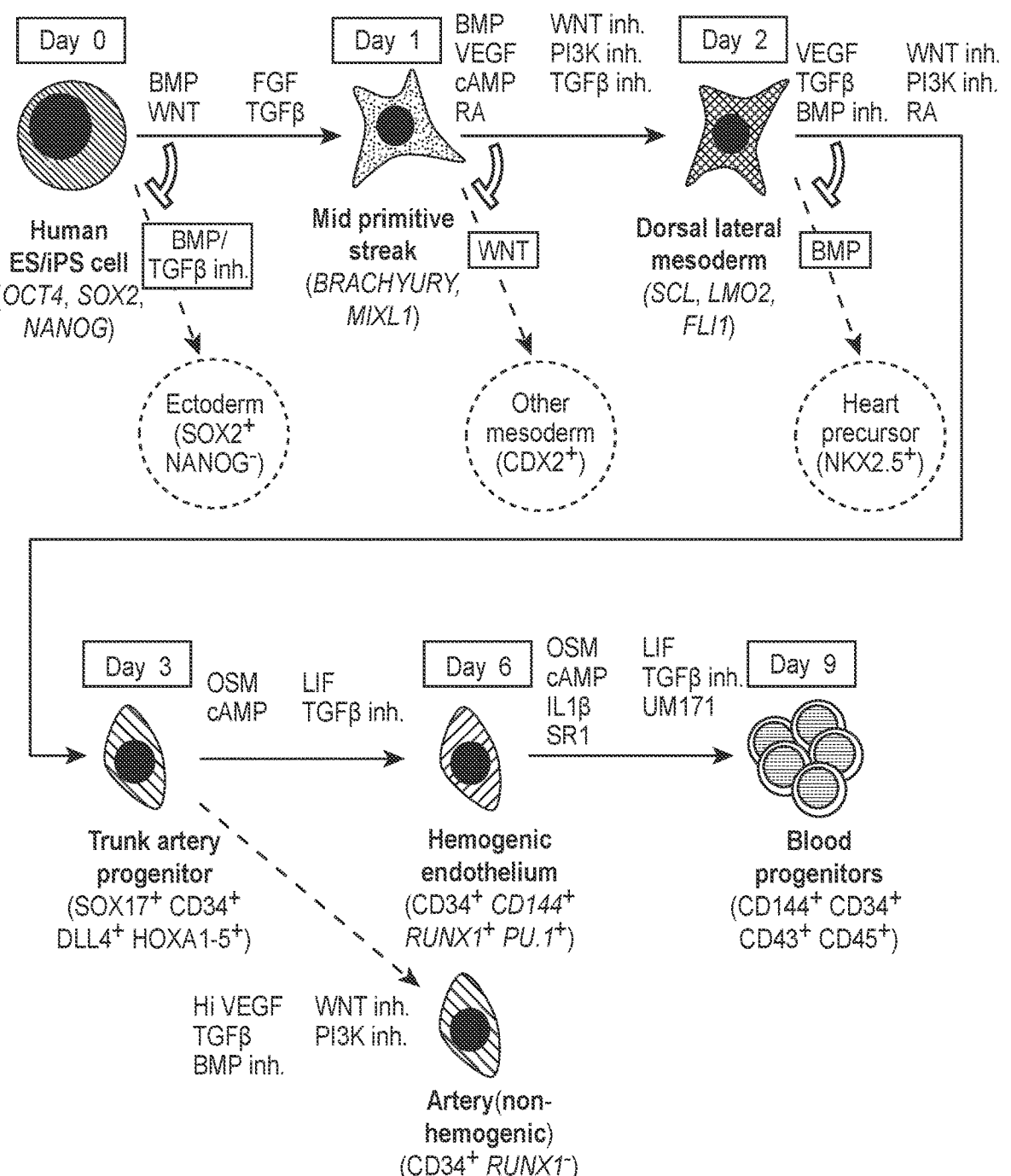
FIG. 4: Efficient generation of trunk artery and hemogenic endothelium from hPSCs within 3 and 6 days, respectively. A) Cartoon of the strategy to generate trunk artery, hemogenic endothelium and HSC-like cells. B) Retinoic acid (RA) signaling induces HOXA1-5 genes in hPSC-derived trunk artery cells; day 1 hPSC-derived primitive streak cells were differentiated into trunk artery cells over the course of 48 hours, in the presence or absence of an RA agonist (TTNPB). C) Flow cytometry (left) and qPCR (right) of hPSC-derived trunk artery cells; for the qPCR data, gene expression is normalized for each gene to undifferentiated hPSCs (gene expression levels in hPSCs=1.0); as a negative control, hPSC-derived artery cells (white bar, generated in the absence of RA agonist) is shown. D) hPSC-derived day-3 trunk artery cells were differentiated into hemogenic endothelium for 24 hours in the complete hemogenic endothelium medium (Forskolin, SB505124, OSM and LIF), or in media where either Forskolin was withheld; SB505124 was withheld; or both OSM and LIF were withheld. E) RUNX1-mOrange knock-in reporter hPSCs were differentiated into hemogenic endothelium, and flow cytometry was performed each 24 hours F) qPCR of hPSC differentiation into hemogenic endothelium every 24 hours of differentiation shows progressive upregulation of mRNAs encoding hemogenic endothelium transcription factors.
Figure 4:
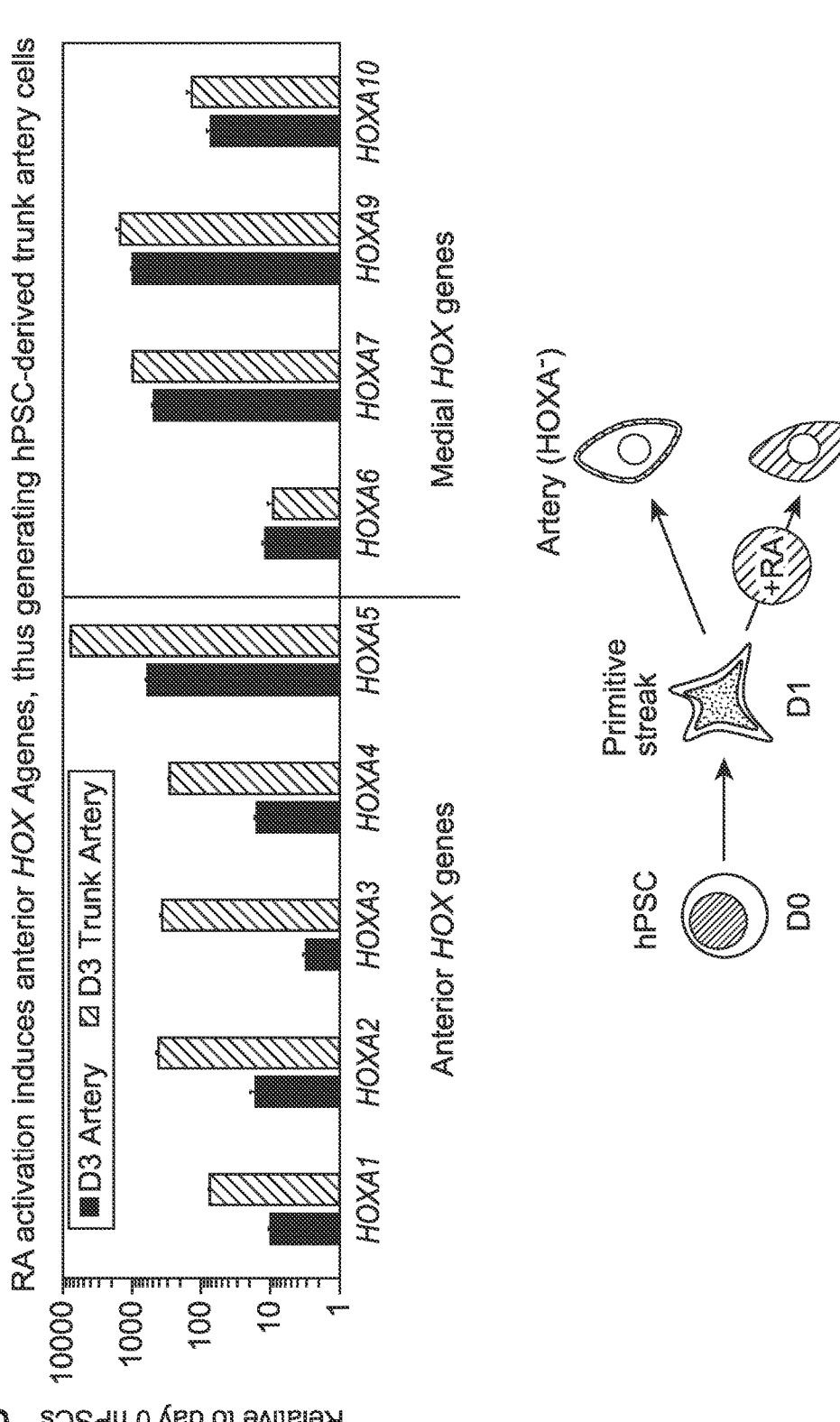
Figure 4:
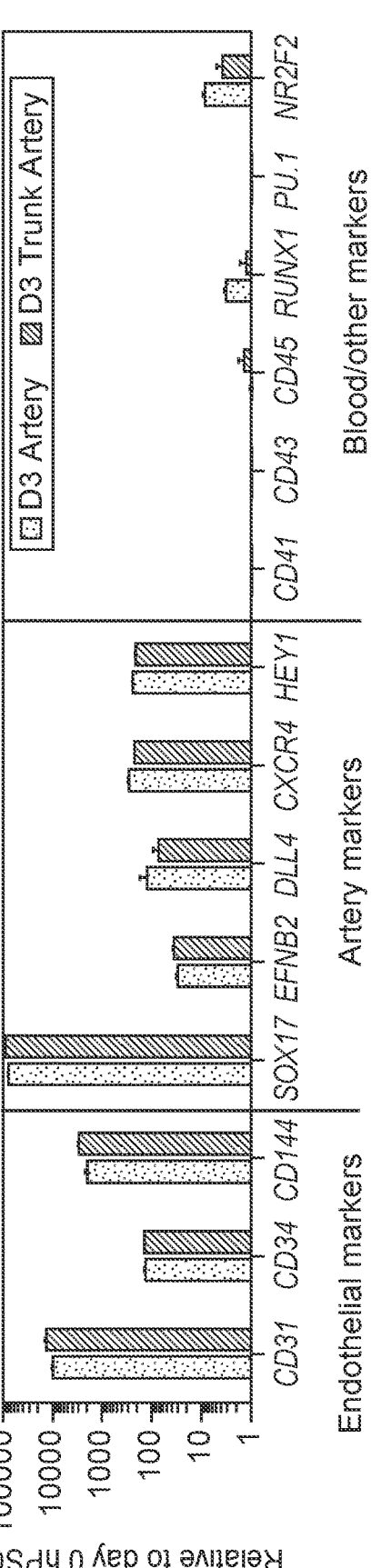
Figure 4:
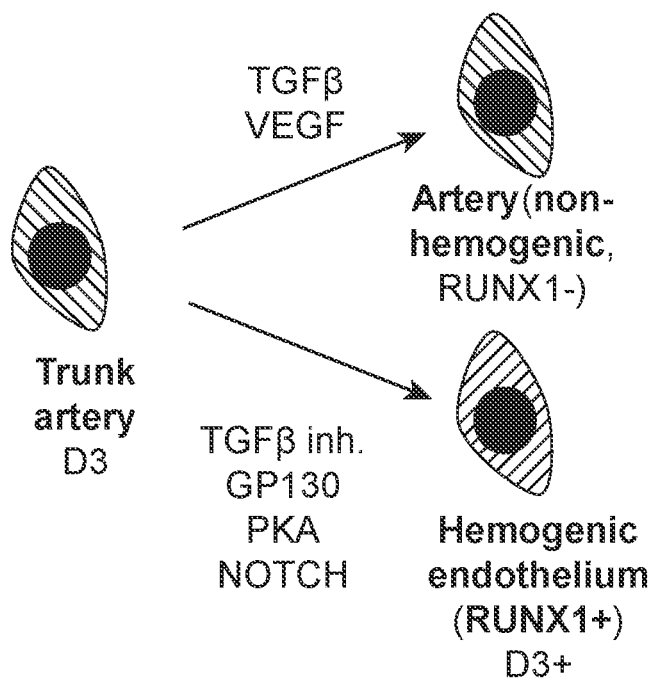
Figure 4:
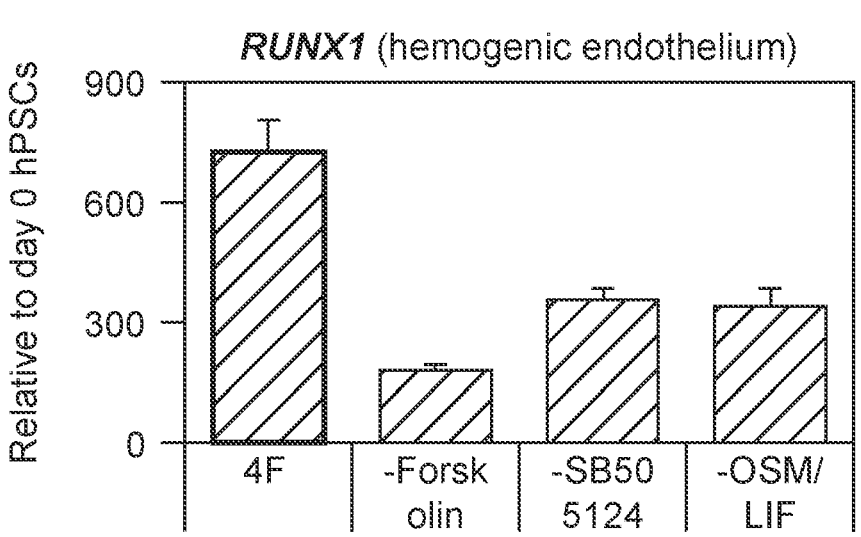
Figure 4:
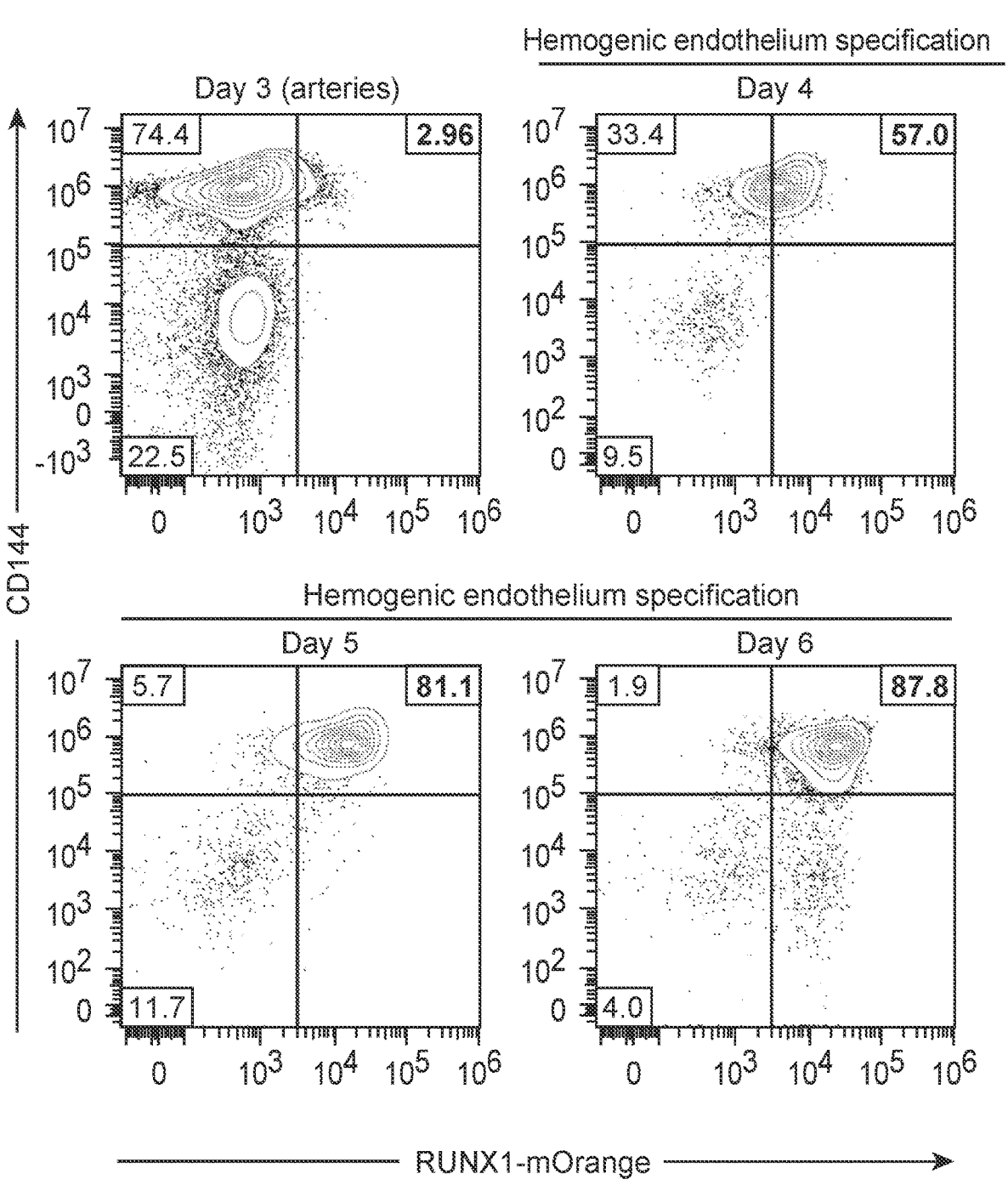
Figure 4:
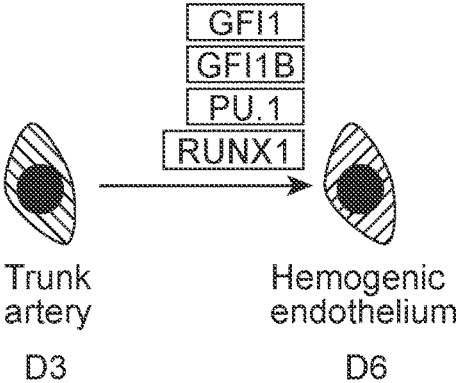
Figure 4:
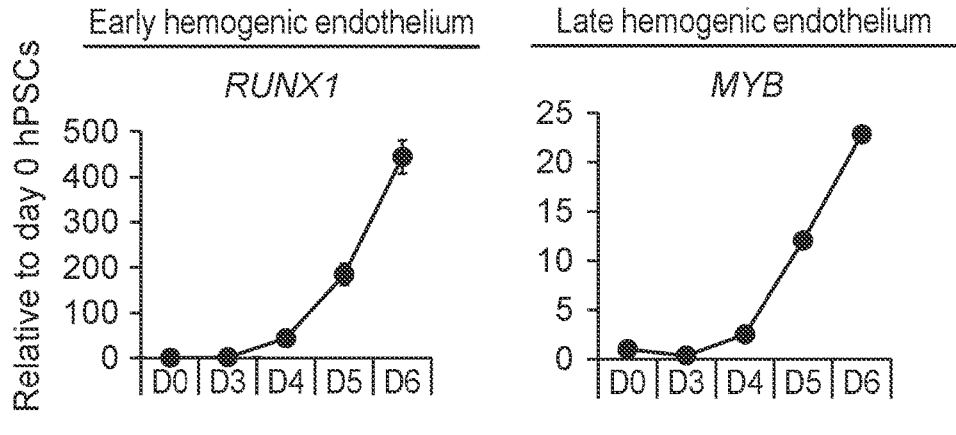
Figure 4:
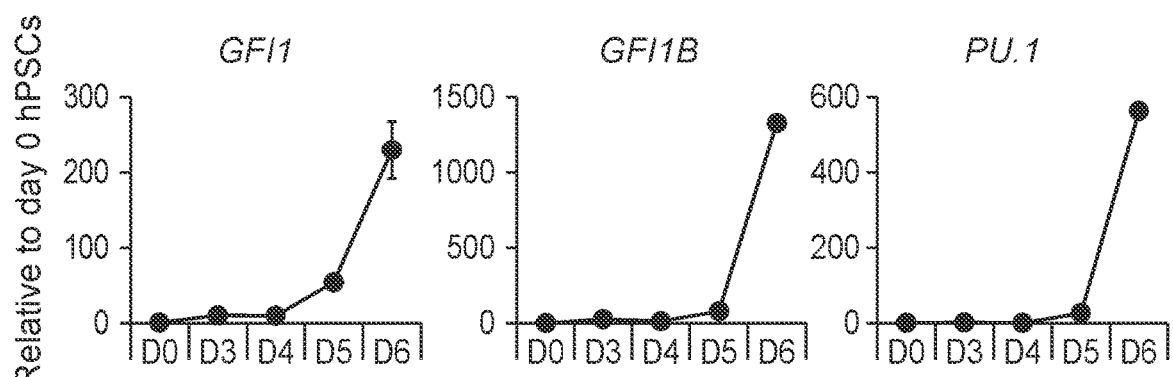

Hemogenic endothelium cells are differentiated from artery progenitor cells by culture at high density in media comprising of a OSM agonist, LIF agonist, CAMP agonist, TGFβ inhibitor, Notch agonist, and serum replacement for about 2 to about 3 days, for example in complete hemogenic endothelium medium (Forskolin, SB505124, OSM and LIF), as shown in FIG. 4.

Figure 5:
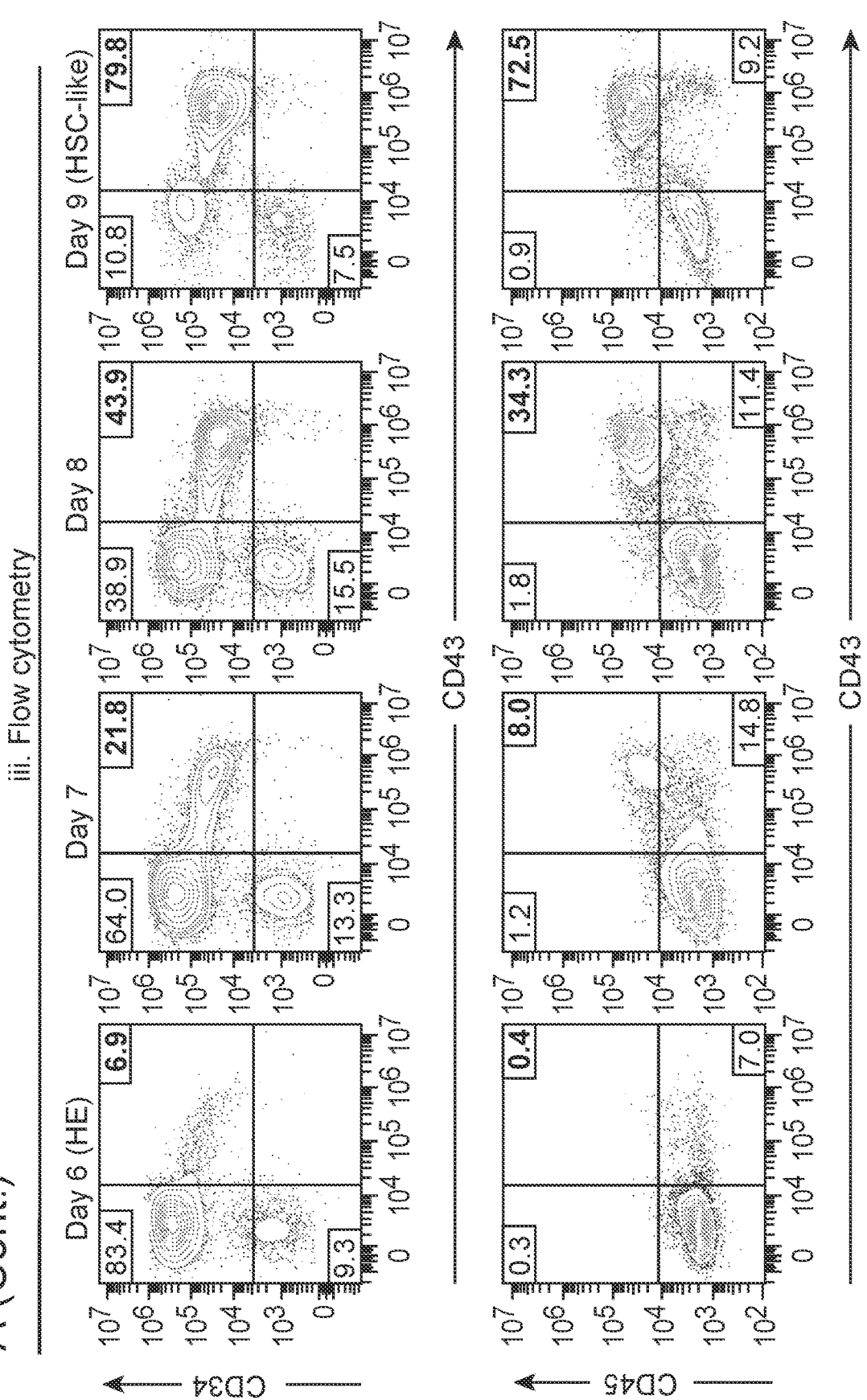
FIG. 5: Efficient generation of HSC-like cells from hPSCs within 9 days. A) hPSC-derived hemogenic endothelium (day 6) was differentiated into HSC-like cells (day 9); i) phase contrast images show that semiadherent blood cells emerge by day 7, and are very abundant by day 9; ii) qPCR every 24 hours of differentiation shows progressive upregulation of blood-associated genes (normalized such that undifferentiated hPSCs=1.0); iii) flow cytometry every 24 hours of differentiation shows progressive emergence of CD34⁺ CD43⁺ CD45⁺ HSC-like cells B, E) Flow cytometry of the hPSC-derived day-9 HSC-like cell population (subgated on the CD43⁺ CD45⁺ HSC-like cells) shows that they express a variety of surface markers and homing receptors expressed on human HSCs (blue shading indicates negative control where the primary antibody was omitted) C, D, F) qPCR comparison of FACS-sorted hPSC-derived day-9 CD34⁺ CD90⁺ CD45RA⁻ HSC-like cells, CD34⁺ CD90⁺ cord blood HSPCs and CD34⁺ CD90⁻ cord blood non-HSPCs; gene expression is normalized for each gene such that expression levels in CD34⁺ CD90⁺ cord blood HSPCs=1.0
Figure 5:
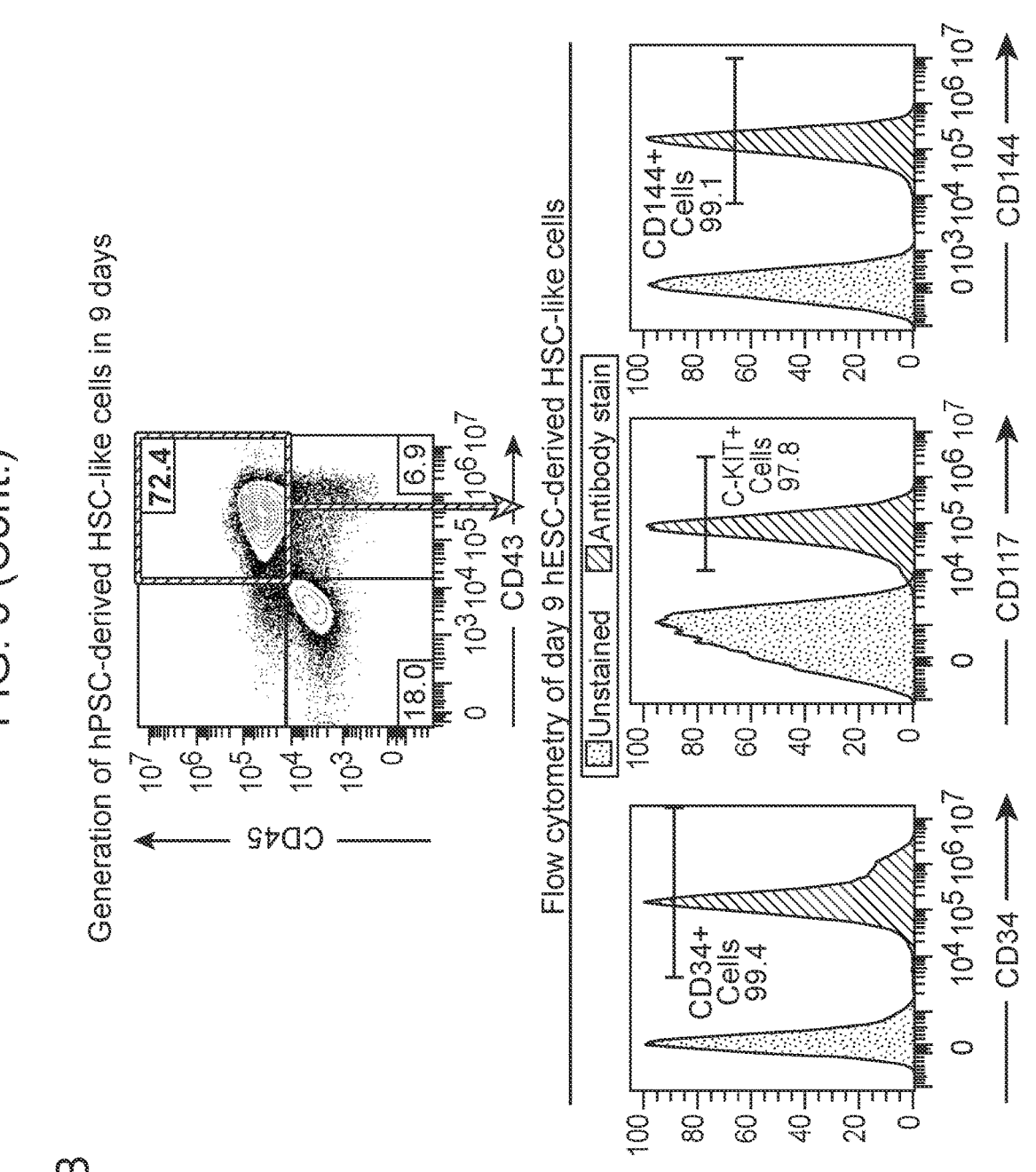
Figure 5:
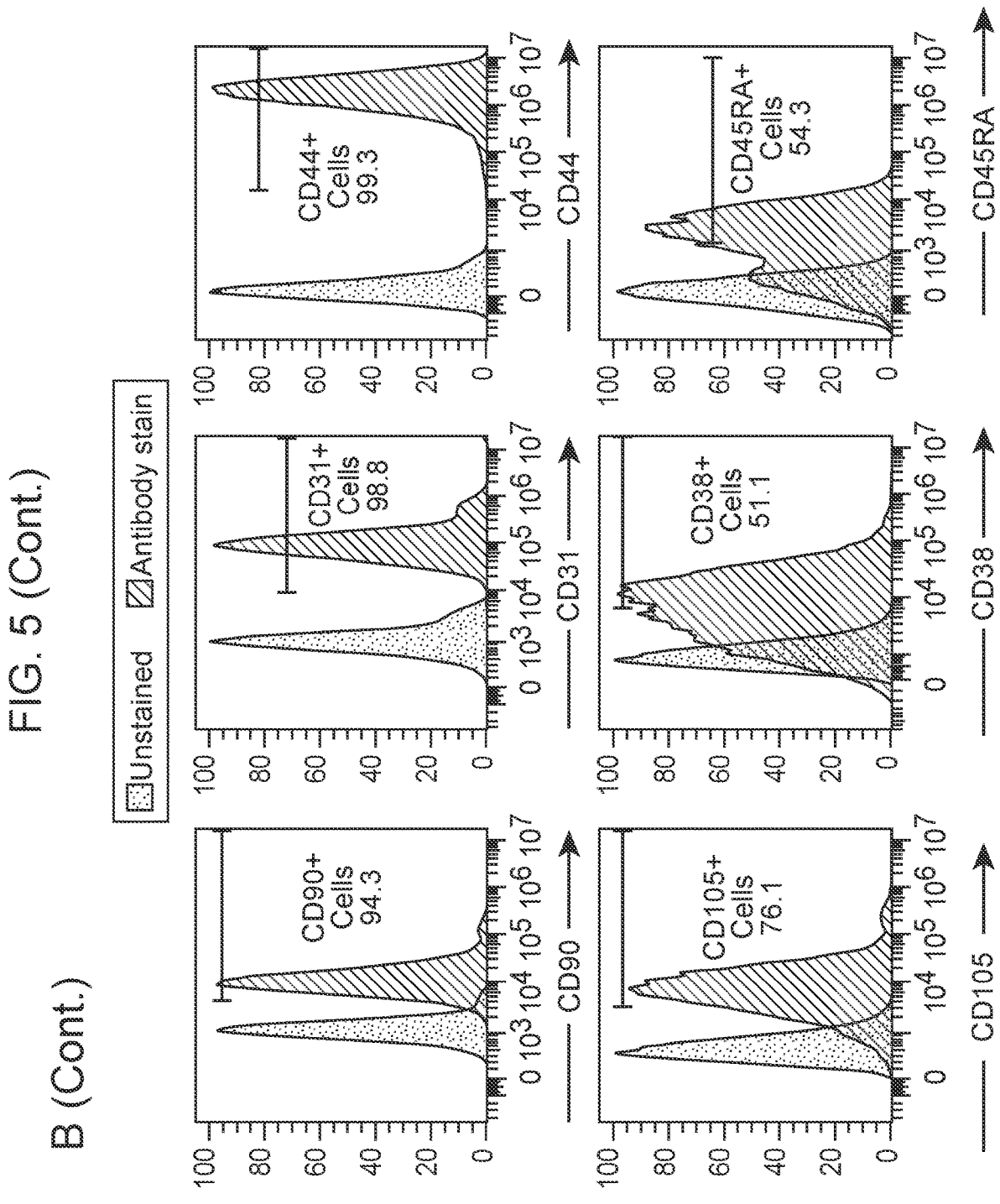
Figure 5:
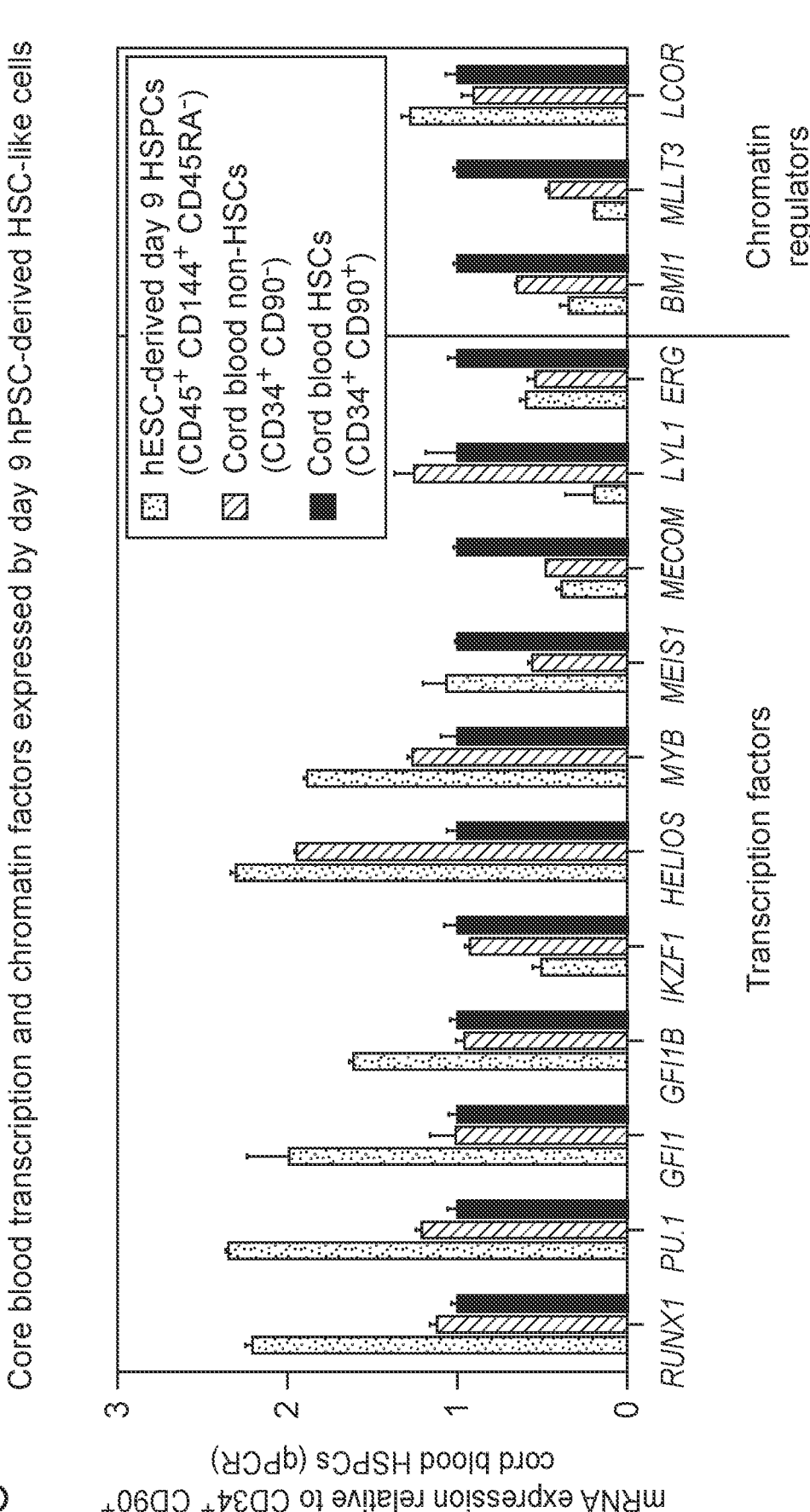
Figure 5:
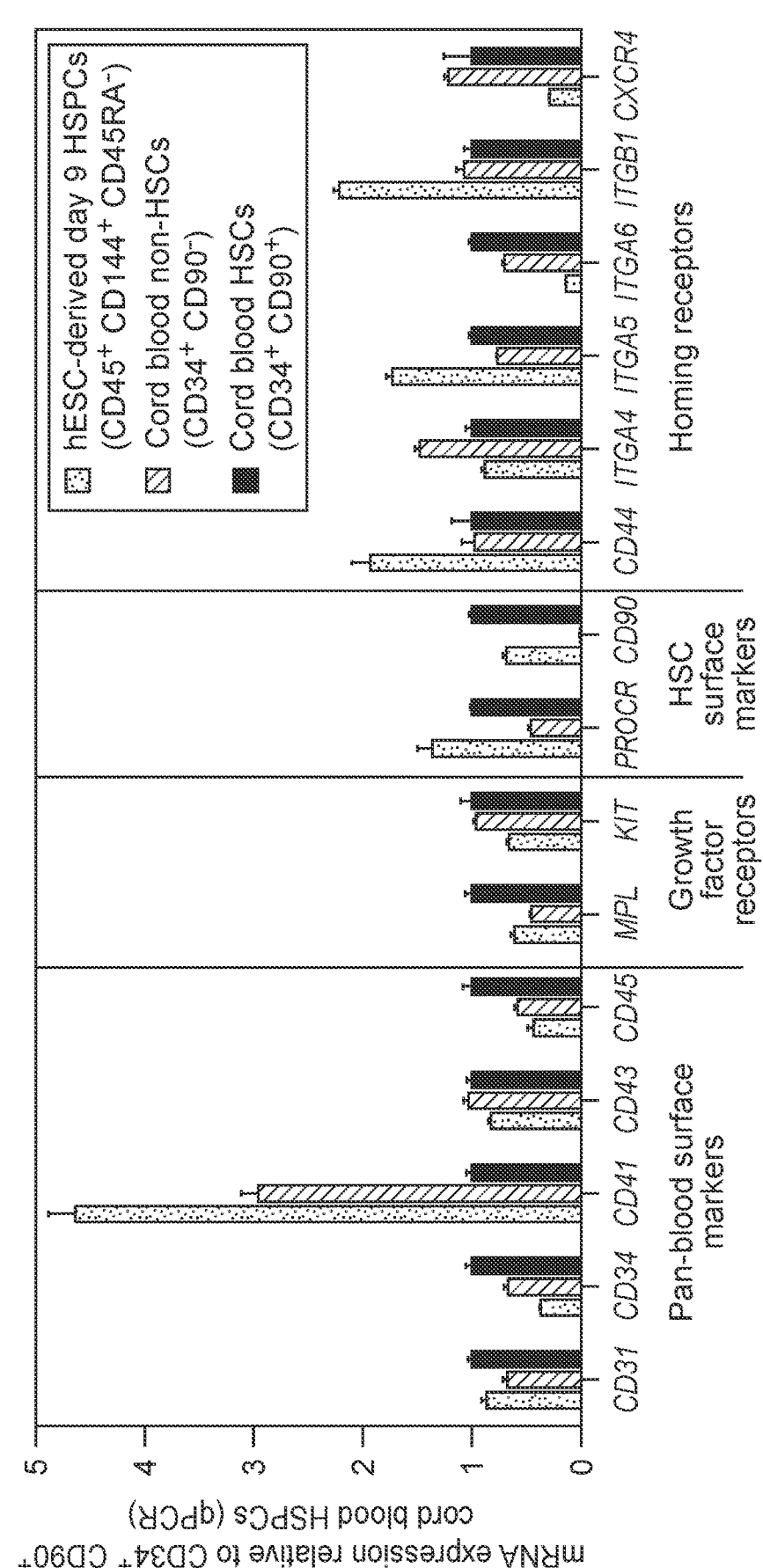
Figure 5:
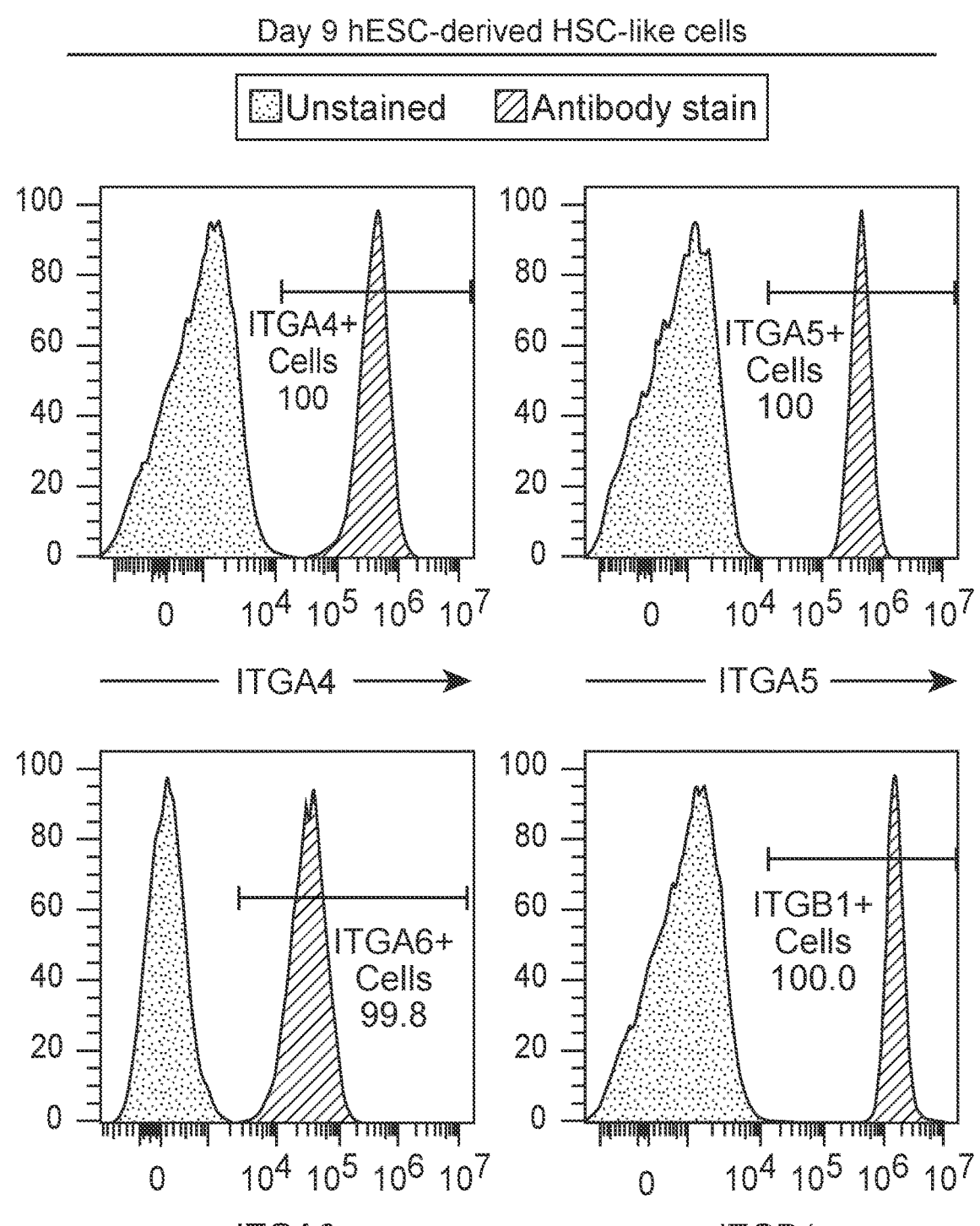
Figure 5:
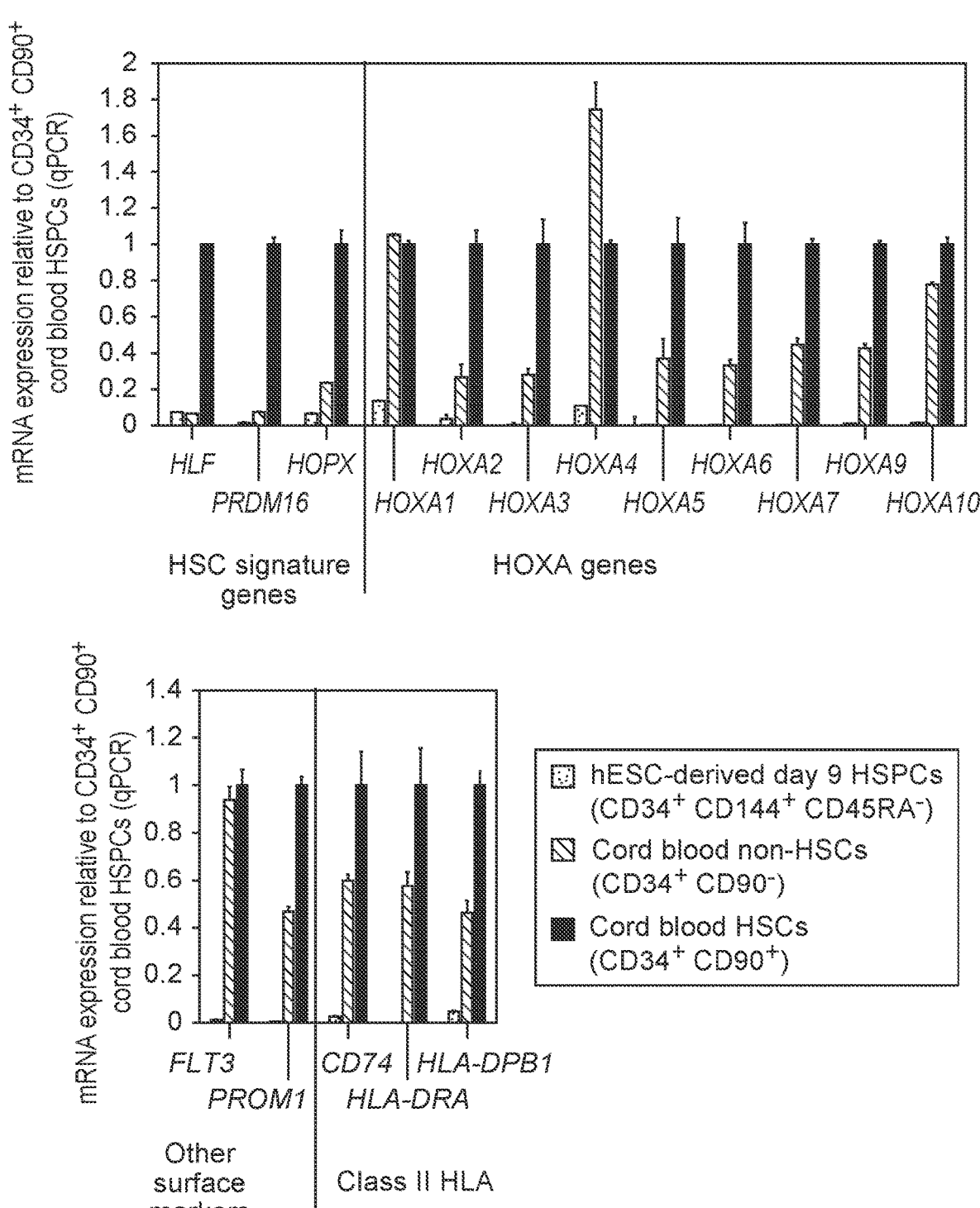

In a final step, the population of hemogenic endothelium cells is cultured in media comprising an OSM agonist, LIF agonist, CAMP agonist, IL-1 agonist, aryl hydrocarbon receptor inhibitor, TGFβ inhibitor, UM171, Notch agonist, and serum replacement, for example KnockOut Serum replacement, for a period of from about 2 to about 3 days to generate a population of hematopoietic stem cells. As shown in FIG. 5, hPSC-derived hemogenic endothelium are differentiated into hHSC over a period of about 3 days, where there is progressive upregulation of blood-associated genes and progressive emergence of CD34⁺ CD43⁺ CD45⁺ HSC-like cells. hPSC-derived HSC-like cells can generate myeloid, erythroid and lymphoid cell-types in vitro.

In other embodiments, the dorsal lateral mesoderm generated as described above are differentiated into pre-vein endothelium cells; and vein endothelium cells in a period of culture of from about 4 to 5 days. The population of dorsal lateral mesoderm cells is cultured at increased density in media comprising a VEGF agonist, TGFβ inhibitor, WNT inhibitor, BMP inhibitor, NOTCH inhibitor, and Vitamin C for a period of about 1 day to produce a population of pre-vein endothelium cells; and the population of pre-vein endothelium cells is cultured in media comprising of a MAPK/ERK inhibitor, TGFβ inhibitor, WNT agonist, NOTCH inhibitor, and Vitamin C for a period of about 1 day to about 2 days to produce a population of vein endothelium cells. The vein endothelium cells are optionally purified by binding to a CD73 binding agent, e.g. a CD73 specific antibody, and selecting for CD73 positive cells.

Figure 3:
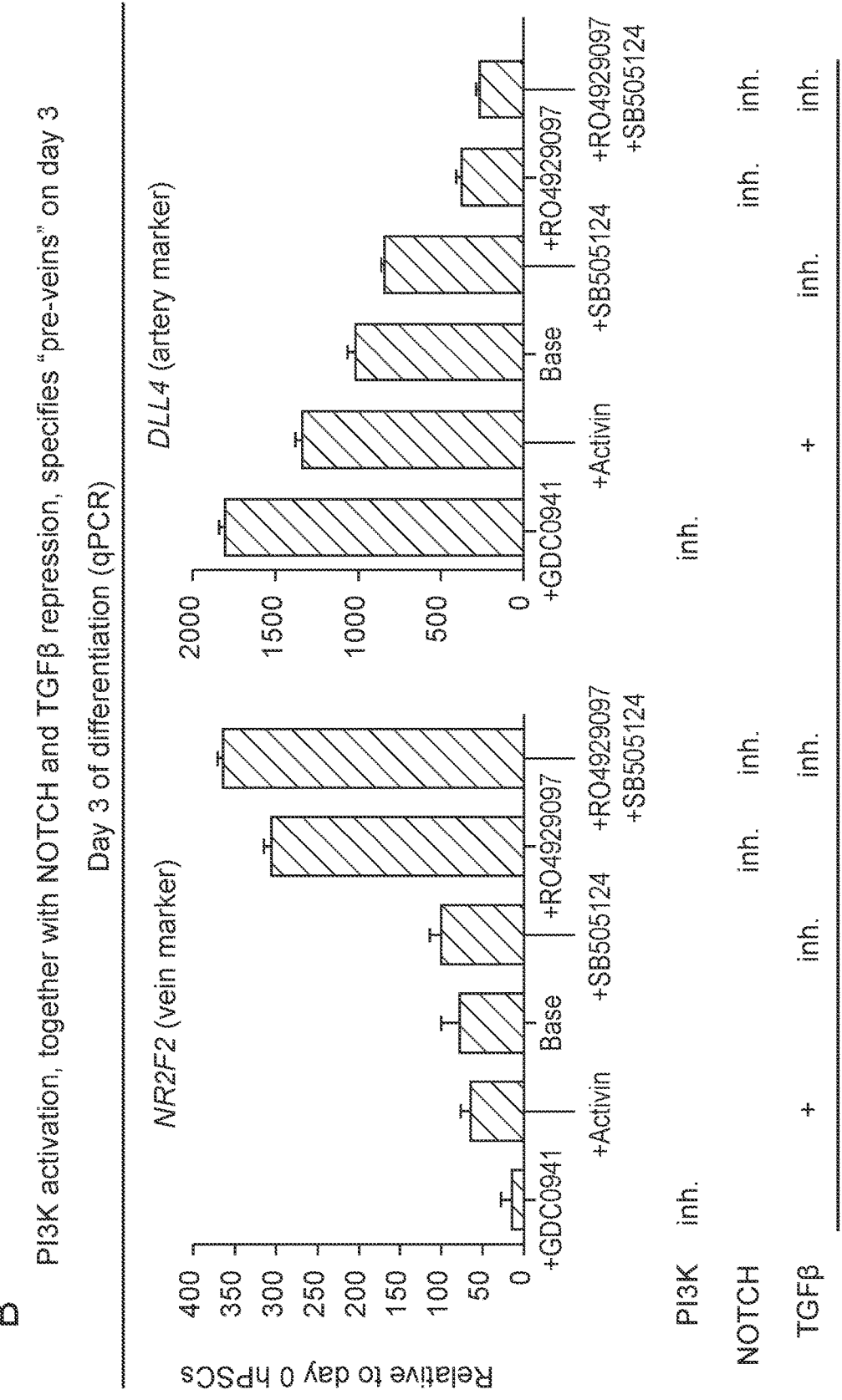
FIG. 3: Efficient generation of human vein endothelial progenitors from hPSCs within 4-5 days. A) Cartoon of downstream differentiation of day 2 hPSC-derived lateral mesoderm into (pre)-vein endothelial cells, while concurrently blocking differentiation into cardiac progenitors or artery endothelial cells. B) Dual inhibition of TGFβ and NOTCH promotes day 3 pre-vein formation; day 2 hPSC-derived dorsal lateral mesoderm was further differentiated in pan-endothelium base media (VEGF+XAV939+DMH1) for 24 hours, in the presence or absence of TGFβ agonist (Activin, 15 ng/mL), TGFβ inhibitor (SB505124, 2 μM), PI3K inhibitor (GDC0941, 2 μM) or NOTCH inhibitor (R04929097, 1 μM); qPCR (right) was performed on day 3 cell populations. C) Cartoon of downstream differentiation of day 2 hPSC-derived lateral mesoderm into pre-vein endothelial cells, and subsequently vein endothelial cells, and the signals that control each lineage transition. D) Temporally-dynamic control of VEGF/ERK signaling is critical for vein differentiation; day 2 hPSC-derived dorsal lateral mesoderm was further differentiated into vein cells using pan-endothelium base media (VEGF+XAV939+ DMH1+AA2P), in the presence or absence of ERK inhibitor (PD0325901, 100 nM) on day 3, day 4 or days 3+4; qPCR was performed on day 4 cell populations. E) Flow cytometry analysis of undifferentiated NR2F2-2A-GFP hESCs or those differentiated into vein endothelial cells for 5 days reveals that >80% of day 4 cells are NR2F2⁺ CD144⁺ vein endothelial cells. F) NR2F2 and VE-CADHERIN (CD144) immunostaining of hPSC-derived day 4 vein endothelial cells (DAPI: nuclear counterstain). G) Percentage of cells expressing selected cell-surface markers among day 0 hPSCs, day 1 mid primitive streak, day 2 dorsal lateral mesoderm, day 3 artery cells or day 4 vein cells, as assessed by robotically-enabled, high-throughput surface marker screening. Artery and vein cells were first pre-gated on their respective CD144⁺ fractions before assessing marker expression. H) DLL4, CD73 and CD144 expression on day 0 hPSCs, day 4 artery cells and day 4 vein cells as shown by flow cytometry. Bottom row depicts DLL4 and CD73 expression on the respective CD144⁺ fractions of artery and vein cells, thus confirming that in these populations, it is the endothelial cells that express DLL4 and CD73.
Figure 3:
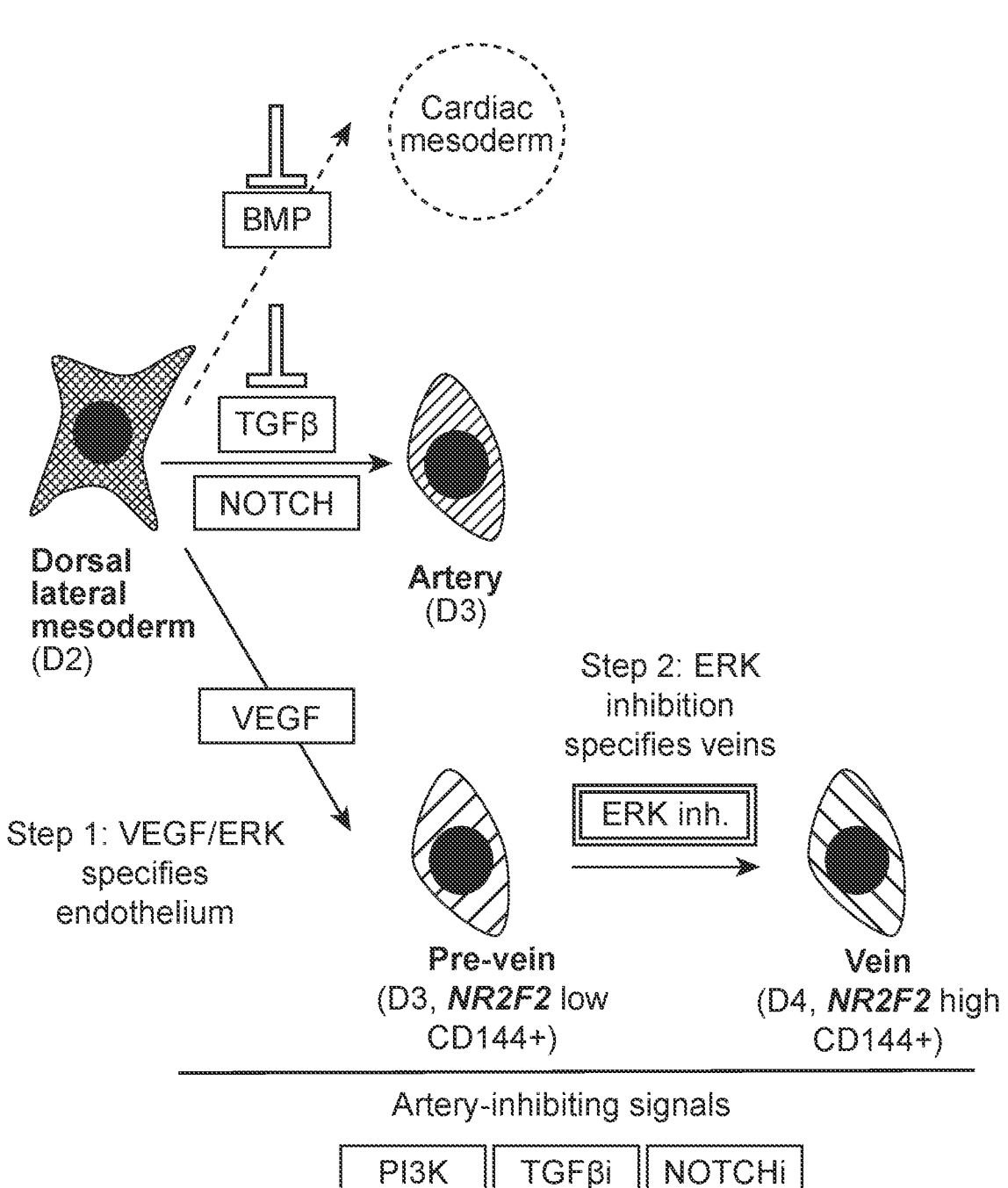
Figure 3:
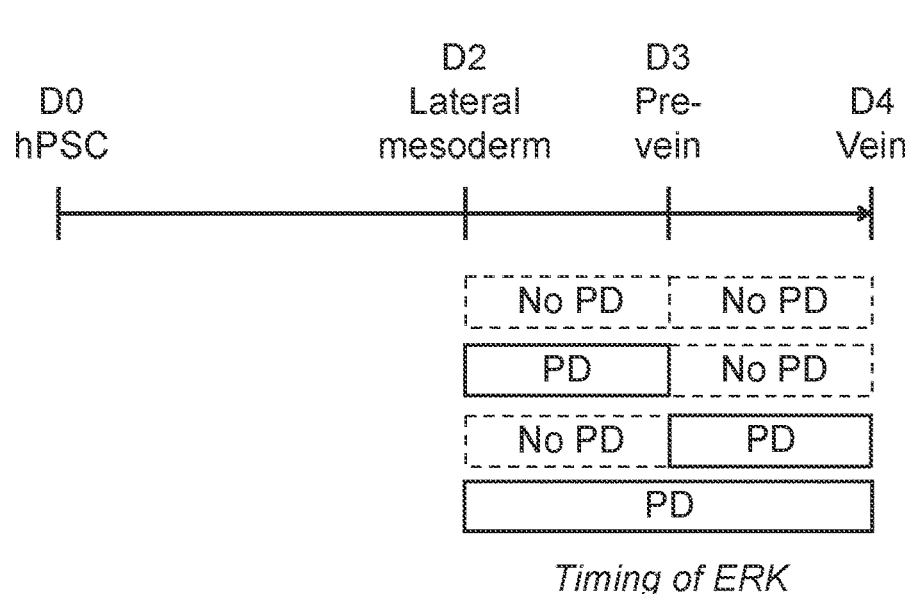
Figure 3:
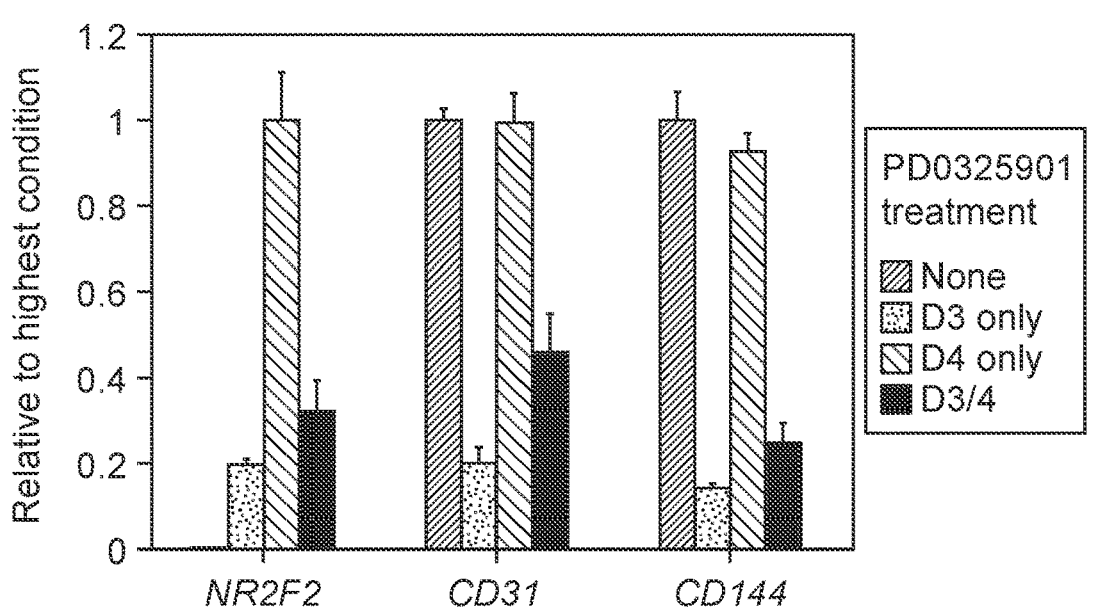
Figure 3:
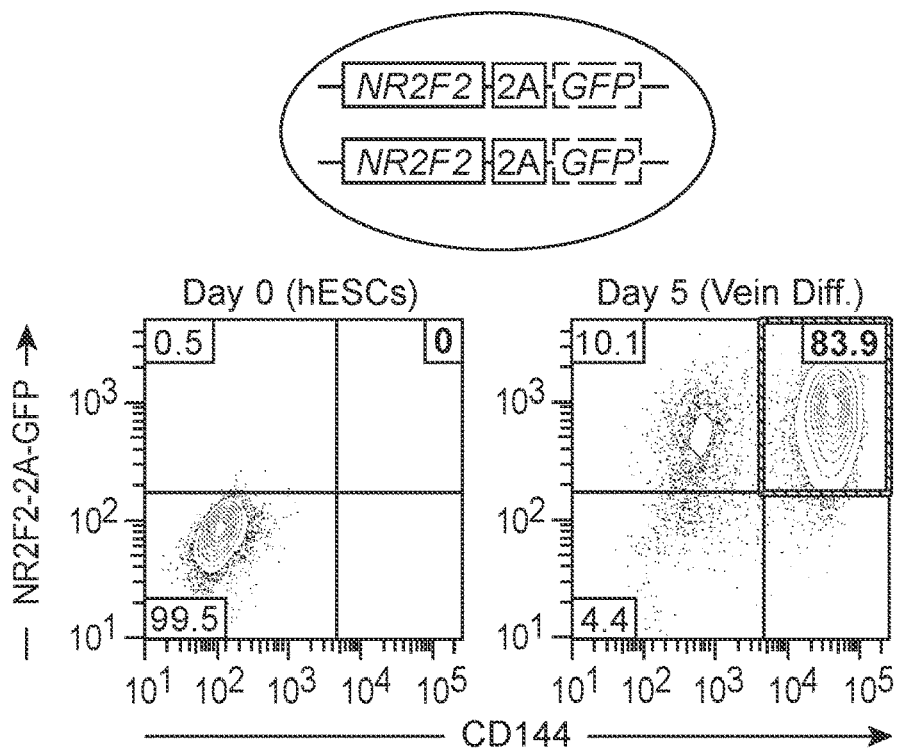
Figure 3:
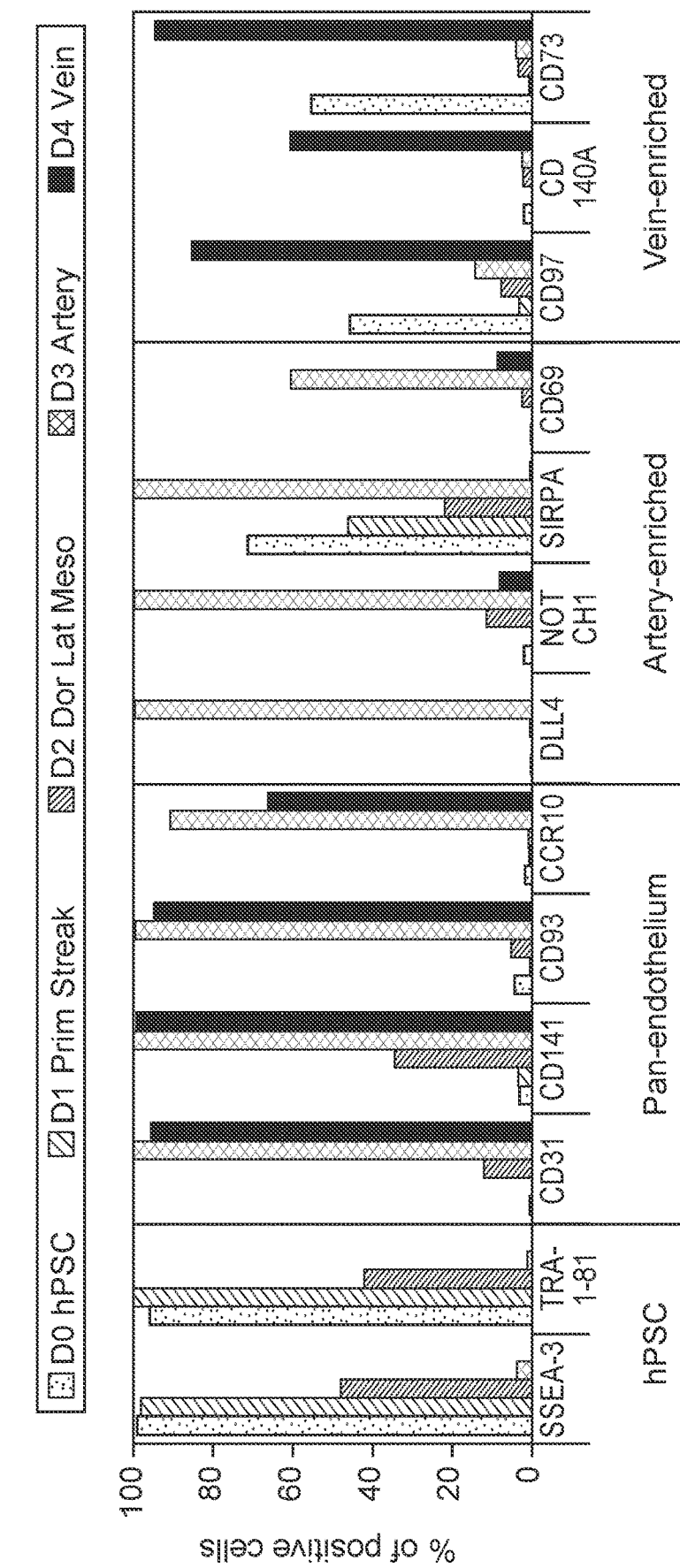

As shown in FIG. 3, dual inhibition of TGFβ and NOTCH promotes day 3 pre-vein formation. hPSC-derived dorsal lateral mesoderm can be further differentiated in pan-endothelium base media (VEGF+XAV939+DMH1) for 24 hours, in the presence or absence of TGFβ agonist (Activin, 15 ng/mL), TGFβ inhibitor (SB505124, 2 μM), PI3K inhibitor (GDC0941, 2 μM) and NOTCH inhibitor (RO4929097, 1 μM). Temporally-dynamic control of VEGF/ERK signaling is critical for vein differentiation; hPSC-derived dorsal lateral mesoderm can be further differentiated into vein cells using pan-endothelium base media (VEGF+XAV939+DMH1+AA2P), in the presence of ERK inhibitor (PD0325901, 100 nM). After differentiating into vein endothelial cells, >80% are NR2F2⁺ CD144⁺ vein endothelial cells.

In some instances, an inducing agent useful in a particular induction composition may include an activator or inhibitor of the TGF-beta (transforming growth factor β (TGF-β)) pathway. Activators and inhibitors of the TGF-beta pathway include small molecule activators, small molecule inhibitors, peptide activators, peptide inhibitors, antibodies, nucleic acid activators, nucleic acid inhibitors, and the like that activate or inhibit at least one component of the TGF-beta pathway resulting in a corresponding activation or inhibition in cellular TGF-beta signaling. Components and downstream effectors of the TGF-beta pathway include but are not limited to, e.g., 14-3-3 e (UniProtID P62258), ark (UniProtID Q6ZNA4), axini (UniProtID O15169), bambi (UniProtID Q13145), beta arrestin 2 (UniProtID P32121), beta catenin (UniProtID P35222), beta glycan (UniProtID Q03167), camkiia (UniProtID Q9UQM7), caveolin-1 (UniProtID O03135), ctgf (UniProtID P29279), dab2 (UniProtID P98082), dapper2 (UniProtID Q5SW24), daxx (UniProtID Q9UER7), eif2a (UniProtID Q9BY44), elf (UniProtID O01082), endofin (UniProtID Q7Z3T8), fkbp12 (UniProtID P62942), gadd34 (UniProtID O75807), grb2 (UniProtID P62993), itch (UniProtID Q96J02), km23-1 (UniProtID Q9NP97), nedd4-2 (UniProtID Q96PU5), ocln (UniProtID Q16625), p70s6k (UniProtID P23443), par6 (UniProtID Q9NPB6), pdk1 (UniProtID 015530), pml (UniProtID P29590), ppp1ca (UniProtID P62136), ppp2ca (UniProtID P67775), ppp2cb (UniProtID P62714), ppp2r2a (UniProtID P63151), rhoa (UniProtID P61586), sara (UniProtID O95405), shc (UniProtID P29353), smad2 (UniProtID Q15796), smad3 (UniProtID P84022), smad4 (UniProtID O13485), smad7 (UniProtID O15105), smurf1 (UniProtID Q9HCE7), smurf2 (UniProtID Q9HAU4), snon (UniProtID P12757), sos1 (UniProtID O07889), strap (UniProtID Q9Y3F4), tab1 (UniProtID 015750), tab2 (UniProtID Q9NYJ8), tak1 (UniProtID 043318), TGFB1 (UniProtID P01137), TGFB2 (UniProtID P61812), TGFB3 (UniProtID P10600), tgfbr1 (UniProtID P36897), tgfbr2 (UniProtID P37173), trap-1 (UniProtID O60466), wwp1 (UniProtID Q9HOMO), xiap (UniProtID P98170), yap65 (UniProtID P46937), and the like.

Activators of the TGF-beta pathway include but are not limited to, e.g., TGF-beta family ligands (e.g., TGF-beta proteins and other activators of TGF-beta receptors) and portions thereof, Activin A, TGF-beta1, TGF-beta2, TGF-beta3, IDE1/2 (IDE1 (1-[2-[(2-Carboxyphenyl)methylene]hydrazide]heptanoic acid), IDE2 (Heptanedioic acid-1-(2-cyclopentylidenehydrazide)), Nodal, and the like. In some instances, activation of the TGF-beta pathway may be achieved through repression of the a TGF-beta pathway inhibitor, e.g., including but not limited to the use of an inhibitory nucleic acid targeting an inhibitor of the TGF-beta pathway or an antibody or small molecule directed to a TGF-beta pathway inhibitor.

Inhibitors of the TGF-beta pathway include but are not limited to, e.g., A-83-01 (3-(6-Methyl-2-pyridinyl)-N-phenyl-4-(4-quinolinyl)-1H-pyrazole-1-carbothioamide), D4476 (4-[4-(2,3-Dihydro-1,4-benzodioxin-6-yl)-5-(2-pyridinyl)-1H-imidazol-2-yl]benzamide), GW 788388 (4-[4-[3-(2-Pyridinyl)-1H-pyrazol-4-yl]-2-pyridinyl]-N-(tetrahydro-2H-pyran-4-yl)-benzamide), LY 364947 (4-[3-(2-Pyridinyl)-1H-pyrazol-4-yl]-quinoline), RepSox (2-(3-(6-Methylpyridine-2-yl)-1H-pyrazol-4-yl)-1,5-naphthyridine), SB431542 (4-[4-(1,3-benzodioxol-5-yl)-5-(2-pyridinyl)-1H-imidazol-2-yl]benzamide), SB-505124 (2-[4-(1,3-Benzodioxol-5-yl)-2-(1,1-dimethylethyl)-1H-imidazol-5-yl]-6-methyl-pyridine), SB 525334 (6-[2-(1,1-Dimethylethyl)-5-(6-methyl-2-pyridinyl)-1H-imidazol-4-yl]quinoxaline), SD208 (2-(5-Chloro-2-fluorophenyl)-4-[(4-pyridyl)amino]pteridine), ITD1 (4-[1,1'-Biphenyl]-4-yl-1,4,5,6,7,8-hexahydro-2,7,7-trimethyl-5-oxo-3-quinolinecarboxylic acid ethyl ester), DAN/Fc, antibodies to TGF-beta and TGF-beta receptors, TGF-beta inhibitory nucleic acids, and the like.

In some instances, an inducing agent useful in a particular induction composition may include an activator or inhibitor of the Wnt pathway. Activators and inhibitors of the Wnt pathway include small molecule activators, small molecule inhibitors, peptide activators, peptide inhibitors, antibodies, nucleic acid activators, nucleic acid inhibitors, and the like that activate or inhibit at least one component of the Wnt pathway resulting in a corresponding activation or inhibition in cellular Wnt signaling. Components and downstream effectors of the Wnt pathway include but are not limited to, e.g., cthrc1 (UniProtID O96CG8), dkk1 (UniProtID O94907), fzd1 (UniProtID Q9UP38), fzd10 (UniProtID Q9ULW2), fzd2 (UniProtID Q14332), fzd4 (UniProtID Q9ULV1), fzd5 (UniProtID Q13467), fzd6 (UniProtID O60353), fzd7 (UniProtID O75084), fzd8 (UniProtID Q9H461), fzd9 (UniProtID O00144), igfbp4 (UniProtID P22692), kremen 1 (UniProtID Q96MU8), kremen 2 (UniProtID Q8NCW0), lrp5 (UniProtID O75197), lrp6 (UniProtID O75581), prr (UniProtID O75787), ror2 (UniProtID Q01974), rspo1 (UniProtID Q2MKA7), ryk (UniProtID P34925), wnt inhibitory 1 (UniProtID Q9Y5W5), wnt1 (UniProtID P04628), wnt2 (UniProtID P09544), wnt3 (UniProtID P56703), wnt3a (UniProtID P56704), wnt5a (UniProtID P41221), wnt7a (UniProtID O00755), wnt7b (UniProtID P56706), CTNNB1 (UniProtID P35222), GSK3A (UniProtID P49840), GSK3B (UniProtID P49841), TNKS1 (UniProtID O95271), TNKS2 (UniProtID Q9H2K2) and the like.

Activators of the WNT pathway include but are not limited to, e.g., CHIR99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), WNT family ligands (e.g., including but not limited to Wnt-1, Wnt-2, Wnt-2b, Wnt-3a, Wnt-4, Wnt-5a, Wnt-5b, Wnt-6, Wnt-7a, Wnt-7a/b, Wnt-7b, Wnt-8a, Wnt-8b, Wnt-9a, Wnt-9b, Wnt-10a, Wnt-10b, Wnt-11, Wnt-16b, etc.), RSPO co-agonists (e.g., RSPO2), lithium chloride, TDZD8 (4-Benzyl-2-methyl-1,2,4-thiadiazolidine-3,5-dione), BIO-Acetoxime ((2'Z,3'E)-6-Bromoindirubin-3'-acetoxime), A1070722 (1-(7-Methoxyquinolin-4-yl)-3-[6-(trifluoromethyl)pyridin-2-yl]urea), HLY78 (4-Ethyl-5,6-Dihydro-5-methyl-[1,3]dioxolo[4,5-j]phenanthridine), CID 11210285 hydrochloride (2-Amino-4-(3,4-(methylenedioxy)benzylamino)-6-(3-methoxyphenyl)pyrimidine hydrochloride), WAY-316606, (hetero)arylpyrimidines, IQ1, QS11, SB-216763, DCA, and the like. In some instances, activation of the Wnt pathway may be achieved through repression of the a Wnt pathway inhibitor, e.g., including but not limited to the use of an inhibitory nucleic acid targeting an inhibitor of the Wnt pathway or an antibody or small molecule directed to a Wnt pathway inhibitor.

Inhibitors of the WNT pathway include but are not limited to, e.g., C59 (4-(2-Methyl-4-pyridinyl)-N-[4-(3-pyridinyl)phenyl]benzeneacetamide), DKK1, IWP-2 (N-(6-Methyl-2-benzothiazolyl)-2-[(3,4,6,7-tetrahydro-4-oxo-3-phenylthieno[3,2-d]pyrimidin-2-yl)thio]-acetamide), Ant1.4Br, Ant 1.4Cl, Niclosamide, apicularen, bafilomycin, XAV939 (3,5,7,8-Tetrahydro-2-[4-(trifluoromethyl)phenyl]-4H-thiopyrano[4,3-d]pyrimidin-4-one), IWR-1 (4-(1,3,3a,4,7,7a-Hexahydro-1,3-dioxo-4,7-methano-2H-isoindol-2-yl)-N-8-quinolinyl-Benzamide), NSC668036 (N-[(1,1-Dimethylethoxy)carbonyl]-L-alanyl-(2S)-2-hydroxy-3-methylbutanoyl-L-Alanine-(1S)-1-carboxy-2-methylpropyl ester hydrate), 2,4-diamino-quinazoline, Quercetin, ICG-001 ((6S,9aS)-Hexahydro-6-[(4-hydroxyphenyl)methyl]-8-(1-naphthalenylmethyl)-4,7-dioxo-N-(phenylmethyl)-2H-pyrazino[1,2-a]pyrimidine-1(6H)-carboxamide), PKF115-584, BML-284 (2-Amino-4-[3,4-(methylenedioxy)benzylamino]-6-(3-methoxyphenyl)pyrimidine), FH-535, iCRT-14, JW-55, JW-67, antibodies to Wnts and Wnt receptors. Wnt inhibitory nucleic acids, and the like.

In some instances, a specific WNT inhibitor may be administered in such a manner as to result in a decrease in PAX3 expression and a promotion of FOXC2 expression.

In some instances, a Wnt activator or inhibitor useful in the methods described herein may include those described in, e.g., Dodge and Lum et al. Annu Rev Pharmacol Toxicol. 2011:51:289-310; Chen et al. Am J Physiol Gastrointest Liver Physiol. 2010 August; 299(2):G293-300; Baker and Clevers, Nat Rev Drug Discov. 2006 December; 5(12):997-1014; Meijer et al. Trends Pharmacol Sci. 2004 September; 25(9):471-80; and Lepourcelet et al. Cancer Cell. 2004 January; 5(1):91-102, the disclosures of which are incorporated herein by reference in their entirety.

In some instances, an inducing agent useful in a particular induction composition may include an activator or inhibitor of the FGF pathway. In some instances, an activator or inhibitor of the FGF pathway may also include activators or inhibitors of related signal transduction pathways including but not limited to, e.g., the MAPK/ERK signal transduction pathway. Activators and inhibitors of the FGF pathway include small molecule activators, small molecule inhibitors, peptide activators, peptide inhibitors, antibodies, nucleic acid activators, nucleic acid inhibitors, and the like that activate or inhibit at least one component of the FGF pathway resulting in a corresponding activation or inhibition in cellular FGF signaling. Components and downstream effectors of the FGF pathway include but are not limited to, e.g., akt1 (UniProtID P31749), beta-klotho (UniProtID Q86Z14), camkiia (UniProtID Q9UQM7), cbl (UniProtID P22681), cortactin (UniProtID Q14247), e-cadherin (UniProtID P12830), erk1 (UniProtID P27361), erk2 (UniProtID P28482), FGF1 (UniProtID P05230), FGF16 (UniProtID O60258), FGF17 (UniProtID O60258), FGF18 (UniProtID O76093), FGF19 (UniProtID O95750), FGF2 (UniProtID P09038), fgf23 (UniProtID Q9GZV9), FGF4 (UniProtID P08620), FGF6 (UniProtID P10767), FGF8 (UniProtID P55075), FGF9 (UniProtID P31371), fgfr1 (UniProtID P11362), fgfr2 (UniProtID P21802), fgfr2b (UniProtID P21802-18), FGFR2c (UniProtID P21802-5), FGFR3c (UniProtID P22607-1), FGFR4 (UniProtID P22455), fos (UniProtID P01100), frs2 (UniProtID Q8WU20), gab1 (UniProtID O13480), grb2 (UniProtID P62993), hgf (UniProtID P14210), jun (UniProtID P05412), klotho (UniProtID Q9UEF7), mapk 14 (UniProtID Q16539), met (UniProtID P08581), mkp-3 (UniProtID Q16828), mmp9 (UniProtID P14780), n-cad-ctf1 (UniProtID P19022), n-cad-ctf2 (UniProtID P19022), n-cadherin (UniProtID P19022), ncam (UniProtID P13591), osteocalcin (UniProtID P02818), osteopontin (UniProtID P10451), p110-alpha (UniProtID P42336), p120ctn (UniProtID Q60716), p90-rsk 1 (UniProtID Q15418), pak4 (UniProtID Q8WYL5), pak4 (UniProtID O96013), pdk1 (UniProtID O15530), pik3r1 (UniProtID P27986), plcgamma1 (UniProtID P19174), pro-e-cadherin (UniProtID P12830), pro-mmp9 (UniProtID P14780), psi (UniProtID gamma), pyk2 (UniProtID Q14289), runx2 (UniProtID Q13950), se-cad (UniProtID P12830), secad-ntf2 (UniProtID P12830), sef (UniProtID Q8NFM7), shc (UniProtID P29353), shp2 (UniProtID O06124), sn-cad (UniProtID P19022), sos1 (UniProtID Q07889), sprouty2 (UniProtID O43597), src (UniProtID P12931), stat1 (UniProtID P42224), stat3 (UniProtID P40763), stat5b (UniProtID P51692), syndecan-2 (UniProtID P34741), syndecan-4 (UniProtID P31431), upa (UniProtID P00749), upar (UniProtID Q03405), and the like. Activators and inhibitors of the MAPK/ERK pathway include small molecule activators, small molecule inhibitors, peptide activators, peptide inhibitors, antibodies, nucleic acid activators, nucleic acid inhibitors, and the like that activate or inhibit at least one component of the MAPK/ERK pathway resulting in a corresponding activation or inhibition in cellular MAPK/ERK signaling. Components and downstream effectors of the MAPK/ERK pathway MAPK/ERK signaling include but are not limited to, e.g., a-raf (EntrezGeneID 369), ask1 (EntrezGeneID 4217), atf2 (EntrezGeneID 1386), cebpa (EntrezGeneID 1050), c-myc (EntrezGeneID 4609), creb (EntrezGeneID 1385), elk1 (EntrezGeneID 2002), erk5 (EntrezGeneID 5598), fos (EntrezGeneID 2353), grb2 (EntrezGeneID 2885), hexokinase type iv glucokinase (EntrezGeneID 2645), ikk-alpha (EntrezGeneID 1147), ikk-beta (EntrezGeneID 3551), jnk (EntrezGeneID 5599), jun (EntrezGeneID 3725), map2k1 (EntrezGeneID 5604), map2k2 (EntrezGeneID 5605), map2k4 (EntrezGeneID 6416), map2k5 (EntrezGeneID 5607), map2k6 (EntrezGeneID 5608), map2k7 (EntrezGeneID 5609), map3k1 (EntrezGeneID 4214), map3k11 (EntrezGeneID 4296), map3k12 (EntrezGeneID 7786), map3k13 (EntrezGeneID 9175), map3k14 (EntrezGeneID 9020), map3k2 (EntrezGeneID 10746), map3k3 (EntrezGeneID 4215), map3k4 (EntrezGeneID 4216), map3k7 (EntrezGeneID 6885), map3k8 (EntrezGeneID 1326), map4k1 (EntrezGeneID 11184), map4k3 (EntrezGeneID 8491), map4k5 (EntrezGeneID 11183), mapk1 (EntrezGeneID 5594), mapk10 (EntrezGeneID 5602), mapk11 (EntrezGeneID 5600), mapk12 (EntrezGeneID 6300), mapk13 (EntrezGeneID 5603), mapk14 (EntrezGeneID 1432), mapk3 (EntrezGeneID 5595), mapk9 (EntrezGeneID 5601), max (EntrezGeneID 4149), mef2 polypeptide a (EntrezGeneID 4205), mef2 polypeptide c (EntrezGeneID 4208), mef2b (EntrezGeneID 4207), mef2 polypeptide d (EntrezGeneID 4209), mek3 (EntrezGeneID 5606), mknk2 (EntrezGeneID 2872), mnk1 (EntrezGeneID 8569), msk1 (EntrezGeneID 9252), ngf r (EntrezGeneID 4804), ngfb (EntrezGeneID 4803), nik (EntrezGeneID 9448), pak1 (EntrezGeneID 5058), pak2 (EntrezGeneID 5062), pp2a (EntrezGeneID 5528), ptprr (EntrezGeneID 5801), rac1 (EntrezGeneID 5879), raf1 (EntrezGeneID 5894), ras (EntrezGeneID 3265), rps6ka1 (EntrezGeneID 6195), shc (EntrezGeneID 6464), sos1 (EntrezGeneID 6654), sp1 (EntrezGeneID 6667), src (EntrezGeneID 6714), stat1 (EntrezGeneID 6772), stat3 (EntrezGeneID 6774), tert (EntrezGeneID 7015), and the like.

Activators of the FGF pathway and/or the MAPK/ERK pathway include but are not limited to, e.g., FGF family ligands (e.g., FGF1, FGF2, FGF-3, FGF-4, FGF-5, FGF-6, KGF/FGF-7, FGF-8, FGF-9, FGF-10, FGF-11, FGF-12, FGF-13, FGF-15, FGF-16, FGF-17, FGF-19, FGF-20, FGF-21, FGF-22, FGF-23, etc.), SUN 11602 (4-[[4-[[2-[(4-Amino-2,3,5,6-tetramethylphenyl)amino]acetyl]methyl-amino]-1-piperidinyl]methy]benzamide), t-Butylhydroquinone, U-46619, C2 Ceramide, Lactosyl Ceramide, Angiotensin II, Baicalin, and the like. In some instances, activation of the FGF pathway and/or the MAPK/ERK pathway may be achieved through repression of the a FGF pathway and/or the MAPK/ERK pathway inhibitor, e.g., including but not limited to the use of an inhibitory nucleic acid targeting an inhibitor of the FGF pathway and/or the MAPK/ERK pathway or an antibody or small molecule directed to a FGF pathway inhibitor and/or MAPK/ERK pathway inhibitor.

Inhibitors of the FGF pathway and/or the MAPK/ERK pathway and or the p38/JNK/MAPK cascade include but are not limited to, e.g., AP 24534 (3-(2-Imidazo[1,2-b]pyridazin-3-ylethynyl)-4-methyl-N-[4-[(4-methyl-1-piperazinyl)methyl]-3-(trifluoromethyl)phenyl]-benzamide), PD173074 (N-[2-[[4-(Diethylamino)butyl]amino]-6-(3,5-dimethoxyphenyl)pyrido[2,3-d]pyrimidin-7-yl]-N'-(1,1-di-methylethyl)urea), FIIN 1 hydrochloride (N-(3-((3-(2,6-di-chloro-3,5-dimethoxyphenyl)-7-(4-(diethylamino)

butylamino)-2-oxo-3,4-dihydropyrimido[4,5-d]pyrimidin-1 (2H)-yl)methyl)phenyl)acrylamide), PD 161570 (N-[6-(2,6-Dichlorophenyl)-2-[[4-(diethylamino)butyl]amino]pyrido [2,3-d]pyrimidin-7-yl]-N'-(1,1-dimethylethyl)urea), SU 5402 (2-[(1,2-Dihydro-2-oxo-3H-indol-3-ylidene)methyl]-4-methyl-1H-pyrrole-3-propanoic acid), SU 6668 (5-[1,2-Dihydro-2-oxo-3H-indol-3-ylidene)methyl]-2,4-dimethyl-1H-pyrrole-3-propanoic acid), PD0325901 (N-[(2R)-2,3-Dihydroxypropoxy]-3,4-difluoro-2-[(2-fluoro-4-iodophenyl)amino]-benzamide), BIX 02189 ((3Z)-3-[[[3-[(Dimethylamino)methyl]phenyl]amino]phenylmethylene]-2,3-dihydro-N,N-dimethyl-2-oxo-1H-indole-6-carboxamide), FR 180204 (5-(2-Phenyl-pyrazolo[1,5-a]pyridin-3-yl)-1H-pyrazolo[3,4-c]pyridazin-3-ylamine), Pluripotin (N-[3-[7-[(1,3-Dimethyl-1H-pyrazol-5-yl)amino]-1,4-dihydro-1-methyl-2-oxopyrimido[4,5-d]pyrimi-din-3(2H)-yl]-4-methylphenyl]-3-(trifluoromethyl)benz-amide), TCS ERK Ile (4-[2-[(2-Chloro-4-fluorophenyl)amino]-5-methyl-4-pyrimidinyl]-N-[(1S)-1-(3-chlorophenyl)-2-hydroxyethyl]-1H-pyrrole-2-carboxamide), TMCB (2-(4,5,6,7-Tetrabromo-2-(dimethylamino)-1H-benzo[d]imidazol-1-yl)acetic acid), XMD 8-92 (2-[[2-Ethoxy-4-(4-hydroxy-1-piperidinyl)phe-nyl]amino]-5,11-dihydro-5,11-dimethyl-6H-pyrimido[4,5-b][1,4]benzodiazepin-6-one), SU5402, AZD4547, BGJ398, AL 8697, AMG 548, CMPD-1, DBM 1285 dihydrochloride, EO 1428, JX 401, ML 3403, RWJ 67657, SB 202190, SB-203580, SB 239063, SB 706504, Scio-469, SKF 86002 dihydrochloride, SX 011, TA 01 (4-(2-(2,6-Difluorophenyl)-4-(fluorophenyl)-1H-imidazol-5-yl)pyridine), TA 02 (4-(2-(2-Fluorophenyl)-4-(fluorophenyl)-1H-imidazol-5-yl)pyri-dine), TAK 715, VX-702, VX-745, antibodies to FGF and/or MAPK pathway components including ligands and receptors, FGF and/or MAPK inhibitory nucleic acids, and the like.

In some instances, a FGF or MAPK activator or inhibitor useful in the methods described herein may include those described in, e.g., English and Cobb, Trends Pharmacol Sci. 2002 January; 23(1):40-5, the disclosure of which is incorporated herein by reference in its entirety.

In some instances, an inducing agent useful in a particular induction composition may include an activator or inhibitor of the BMP pathway. Activators and inhibitors of the BMP pathway include small molecule activators, small molecule inhibitors, peptide activators, peptide inhibitors, antibodies, nucleic acid activators, nucleic acid inhibitors, and the like that activate or inhibit at least one component of the BMP pathway resulting in a corresponding activation or inhibition in cellular BMP signaling. Components and downstream effectors of the BMP pathway include but are not limited to, e.g., bambi (UniProtID Q13145), bmp2 (UniProtID P12643), bmp4 (UniProtID P12644), bmp6 (UniProtID P22004), bmp7 (UniProtID P18075), bmpr1a (UniProtID P36894), bmpr1b (UniProtID O00238), bmpr2 (UniProtID Q13873), cer1 (UniProtID O95813), chrd (UniProtID Q9H2X0), chrdl1 (UniProtID Q9BU40), endofin (UniProtID Q7Z3T8), erk2 (UniProtID P28482), fetua (UniProtID P02765), fs (UniProtID P19883), gadd34 (UniProtID O75807), grem1 (UniProtID O60565), gsk3beta (UniProtID P49841), nog (UniProtID Q13253), nup214 (UniProtID P35658), ppm1a (UniProtID P35813), ppp1ca (UniProtID P62136), rgma (UniProtID Q96B86), rgmb (UniProtID Q6NW40), rgmc (UniProtID Q6ZVN8), scp1 (UniProtID Q9GZU7), scp2 (UniProtID O14595), scp3 (UniProtID O15194), ski (UniProtID P12755), smad1 (UniProtID Q15797), smad4 (UniProtID O13485), smad5 (UniProtID Q99717), smad6 (UniProtID O43541), smad7 (UniProtID O15105), smad8a (UniProtID O15198), smurf1 (UniProtID Q9HCE7), smurf2 (UniProtID Q9HAU4), tab1 (UniProtID O15750), tab2 (UniProtID Q9NYJ8), tak1 (UniProtID O43318), usag1 (UniProtID Q6X4U4), xiap (UniProtID P98170), and the like.

Activators of the BMP pathway include but are not limited to, e.g., BMP family ligands (e.g., BMP2, BMP4, BMP7, etc.), Alantolactone, FK506, isoliquiritigenin, 4'-hydroxychalcone, and the like. In some instances, activation of the BMP pathway may be achieved through repression of the a BMP pathway inhibitor, e.g., including but not limited to the use of an inhibitory nucleic acid targeting an inhibitor of the BMP pathway or an antibody or small molecule directed to a BMP pathway inhibitor.

Inhibitors of the BMP pathway include but are not limited to, e.g., NOGGIN, CHORDIN, LDN-193189 (4-[6-[4-(1-Piperazinyl)phenyl]pyrazolo[1,5-a]pyrimidin-3-yl]-quinoline hydrochloride), DMH1 (4-[6-[4-(1-Methylethoxy)phenyl]pyrazolo[1,5-a]pyrimidin-3-yl]-quinoline), Dorsomorphin (6-[4-[2-(1-Piperidinyl)ethoxy]phenyl]-3-(4-pyridinyl)-pyrazolo[1,5-a]pyrimidine dihydrochloride), K 02288 (3-[(6-Amino-5-(3,4,5-trimethoxyphenyl)-3-pyridinyl]phenol), ML 347 (5-[6-(4-Methoxyphenyl)pyrazolo[1, 5-a]pyrimidin-3-yl]quinoline), DMH-1, antibodies to BMPs and BMP receptors, BMP inhibitory nucleic acids, and the like.

In some instances, an inducing agent useful in a particular induction composition may include an activator or inhibitor of the retinoic acid signaling pathway. Activators and inhibitors of the retinoic acid signaling pathway include small molecule activators, small molecule inhibitors, peptide activators, peptide inhibitors, antibodies, nucleic acid activators, nucleic acid inhibitors, and the like that activate or inhibit at least one component of the retinoic acid signaling pathway resulting in a corresponding activation or inhibition in cellular retinoic acid signaling. Components and downstream effectors of the retinoic acid signaling pathway include but are not limited to, e.g., CRABP (e.g., Accession: NP_004369), TRAIL (e.g., Accession: NP_003801), TRAILR1 (e.g., Accession: NP_003835), TRAILR2 (e.g., Accession: NP_003833), DAP3 (e.g., Accession: NP_001186780), FADD (e.g., Accession: CAG33019), FLIP (e.g., Accession: NP_001294972), Caspase 8 (e.g., Accession: AAD24962), BID (e.g., Accession: NP_001304162), tBID (e.g., Accession: P55957), APAF1 (e.g., Accession: ABQ59028), Caspase 9 (e.g., Accession: P55211). PARPs (e.g., Accession: AAH14206), RAR (e.g., Accession: NP_001138773 and components thereof e.g., AF2 domain, AF1 domain, DBD domain, and the like. Activators and inhibitors of the retinoic acid signaling include but are not limited to e.g., Tretinoin, Retinol palmitate, Etretinate, Isotretinoin, Adapalene, Tazarotene, Tamibarotene, Retinol acetate, Acitretin, Alitretinoin, Bexarotene, Isotretinoin anisatil, Motretinide, Vitamin A, Retinol propionate, and the like. In some instances, useful modulators of the retinoic acid signaling pathway include retinoid agonist, including but not limited to e.g., all-trans retinoic acid, TTNPB, AM580 and the like. In some instances, an inducing agent useful in a particular induction composition may include an activator or inhibitor of the Hedgehog pathway. Activators and inhibitors of the Hedgehog pathway include small molecule activators, small molecule inhibitors, peptide activators, peptide inhibitors, antibodies, nucleic acid activators, peptide inhibitors, and the like that activate or inhibit at least one component of the Hedgehog pathway resulting in a corresponding activation or inhibition in cellular Hedgehog signaling. Components and downstream effectors of the Hedgehog pathway include but are not limited to, e.g., akt1 (UniProtID P31749), beta arrestin2 (UniProtID P32121), boc (UniProtID Q9BWV1), cdo (UniProtID Q4KMG0), dhh (UniProtID O43323), gas1 (UniProtID P54826), gli2 (UniProtID P10070), grk2 (UniProtID P25098), hhat (UniProtID Q5VTY9), hhip (UniProtID Q96QV1), ihh (UniProtID Q14623), Irpap1 (UniProtID P30533), megalin (UniProtID P98164), p110-alpha (UniProtID P42336), pik3r1 (UniProtID P27986), ptch1 (UniProtID Q13635), ptch2 (UniProtID Q9Y6C5), pthrp (UniProtID P12272), shh (UniProtID Q15465), sil (UniProtID Q15468), smo (UniProtID Q99835), tgf-beta2 (UniProtID P61812), and the like.

Activators of the Hedgehog pathway include but are not limited to, e.g., Hedgehog family ligands (Hh, Shh, Ihh, Dhh, etc.) and fragments thereof, benzothiophene smoothened agonists, SAG (Hh-Ag1.3), SAG21k (3-chloro-4,7-difluoro-N-(4-methoxy-3-(pyridin-4-yl)benzyl)-N-((1r,4r)-4-(methylamino)cyclohexyl)benzo[b]thiophene-2-carboxamide), Hh-Ag1.1, Hh-Ag1.5, purmorphamine, and the like. In some instances, activation of the Hedgehog pathway may be achieved through repression of the a Hedgehog pathway inhibitor, e.g., including but not limited to the use of an inhibitory nucleic acid targeting an inhibitor of the Hedgehog pathway or an antibody or small molecule directed to a Hedgehog pathway inhibitor.

Inhibitors of the Hedgehog pathway include but are not limited to, e.g., Hedgehog antagonists that target smoothened (SMO), Hedgehog antagonists that target patched (PTCH), Hedgehog antagonists that target Gli, cyclopamine and analogs and derivatives thereof, cyclopamine-competitive antagonists, IPI-926 (Saridegib), LDE225 (sonidegib), itraconazole, GDC-0449 (vismodegib), SANT1, KAAD-cyclopamine, LEQ506, PF-04449913, TAK-441, BMS833923 (XL-139), LY2940680, and inhibitory nucleic acids targeting SMO, inhibitory nucleic acids targeting a Hedgehog, inhibitory nucleic acids targeting PTCH, inhibitory nucleic acids targeting Gli (e.g., siRNA targeting Gli1), arsenic trioxide, and the like.

In some instances, Hedgehog pathway activators and Hedgehog pathway inhibitors include those agents described in, e.g., Chen et al. (2002) PNAS. 99(22):14071-14076; Frank-Kamenetsky, et al. (2002) J Biol. 1(2):10; Paladini et al. (2005) J Invest Dermatol. 125(4):638-46; Nakamura et al. (2014) J Cell. Physiol. ePub, Yun et al., Arch Pharm Res. 2012 August; 35(8):1317-33; the disclosures of which are incorporated herein by reference in their entirety.

In some instances, an inducing agent useful in a particular induction composition may include an activator or inhibitor of the PI3K pathway. Activators and inhibitors of the PI3K pathway include small molecule activators, small molecule inhibitors, peptide activators, peptide inhibitors, antibodies, nucleic acid activators, nucleic acid inhibitors, and the like that activate or inhibit at least one component of the PI3K pathway resulting in a corresponding activation or inhibition in cellular PI3K signaling. Components and downstream effectors of the PI3K pathway include but are not limited to, e.g., arap3 (UniProtID Q8WWN8), arf1 (UniProtID P84077), arf5 (UniProtID P84085), arf6 (UniProtID P62330), amo (UniProtID Q99418), bam32 (UniProtID Q9UN19), blk (UniProtID P51451), blnk (UniProtID Q8WV28), btk (UniProtID Q06187), cental (UniProtID 075689), cytohesin-1 (UniProtID O15438), fgr (UniProtID P09769), foxo3a (UniProtID O43524), fyn (UniProtID P06241), grp1 (UniProtID O43739), hck (UniProtID P08631), h-ras isoform 1 (UniProtID P01112), h-ras isoform 2 (UniProtID P01112), hsp90 (UniProtID P07900), itk (Uni- ProtID O08881), k-ras isoform 2a (UniProtID P01116-1), k-ras isoform 2b (UniProtID P01116-2), lat (UniProtID O43561-2), lck (UniProtID P06239), lyn (UniProtID P07948), n-ras (UniProtID P01111), p101 (UniProtID Q8WYR1), p110-alpha (UniProtID P42336), p110-beta (UniProtID P42338), p110D (UniProtID O00329), p55-gamma (UniProtID Q92569), p84 (UniProtID Q5UE93), p85-beta (UniProtID O00459), pdk1 (UniProtID O15530), PI3Kgamma (UniProtID P48736), PIK3R1 (UniProtID P27986), plcgamma1 (UniProtID P19174), plcgamma2 (UniProtID P16885), pten (UniProtID P60484), rac1 (UniProtID P63000), rap1a (UniProtID P62834), rhoa (UniProtID P61586), sgk1 (UniProtID O00141), ship (UniProtID O00145), ship2 (UniProtID O15357), src (UniProtID P12931), syk (UniProtID P43405), tapp1 (UniProtID Q9HB19), tapp2 (UniProtID Q9HB21), yes (UniProtID P07947), zap-70 (UniProtID P43403), and the like.

Activators of the PI3K pathway include but are not limited to, e.g., PI3K family ligands, 740 Y-P, Insulin receptor substrate (Tyr608) peptide (KKHTDDGYMPMSPGVA, SEQ ID NO:1), and the like. In some instances, an FGF signaling protein may serve as an activator of the PI3K pathway. In some instances, activation of the a PI3K pathway may be achieved through repression of the a PI3K pathway inhibitor, e.g., including but not limited to the use of an inhibitory nucleic acid targeting an inhibitor of the PI3K pathway or an antibody or small molecule directed to a PI3K pathway inhibitor.

Inhibitors of the PI3K pathway include but are not limited to, e.g., AS 252424 (5-[[5-(4-Fluoro-2-hydroxyphenyl)-2-furanyl]methylene]-2,4-thiazolidinedione), AS 605240 (5-(6-Quinoxalinylmethylene)-2,4-thiazolidine-2,4-dione), AZD 6482 ((−)-2-[[(1R)-1-[7-Methyl-2-(4-morpholinyl)-4-oxo-4H-pyrido[1,2-a]pyrimidin-9-yl]ethyl]amino]benzoic acid), BAG 956 (α,α,-Dimethyl-4-[2-methyl-8-[2-(3-pyridinyl)ethynyl]-1H-imidazo[4,5-c]quinolin-1-yl]-benzeneac-etonitrile), CZC 24832 (5-(2-Amino-8-fluoro[1,2,4]triazolo[1,5-a]pyridin-6-yl)-N-(1,1-dimethylethyl)-3-pyridinesulfonamide), GSK 1059615 (5-[[4-(4-Pyridinyl)-6-quinolinyl]methylene]-2,4-thiazolidenedione), KU 0060648 (4-Ethyl-N-[4-[2-(4-morpholinyl)-4-oxo-4H-1-benzopyran-8-yl]-1-dibenzothienyl]-1-piperazineacet-amide), LY 294002 hydrochloride (2-(4-Morpholinyl)-8-phenyl-4H-1-benzopyran-4-one hydrochloride), 3-Methyladenine (3-Methyl-3H-purin-6-amine), PF 04691502 (2-Amino-8-[trans-4-(2-hydroxyethoxy)cyclo-hexyl]-6-(6-methoxy-3-pyridinyl)-4-methyl-pyrido[2,3-d]pyrimidin-7(8H)-one), PF 05212384 (N-[4-[[4-(Dimethyl-amino)-1-piperidinyl]carbonyl]phenyl]-N'-[4-(4,6-di-4-morpholinyl-1,3,5-triazin-2-yl)phenyl]urea), PI 103 hydrochloride (3-[4-(4-Morpholinylpyrido[3',2':4,5]furo[3,2-d]pyrimidin-2-yl]phenol hydrochloride), PI 828 (2-(4-Morpholinyl)-8-(4-aminophenyl)-4H-1-benzopyran-4-one), PP 121 (1-Cyclopentyl-3-(1H-pyrrolo[2,3-b]pyridin-5-yl)-1H-pyrazolo[3,4-d]pyrimidin-4-amine), Quercetin, TG 100713 (3-(2,4-Diamino-6-pteridinyl)-phenol), Wortman-nin, PIK90, GDC-0941, antibodies to PI3K and PI3K recep-tors, PI3K inhibitory nucleic acids, and the like.

In some instances, an inducing agent useful in a particular induction composition may include an activator or inhibitor of the PDGF pathway. Activators and inhibitors of the PDGF pathway include small molecule activators, small molecule inhibitors, peptide activators, peptide inhibitors, antibodies, nucleic acid activators, nucleic acid inhibitors, and the like that activate or inhibit at least one component of the PDGF pathway resulting in a corresponding activation or inhibition in cellular PDGF signaling. Components and downstream effectors of the PDGF pathway include but are not limited to, e.g., 14-3-3 e (UniProtID P62258), abi1 (UniProtID Q81ZP0), acta2 (UniProtID P62736), afadin (UniProtID P55196), alpha actinin 4 (UniProtID O43707), alphav inte-grin (UniProtID P06756), arap1 (UniProtID Q96P48), arp2 (UniProtID P61160), arp3 (UniProtID P61158), arpc1b (UniProtID O15143), arpc2 (UniProtID O15144), arpc3 (UniProtID O15145), arpc4 (UniProtID P59998), arpc5 (UniProtID O15511), beta3 integrin (UniProtID P05106), blk (UniProtID P51451), braf (UniProtID P15056), c3g (UniProtID Q13905), c-abl (UniProtID P00519), caveolin-1 (UniProtID O03135), caveolin-3 (UniProtID P56539), cbl (UniProtID P22681), ck2a1 (UniProtID P68400), cortactin (UniProtID O14247), crk (UniProtID P46108), crkl (Uni-ProtID P46109), csk (UniProtID P41240), dep1 (UniProtID O12913), dock4 (UniProtID 8N1I0), dynamin 2 (UniProtID P50570), elk1 (UniProtID P19419), eps8 (UniProtID Q12929), erk1 (UniProtID P27361), erk2 (UniProtID P28482), fgr (UniProtID P09769), fos (UniProtID P01100), fyn (UniProtID P06241), gab1 (UniProtID Q13480), grb10 (UniProtID Q13322), grb2 (UniProtID P62993), hck (Uni-ProtID P08631), h-ras isoform 1 (UniProtID P01112), h-ras isoform 2 (UniProtID P01112), hspc300 (UniProtID Q8WUW1), ifn-gamma (UniProtID P01579), iqgap1 (Uni-ProtID P46940), irsp53 (UniProtID Q9UQB8), jak1 (Uni-ProtID P23458), jak2 (UniProtID O60674), jnk1 (UniProtID P45983), jnk2 (UniProtID P45984), jnk3 (UniProtID P53779), jun (UniProtID P05412), jund (UniProtID P17535), k-ras isoform 2a (UniProtID P01116-1), k-ras isoform 2b (UniProtID P01116-2), ksr (UniProtID Q81VT5), lck (UniProtID P06239), lrp1 (UniProtID O07954), lyn (UniProtID P07948), mek1 (UniProtID O02750), mek2 (UniProtID P36507), mkk4 (UniProtID P45985), mkk7 (UniProtID O14733), myc (UniProtID P01106), myocardin (UniProtID Q81ZQ8), nap1 (UniPro-tID Q9Y2A7), nck1 (UniProtID P16333), nck2 (UniProtID O43639), nherf1 (UniProtID 014745), nherf2 (UniProtID O15599), n-ras (UniProtID P01111), n-wasp (UniProtID O00401), p101 (UniProtID Q8WYR1), p110-alpha (Uni-ProtID P42336), p110-beta (UniProtID P42338), p110D (UniProtID O00329), p130 cas (UniProtID P56945), p190rhogap (UniProtID Q9NRY4), p52 shc (UniProtID P29353-2), p55-gamma (UniProtID Q92569), p62dok (Uni-ProtID Q99704), p84 (UniProtID Q5UE93), p85-beta (Uni-ProtID O00459), pag1 (UniProtID Q9NWQ8), pak1 (Uni-ProtID O13153), pdgfa (UniProtID P04085), pdgfb (UniProtID P01127), pdgfc (UniProtID Q9NRA1), pdgfd (UniProtID Q9GZP0), pdgfra (UniProtID P16234), pdgfrb (UniProtID P09619), PI3Kgamma (UniProtID P48736), pik3r1 (UniProtID P27986), pin1 (UniProtID Q13526), pkc alpha (UniProtID P17252), pkc delta (UniProtID Q05655), pkc epsilon (UniProtID Q02156), pkr (UniProtID P19525), pla2g4a (UniProtID P47712), plcgamma1 (UniProtID P19174), ppp2ca (UniProtID P67775), ppp2r1a (UniProtID P30153), ppp2r2b (UniProtID O00005), pten (UniProtID P60484), ptp1b (UniProtID P18031), rab4a (UniProtID P20338), rab5 (UniProtID P20339), rac1 (UniProtID P63000), raf1 (UniProtID P04049), rap1a (UniProtID P62834), rap1b (UniProtID P61224), rasgap (UniProtID P20936), rhoa (UniProtID P61586), rhogdi (UniProtID P52565), mtre (UniProtID Q92738), rsk2 (UniProtID P51812), s1p1 (UniProtID P21453), shb (UniProtID O15464), shc (UniProtID P29353), shf (UniProtID Q7M4L6), shp2 (UniProtID Q06124), slap (UniProtID O13239), sm22 (UniProtID Q01995), sos1 (UniProtID Q07889), spa-1 (UniProtID Q96FS4), sphk1 (UniProtID Q9NYA1), sra1 (UniProtID Q96F07), src (UniProtID P12931), srf (UniProtID P11831), stat1 (UniProtID P42224), stat3 (UniProtID P40763), STAT5A (UniProtID P42229), STAT5B (UniProtID P51692), tcptp p45 (UniProtID P17706-1), vav2 (UniProtID P52735), wave2 (UniProtID Q9Y6W5), yes (UniProtID P07947), ywhab (UniProtID P31946), ywhag (UniProtID P61981), ywhah (UniProtID O04917), ywhaq (UniProtID P27348), ywhas (UniProtID P31947), ywhaz (UniProtID P63104), and the like.

Activators of the PDGF pathway include but are not limited to, e.g., PDGF family ligands (e.g., PDGF, PDGF A, PDGF B, PDGF C, PDGF D, etc.) and fragments thereof and/or dimers thereof (e.g., PDGF-AA, PDGF-BB, PDGF-CC, PDGF-DD, PDGF-AB, etc.), and the like. In some instances, activation of the PDGF pathway may be achieved through repression of the a PDGF pathway inhibitor, e.g., including but not limited to the use of an inhibitory nucleic acid targeting an inhibitor of the PDGF pathway or an antibody or small molecule directed to a PDGF pathway inhibitor.

Inhibitors of the PDGF pathway include but are not limited to, e.g., AG 18 ([(3,4-Dihydroxyphenyl)methylene]-propenedinitrile), AG1295, AG1296, AGL2043, AP 24534 (3-(2-Imidazo[1,2-b]pyridazin-3-ylethynyl)-4-methyl-N-[4-[(4-methyl-1-piperazinyl)methyl]-3-(trifluoromethyl)phenyl]-benzamide), CDP860, DMPQ dihydrochloride (5,7-Dimethoxy-3-(4-pyridinyl)quinoline dihydrochloride), Imatinib, PD 166285 dihydrochloride (6-(2,6-Dichlorophenyl)-2-[[4-[2-(diethylamino)ethoxy]phenyl]amino]-8-methylpyrido[2,3-d]pyrimidin-7(8H)-one dihydrochloride), SU 16f (5-[1,2-Dihydro-2-oxo-6-phenyl-3H-indol-3-ylidene) methyl]-2,4-dimethyl-1H-pyrrole-3-propanoic acid), SU 6668 (5-[1,2-Dihydro-2-oxo-3H-indol-3-ylidene)methyl]-2,4-dimethyl-1H-pyrrole-3-propanoic acid), SU11248, Sunitinib malate (N-[2-(Diethylamino)ethyl]-5-[(Z)-(5-fluoro-1,2-dihydro-2-oxo-3H-indol-3-ylidine)methyl]-2,4-dimethyl-1H-pyrrole-3-carboxamide (2S)-2-hydroxybutanedioate salt), Toceranib (5-[(Z)-(5-Fluoro-1,2-dihydro-2-oxo-3H-indol-3-ylidene)methyl]-2,4-dimethyl-N-[2-(1-pyrrolidinyl) ethyl]-1H-pyrrole-3-carboxamide), antibodies targeting PDGF and/or PDGF receptor, PDGF inhibitory nucleic acids, and the like.

In some instances, an inducing agent useful in a particular induction composition may include an activator of the NOTCH pathway. Activators of the NOTCH pathway include small molecule activators, peptide activators, antibodies against NOTCH repressors, nucleic acid activators, nucleic acid inhibitors of NOTCH repressors, and the like that activate at least one component of the NOTCH pathway resulting in a corresponding activation in cellular NOTCH signaling.

Activators of the NOTCH pathway include but are not limited to, e.g., NOTCH family ligands, including both canonical and non-canonical NOTCH family ligands, and portions or fragments thereof. Canonical and non-canonical NOTCH family ligands include but are not limited to, e.g., Delta-like ligands, Jagged ligands, homologous vertebrate proteins and polypeptides to invertebrate NOTCH ligands (e.g., delta, serrate, LAG-2, APX-1, ARG-1, DSL-1, and the like), and the like. NOTCH ligands and methods of activating NOTCH signaling are known in the art and include, e.g., those described in D'Souza et al. (Curr Top Dev Biol. 2010; 92:73-129) Li et al. (J Biol Chem. 2008; 283(12):8046-54), the disclosures of which is incorporated herein by reference in their entirety. In some instances, activation of the NOTCH pathway may be achieved through repression of the a NOTCH pathway inhibitor, e.g., including but not limited to the use of an inhibitory nucleic acid targeting an inhibitor of the NOTCH pathway or an antibody or small molecule directed to a NOTCH pathway inhibitor.

In some instances, an inducing agent useful in a particular induction composition may include an activator or inhibitor of the PKA/cAMP pathway (i.e., the cAMP-dependent pathway, adenylyl cyclase pathway, PAK signaling, etc.). Activators and inhibitors of the PKA/cAMP pathway include small molecule activators, small molecule inhibitors, peptide activators, peptide inhibitors, antibodies, nucleic acid activators, nucleic acid inhibitors, and the like that activate or inhibit at least one component of the PKA/cAMP pathway resulting in a corresponding activation or inhibition in cellular PKA/cAMP signaling. Components and downstream effectors of the PKA/cAMP pathway include but are not limited to, e.g., G-protein alpha-12 family, WASF1 (WAVE1), LBC, G-protein alpha-i family, AKAP2, ATP cytosol, PDE3B, SMAD3, Androgen receptor, KDELR, AKAP7 gamma, PCTK1, 4.6.1.1, AKAP12, SMAD4, Anaphase-promoting complex (APC), GABA-A receptor beta-2 subunit, Ryanodine receptor 1, Troponin I, cardiac, AKAP8, 3.1.4.17, AKAP11, PHK beta, GABA-A receptor beta-3 subunit, PKA-cat alpha, CREB1, cAMP, G-protein alpha-s, GSK3 alpha/beta, AKAP3, Adenylate cyclase, PDK (PDPK1), GABA-A receptor beta-1 subunit, PKA-reg (cAMP-dependent), PDE4D, PKA-cat (cAMP-dependent), DARPP-32, PKA-reg type II (cAMP-dependent), NFKBIA, Meprin A, beta, AKAP82, AMP, PDE3A, PKI, PHK gamma, PDE4A, NFKBIB, PP2A regulatory, BAD, p90RSK1, G-protein alpha-13, Phospholamban, G-protein alpha-i family, RAP-1A, Adenylate cyclase type II, cAMP, G-protein beta/gamma, Calcineurin A (catalytic), PKC, Calmodulin, GSK3 alpha/beta, Adenylate cyclase type VII, Adenylate cyclase type IV, Adenylate cyclase type VIII, CREB1, ATP cytosol, Ca('2+) cytosol, 4.6.1.1, Ryanodine receptor 1, G-protein alpha-s, PKC-alpha, RAP-2A, CaMK IV, PHK alpha, PKA-reg (cAMP-dependent), Adenylate cyclase type III, cAMP-GEFII, Adenylate cyclase type V, LIPS, KDELR, cAMP-GEFI, Adenylate cyclase type VI, PKA-cat (cAMP-dependent), PHK gamma, CaMK II, PKC-zeta, PKC-delta, Adenylate cyclase type I, Adenylate cyclase type IX, and the like.

Activators of the PKA/cAMP pathway include but are not limited to, e.g., forskolin, dibutyryl-cAMP (bucladesine), 8-bromo-cAMP, 8-CPT-cAMP, taxol, Adenosine 3',5'-cyclic Monophosphate, N6-Benzoyl, Adenosine 3',5'-cyclic monophosphate, belinostat, 8-Chloroadenosine 3',5'-Cyclic Monophosphate, (S)-Adenosine, cyclic 3',5'-(hydrogen-phosphorothioate), Sp-Adenosine 3',5'-cyclic monophosphorothioate, Sp-5,6-DCI-cBiMPS, Adenosine 3',5'-cyclic Monophosphorothioate, 8-Bromo-, Sp-Isomer, Sp-8-pCPT-cyclic GMPS Sodium, N6-Monobutyryladenosine 3':5'-cyclic monophosphate, 8-PIP-cAMP, Sp-cAMPS caffeine, theophylline, pertussis toxin and the like. In some instances, activation of the PKA/cAMP pathway may be achieved through repression of the a PKA/cAMP pathway inhibitor, e.g., including but not limited to the use of an inhibitory nucleic acid targeting an inhibitor of the PKA/cAMP pathway or an antibody or small molecule directed to a PKA/cAMP pathway inhibitor.

In some instances, an inducing agent useful in a particular induction composition may include an activator or inhibitor of the VEGF pathway. Activators and inhibitors of the VEGF pathway include small molecule activators, small molecule inhibitors, peptide activators, peptide inhibitors, antibodies, nucleic acid activators, nucleic acid inhibitors, and the like that activate or inhibit at least one component of the VEGF pathway resulting in a corresponding activation or inhibition in cellular VEGF signaling. Components and downstream effectors of the VEGF pathway include but are not limited to, e.g., VEGFA, KDR, SH2D2A, PLCG1, PLCG2, PRKCA, PRKCB, PRKCG, SPHK1, SPHK2, HRAS, KRAS, NRAS, RAF1, MAP2K1, MAP2K2, MAPK1, MAPK3, PLA2G4E, PLA2G4A, JMJD7-PLA2G4B, PLA2G4B, PLA2G4C, PLA2G4D, PLA2G4F, PPP3CA, PPP3CB, PPP3CC, PPP3R1, PPP3R2, NFATC2, PTGS2, PTK2, SHC2, PXN, CDC42, MAPK11, MAPK12, MAPK13, MAPK14, MAPKAPK2, MAPKAPK3, HSPB1, SRC, PIK3CA, PIK3CD, PIK3CB, PIK3CG, PIK3R1, PIK3R5, PIK3R2, PIK3R3, RAC1, RAC2, RAC3, AKT1, AKT2, AKT3, NOS3, CASP9, BAD, and the like.

Modulators of the VEGF signaling pathway include but are not limited to e.g., Aspirin, Naproxen, Sulindac, Ibuprofen, Piroxicam, Diflunisal, Ketoprofen, Indometacin, Mefenamic acid, Tolmetin sodium, Meclofenamate sodium, Etodolac, Flurbiprofen, Nabumetone, Sasapyrine, Oxaprozin, Phenylbutazone, Sodium salicylate, Celecoxib, Rofecoxib, Axitinib, Bosutinib, Dasatinib, Doramapimod, Pegaptanib sodium, Ranibizumab, Semaxanib, Sorafenib tosilate, Vatalanib, Sunitinib malate, Vandetanib, Bevacizumab, Dasatinib hydrate, Motesanib, Dexketoprofen, Ketoprofen sodium, Meclofenamate sodium, Piketoprofen, Piketoprofen hydrochloride, Toceranib, Sorafenib, Toceranib phosphate, Sunitinib, Bevasiranib sodium, Brivanib alaninate, Cediranib, Cediranib maleate, Motesanib phosphate, Pamapimod, Ramucirumab, Talmapimod, Aflibercept, Dilmapimod, Dilmapimod tosylate, Foretinib, Linifanib, Losmapimod, Saracatinib, Saracatinib difumarate, Tivozanib, Bosutinib hydrate, Pegdinetanib, Naproxen etemesil, Cabozantinib, Tivozanib hydrochloride, Golvatinib, Pimasertib, Pimasertib hydrochloride, and the like. In some instances, VEGF activators useful in the subject methods include but are not limited to e.g., a VEGF polypeptide and/or a nucleic acid encoding a VEGF polypeptide.

In some instances, activation of the PKA/cAMP pathway may be achieved through repression of the a PKA/cAMP pathway inhibitor, e.g., including but not limited to the use of an inhibitory nucleic acid targeting an inhibitor of the PKA/cAMP pathway or an antibody or small molecule directed to a PKA/cAMP pathway inhibitor.

In some instances, an inducing agent useful in a particular induction composition may include a SCF agonist. SCF activators (i.e., SCF agonists) with vary and may include small molecule activators, peptide activators, agonist antibodies, nucleic acid activators, and the like that activate a molecule that responds to SCF or promotes the expression or functional bioactivity of SCF. In some instances, activation of SCF may be achieved through repression of a SCF inhibitor, e.g., including but not limited to the use of an inhibitory nucleic acid targeting an inhibitor of SCF or an antibody or small molecule directed to a SCF inhibitor. SCF agonists include but are not limited to, e.g., a SCF protein or polypeptide, an agonistic SCF peptide, a nucleic acid encoding a SCF protein or polypeptide, a nucleic acid encoding an agonistic SCF peptide, and the like.

In some instances, an inducing agent useful in a particular induction composition may include a gp130/IL6 superfamily agonist. Gp130/IL6 superfamily agonists will vary and may include small molecules, peptides, nucleic acids, and the like that activate Gp130/IL6 signaling or promotes the functional bioactivity of Gp130/IL6. In some instances, activation of Gp130/IL6 may be achieved through repression of a Gp130/IL6 inhibitor, e.g., including but not limited to the use of an inhibitory nucleic acid targeting an inhibitor of Gp130/IL6 or an antibody or small molecule directed to a Gp130/IL6 inhibitor.

Gp130/IL6 agonists will include a gp130/IL6 agonist binding-pair where such a binding-pair includes a first binding partner and a second binding partner that, when both binding partners are present in the culture medium function as a gp130/IL6 agonist. In some instances, one or more component of the gp130/IL6 agonist binding-pair may be added to the culture media. In other instances, one or more component of the gp130/IL6 agonist binding-pair may be expressed from a cell of the culture. The first and second binding partners of the a gp130/IL6 agonist binding-pair may be ligand receptor pairs, including soluble ligand and soluble receptor pairs that are capable of functioning as a gp130/IL6 agonist including extracellularly activating gp130/IL6.

Exemplary gp130/IL6 agonist binding-pairs include but are not limited to e.g., soluble IL6 and soluble IL6 receptor or a portion thereof (including e.g., soluble IL6 receptor alpha (IL6RA) ectodomain), soluble IL11 and soluble IL11 receptor (IL11R) or a portion thereof, soluble LIF and soluble LIF receptor (LIFR) or a portion thereof, soluble OSM and soluble OSM receptor (OSMR) or a portion thereof, soluble CNTF and soluble CNTF receptor (CNTFR) or a portion thereof, soluble CT1 and soluble CT1 receptor (i.e., LIF receptor (LIFR)) or a portion thereof. In some instances, gp130/IL6 agonist binding-pairs include those pairs containing component parts selected from those described in Taga & Kishimoto (Annu Rev Immunol. 1997; 15:797-81), the disclosure of which is incorporated herein by reference in its entirety.

In some instances, pathway modulating agents, as described above and including pathway activators and pathway inhibitors include, e.g., those that are commercially available, e.g., from such suppliers such as Tocris Bioscience (Bristol, UK), Sigma-Aldrich (St. Louis, MO), Santa Cruz Biotechnology (Santa Cruz, CA), and the like.

Pluripotent progenitors and derivatives thereof may be contacted with induction agents by any convenient means. Generally an induction agent is added to culture media, as described herein, within which cells of the instant disclosure are grown or maintained, such that the induction agent is present, in contact with the cells, at an effective concentration to produce the desired effect, e.g., induce a desired lineage restriction event. In other instances, e.g., where the existing culture media is not compatible with a particular induction agent, the culture media in which the cells are being grown is replaced with fresh culture media containing the particular induction agent present in the fresh media at an effective concentration to produce the desired effect. In instances where fresh or specific culture media is provided with a particular induction agent the culture agent may, in some instances, be specifically formulated for the particular induction agent, e.g., containing one or more specific additional reagents to, e.g., aid in the delivery of the induction agent, aid in the solubility of the induction agent, aid in the stability of the induction agent, etc.

In instances where a particular induction agent may consists of two or more parts, e.g., in the instance of a specific binding pair including but not limited to e.g., a gp130/IL6 agonist binding pair, both components may be administered simultaneously or the components may be added sequentially provided both components are present together in an effective concentration in the culture medium at the time necessary to perform the desired induction.

The effective concentration of a particular induction agent will vary and will depend on the agent. In addition, in some instances, the effective concentration may also depend on the cells being induced, the culture condition of the cells, other induction agents co-present in the culture media, etc. As such, the effective concentration of induction agents will vary and may range from 1 ng/mL to 10 µg/mL or more, including but not limited to, e.g., 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 ng/mL, 15 ng/mL, 16 ng/mL, 17 ng/mL, 18 ng/mL, 19 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, 30 ng/mL, 31 ng/mL, 32 ng/mL, 33 ng/mL, 34 ng/mL, 35 ng/mL, 36 ng/mL, 37 ng/mL, 38 ng/mL, 39 ng/mL, 40 ng/mL, 41 ng/mL, 42 ng/mL, 43 ng/mL, 44 ng/mL, 45 ng/mL, 46 ng/mL, 47 ng/mL, 48 ng/mL, 49 ng/mL, 50 ng/mL, 1-5 ng/mL, 1-10 ng/mL, 1-20 ng/mL, 1-30 ng/mL, 1-40 ng/mL, 1-50 ng/mL, 5-10 ng/mL, 5-20 ng/mL, 10-20 ng/mL, 10-30 ng/mL, 10-40 ng/mL, 10-50 ng/mL, 20-30 ng/mL, 20-40 ng/mL, 20-50 ng/mL, 30-40 ng/mL, 30-50 ng/mL, 40-50 ng/mL, 1-100 ng/mL, 50-100 ng/mL, 60-100 ng/mL, 70-100 ng/mL, 80-100 ng/mL, 90-100 ng/mL, 10-100 ng/mL, 50-200 ng/mL, 100-200 ng/mL, 50-300 ng/mL, 100-300 ng/mL, 200-300 ng/mL, 50-400 ng/mL, 100-400 ng/mL, 200-400 ng/mL, 300-400 ng/mL, 50-500 ng/mL, 100-500 ng/mL, 200-500 ng/mL, 300-500 ng/mL, 400 to 500 ng/mL, 0.001-1 µg/mL, 0.001-2 µg/mL, 0.001-3 µg/mL, 0.001-4 µg/mL, 0.001-5 µg/mL, 0.001-6 µg/mL, 0.001-7 µg/mL, 0.001-8 µg/mL, 0.001-9 µg/mL, 0.001-10 µg/mL, 0.01-1 µg/mL, 0.01-2 µg/mL, 0.01-3 µg/mL, 0.01-4 µg/mL, 0.01-5 µg/mL, 0.01-6 µg/mL, 0.01-7 µg/mL, 0.01-8 µg/mL, 0.01-9 µg/mL, 0.01-10 µg/mL, 0.1-1 µg/mL, 0.1-2 µg/mL, 0.1-3 µg/mL, 0.1-4 µg/mL, 0.1-5 µg/mL, 0.1-6 µg/mL, 0.1-7 µg/mL, 0.1-8 µg/mL, 0.1-9 µg/mL, 0.1-10 µg/mL. 0.5-1 µg/mL, 0.5-2 µg/mL, 0.5-3 µg/mL, 0.5-4 µg/mL, 0.5-5 µg/mL, 0.5-6 µg/mL, 0.5-7 µg/mL, 0.5-8 µg/mL, 0.5-9 µg/mL, 0.5-10 µg/mL, and the like.

In some instances, the effective concentration of an induction agent in solution, e.g., cell culture media, may range from 1 nM to 100 µM or more, including but not limited to, e.g., 1 nM, 2 nM, 3 nM, 4 nM, 5 nM, 6 nM, 7 nM, 8 nM, 9 nM, 10 nM, 11 nM, 12 nM, 13 nM, 14 nM, 15 nM, 16 nM, 17 nM, 18 nM, 19 nM, 20 nM, 21 nM, 22 nM, 23 nM, 24 nM, 25 nM, 26 nM, 27 nM, 28 nM, 29 nM, 30 nM, 31 nM, 32 nM, 33 nM, 34 nM, 35 nM, 36 nM, 37 nM, 38 nM, 39 nM, 40 nM, 41 nM, 42 nM, 43 nM, 44 nM, 45 nM, 46 nM, 47 nM, 48 nM, 49 nM, 50 nM, 1-2 nM, 1-3 nM, 1-4 nM, 1-5 nM, 1-6 nM, 1-7 nM, 1-8 nM, 1-9 nM, 1-10 nM, 1.5 nM, 1.5-2 nM, 1.5-3 nM, 1.5-4 nM, 1.5-5 nM, 1.5-6 nM, 1.5-7 nM, 1.5-8 nM, 1.5-9 nM, 1.5-10 nM, 2-3 nM, 2-4 nM, 2-5 nM, 2-6 nM, 2-7 nM, 2-8 nM, 2-9 nM, 2-10 nM, 3-4 nM, 3-5 nM, 3-6 nM, 3-7 nM, 3-8 nM, 3-9 nM, 3-10 nM, 4-5 nM, 4-6 nM, 4-7 nM, 4-8 nM, 4-9 nM, 4-10 nM, 5-6 nM, 5-7 nM, 5-8 nM, 5-9 nM, 5-10 nM, 6-7 nM, 6-8 nM, 6-9 nM, 6-10 nM, 7-8 nM, 7-9 nM, 7-10 nM, 8-9 nM, 8-10 nM, 9-10 nM, 5-15 nM, 5-20 nM, 5-25 nM, 5-30 nM, 5-35 nM, 5-40 nM, 5-45 nM, 5-50 nM, 10-15 nM, 10-20 nM, 10-25 nM, 10-30 nM, 10-35 nM, 10-40 nM, 10-50 nM, 15-20 nM, 15-25 nM, 15-30 nM, 15-35 nM, 15-40 nM, 15-45 nM, 15-50 nM, 20-25 nM, 20-30 nM, 20-35 nM, 20-40 nM, 20-45 nM, 20-50 nM, 25-30 nM, 25-35 nM, 25-40 nM, 25-45 nM, 25-50 nM, 30-35 nM, 30-40 nM, 30-45 nM, 35-50 nM, 40-45 nM, 40-50 nM, 45-50 nM, 10-100 nM, 20-100 nM, 30-100 nM, 40-100 nM, 50-100 nM, 60-100 nM, 70-100 nM, 80-100 nM, 90-100 nM, 50-150 nM, 50-200 nM, 50-250 nM, 50-300 nM, 50-350 nM, 50-400 nM, 50-450 nM, 50-500 nM, 10-150 nM, 10-200 nM, 10-250 nM, 10-300 nM, 10-350 nM, 10-400 nM, 10-450 nM, 10-500 nM, 100-150 nM, 100-200 nM, 100-250 nM, 100-300 nM, 100-350 nM, 100-400 nM, 100-450 nM, 100-500 nM, 200-500 nM, 300-500 nM, 400-500 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 200-400 nM, 300-500 nM, 400-600 nM, 500-700 nM, 600-800 nM, 700-900 nM, 800 nM to 1 µM, 0.5-1 µM, 0.5-1.5 µM, 0.5-2 µM, 0.5-2.5 µM, 0.5-3 µM, 0.5-3.5 µM, 0.5-4 µM, 0.5-4.5 µM, 0.5-5 µM, 1 µM, 2 µM, 3 µM, 4 µM, 5 µM, 6 µM, 7 µM, 8 µM, 9 µM, 10 µM, 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40 µM, 41 µM, 42 µM, 43 µM, 44 µM, 45 µM, 46 µM, 47 µM, 48 µM, 49 µM, 50 µM, 1-2 µM, 1-3 µM, 1-4 µM, 1-5 µM, 1-6 µM, 1-7 µM, 1-8 µM, 1-9 µM, 1-10 µM, 1.5 µM, 1.5-2 µM, 1.5-3 µM, 1.5-4 µM, 1.5-5 µM, 1.5-6 µM, 1.5-7 µM, 1.5-8 µM, 1.5-9 µM, 1.5-10 µM, 2-3 µM, 2-4 µM, 2-5 µM, 2-6 µM, 2-7 µM, 2-8 µM, 2-9 µM, 2-10 µM, 3-4 µM, 3-5 µM, 3-6 µM, 3-7 µM, 3-8 µM, 3-9 µM, 3-10 µM, 4-5 µM, 4-6 µM, 4-7 µM, 4-8 µM, 4-9 µM, 4-10 µM, 5-6 µM, 5-7 µM, 5-8 µM, 5-9 µM, 5-10 µM, 6-7 µM, 6-8 µM, 6-9 µM, 6-10 µM, 7-8 µM, 7-9 µM, 7-10 µM, 8-9 µM, 8-10 µM, 9-10 µM, 5-15 µM, 5-20 µM, 5-25 µM, 5-30 µM, 5-35 µM, 5-40 µM, 5-45 µM, 5-50 µM, 10-15 µM, 10-20 µM, 10-25 µM, 10-30 µM, 10-35 µM, 10-40 µM, 10-50 µM, 15-20 µM, 15-25 µM, 15-30 µM, 15-35 µM, 15-40 µM, 15-45 µM, 15-50 µM, 20-25 µM, 20-30 µM, 20-35 µM, 20-40 µM, 20-45 µM, 20-50 µM, 25-30 µM, 25-35 µM, 25-40 µM, 25-45 µM, 25-50 µM, 30-35 µM, 30-40 µM, 30-45 µM, 30-50 µM, 35-40 µM, 35-45 µM, 35-50 µM, 40-45 µM, 40-50 µM, 45-50 µM, 10-100 µM, 20-100 µM, 30-100 µM, 40-100 µM, 50-100 µM, 60-100 µM, 70-100 µM, 80-100 µM, 90-100 µM, and the like.

In some instances, the effective concentration of an induction agent will be below a critical concentration such that the induction produces the desired effect essentially without undesirable effects. As used herein, the term "critical concentration" refers to a concentration of induction agent above which undesirable effects are produced. Undesirable effects that may be the result of a concentration exceeding the critical concentration include but are not limited to, e.g., off-target effects (off-target activation of signaling, off-target inhibition of signaling), reduction or loss of function (e.g., loss of desired activator function, loss of desired inhibitor function) reduction of cell viability, increase in cell mortality, lineage restriction towards an undesired cell type, differentiation into an undesired cell type, loss of expression of a particular desired marker, etc. Whether a particular induction agent will have a critical concentration and what the critical concentrations of those agents having a critical concentration are will depend on the agent and the specific conditions in which the agent is used.

In some instances, cells of the instant disclosure may be contacted with multiple induction agents and/or multiple induction compositions in order achieve a desired mesodermal cell type of derivative thereof. In some instances, a particular induction composition will contain two or more induction agents such that a particular cell culture is simultaneously contacted with multiple induction agents. In some instances, a particular series of induction compositions may be used, one at a time, in generating a desired mesodermal cell type such that a particular cell culture is successively contacted with multiple induction agents.

The duration of contact of a particular induction composition with a particular cell type will vary and will depend, e.g., on the desired mesodermal cell type, the cell type being induced, and the components of the induction composition. In some instances, a particular induction composition may be introduced for different exposure times depending on the context of use, e.g., cell type X may be contacted with induction composition Y for time Z whereas cell type A may be contacted with induction composition Y for time B, wherein cell type X is different than cell type A and time Z is different than time B. As such, the time cells are contacted with a particular induction composition may vary, e.g., when being used on different cells, when being used to generate different cells, or when being used at different steps of a differentiation process.

The duration of contact of a particular induction composition with a particular cell type, in some instances, may be referred to as the "exposure time" and exposure times may range from a day to weeks or more, including but not limited to e.g., 1 day, 1.5 days, 2 days, 2.5 days, 3 days, 3.5 days, 4 days, 4.5 days, 5 days, 5.5 days, 6 days, 6.5 days, 7 days, 7.5 days, 8 days, 8.5 days, 9 days, 9.5 days, 10 days, 11 days, 12, days, 13, days, 14 days, 15, days, etc. As used herein, exposure times are, in some instances, referred as consisting essentially of, e.g., 24 hours, indicating that the exposure time may be longer or shorter than that specified including those exposure times that are longer or shorter but do not materially affect the basic outcome of the particular exposure. As such, in some instances where a particular exposure is more time sensitive such that under or over exposure, e.g., of more or less than 1 hour, materially affects the outcome of the exposure, a time period consisting essentially of, e.g., 24 hours, will be interpreted to refer to a time period ranging from about 23 hours to about 25 hours. In some other instances where a particular exposure is less time sensitive such that under or over exposure, e.g., of more than 12 hours, does not materially affect the outcome of the exposure, a time period consisting essentially of, e.g., 24 hours will mean a time period ranging from about 12 hours or less to about 36 hours or more. In some instances, depending on the context, an exposure period consisting essentially of 24 hours may refer to an exposure time of 22-26 hours, 21-27 hours, 20-28 hours, 19-29 hours, 18-30 hours, etc.

In some instances, time periods of exposure may be pre-determined such that cells are contacted with an induction composition according to a schedule set forth prior to the contacting. In some instances, the time period of exposure, whether pre-determined or otherwise, may be modulated according to some feature or characteristic of the cells and/or cell culture, including but not limited to, e.g., cell morphology, cell viability, cell appearance, cellular behaviors, cell number, culture confluence, marker expression, etc.

In some instances, cells are grown in densities that may range from but not limited to 100 cells/cm$^2$, 10$^3$ cells/cm$^2$, 10$^4$ cells/cm$^2$, 10$^5$ cells/cm$^2$, 10$^6$ cells/cm$^2$, 10$^7$ cells/cm$^2$, 10$^8$ cells/cm$^2$, 10$^9$ cells/cm$^2$, 10$^{10}$ cells/cm$^2$.

Markers

Aspects of the present disclosure include identifying cells based on the presence or absence or relative amount of one or more markers. In some instances, markers of interest include cell surface markers that may be detected, e.g., on live cells. In other instances, markers of interest include expression markers, e.g., cellular expression markers indicative of cell type.

Markers may be detected or measured by any convenient means as such marker detection is well-known in the art and may make use of one or more detection reagents including but not limited to, e.g., antibodies, antibody fragments, binding partners (e.g., ligands, binding pairs, etc), hybridizable nucleic acids, aptamers, etc. In some instances, a marker may be a cell surface marker and detection of the marker may be performed based on the use of one or more detection reagents that specifically bind to the marker. Detection reagents, e.g., antibodies, may be detectably labeled (e.g., fluorescently labeled through the attachment of a fluorescent molecule, fluorescent bead, or other fluorescent label) or may be detected through the use of a second detectably labeled detection reagent that specifically binds to the first detection reagent (e.g., a fluorescently labeled secondary antibody). In some instances, a detection agent, e.g., having a detectable label or having been bound by a second agent having a detectable label, can be visualized or otherwise observed or detected based on the visual characteristics of the label, including e.g., fluorescent detection, colorimetric detection, and the like. Detectable labels useful in detection reagents need not be visually detectable and may, in some instances, be detected by a detection device configured to detect a non-visual detectable label including but not limited to, e.g., a magnetic label, a radioactive label, etc. In some instances, detectable labels may be detected through the use of one or more detection reactions, including but not limited to, e.g., enzymatic detection reactions (enzymatic reactions generating a detectable substrate, e.g., a fluorescent or colorimetric substrate), amplification reactions (PCR amplification, fluorescent signal amplification (e.g., tyramide signal amplification, etc.), etc.)

In certain aspects of the instant disclosure, methods described make use of cell surface markers detectable on the surface of cells using one or more appropriate detection reagents. Cell surface markers of interest may vary and depend on the type of cell to be detected or the desired cell type being derived.

In some instances, identification and/or selection for sorting of cells may be performed using a combination of markers. Such combinations may include but combinations of positive selection markers, combinations of negative selection markers or mixed combinations of positive and negative selection markers.

In certain embodiments marker detection and/or measurement of marker level is performed using flow cytometry. Flow cytometry is a technique for counting, examining, and sorting microscopic particles suspended in a stream of fluid. It allows simultaneous multi-parametric analysis of the physical and/or chemical characteristics of single cells flowing through an optical and/or electronic detection apparatus. Fluorescence-activated cell sorting (FACS) is a specialized type of flow cytometry. FACS provides a method for sorting a heterogeneous mixture of biological cells into two or more containers, generally one cell at a time, based upon the specific light scattering and fluorescent characteristics of each cell. The flow cytometer and the FACS machine are useful scientific instruments as they provide fast, objective and quantitative recording of signals, e.g., fluorescent signals, and/or detection of cellular characteristics, e.g., size, granularity, viability, etc., from individual cells as well as physical separation of cells of particular interest. Fluorescent signals used in flow cytometry, for instance when quantifying and/or sorting cells by any marker present on or in the cell, typically are fluorescently-tagged antibody preparations or fluorescently-tagged ligands for binding to antibodies or other antigen-, epitope- or ligand-specific agent, such as with biotin/avidin binding systems or fluo-rescently-labeled and optionally addressable beads (e.g. microspheres or microbeads). The markers or combinations of markers detected by the optics and/or electronics of a flow cytometer vary and in some cases include but are not limited to: cell surface markers, intracellular and nuclear antigens, DNA, RNA, cell pigments, cell metabolites, protein modi-fications, transgenic proteins, enzymatic activity, apoptosis indicators, cell viability, cell oxidative state, etc.

In certain instances, flow cytometry is performed using a detection reagent, e.g., a fluorochrome-labeled antibody, e.g., a monoclonal antibody, with specific avidity against a cell surface maker of interest. A cellular sample is contacted with a detection reagent under conditions sufficient to allow the detection reagent to bind the cell surface maker and the cells of the sample are loaded into the flow cytometer, e.g., by first harvesting the cells from a cell culture using methods known in the art or described herein and re-suspending the isolated cells in a suitable buffer, e.g., running buffer. The cells loaded into the flow cytometer are run through the flow cytometer, e.g., by flowing cell containing buffer or liquid sample through the flow cell of the flow cytometer. The flow cytometer detects events as the cell passes one or more detection areas of the flow cytometer. For example, the flow cytometer may detect fluorescence emitted from a fluoro-chrome of a detection reagent upon excitation of the fluo-rochrome with a particular wavelength of light. In some instances, the flow cytometer detects the relative intensity of a particular signal, e.g., fluorescence of a particular detection reagent, of a particular cell, e.g., to quantify the level of a marker present on the surface of the cell and/or to qualita-tively categorize the cell, e.g., as a cell that is positive for a particular marker or a cell that is negative for a particular marker. Detected events are counted or otherwise evaluated by the flow cytometer with or without input from an operator and used to determine, e.g., the total number of cells, the number or proportion of cells bound to a particular detection reagent, etc. In instances where FACS is utilized cells may be sorted, e.g., into separate containers, based on the detec-tion or measurement of a particular marker. In some instances, cell sorting, e.g., by FACS, may be utilized to generate a purified population of a desired cell type.

In some instances, a threshold level of a particular detect-able marker is used to categorize cells for sorting by FACS. Threshold levels may be used to categorize cells as "posi-tive", "negative, "high", "low", etc. for a particular marker based on the level of detection of the marker. In some instances, a marker threshold level is determined by making a comparison of the levels of marker within a population of cells. e.g., a population of cells of unknown expression levels of Marker X or a population of cells suspected of containing subpopulations of cells having different expres-sion levels of Marker X. For example, the expression level of Marker X is measured on a flow cytometer of at least a sufficient number of cells such that the measurements may be plotted, e.g., on a histogram, and separation between two or more subpopulations of cells is revealed based on indi-vidual cell expression levels of Marker X. Accordingly, the flow cytometer operator may then determine a threshold level between the subpopulations that may be used to categorize cells as belonging to a particular subpopulation, e.g., a subpopulation having a low level of expression of Marker X or a subpopulation having high level of expression of Marker X.

In other instances, a threshold is predetermined based on a known or expected difference in marker level between cells of different populations. In some instances, a threshold is pre-calibrated or saved, e.g., in computer readable form, in a device, e.g., a flow cytometer, used in detecting or measuring a marker and/or sorting cells based on marker detection and/or measurement.

In some instances, the marker threshold is based on the limit of detection of the flow cytometer. For example, cells of a population of cells may be identified as expressing a particular marker (i.e. being positive for a particular marker) if the cells have any detectable level of a particular marker. Likewise, cells of a population of cells may be identified as not expressing a particular marker (i.e. being negative for a particular marker) if the cells do not have a detectable level of a particular biomarker. Accordingly, the detection level of the flow cytometer may be used to determine the biomarker threshold.

Expression markers of interest may be used to identify a particular cell type or verify that a derived cell type expresses a characteristic component of the derived cell type. In some instances, detection of expression markers may allow for optimization of a particular differentiation protocol, e.g., to optimize production of a desired cell type based on detection of one or more expression markers. Expression markers will vary depending on the type of cell to be identified or verified and/or desired downstream uses of the cell following identification or verification with the expression marker. Types of expression markers will include but are not limited to, e.g., gene expression marker, protein expression markers, expressed reporters, and the like. Expression marker detection and/or measurement may be detrimental to cell viability (e.g., wherein detection requires lysing or fixing a cell of interest) or may be essentially neutral to cell viability (e.g., wherein detection does not require lysing or fixing a cell of interest and may be performed on live cells).

Gene expression markers include but are not limited to the presence, absence, and/or relative amounts of a particular gene transcript that is indicative of particular cell type. Protein expression markers include but are not limited to the presence, absence, and/or relative amounts of a particular expression product that is indicative of particular cell type. Protein expression markers may be intercellular proteins, intracellular proteins or cell surface proteins. In some instances, a gene expression marker and a protein expression marker derived from the same gene may be indicative of a particular cell type.

Methods of detecting and/or measuring gene expression and/or protein expression are well-known in the art and include but are not limited to, e.g., Northern blot, Western blot, ELISA, PCR, quantitative PCR, in situ hybridization, fluorescent in situ hybridization, immunohistochemistry, immunofluorescence, microarray, quantitative sequencing, RNAseq, quantitative mass spectrometry, and the like.

Gene and protein expression markers useful in character-izing and/or identifying arterial endothelial cells, e.g., derived as described herein, include but are not limited to, e.g., CD31, CD34, CD144 (VE-cadherin), SCL, LMO2, FLI1, AA4.1, ESAM1, artery markers (SOX17, DLL4, JAG1, EFNB2), hemogenic markers (RUNX1, MYB), and the like. In some instances, the measurement of one or more such arterial endothelial markers above a particular thresh-old is indicative of an increased likelihood that an analyzed cell or cell population is an arterial endothelial cell or are arterial endothelial mesoderm cells. Generally, the detection and/or measurement of more such markers increases confi-dence in such determinations. In certain instances, measure-ment of one or more arterial endothelial markers above a particular threshold indicates that a cell is an arterial endothelial cell or a population of cells are arterial endothelial cells.

Arterial endothelial cells may also be differentiated on the basis of morphological characteristics including e.g., a distinctive network appearance. In some instances, arterial endothelial cells may also be differentiated on the basis of functional characteristics including e.g., the ability to subsequently form monocytes, the ability to subsequently form macrophages, the ability to subsequently form monocytes and macrophages, etc.

Expressed markers useful in identifying the above cell types as well as other cell types described herein are not limited to those specifically disclosed as other markers are known in the art may be deployed either independently to identify or characterize a particular cell type or in combination with one or more markers described herein. Furthermore, expressed markers are not limited to those gene products that produce a polypeptide and may include e.g., non-coding RNAs, non-coding transcripts, microRNAs, and the like. For example, in some instances identification and/or characterization of a cell type of interest may make use of one or more differentially expressed long noncoding RNAs as described herein.

In some instances, cells may be identified based on an expressed reporter wherein the expressed reporter may be heterologous sequence introduced into a cell. For example, in some instances, heterologous sequence encoding a detectable reporter may be introduced into a cell such that upon differentiation and/or lineage restriction to a mesodermal cell type of interest the reporter, e.g., a fluorescent molecule, becomes alternatively active or inactive. As describe herein, heterologous sequence may be stably or transiently introduced. Such introduced heterologous sequence may be configured to be responsive to activation of a marker, e.g., a marker of a particular cell type as described herein or known in the art, such that upon expression of the marker the reporter is activated. Alternatively, such introduced heterologous sequence may be configured to be responsive to activation of a marker, e.g., a marker of a particular cell type as described herein or known in the art, such that the reporter is active independent of expression of the marker but upon expression of the marker the reporter is deactivated. Methods of creating and using expression reporters are well-known in art.

Cell Modification

Methods of modification of cells, including modification of pluripotent cells and modification of hematopoietic stem cells are well-known in the art and include but are not limited to e.g., genetic modification (e.g., through deletion mutagenesis, through substitution mutagenesis), through insertional mutagenesis (e.g., through the introduction of heterologous nucleic acid into the pluripotent cell, etc.), non-mutagenic genetic modification (e.g., the non-mutagenic insertion of heterologous nucleic acid, etc.), epigenetic modification (e.g., through the treatment with one or more specific or general epigenetic modifying agents (e.g., methylation inhibitors, methylation activators, demethylases, etc.), other modifications (e.g., non-genetic labeling, etc.).

Modifications of cells may be transient or stable. In some instances, a modification of a particular pluripotent cell or mesodermal progenitor cell may be stable such that the modification persists through derivation of a desired mesodermal cell type from the pluripotent cell or progenitor cell as described herein. In some instances, stable modifications may persist through introduction of a mesodermally derived cell type into a host. In some instances, stable modifications may persist through proliferation of the cell such that all progenitors of a particular modified cell also contain the subject modification. In some instances, a modification of a particular pluripotent cell or progenitor cell may be transient such that the modification is lost after derivation of a mesodermal cell type of interest from the transiently modified pluripotent cell. In certain instances, transient modifications may persist through one or more rounds of proliferation of the modified cell such that some but not all of the progeny of the modified cell contain the subject modification. In some instances, a transient modification will not persist during proliferation such that none of the progeny of a modified cell will contain the subject modification. In some instances, a transiently modified cell may be configured such that the modification persists through certain aspects of derivation of the cell type of interest, e.g., through derivation of a particular mesodermal cell type of interest, but is lost prior to introduction of the derived cell into a host.

Screening

Aspects of the instant disclosure include method of screening pharmacological agents using hematopoietic stem cells derived according to the methods described herein. In some instances, a plurality cell populations derived according to the methods as described herein are contacted with a plurality of pharmacological agents in order to screen for agents producing a cellular response of interest. A cellular response of interest may be any cellular response including but not limited to, e.g., cell death, cell survival, cell self-renewal, proliferation, differentiation, expression of one or more markers, loss of expression of one or more markers, change in morphology, change in cellular physiology, cellular engraftment, change in cell motility, change in cell migration, production of a particular cellular component, cease of production of a particular cellular component, change in metabolic output, response to stress, and the like.

Screening pharmacological agents using cells described herein may be performed in vitro, e.g., in a tissue culture chamber, on a slide, etc., or may be performed in vivo, e.g., in an animal host, etc. Cells used in such screening assays may be genetically altered or may an unaltered. In some instances, cells generated according to the methods as described herein are used in multiplexed in vitro pharmacological screening. Methods for evaluating cellular responses during in vitro screening are well-known in the art and include but are not limited to, e.g., microscopic methods (e.g., light microscopy, electron microscopy, etc.), expression assays, enzymatic assays, cytological assays (e.g., cellular staining), genomics, transcriptomics, metabolomics, and the like.

In some instances, cells generated according to the methods as described herein are introduced into a host animal and the host animal may be administered a pharmacological agent in order to screen for a response from the introduced cells. In some instances, the cells of the in vivo assay may be directly evaluated, e.g., for an intrinsic response to a pharmacological agent. In some instances, the host animal of the in vivo assay may be evaluated as an indirect measurement of the response of the cells to the pharmacological agent.

In certain embodiments, the subject disclosure includes screening cells derived according to the methods described herein as a method of therapy of an animal model of disease and/or a human disease. Methods of screening cells derived according to the methods described herein as a method of therapy may be, in some instances, performed according to those methods described below regarding using such cells in therapeutic protocols.

In certain embodiments, the subject disclosure includes screening cells derived according to the methods described herein introduced to a host animal as a method of directly evaluating the cells or particular cellular behaviors, e.g., due to an introduced genetic modification or a naturally derived mutation. In one embodiment, genetically modified cells, e.g., having at least one modified genomic locus, derived according to the methods described herein may be introduced into a host animal and the ability of the cells to differentiate into a particular tissue or cell type may be evaluated. In another embodiment, genetically modified cells derived according to the methods described herein may be introduced into a host animal and the behavior of the cells within the host animal and/or within a tissue of the host animal may be evaluated. In another embodiment, cells derived from a donor organism having a particular mutation or phenotype and lineage restricted according to the methods described herein may be introduced into a host animal and the behavior of the cells within the host animal and/or within a tissue of the host animal may be evaluated, including, e.g., the ability of the cells to differentiate into one or more tissue or cell types. The cells may introduced into the host animal in a autologous graft, an allograft, or a xenograft such that the introduced cells may be derived from the host animal, a separate donor of the same species as the host animal, or a separate donor of a different species as compared to the host animal, respectively.

Therapy

Aspects of the disclosure include methods for lessening the symptoms of and/or ameliorating a dysfunction in hematopoietic stem cells and cells derived therefrom. Treatment methods described herein include therapeutic treatments, in which the subject is inflicted prior to administration, and prophylactic treatments, in which the subject is not inflicted prior to administration. In some embodiments, the subject has an increased likelihood of becoming inflicted or is suspected of having an increased likelihood of becoming inflicted (e.g., relative to a standard, e.g., relative to the average individual, e.g., a subject may have a genetic predisposition to mesodermal dysfunction or disorder and/or a family history indicating increased risk of mesodermal dysfunction or disorder), in which case the treatment can be a prophylactic treatment. Any and all forms of dysfunction, whether treated or untreated, or resulting from any primary condition, whether treated or untreated, are suitable dysfunctions or disorders to be treated by the subject methods described herein.

In some instances, the treatment methods described herein include the alleviation or reduction or prevention of one or more symptoms of dysfunction or disorder. Symptoms of dysfunction or disorder will vary, may be infrequent, occasional, frequent, or constant.

The methods of treatment described herein include administering a therapeutically effective amount of a population, e.g., an essentially homogenous population, of hematopoietic stem cells to a subject in need thereof in order to treat the subject for a dysfunction or deficiency.

The effective amount administered varies depending upon the goal of the administration, the health and physical condition of the individual to be treated, age, the taxonomic group of individual to be treated (e.g., human, non-human primate, primate, etc.), the degree of resolution desired (e.g., the amount of alleviation or reduction of symptoms), the formulation of the cell composition, the treating clinician's assessment of the medical situation, and other relevant factors.

A "therapeutically effective dose" or "therapeutic dose" is an amount sufficient to effect desired clinical results (i.e., achieve therapeutic efficacy) or reduce, alleviate, or prevent symptoms to a desired extent as determined by the patient or the clinician. A therapeutically effective dose can be administered in one or more administrations. For purposes of this disclosure, a therapeutically effective dose of cells is an amount that is sufficient, when administered to (e.g., transplanted into) the individual, to palliate, ameliorate, stabilize, reverse, prevent, slow or delay the progression of the disease state by, for example, inducing stabilization, repair, or regeneration.

In some embodiments, a therapeutically effective dose of cells is one cell or more (e.g., $1 \times 10^2$ or more, $5 \times 10^2$ or more, $1 \times 10^3$ or more, $5 \times 10^3$ or more, $1 \times 10^4$ cells, $5 \times 10^4$ or more, $1 \times 10^5$ or more, $5 \times 10^5$ or more, $1 \times 10^6$ or more, $2 \times 10^6$ or more, $5 \times 10^6$ or more, $1 \times 10^7$ cells, $5 \times 10^7$ or more, $1 \times 10^8$ or more, $5 \times 10^8$ or more, $1 \times 10^9$ or more, $5 \times 10^9$ or more, or $1 \times 10^{10}$ or more).

In some embodiments, a therapeutically effective dose of cells is in a range of from $1 \times 10^3$ cells to $1 \times 10^{10}$ cells (e.g., from $5 \times 10^3$ cells to $1 \times 10^{10}$ cells, from $1 \times 10^4$ cells to $1 \times 10^{10}$ cells, from $5 \times 10^4$ cells to $1 \times 10^{10}$ cells, from $1 \times 10^5$ cells to $1 \times 10^{10}$ cells, from $5 \times 10^5$ cells to $1 \times 10^{10}$ cells, from $1 \times 10^6$ cells to $1 \times 10^{10}$ cells, from $5 \times 10^8$ cells to $1 \times 10^{10}$ cells, from $1 \times 10^7$ cells to $1 \times 10^{10}$ cells, from $5 \times 10^7$ cells to $1 \times 10^{10}$ cells, from $1 \times 10^8$ cells to $1 \times 10^{10}$ cells, from $5 \times 10V$ cells to $1 \times 10^{10}$, from $5 \times 10^3$ cells to $5 \times 10^9$ cells, from $1 \times 10^4$ cells to $5 \times 10^9$ cells, from $5 \times 10^4$ cells to $5 \times 10^9$ cells, from $1 \times 10^5$ cells to $5 \times 10^9$ cells, from $5 \times 10^5$ cells to $5 \times 10^9$ cells, from $1 \times 10^8$ cells to $5 \times 10^9$ cells, from $5 \times 10^8$ cells to $5 \times 10^9$ cells, from $1 \times 10^7$ cells to $5 \times 10^9$ cells, from $5 \times 10^7$ cells to $5 \times 10^9$ cells, from $1 \times 10^8$ cells to $5 \times 10^9$ cells, from $5 \times 10^8$ cells to $5 \times 10^9$, from $5 \times 10^3$ cells to $1 \times 10^9$ cells, from $1 \times 10^4$ cells to $1 \times 10^9$ cells, from $5 \times 10^4$ cells to $1 \times 10^9$ cells, from $1 \times 10^5$ cells to $1 \times 10^9$ cells, from $5 \times 10^5$ cells to $1 \times 10^9$ cells, from $1 \times 10^4$ cells to $1 \times 10^9$ cells, from $5 \times 10^{10}$ cells to $1 \times 10^9$ cells, from $1 \times 10^7$ cells to $1 \times 10^9$ cells, from $5 \times 10^7$ cells to $1 \times 10^9$ cells, from $1 \times 10^8$ cells to $1 \times 10^9$ cells, from $5 \times 10^8$ cells to $1 \times 10^9$, from $5 \times 10^3$ cells to $5 \times 10^8$ cells, from $1 \times 10^4$ cells to $5 \times 10^8$ cells, from $5 \times 10^4$ cells to $5 \times 10^8$ cells, from $1 \times 10^5$ cells to $5 \times 10^8$ cells, from $5 \times 10^5$ cells to $5 \times 10^8$ cells, from $1 \times 10^8$ cells to $5 \times 10^8$ cells, from $5 \times 10^6$ cells to $5 \times 10^8$ cells, from $1 \times 10^7$ cells to $5 \times 10^8$ cells, from $5 \times 10^7$ cells to $5 \times 10^8$ cells, or from $1 \times 10^8$ cells to $5 \times 10^8$ cells).

In some embodiments, the concentration of cells to be administered is in a range of from $1 \times 10^5$ cells/ml to $1 \times 10^9$ cells/ml (e.g., from $1 \times 10^5$ cells/ml to $1 \times 10^8$ cells/ml, from $5 \times 10^5$ cells/ml to $1 \times 10^8$ cells/ml, from $5 \times 10^5$ cells/ml to $5 \times 10^7$ cells/ml, from $1 \times 10^8$ cells/ml to $1 \times 10^8$ cells/ml, from $1 \times 10^8$ cells/ml to $5 \times 10^7$ cells/ml, from $1 \times 10^8$ cells/ml to $1 \times 10^7$ cells/ml, from $1 \times 10^6$ cells/ml to $6 \times 10^6$ cells/ml, or from $2 \times 10^0$ cells/ml to $8 \times 10^8$ cells/ml).

In some embodiments, the concentration of cells to be administered is $1 \times 10^5$ cells/ml or more (e.g., $1 \times 10^5$ cells/ml or more, $2 \times 10^5$ cells/ml or more, $3 \times 10^5$ cells/ml or more, $4 \times 10^5$ cells/ml or more, $5 \times 10^5$ cells/ml or more, $6 \times 10^5$ cells/ml or more, $7 \times 10^5$ cells/ml or more, $8 \times 10^5$ cells/ml or more, $9 \times 10^5$ cells/ml or more, $1 \times 10^8$ cells/ml or more, $2 \times 10^8$ cells/ml or more, $3 \times 10^8$ cells/ml or more, $4 \times 10^6$ cells/ml or more, $5 \times 10^8$ cells/mi or more, $6 \times 10^8$ cells/ml or more, $7 \times 10^6$ cells/ml or more, or $8 \times 10^8$ cells/ml or more).

A therapeutically effective dose of cells may be delivered or prepared and any suitable medium, including but not limited to, e.g., those described herein. Suitable medium for the delivery of a therapeutically effective dose of cells will vary and may depend on, e.g., the type of pluripotent cells from which the effective dose of cells is derived or the type of derived cells of the effective dose. In some instances, a suitable medium may be a basal medium. "Cell medium" as used herein are not limited to liquid media may, in some instances, include non-liquid components or combinations of liquid media and non-liquid components. Non-liquid components that may find use a delivery or preparation medium include those described herein and those known in the art. In some instances, non-liquid components include natural or synthetic extra cellular matric components including but not limited to, e.g., basement membrane matrix components and the like.

In some instances, an effective dose of the cells described herein may be co-administered with one or more additional agents (e.g., prepared in a suitable medium). Additional agents useful in such co-administration include agents that improve the overall effectiveness of the effective dose of cells or decrease the dose of cells necessary to achieve an effect essentially equal to administration of an effective dose of the cells without the additional agent. Non-limiting examples of additional agents that may be co-administered include: conventional agents for treating diseases, pro-survival factors, pro-engraftment factors, functional mobilization agents, and the like. By conventional agents for treating diseases or dysfunction of mesodermally derived tissue is meant agents known in the art that prevent or inhibit disease or dysfunction.

By pro-survival factors is meant a factor or agent that may be added to the medium, culture media, delivery excipient, or storage solution that promotes the survival of a desired cell type. Such pro-survival factors may be general pro-survival factors that generally promote the survival of most cell types or may be specific pro-survival factors that only promote the survival of certain specific cell types. In some instances, pro-survival factors of the subject disclosure include but are not limited to, e.g., Rho-associated kinase (ROCK) inhibitor, pinacidil, allopurinol, uricase, cyclosporine (e.g., low does, i.e., sub-immunosuppressive dose, cyclosporine), ZVAD-fmk, pro-survival cytokines (e.g., insulin-like growth factor-1 (IGF-1)), extra cellular matrix (ECM) components, hydrogels, matrigel, collagen, gelatin, agarose, alginate, poly(ethylene glycol), hyaluronic acid, etc.

By pro-engraftment factors is meant a factor or agent that may be added to the administered dose or the delivery excipient or the cell storage solution that, upon delivery of the cells into a subject for treatment, increase the engraftment of the administered cells into the tissue targeted for engraftment and therapy. In some instances, pro-engraftment factors include factors that physically retain the administered cells at the delivery site, e.g., the injection site in the case of direct injection to the affected area, including but not limited to, e.g., gels, polymers, and highly viscous liquids that have physical properties that prevent the administered cells from freely diffusing. Such gels, polymers, and highly viscous liquids include but are not limited to e.g., ECM components, hydrogels, matrigel, collagen, gelatin, agarose, alginate, poly(ethylene glycol), and the like.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks. 3 weeks. 4 weeks, 5 weeks, 6 weeks, 8 weeks, or 12 weeks after) the administration of a second therapeutic agent.

The cells may be introduced by injection, catheter, intravenous perfusion, or the like. The cells may be frozen at liquid nitrogen temperatures and stored for long periods of time, being capable of use upon thawing. Once thawed, the cells may be expanded by use of growth factors and/or feeder cells or in feeder-free conditions associated with progenitor cell proliferation and differentiation. In some instances, the cells may be administered fresh such that the cells are expanded and differentiated and administer without being frozen.

The cells of this disclosure can be supplied in the form of a pharmaceutical composition, comprising an isotonic excipient or buffer or media prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cells. Suitable ingredients include matrix proteins that support or promote adhesion of the cells, or complementary cell types.

Cells of the subject methods may be autologously derived. By autologously derived it is meant that the cells are derived from the subject that is to be treated with the cells. The cells may be derived from a tissue sample obtained from the subject including but not limited to, e.g., a blood sample (e.g., a peripheral blood sample), a skin sample, a bone marrow sample, and the like. In some instances, the sample from which cells are derived may be a biopsy or swab, e.g., a biopsy or swab collected to diagnose, monitor, or otherwise evaluate the subject, e.g., diagnose the subject for a mesodermal dysfunction or deficiency. e.g., bone disease or a muscle disease or a cartilage disease or a related condition, or for cell collection. In some instances, the autologous sample from which the cells are derived may be a previously collected and stored sample, e.g., a banked tissue sample, from the subject to be treated, including but not limited to e.g., banked cardiac tissue or cells, banked musculoskeletal tissue or cells, banked reproductive tissue or cells, banked skin tissue or cells, banked bone tissue or cells, banked bone marrow tissue or cells, banked vascular tissue or cells, banked umbilical cord blood tissue or cells, and the like.

In some instances, cells of the subject methods are non-autologously derived. By non-autologously derived it is meant that the cells are not derived from the subject that is to be treated with the cells. In some instances, non-autologously derived cells may be xeno-derived (i.e., derived from a non-human animal) or allo-derived (i.e. derived from a human donor other than the subject to be treated). Non-autologously derived cells or tissue may be derived from any convenient source of cells or tissue collected by any convenient means.

Whether to use autologously derived or non-autologously derived cells may be determined according to the discretion of the subject's clinician and may depend on, e.g., the health, age, genetic predisposition or other physical state of the subject. In some instances, autologous cells may be preferred, including, e.g., to decrease the risk or immune rejection of the transplanted cells. In some instances, non-autologous cells may be preferred, including, e.g., when the subject has a genetic defect that affects mesodermally derived tissues.

Methods of derivation of pluripotent progenitor cells from an autologous or non-autologous tissue useful in the methods described herein include but are not limited to, e.g., methods of embryonic stem cell derivation and methods of induced pluripotent stem cell derivation. In some instances, methods as described herein may be performed using non-autologous pluripotent progenitor cells previously derived including, e.g., those publically or available or commercially available (e.g., from Biotime, Inc., Alameda, CA). In some instances, methods as described herein may be performed using newly derived non-autologous pluripotent progenitor cells or newly derived autologous pluripotent progenitor cells including but not limited to, e.g., newly derived embryonic stem cells (ESC) (including. e.g., those derived under xeno-free conditions as described in, e.g., Lei et al. (2007) *Cell Research*, 17:682-688) and newly derived induced pluripotent stem cells (iPS). General methods of inducing pluripotency to derive pluripotent progenitor cells are described in, e.g., Rodolfa K T, (2008) *Inducing Pluripotency*, StemBook, ed. The Stem Cell Research Community, doi/10.3824/stembook.1.22.1 and Selvaraj et al. (2010) *Trends Biotechnol*, 28(4)214-23, the disclosures of which are incorporated herein by reference. In some instances, pluripotent progenitor cells, e.g., iPS cells, useful in the methods described herein are derived by reprogramming and are genetically unmodified, including e.g., those derived by integration-free reprogramming methods, including but not limited to those described in Goh et al. (2013) *PLoS ONE* 8(11): e81622; Awe et al (2013) *Stem Cell Research & Therapy*. 4:87; Varga (2014) *Exp Cell Res*, 322(2)335-44; Jia et al. (2010) *Nat Methods*, 7(3):197-9; Fusaki et al. (2009) *Proc Jpn Acad Ser B Phys Biol Sci*. 85(8):348-62; Shao & Wu, (2010) *Expert Opin Biol Ther*. 10(2):231-42; the disclosures of which are incorporated herein by reference.

In some instances, the derived or obtained pluripotent progenitor cells are prepared, dissociated, maintained and/or expanded in culture prior to being differentiated and/or lineage restricted as described herein.

In some instances, before differentiation or lineage restriction of the pluripotent progenitor cells the pluripotent progenitor cells are dissociated, e.g., to generate a single-cell suspension. In some instances, the dissociation of the pluripotent progenitors is chemical, molecular (e.g., enzyme mediated), or mechanical dissociation. Methods of chemical, molecular, and/or enzyme mediated dissociation will vary and in some instances may include but are not limited to the use of, e.g., trypsin, TrypLE Express™, TrypLE Select™, Accutase®, StemPro® (Life Technologies, Inc., Grand Island, NY), calcium and magnesium free media, low calcium and magnesium medium, and the like. In some instances the dissociation media may further include pro-survival factors including but not limited to, e.g., Rho-associated kinase (ROCK) inhibitor, pinacidil, allopurinol, uricase, cyclosporine (e.g., low does, i.e., sub-immunosuppressive dose, cyclosporine), ZVAD-fmk, pro-survival cytokines (e.g., insulin-like growth factor-1 (IGF-1)), Thiazovivin, etc.

In some instances, methods of culturing pluripotent stem cells include xeno-free culture conditions wherein, e.g., human cells are not cultured with any reagents derived from non-human animals. In some instances, methods culturing of pluripotent stem cells include feeder-free culture conditions, wherein the pluripotent stem cells are cultured under conditions that do not require feeder cells and/or in feeder cell free medium, including e.g., commercially available feeder-free mediums, such as, e.g., those available from STEM-CELL Technologies, Inc. (Vancouver, BC). In some instances, methods culturing of pluripotent stem cells include culture conditions that include supplemental serum, including e.g. supplement of autologously derived serum, e.g., as described in Stute et al. (2004) *Exp Hematol*, 32(12):1212-25. In some instances, methods of culturing of pluripotent cells or derivatives thereof include culture conditions that are serum-free, meaning the culture media does not contain animal, mammal, or human derived serum. Serum-free culture conditions may be performed for only a portion of the life of the culture or may performed for the entire life of the culture. In some instances, serum-free culture conditions are used for a particular method step or procedure, e.g., during differentiation, during lineage restriction, prior to or during harvesting, etc. As is known in the art, in some instances, cells may be cultured in two dimensional or three dimensional formats (e.g., on non-coated or coated surfaces or within a solid or semi-solid matrix). Instances where two dimensional or three dimensional culture is appropriate for use in the methods as described herein, e.g., to promote survival or differentiation of a desired cell type, will be readily apparent to the ordinary skilled artisan. In some instance the pluripotent progenitor cell media includes one or more pro-survival factors, e.g., including those described herein. General methods of culturing human pluripotent progenitor cells are described in, e.g., Freshney et al. (2007) *Culture of human stem cells*, Wiley-Interscience, Hoboken, NJ and Borowski et al. (2012) *Basic pluripotent stem cell culture protocols*, StemBook, ed. The Stem Cell Research Community, StemBook, doi/10.3824/stembook, the disclosures of which are incorporated herein by reference.

In some instances, the pluripotent progenitor cells used according to the methods described herein may be genetically unmodified. By "genetically unmodified" is meant that essentially no modification of the genome of the cells transplanted into the subject has been performed. Encompassed within the term genetically unmodified are instances wherein transient genetic modification is performed at some point during the derivation of the cells but essentially no genetic modification persists in the cells that are eventually transplanted into the subject (i.e. the cells are essentially indistinguishable before the transient genetic modification and after the course of the transient modification). Also encompassed within the term genetically unmodified are instances wherein the genome of the cells is not transiently or stably modified, e.g., where the cells are manipulated, e.g., pluripotent progenitors are derived or cells are transformed, without genetic modification (e.g., modification of the nucleotide sequence of the genome) of the cells.

In some instances, the cells used according to the methods described herein may be genetically modified. By "genetically modified" is meant that at least one nucleotide is added to, changed within, or deleted from of the genome of the cell. In some instances, the genetic modification may be an insertion of a heterologous sequence, e.g., a sequence that encodes a tag, a label sequence, a reporter, a selectable marker, a gene encoding a protein from a species different from that of the host cell, etc. In some instances, the genetic modification corrects a defect or a mutation within the cell, e.g., corrects an anomalous mutation that confers a meso-dermally derived tissue dysfunction or deficiency. In some instances, the genetic modification deletes or renders inoperable an endogenous gene of the host cell. In some instances, the genetic modification enhances an endogenous gene of the host cell. In some instances, the genetic modification represents a change that enhances survival, control of proliferation, and the like. Cells may be genetically altered by transfection or transduction with a suitable vector, homologous recombination, or other appropriate technique, so that they express a heterologous sequence or have altered expression of an endogenous gene.

For further elaboration of general techniques useful in the practice of this disclosure, the practitioner can refer to standard textbooks and reviews in cell biology, tissue culture, and embryology. With respect to tissue culture and stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

Systems

Also provided are systems for use in practicing the subject methods. Systems of the subject disclosure may include a cell production system, e.g., for the production of a homogenous or highly pure population of hematopoietic stem cells from pluripotent progenitor cells.

In some instances, the cell production system includes a cell culture chamber or cell culture vessel for the culture of desired cell types. Such cell culture chambers may be configured for the expansion of pluripotent progenitor cells and for the differentiation and/or lineage restriction of such pluripotent progenitor cells into desired cell types. In some instances, the cell culture chamber is also configured for the expansion of hematopoietic stem cells. In certain embodiments, the cell culture chamber or cell culture vessel may be an open culture system, including but not limited to e.g., tissue culture dishes, tissue culture plates, tissue culture multi-well plates, tissue culture flasks, etc. In certain embodiments, the cell culture chamber or cell culture vessel may be a closed culture system, including e.g., a bioreactor, a stacked tissue culture vessel (e.g., CellSTACK Culture Chambers available from Corning, Inc. Corning, NY). In some instances, culture media and or other factors or agents may be exchanged in and out of the cell culture chamber through the use of one or more pumps (e.g., syringe pumps, peristaltic pumps, etc.) or gravity flow devices. In instances where the cells are cultured under sterile conditions the culture system may allow for the sterile exchange of culture media, e.g., through the use of sterile tubing connected, sealed, and reconnected through the use of a sterile devices, including but not limited to, e.g., a sterile tube welder and/or a sterile tube sealer. The cell culture system may be configured to control certain environmental conditions, including but not limited to e.g., temperature, humidity, light exposure, air composition (e.g., oxygen levels, carbon dioxide levels, etc.) to achieve the conditions necessary for expansion and/or differentiation of desired cell types. In some instances, the cell culture chamber may include a cell culture vessel that includes one or more patterned cell culture substrates or one or more arrays of patterned cell culture substrates as described herein.

The cell culture chamber may be configured for the production of cells for clinical use, e.g., according to current good manufacturing practice (cGMP) compliant cell culture practices, including the methods and configurations described in e.g., Fekete et al. *PLoS ONE* (2012) 7(8): e43255; Pham et al. (2014) *J Trans Med* 12:56; Gastens et al. (2007) *Cell Transplant* 16(7):685-96; Fernandes et al. (2013) *Stem Cell Bioprocessing: For Cellular Therapy, Diagnostics and Drug Development*, Burlington, Oxford: Elsevier Science: Woodhead Publishing, the disclosures of which are incorporated herein by reference.

The cell production system may, in some instances, by computer controlled and/or automated. Automated and/or computer controlled cell production systems may include a "memory" that is capable of storing information such that it is accessible and retrievable at a later time or date by a computer. Any convenient data storage structure may be chosen, based on the means used to access the stored information. In certain aspects, the information may be stored in a "permanent memory" (i.e. memory that is not erased by termination of the electrical supply to a computer or processor) or "non-permanent memory". Computer hard-drive, CD-ROM, floppy disk, portable flash drive and DVD are all examples of permanent memory. Random Access Memory (RAM) is an example of non-permanent memory. A file in permanent memory may be editable and re-writable.

In in certain instances, a computer controlled and/or automated cell culture system may include a module or program stored in memory for production of cells according to the methods described herein. Such a module may include instructions for the administration of induction agent and/or induction compositions, e.g., at particular timing intervals or according to a particular schedule, in order to generate a desired mesodermally derived cell type. In some instances, such a computer module may further include additional modules for routine cell culture tasks including but not limited to, e.g., monitoring and record keeping, media changes, environmental monitoring, etc.

Systems of the present disclosure include components and/or devices for delivering cells produced according to the methods described herein to a subject in need thereof. For example, in some instances a system for treating a subject with a mesodermal derived tissue dysfunction or deficiency includes a cell injection system for delivering cells in a carrier, with or without optional adjuvants, to a desired injection site, including diseased tissue, adjacent to diseased tissue, and/or within, on or near a dysfunctioning organ. Such systems utilize known injection devices (e.g., including but not limited to needles, bent needles, cannulas, syringes, pumps, infusion devices, diffusion devices, etc.) and techniques (e.g., including but not limited to intramuscular injection, subcutaneous injection, device-guided injection, etc.). In some instances, a device or technique used for the delivery of a cell scaffold or other bioengineered device may be configured or adapted for use in a cell delivery system for use in delivering cells derived according to the methods described herein In addition to the above described components systems of the subject disclosure may include a number of additional components, such as data output devices, e.g., monitors and/or speakers, data input devices, e.g., interface ports, keyboards, etc., fluid handling components, power sources, controllers, etc.

45

46

Compositions and Kits

Also provided are compositions and kits for use in the subject methods. The subject compositions and kits include any combination of components for performing the subject methods. In some embodiments, a composition can include, but is not limited to and does not require, the following: cell dissociation agents and/or media, cell reprogramming agents and/or media, pluripotent progenitor cells, cell culture agents and/or media, cell differentiation agents and/or media; lineage restriction agents (e.g., induction agents) and/or media; conventional agents for treating diseases and/or dysfunctions, pro-survival factors, pro-engraftment factors, functional mobilization agents and any combination thereof.

In some embodiments, a kit can include, but is not limited to and does not require, the following: any of the above described composition components, a sample collection container, a sample collection device (e.g., a sample collection container that includes a sample enrichment mechanism including, e.g., a filter), a tissue collection device (e.g., a biopsy device), a tissue dissociation device, a cell culture vessel, a cell production system; and any combination thereof.

In some embodiments, a kit can include, but is not limited to and does not require, a cell delivery system and/or a cell injection system configured for delivery of cells derived according to the methods described herein. For example, a kit may include a cell injection system configured for injection or delivery of cells into a desired area of the subject in order to effectively treat the subject for a mesodermally derived tissue dysfunction or deficiency. e.g., through delivery of cells to the mesodermally derived tissue. Such kits may include a cell delivery or injection system, as described herein, including individual components of such systems in assembled or unassembled form. In some instances, cells derived according to the methods described herein may be "preloaded" into a cell injection or delivery system such that the system is provided in a "ready-to-use" configuration. In other instances, a cell injection or delivery system may be provided in an "unloaded" configuration such that cells derived according to the methods described herein must be loaded into the system, with any desired carrier or vehicle, prior to use.

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is electronic, e.g., a website address which may be used via the internet to access the information at a removed site.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., room temperature (RT); base pairs (bp); kilobases (kb); picoliters (pl); seconds (s or sec); minutes (m or min); hours (h or hr); days (d); weeks (wk or wks); nanoliters (n); microliters (ul); milliliters (ml); liters (L); nanograms (ng); micrograms (ug); milligrams (mg); grams ((g), in the context of mass); kilograms (kg); equivalents of the force of gravity ((g), in the context of centrifugation); nanomolar (nM); micromolar (uM), millimolar (mM); molar (M); amino acids (aa); kilobases (kb); base pairs (bp); nucleotides (nt); intramuscular (i.m.); intraperitoneal (i.p.); subcutaneous (s.c.); and the like.

Example 1

Efficient and Rapid Generation of Human Blood Vessel Progenitors and Blood Progenitors from Pluripotent Stem Cells Generation of blood-forming hematopoietic stem cells (HSCs) from human pluripotent stem cells (hPSCs) can provide a powerful platform to replace patients' diseased blood and immune systems with healthy ones in vivo and to mass-produce desired immune cells in vitro. However it has been heretofore challenging to differentiate hPSCs into HSCs. The sequence of developmental intermediates through which pluripotent cells differentiate into HSCs and the extrinsic signals that induce or repress the formation of each successive intermediate remain incompletely understood. Here we demonstrate that blood-vessel (endothelial) cells, specifically artery endothelial cells, are the developmental precursor to HSCs. First, we efficiently and rapidly differentiate hPSCs into primitive streak and dorsal-lateral mesoderm progenitors, subsequently generating enriched populations of either artery or vein endothelial cells. Next, we further differentiate these artery endothelial cells into hemogenic endothelium and finally >70% pure CD34$^+$ CD90$^+$CD144$^+$ CD43$^+$CD45$^+$ HSC-like cells in defined, monolayer culture, within 9 total days of hPSC differentiation. During this sequential differentiation process, differentiation-inducing signals change sharply within 24 hours. The hPSC-derived HSC-like cells generate T cells, platelets, red blood cells and myeloid cells in vitro, with ramifications for regenerative medicine and cancer immunotherapy. We show that artery endothelial cells are the developmental precursor to HSCs and that transition through an artery state instills the competence to differentiate into hemogenic endothelium and eventually, HSCs. Taken together, the ability to efficiently generate human endothelial cells and blood progenitors in vitro has widespread ramifications for regenerative medicine, tissue engineering, cancer immunotherapy, disease modeling and other applications that hinge on a supply of such cells.

We address the origins of definitive blood in human development, and we show that artery cells are the upstream developmental precursor to HSCs. First, we efficiently differentiated hPSCs into primitive streak, dorsal-lateral mesoderm, and subsequently a >90% pure population of artery endothelial cells (within 3 days of differentiation) or a >80% pure population of NR2F2$^+$ CD144$^+$ vein endothelial cells (within 4 days of differentiation). Second, we found that these artery cells could subsequently evolve into HSC-like cells and we mapped the steps through which these cells differentiated. We found that day 3 hPSC-derived artery cells faced a branching lineage choice to remain as arteries (instructed by VEGF and TGFβ) or to convert into hemogenic endothelium (specified by the absence of VEGF and TGFβ together with activation of GP130, NOTCH and PKA signaling). Hemogenic endothelium cells were endothelial in nature but progressively upregulated a number of hematopoietic transcription factors (first RUNX1, then GFI1 and followed by GFI1B and PU.1), becoming a >80% pure population of CD144⁺ RUNX1⁺ hemogenic endothelium cells by day 6 of differentiation. Subsequently, by day 9 of differentiation, a >60% pure population of CD34⁺ CD90⁺ CD144⁺ CD45⁺ HSC-like cells emerged. These hPSC-derived HSC-like cells could generate monocytes, red blood cells, platelets and T cells in vitro, indicating that they are multipotent blood progenitors at the population level.

Results

Efficient differentiation of hPSCs into primitive streak and dorsal lateral mesoderm by repressing unwanted fates. In vivo, pluripotent cells (corresponding to day 5.5 of mouse embryonic development [~E5.5]) first differentiate into primitive streak (~E6.5) and lateral mesoderm (~E7-7.5) before forming endothelial cells, including DLL4⁺ artery endothelial cells (~E8-E8.25) and NR2F2⁻ vein endothelial cells (~E8.5-E9.5) (FIG. 1a). We sought to efficiently recreate this sequence of steps in vitro starting from hPSCs (FIG. 1a). First, we found that simultaneous activation of BMP, FGF, TGFβ and WNT for 24 hours efficiently differentiated hPSCs into 97.3±0.3% pure MIXL1-GFP⁺ mid primitive streak, while suppressing ectoderm formation (FIG. 1b), as previously reported (Loh et al., 2016).

Second, we further differentiated hPSC-derived day 1 mid primitive streak into day 2 dorsal lateral mesoderm. In *Xenopus*, lateral mesoderm is heterogeneous and only dorsal lateral mesoderm expresses SCL, LMO2 and FLI1 and is fated to become endothelium and blood (Ciau-Uitz et al., 2013). Our analysis of E7 mouse embryo single-cell RNA-sequencing data (Pijuan Sala et al., 2019) suggested that in mammals, lateral mesoderm is likewise heterogeneous, with only a subset expressing Scl, Lmo2 and Fli1 (FIG. 1c). While signals that induce lateral mesoderm from hPSCs are known (Cheung et al., 2012; Loh et al., 2016), how dorsal lateral mesoderm is specifically induced remains unknown.

Figure 7:
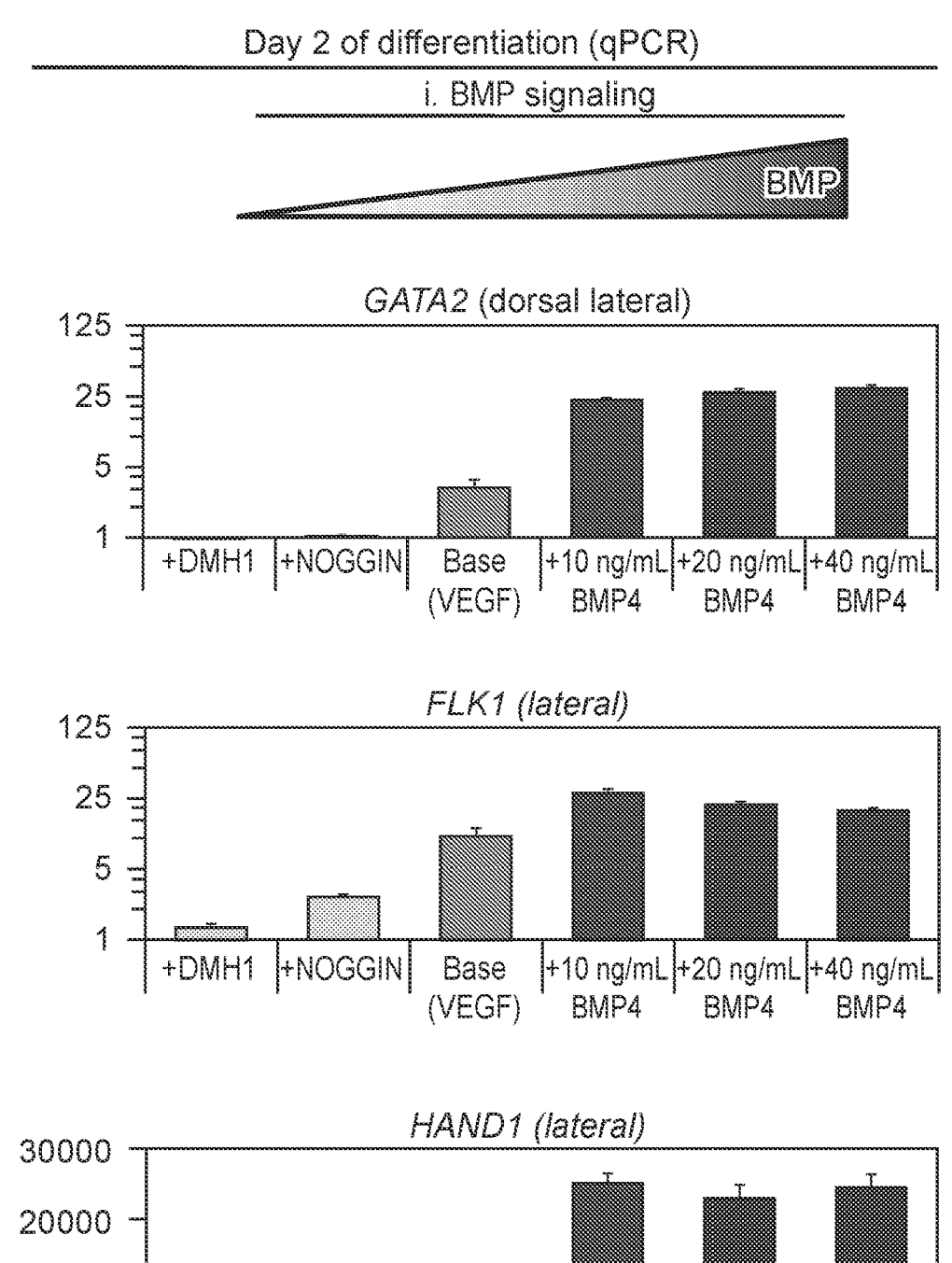
FIG. 7: Optimization of dorsal lateral mesoderm generation from hPSCs (related to FIG. 1). A) BMP specifies, whereas TGFβ and WNT repress, day 2 dorsal lateral mesoderm; i) day 1 hPSC-derived primitive streak was treated with VEGF for 24 hours in the presence or absence of BMP4 (10-40 ng/mL) or BMP inhibitors (DMH1 or NOGGIN); ii) day 1 hPSC-derived primitive streak was treated with BMP4+VEGF for 24 hours in the presence or absence of a WNT agonist (CHIR99021, 1-6 μM) or WNT inhibitors (C59 or XAV939); iii) day 1 hPSC-derived primitive streak was treated with BMP4+VEGF for 24 hours in the presence or absence of a TGFβ agonist (Activin, 5-100 ng/mL) or TGFβ inhibitors (SB505124 or SB431542); qPCR was performed on day 2 cell populations. B) PKA agonists specify day 2 dorsal lateral mesoderm; day 1 hPSC-derived primitive streak was treated with BMP+ GDC0941+VEGF+XAV939 in the presence or absence of PKA agonists (8-bromo-cAMP [1 mM] or Forskolin [10 μM]) or PKA inhibitor (KT5720 [1 μM]) for 24 hours to generate candidate dorsal lateral mesoderm, which was then further differentiated into artery endothelial cells for 24 additional hours (using GDC0941+VEGF+XAV939); flow cytometry was performed on day 3 artery populations (top) and qPCR was performed on day 2 dorsal lateral mesoderm populations (bottom). C) PI3K inhibitors specify day 2 dorsal lateral mesoderm; day 1 hPSC-derived primitive streak was treated with BMP+VEGF+XAV939 in the presence or absence of PI3K inhibitors (PIK90 or GDC0941) for 24 hours to generate candidate dorsal lateral mesoderm, which was then further differentiated into artery endothelial cells for 24 additional hours (using VEGF alone); flow cytometry was performed on day 3 artery populations.
Figure 7:
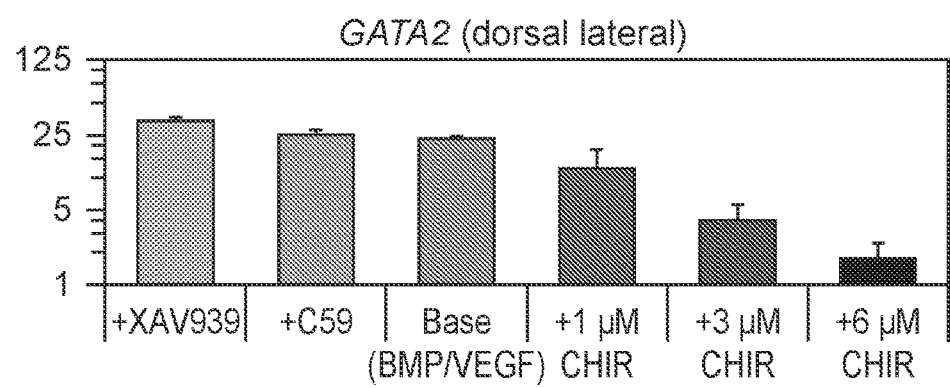
Figure 7:
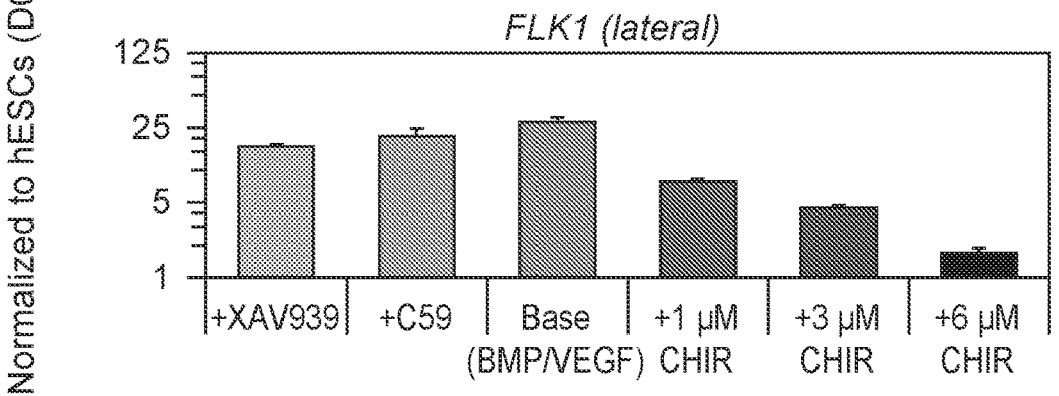
Figure 7:
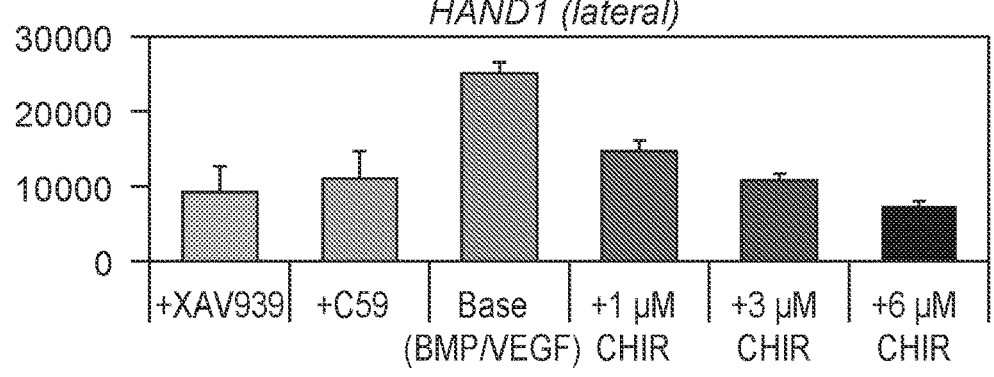
Figure 7:
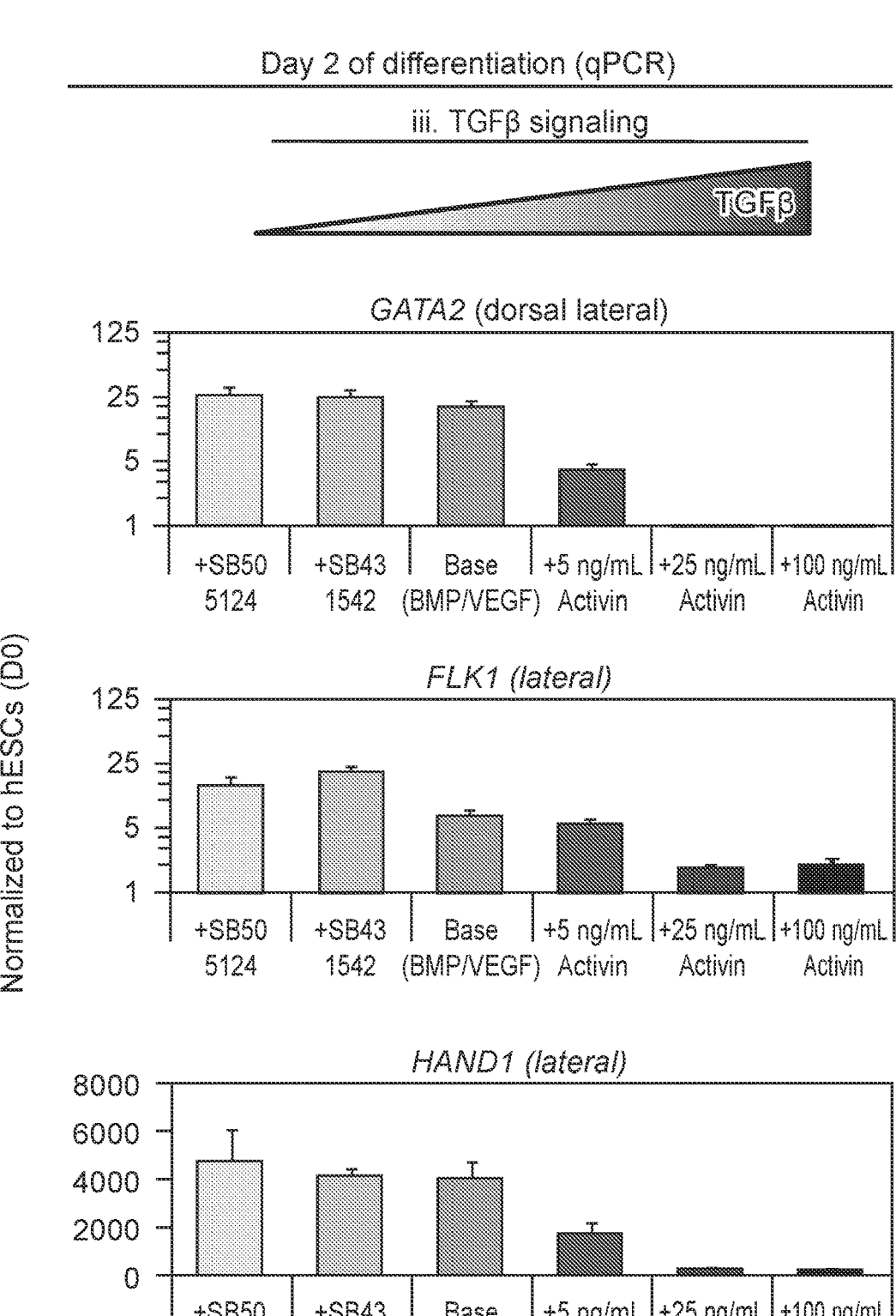
Figure 7:
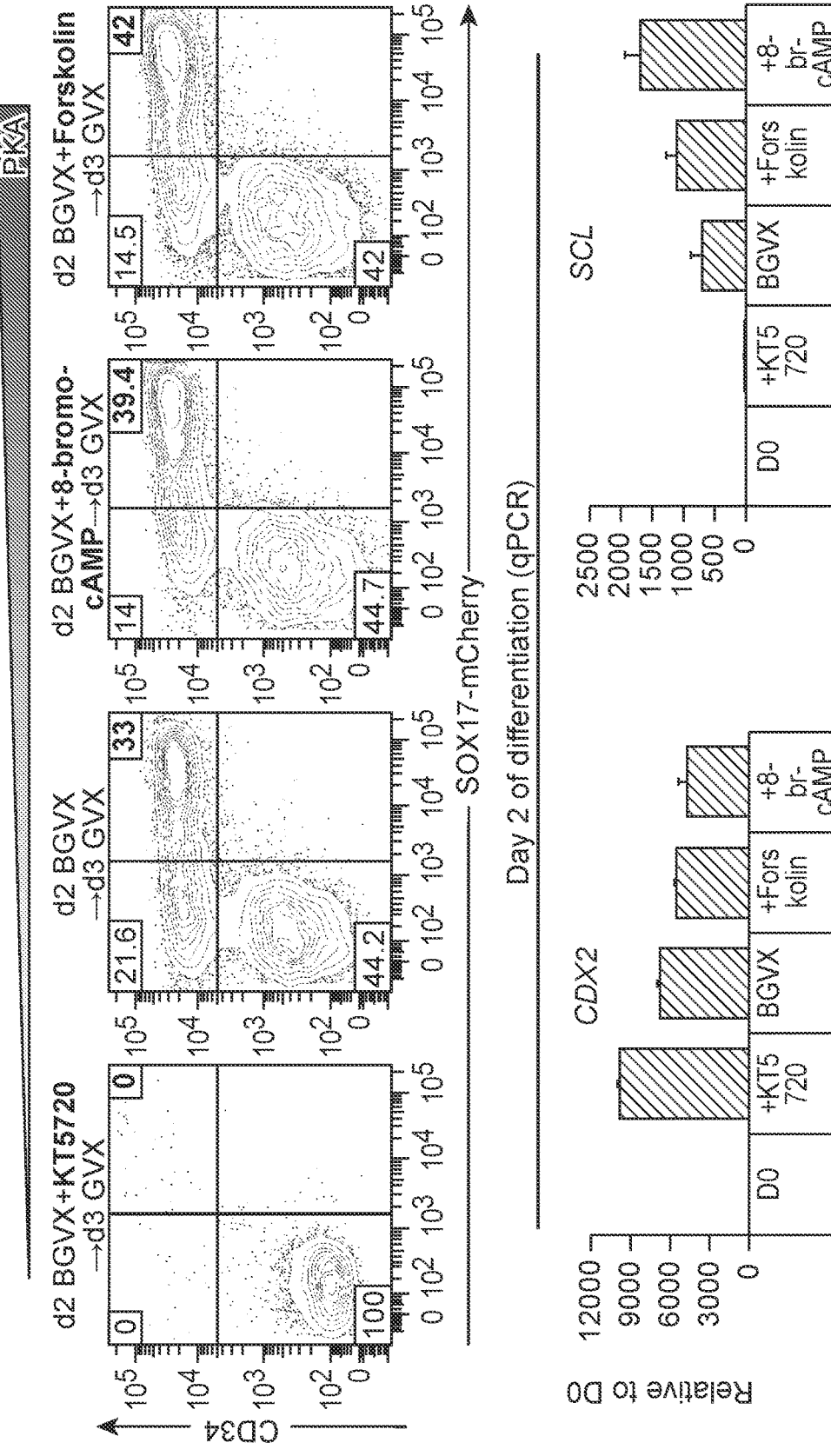
Figure 7:
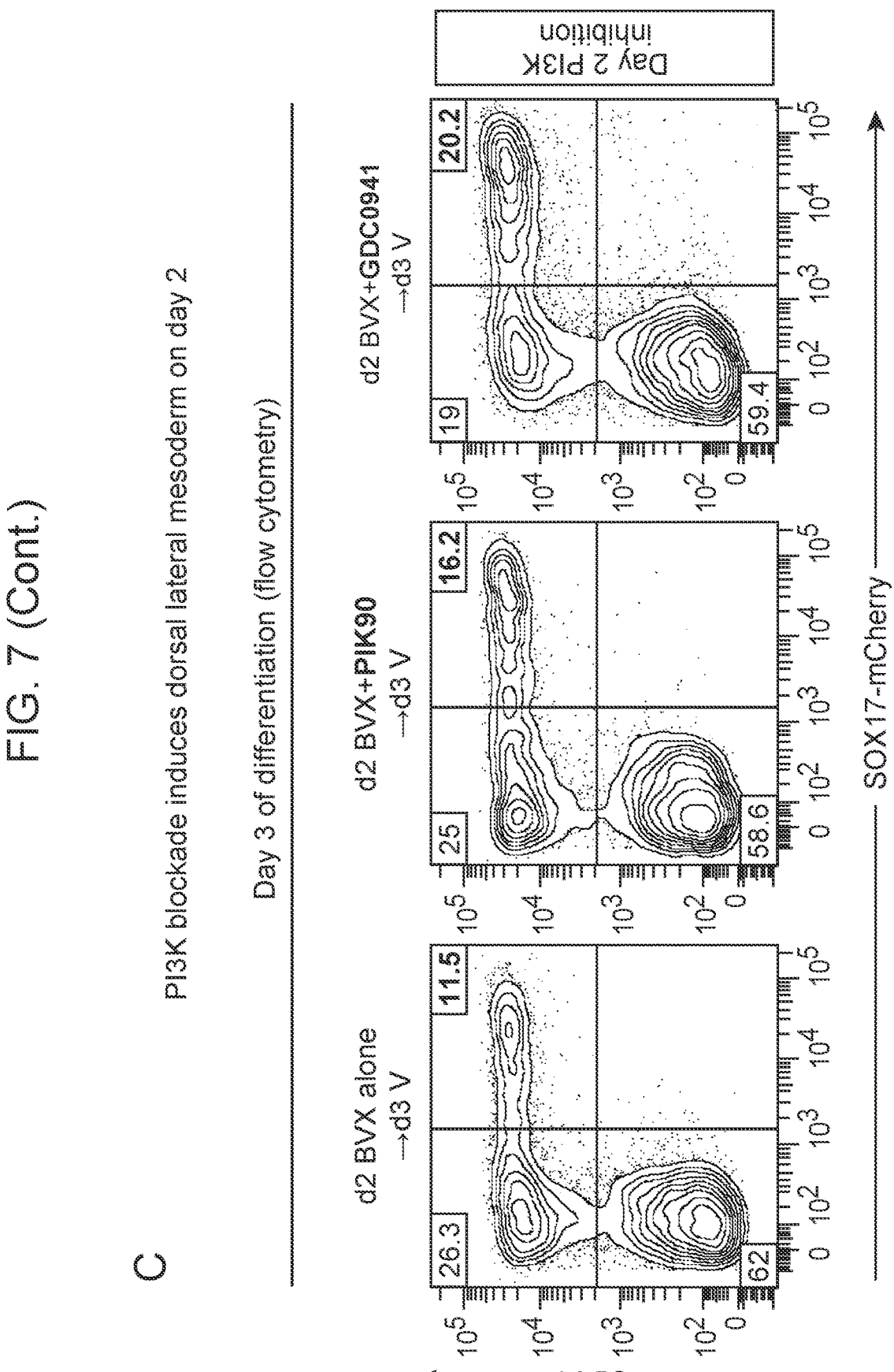

During day 2 of differentiation, we found that VEGF (FIG. 1c) and BMP (FIG. 1di; FIG. 7ai) upregulated SCL, LMO2 and FLI1, thus specifying dorsal lateral mesoderm. This is consistent with how VEGF specifies *Xenopus* dorsal lateral mesoderm (Ciau-Uitz et al., 2013) and explains the total loss of blood vessels in Vegfr2⁻/⁻ (Flk1⁻/⁻) mice (Shalaby et al., 1995). Conversely, WNT and TGFβ respectively induced paraxial mesoderm and endoderm (Loh et al., 2014; Loh et al., 2016). Therefore inhibiting both WNT and TGFβ enhanced dorsal lateral mesoderm specification by repressing these unwanted fates (FIG. 1dii,iii; FIG. 7aii,iii). Finally, PKA/cAMP activation (FIG. 7b) together with PI3K inhibition (FIG. 7c) further enhanced formation of dorsal lateral mesoderm that was competent for subsequent endothelial differentiation. Taken together, we found that BMP, PKA/cAMP and VEGF activation together with inhibition of WNT, TGFβ 1 and PI3K signaling for 24 hours differentiated day 1 mid primitive streak into day 2 dorsal lateral mesoderm (corresponding to ~E7-E7.5 of mouse embryogenesis), while simultaneously repressing unwanted endoderm or paraxial mesoderm differentiation.

Efficient differentiation of hPSC-derived dorsal lateral mesoderm into arteries: artery-instructive signals. Day 2 hPSC-derived dorsal lateral mesoderm was further differentiated into day 3 artery progenitors. To track artery specification in vitro, we exploited SOX17-mCherry (Loh et al., 2014) or SOX17-GFP (Wang et al., 2011) knock-in reporter hESC lines and screened for signals to induce SOX17⁺ CD34⁺ arterial progenitors in vitro. In the mouse embryo, artery cells emerge at ~E8.0-E8.25 (Chong et al., 2011) and express Sox17, which specifies arterial fate; conditional Sox17 deletion converts arteries into veins (Corada et al., 2013; Sakamoto et al., 2007).

At this juncture, we found that day 2 dorsal lateral mesoderm could differentiate into arteries; pre-veins (a transitional intermediate to veins [see below]); and heart progenitors by day 3 (FIG. 2a). We found that BMP specified NKX2.5⁺ cardiac progenitors (Loh et al., 2016) (FIG. 8a), whereas WNT specified non-endothelial CDX2⁺ mesoderm (FIG. 8b). Consequently the activation of VEGF together with dual BMP and WNT blockade broadly promoted pan-endothelial specification. In this permissive, pro-endothelial signaling context, we next asked what uniquely instructs arterial fate.

We found that TGFβ was a crucial artery-specifying signal that induced CD34⁺ SOX17⁺ artery cells, and repressed venous fate, on day 3 (FIG. 2b, FIG. 8c). Conversely, TGFβ inhibition on day 3 downregulated arterial markers (SOX17, DLL4 and EFNB2) and induced NR2F2 (FIG. 2b). Our results suggest that the earlier use of TGFβ inhibitors to generate hPSC-derived putative arterial cells (Zhang et al., 2017) may have instead inhibited arterial formation. Extracellular signals specifying arterial fate were temporally dynamic and sharply changed every 24 hours: during 3 days of hPSC differentiation, the same signals were re-interpreted to specify 3 distinct cell-types. For instance, TGFβ activation differentiated hPSCs towards mid primitive streak on day 1 (FIG. 1b); subsequently TGFβ had to be inhibited to differentiate mid primitive streak into dorsal lateral mesoderm on day 2 (FIG. 1e); finally TGFβ had to be activated again to specify arterial fate (FIG. 2b).

Conversely, PI3K specified veins and therefore we inhibited PI3K to specify hPSC-derived arterial progenitors from dorsal lateral mesoderm and to downregulate venous marker NR2F2 (FIG. 2c). This is consistent with how PI3K inhibition expands arteries, and represses veins, in zebrafish embryos (Hong et al., 2006).

Taken together, activation of TGFβ and inhibition of PI3K constituted artery-instructive signals that acted together with permissive, pan-endothelial signals (VEGF activation together with BMP and WNT inhibition) that differentiated day 2 dorsal lateral mesoderm into day 3 hPSC-derived arterial progenitors, while inhibiting unwanted differentiation into either heart or vein precursors (FIG. 8d). This delineates a complex signaling code for arterial specification beyond simply activation of VEGF and NOTCH (reviewed by Fish and Wythe, 2015).

This signaling combination generated a >90% pure SOX17⁺ CD34⁺ artery progenitor population by day 3 of hPSC differentiation (FIG. 2d,e). These artery progenitors coexpressed pan-endothelial marker proteins CD31/PE-CAM1 and CD144/VE-CADHERIN (FIG. 2d,e), indicating that they were endothelial and not other SOX17⁺ lineages, such as endoderm (Loh et al., 2014). hPSC-derived day 3 SOX17⁺ CD34⁺ artery progenitors expressed multiple artery-specific markers, including EFNB2 (Wang et al., 1998), DLL4 (Shutter et al., 2000), JAG1, NOTCH1, NRP1 (Herzog et al., 2001) and FOXC1 (Seo et al., 2006) but not the vein-specific marker NR2F2/COUP-TFII (You et al., 2005) (FIG. 2f, FIG. 8e). Indeed, hPSC-derived arterial cells homogeneously expressed the arterial marker DLL4 at a single-cell level, as shown by flow cytometry (FIG. 2g). Furthermore, hPSC-derived arterial cells expressed pan-endothelial transcription factors (SCL, LMO2 and FL1) and pan-endothelial surface markers (CD31, CD34, CD93/AA4.1, CD144 and ESAM1), but minimally expressed markers of other mesoderm subtypes (CDX2, FOXF1) and pluripotent cells (POU5F1/OCT4, SOX2 and NANOG) (FIG. 2f, FIG. 8e).

Figure 9:
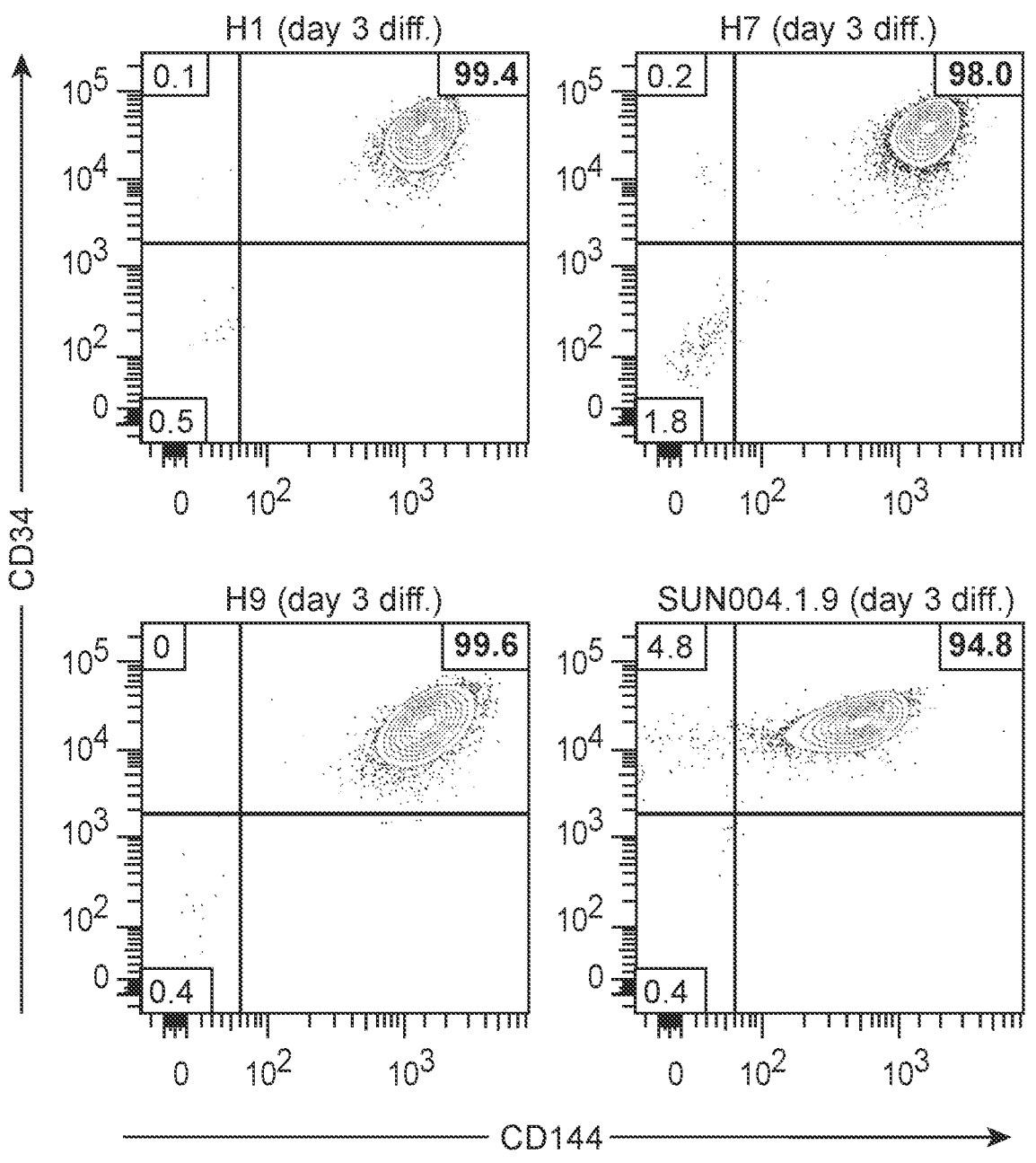
FIG. 9: Comparison of endothelial differentiation protocols (related to FIG. 2). A) Flow cytometry of H1, H7, H9 and SUN004.1.9 hPSCs differentiated into arteries for 3 days reveals that >94% of cells are CD34$^+$ CD144$^+$ arterial cells. B,C) Side-by-side comparison of our artery differentiation system against 4 prevailing methods for endothelial differentiation in the H1 and SUN004.1.9 hPSC lines; flow cytometry to assess the percentage of CD34$^+$ CD144$^+$ endothelial cells was performed on days 3, 5 and 6 of differentiation.
Figure 9:
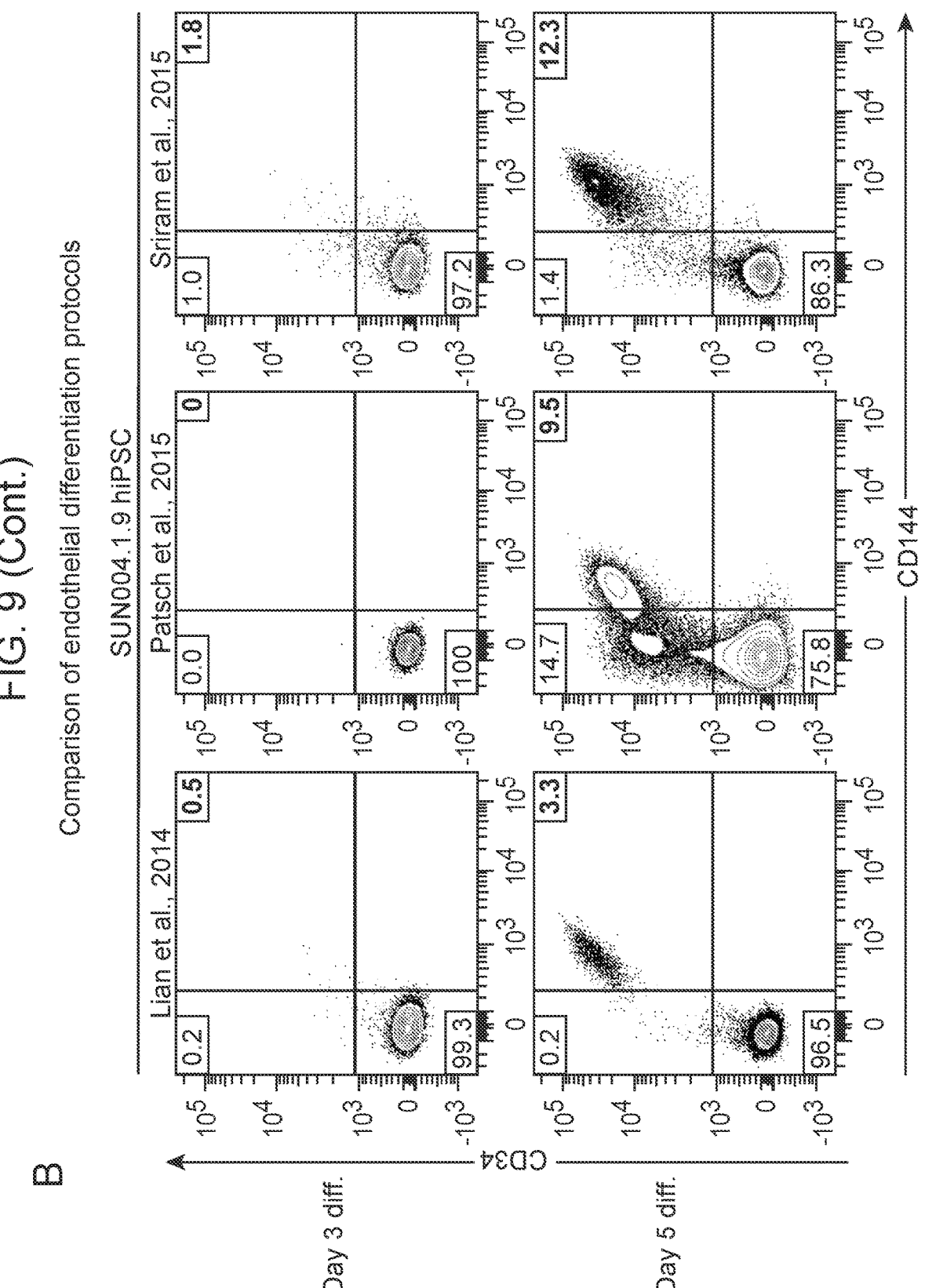
Figure 9:
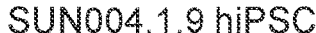
Figure 9:
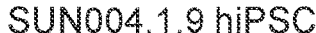
Figure 9:
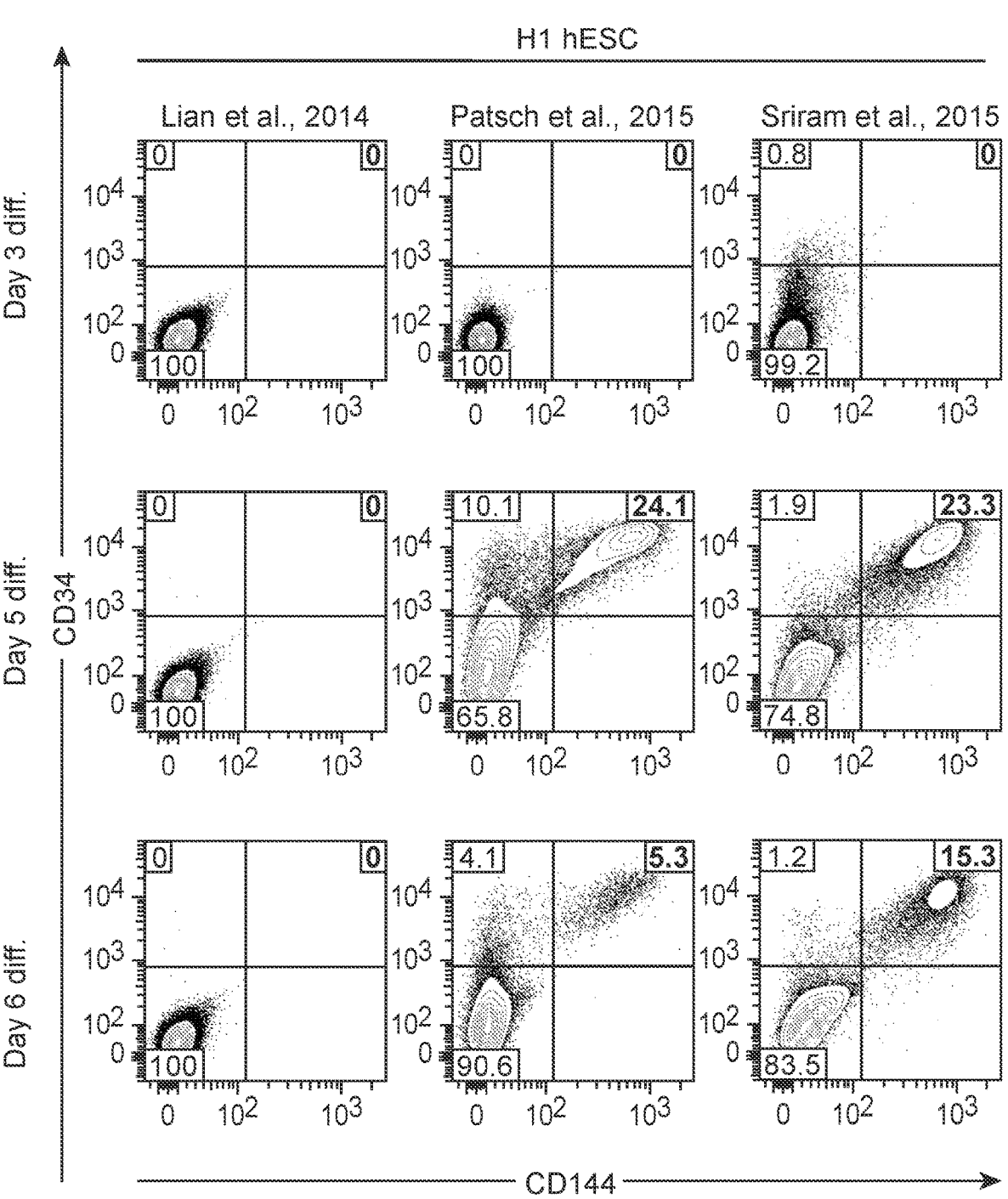
Figure 9:
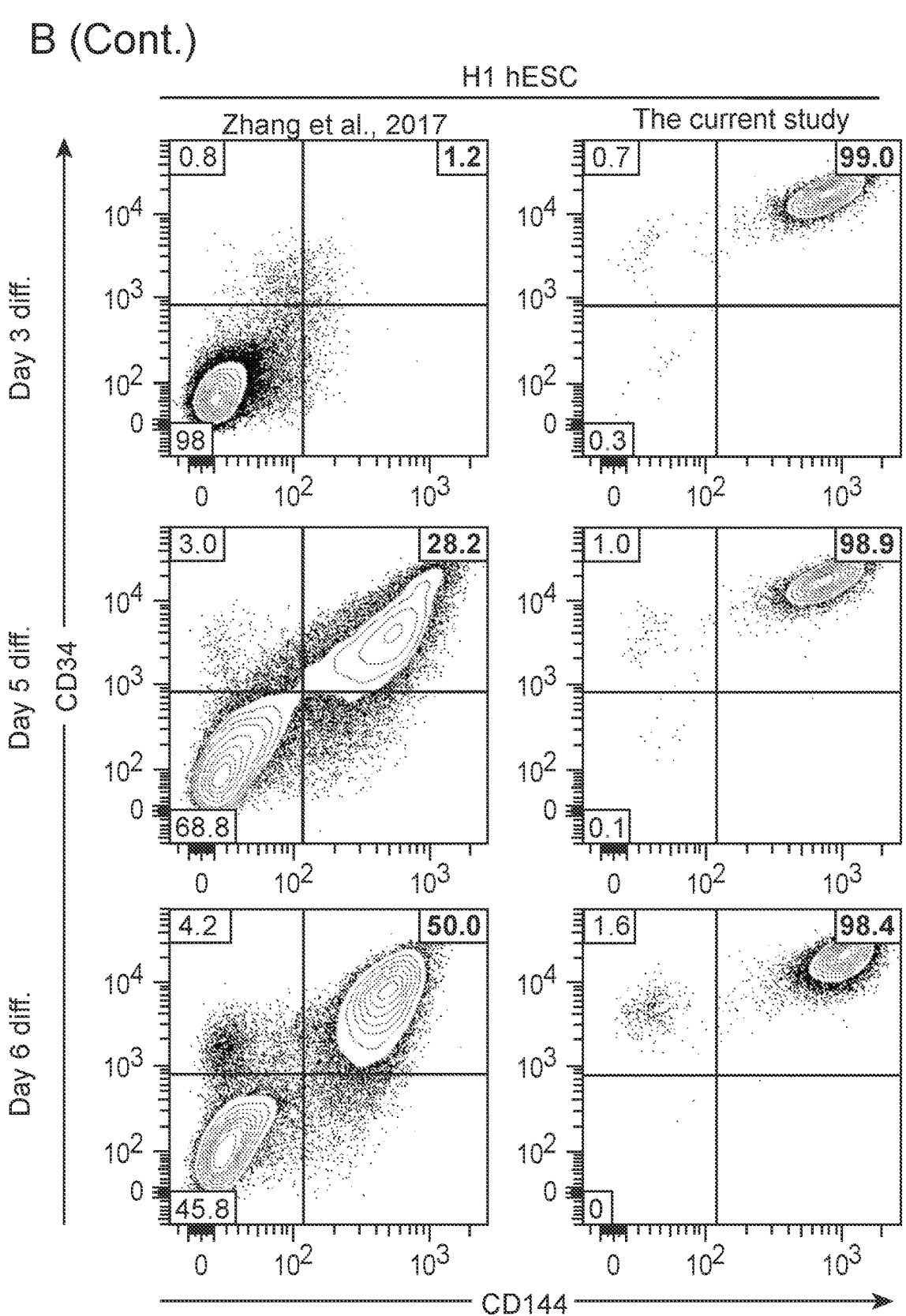
Figure 9:
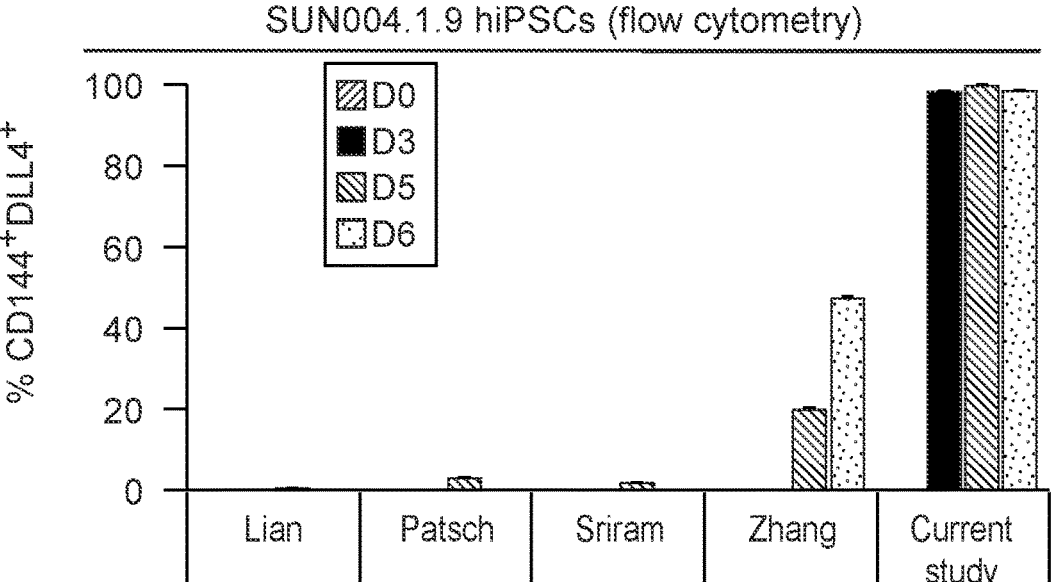
Figure 9:
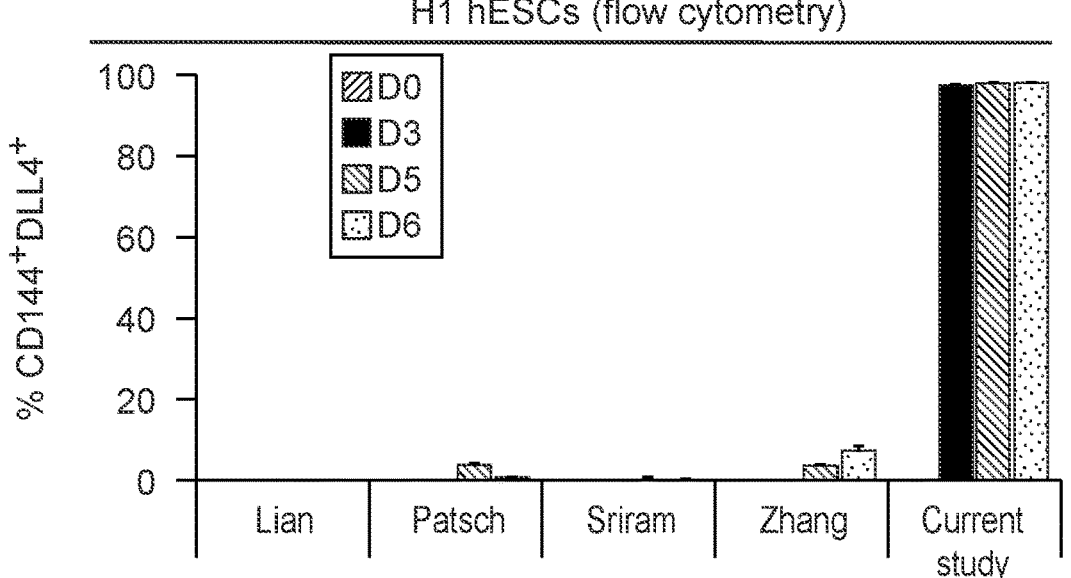

Artery differentiation was highly reproducible and efficient across 4 wild-type hESC and hiPSC lines, generating a >94% pure CD144$^+$ DLL4$^+$ arterial population within 3 days (FIG. 2g, FIG. 9a). Moreover, this differentiation strategy yielded arterial cells with significantly higher homogeneity and rapidity than 4 prevailing methods for endothelial differentiation (Lian et al., 2014; Patsch et al., 2015; Sriram et al. 2015; Zhang et al., 2017) (FIG. 2h, FIG. 9b,c). We conclude that activation of artery-specifying signals, together with repression of vein-specifying signals, establishes arterial fate with high efficiency and rapidity.

Figure 10:
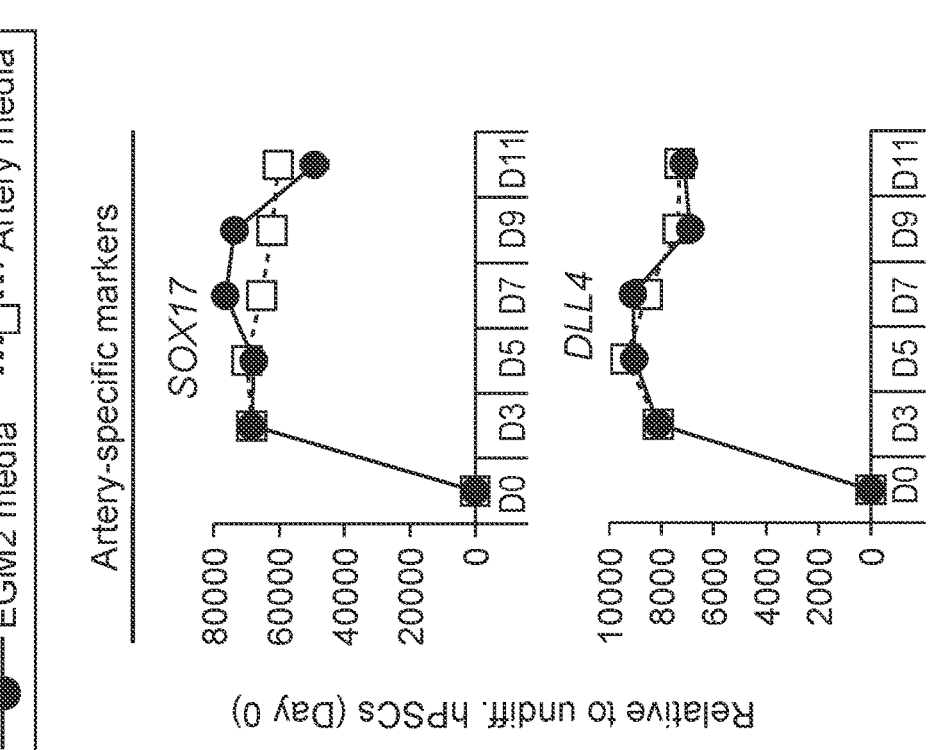
FIG. 10: Functional assessment of, and in vitro expansion of, hPSC-derived artery endothelial cells (related to FIG. 2). A) hPSC-derived artery endothelial cells can be maintained in culture for up to 8 days; day 3 hPSC-derived artery endothelial cells were cultured in artery-specification media (defined) or EGM2 media (undefined) for up to 8 further days (3+8=11 total days of differentiation); qPCR was performed on days 0, 3, 5, 7, 9 and 11. B) hPSC-derived artery endothelial cells can be maintained in culture for up to 8 days; day 3 hPSC-derived artery endothelial cells were cultured in artery-specification media (defined) or EGM2 media (undefined) for up to 8 further days (3+8=11 total days of differentiation); flow cytometry was performed on days 0, 3, 5, 7, 9 and 11. C) hPSC-derived artery cells and human fibroblasts were mixed (1:2 ratio) and cultured in a 3D fibrin gel with EGM2 media as described previously; after 1 week, hPSC-derived artery endothelial cells formed elaborate, branching CD31$^+$ networks in 3D, as assessed by immunostaining. D) hPSC-derived artery cells were dissociated and reaggregated into 3D spheres (containing ~1000 cells/sphere) in AggreWell plates to increase the density of cells, and then cultured with FGF2 and VEGF for 24 hours, after which they robustly formed sprouts in response to these signals. E) hPSC-derived day 3 artery cells were exposed to EGM2 medium for 24 hours either in static conditions or shear stress; the application of shear stress led to the intracellular polarization of these artery endothelial cells, as quantified by the location of the Golgi body (GOLPH4$^+$) relative to the nucleus. F) hPSC-derived artery cells were exposed to EGM2 media for 24 hours either in static culture (negative control) or shear stress; subsequently, the localization of the Golgi body (assessed by GOLPH4 immunostaining) relative to the nucleus was quantified. G) $10^6$ constitutively-GFP-expressing hPSC-derived artery cells were transplanted under the kidney capsule of adult NOD-SCID Il2ng$^{-/-}$ mice in a 2 μL drop of Matrigel; 1 month later, the transplanted cells formed endothelial networks. G) $10^4$ constitutively-GFP-expressing hPSC-derived artery cells were injected in utero into E11.5 rat embryos via in utero transplantation; after two days (i.e., at E13.5), injected rat embryos were collected for confocal imaging.
Figure 10:
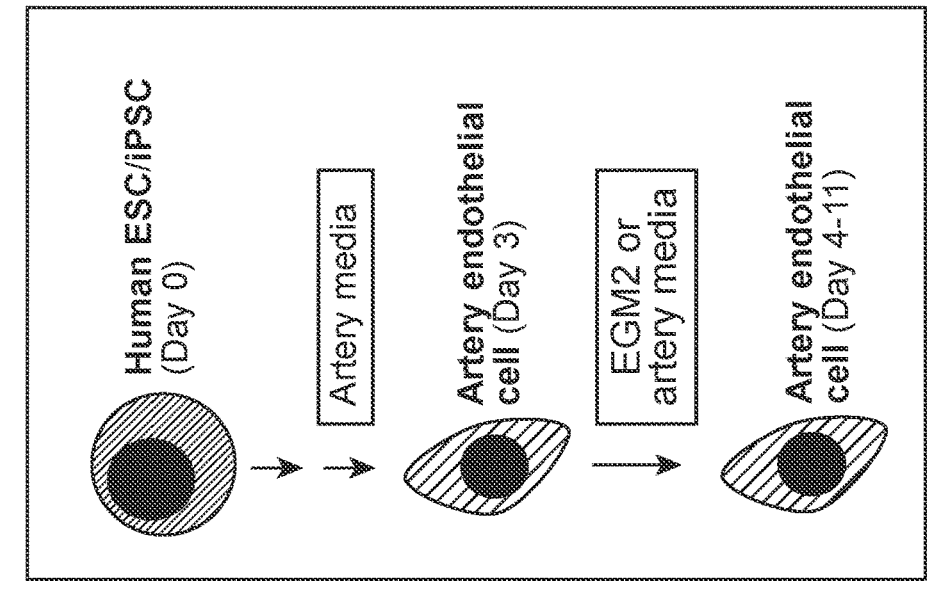
Figure 10:
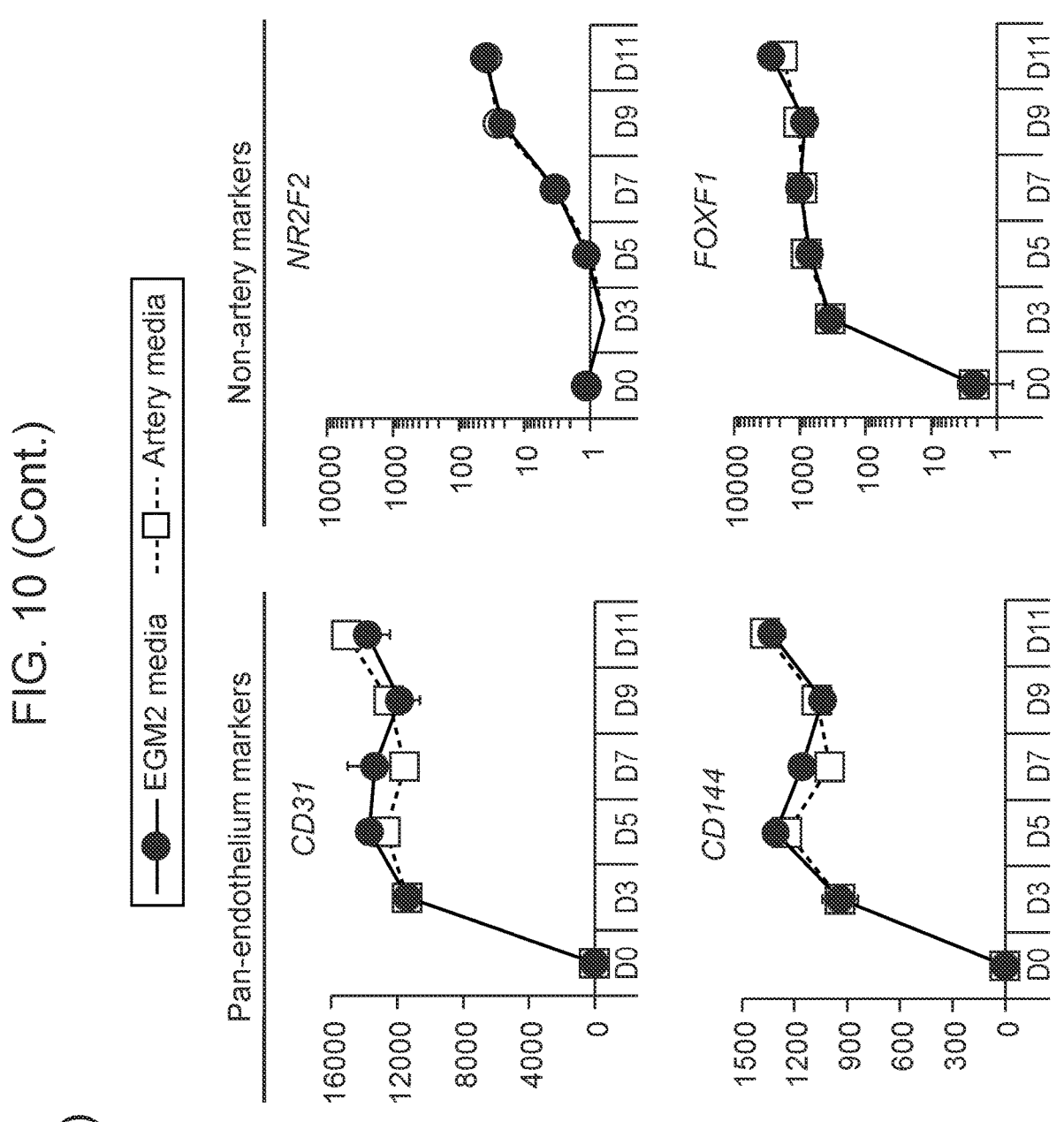
Figure 10:
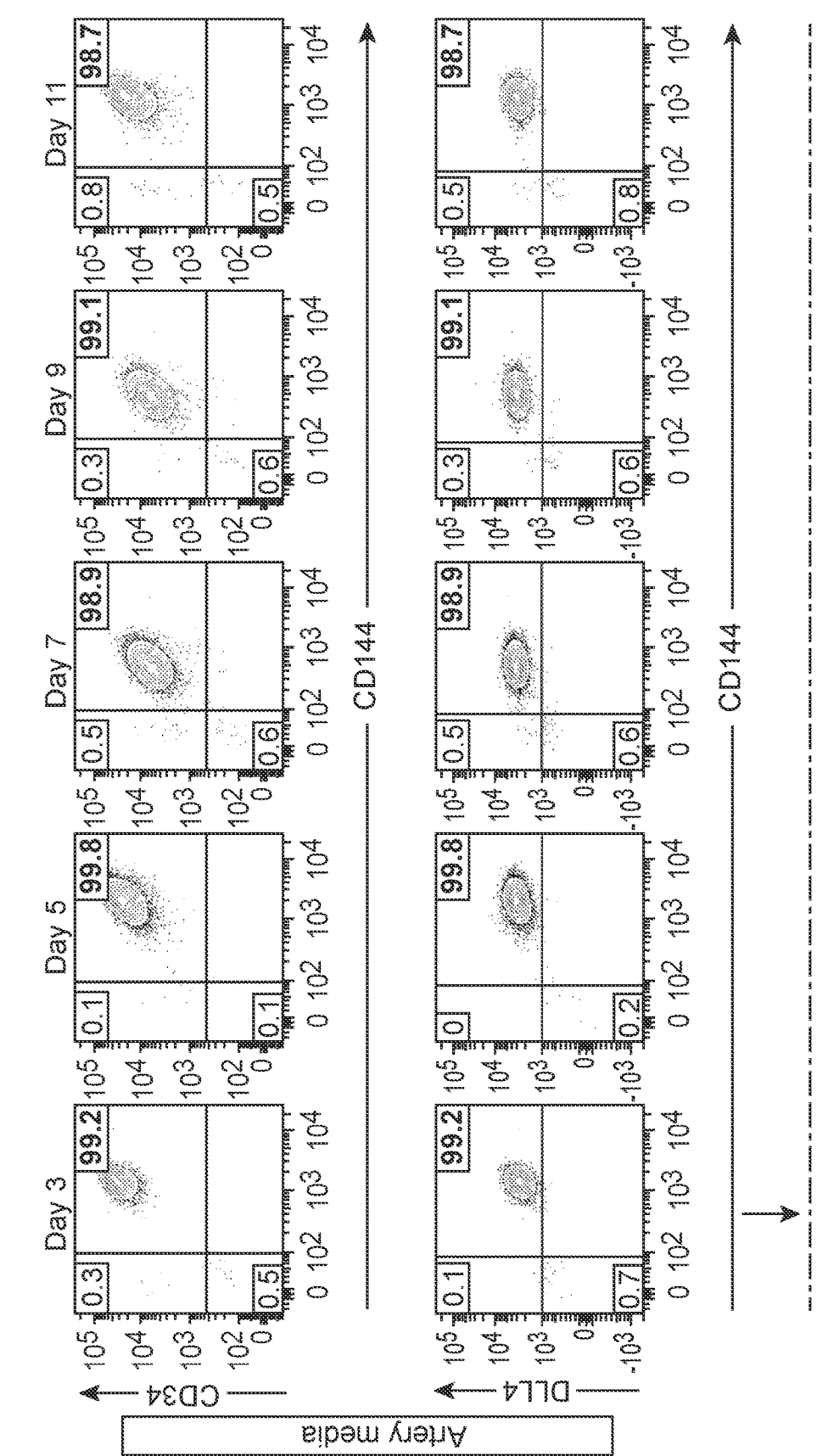
Figure 10:
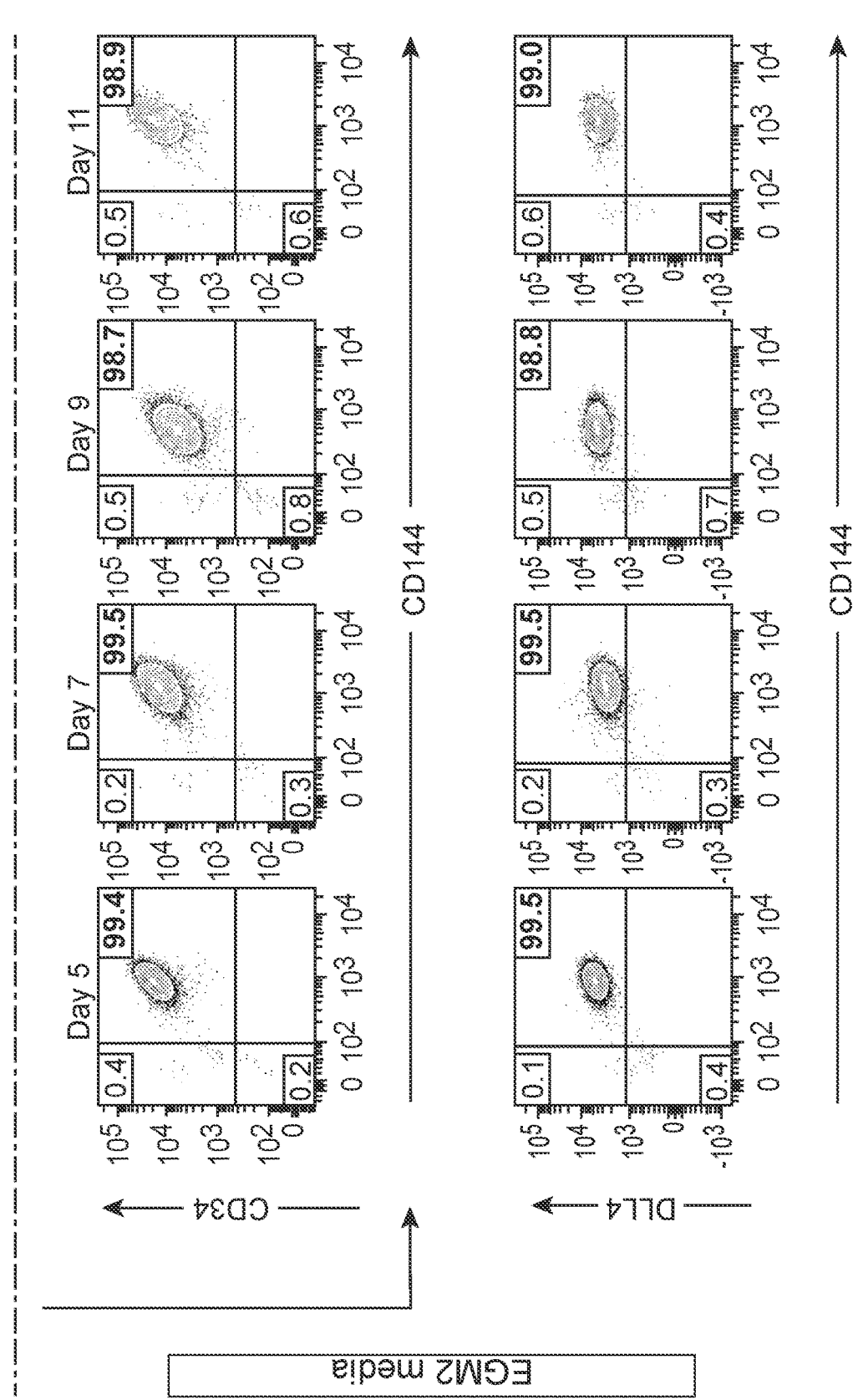
Figure 10:
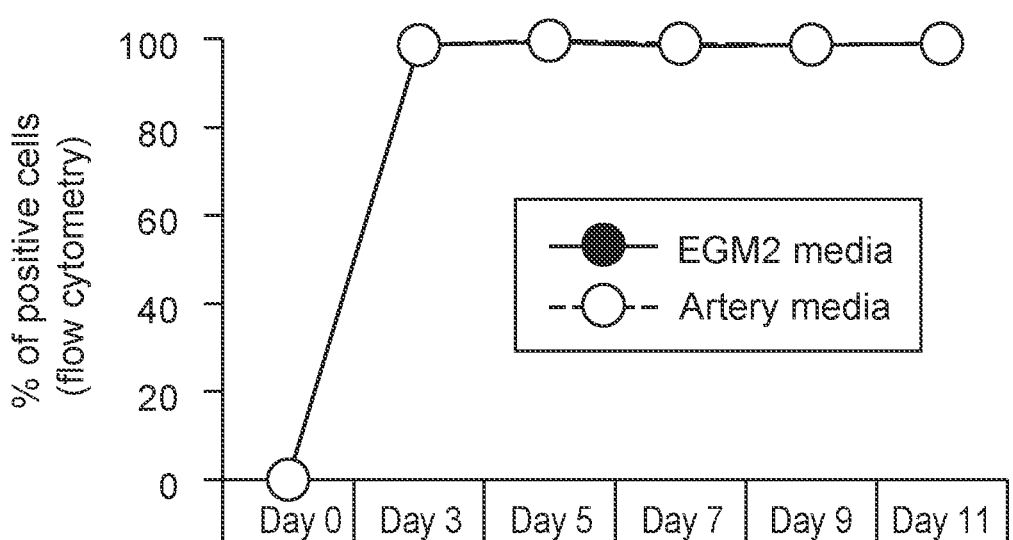
Figure 10:
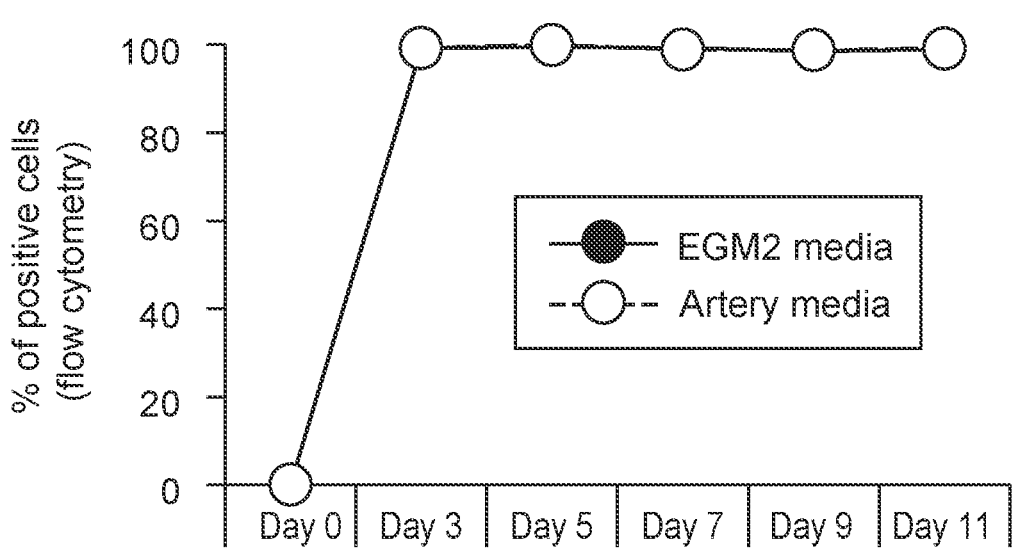
Figure 10:
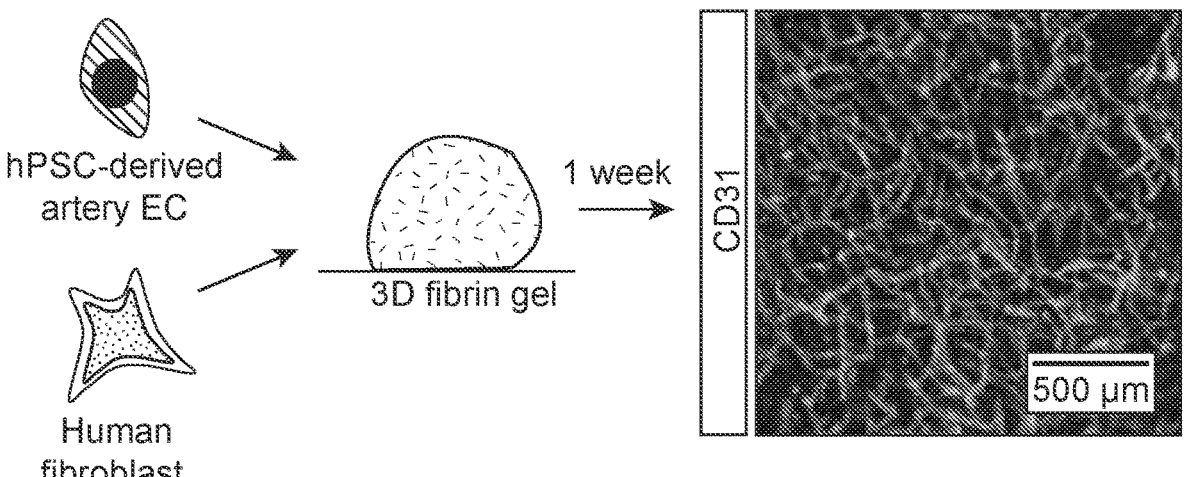
Figure 10:
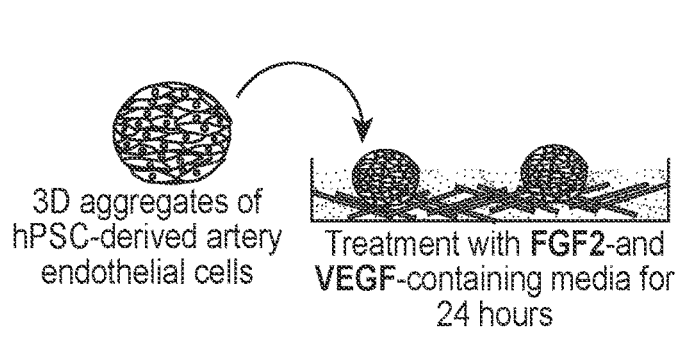
Figure 10:
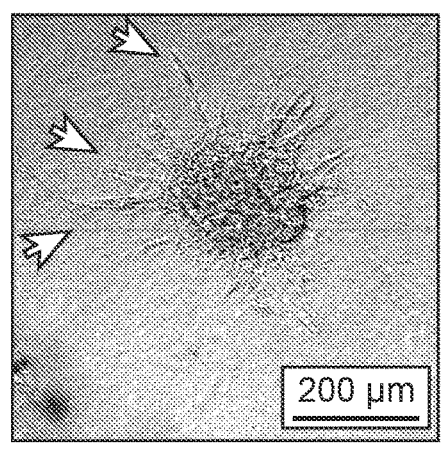
Figure 10:
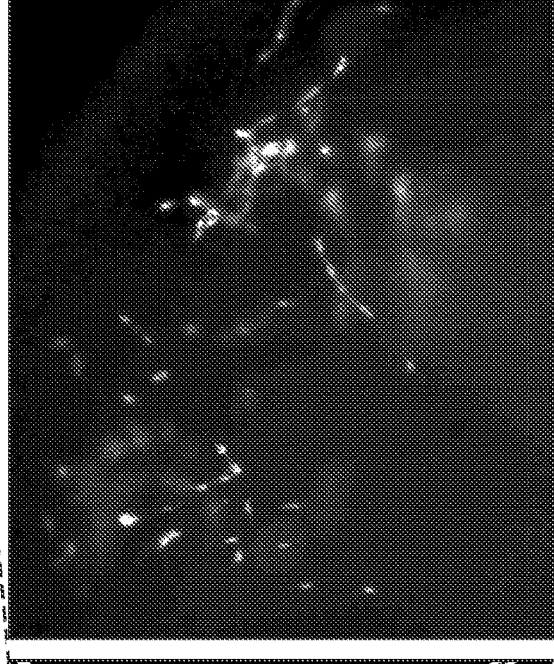
Figure 10:
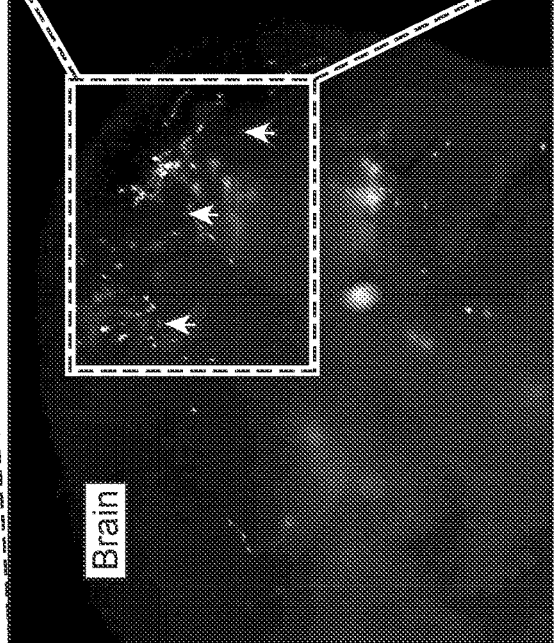

Functionality and in vitro expansion of hPSC-derived artery endothelial cells. After the initial specification of hPSC-derived artery endothelial cells by day 3 of differentiation, we found that they could be maintained and further expanded in culture. Upon continued culture in either the fully-defined, artery-specification media (FIG. 2) or in widely-used but serum-containing endothelium media (Endothelial Cell Growth Medium 2 [EGM2]), we found that hPSC-derived day 3 artery cells maintained the expression of key endothelial and arterial markers for at least 8 additional days (FIG. 10a). At this point, hPSC-derived artery endothelium cultures remained >98% CD34$^+$ CD144$^+$ DLL4$^+$ pure in either the artery-specification or EGM2 media, as assessed by flow cytometry (FIG. 10b).

Next, we found that hPSC-derived artery endothelial cells were functional in 5 independent in vivo and in vitro functional assays. First, to assess their ability to form endothelial networks in vitro, we mixed hPSC-derived artery cells and human fibroblasts (1:2 ratio) and cultured them in a 3D fibrin gel with EGM2 media as described previously (Kurokawa et al., 2017). In 1 week, hPSC-derived artery endothelial cells formed elaborate, branching CD31$^+$ networks in 3D (FIG. 10c). Second, we found that hPSC-derived artery endothelial cells could sprout and migrate in response to chemotactic cues—a key feature of endothelial cells critical for blood-vessel growth (Kiefer and Siekmann, 2011). Specifically, 3D spheres of hPSC-derived artery endothelial cells were treated with the endothelial cytokines FGF2 and VEGF for 24 hours, and we found that they robustly formed sprouts in response to these signals (FIG. 10d). Third, endothelial cells are distinguished by their ability to mechanically sense shear stress (i.e., fluid flow) (Baratchi et al., 2017) and they respond in multiple ways, including orienting their Golgi body relative to the axis of flow (Poduri et al., 2017). To assess the mechanoresponsiveness of our hPSC-derived day 3 artery endothelial cells, we exposed them to shear stress for 24 hours in EGM2 media, and found that this led to the spatial polarization of the Golgi body relative to the nucleus in these cells (FIG. 10e). Cells cultured in static conditions without shear stress showed a random localization of their Golgi body relative to the nucleus (FIG. 10e). Fourth, we showed that our hPSC-derived artery endothelial cells formed networks in vivo upon subcutaneous transplantation. 1 month post-transplantation into adult immunodeficient NOD-SCID Il2rg$^{/-}$ mice, artery endothelial cells derived from constitutively-GFP-expressing hPSCs formed endothelial networks (FIG. 10f). Fifth, we transplanted our hPSC-derived artery endothelial cells into rodent embryos in utero and found that they could similarly form endothelial networks within 2 days (FIG. 10g). Taken together, hPSC-derived artery endothelial cells are functional.

Efficient differentiation of hPSC-derived dorsal lateral mesoderm into pre-veins and subsequently, veins: a two-step model for vein specification. Having defined artery-specifying signals, next we asked what signal(s) confer vein identity (FIG. 3a). Starting from day 2 hPSC-derived dorsal lateral mesoderm, we found that dual inhibition of the artery-specifying signals TGFβ and NOTCH repressed arterial fate, leading to the upregulation of the venous marker NR2F2 (FIG. 3b). This is altogether consistent with how genetic abrogation of NOTCH signaling converts artery cells into vein cells in vivo (Duarte et al., 2004; Gale et al., 2004; Krebs et al., 2004; Lawson et al., 2001).

Strikingly, we found that VEGF/ERK signaling had a temporally-dynamic role in vein specification, thus defining two discrete steps in vein development which we refer to "pre-vein" followed by "vein" specification on days 3 and 4 of hPSC specification, respectively (FIG. 3c). VEGF has been ascribed contradictory roles in vein development in vivo: while disrupting VEGF signaling in Vegfr2$^{-/-}$ (Flk1$^{-/-}$) mice leads to complete loss of endothelium, including vein cells (Shalaby et al., 1995), inhibition of VEGF has been reported to paradoxically increase vein specification (Lawson et al., 2002). How can the same signal exert different effects? We reconciled these divergent observations by showing that VEGF promotes or inhibits vein formation depending on what exact time it is activated. Specifically, we found that VEGF/ERK signaling for 24 hours was paramount for day 2 dorsal lateral mesoderm to acquire endothelial identity ("pre-vein" fate) by day 3; at this stage, ERK inhibition strongly inhibited expression of endothelial genes (FIG. 3d). Yet, after pre-vein cells had committed to an endothelial identity by day 3, the subsequent inhibition of ERK on day 4 did not impair endothelial identity but rather induced the venous marker NR2F2 (FIG. 3d). Hence, VEGF/ERK must be initially activated to induce pre-vein endothelial cells, but subsequent ERK inhibition induces vein identity. The importance of temporally-dynamic VEGF/ERK modulation is illustrated by how activation of VEGF for 48 hours did not yield vein endothelial cells; moreover, inhibition of VEGF for 48 hours also failed to generate endothelial cells altogether (FIG. 3d).

Figure 8:
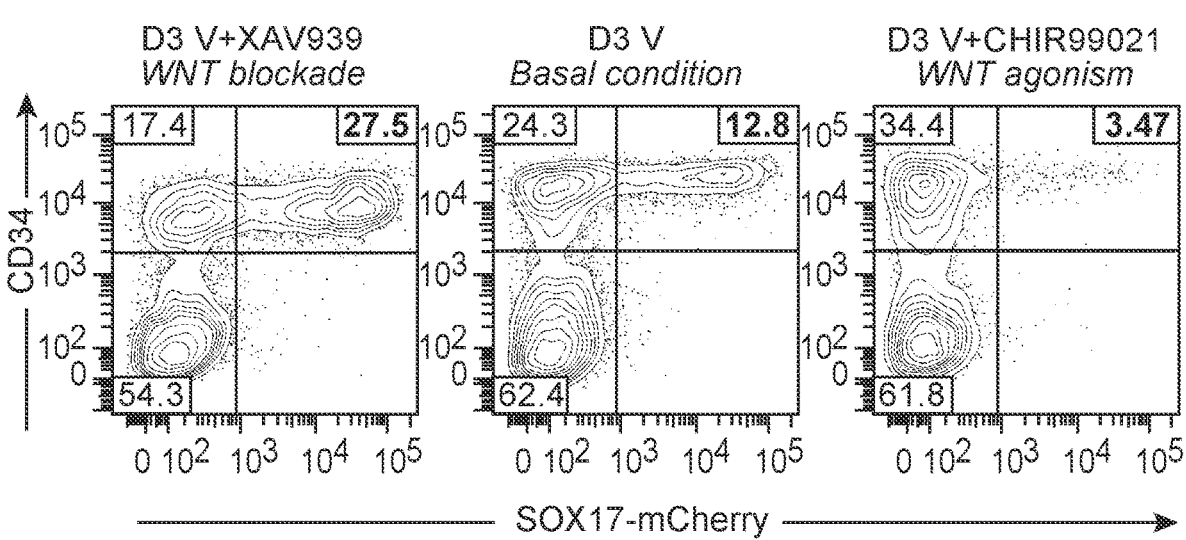
FIG. 8: Optimization of human artery endothelial progenitor generation from hPSCs (related to FIG. 2). A) BMP represses day 3 artery formation; day 2 hPSC-derived dorsal lateral mesoderm was treated with Activin+GDC0941+ VEGF+XAV939+Vitamin C for 24 hours, in the presence or absence of BMP4 (5-40 ng/mL) or BMP inhibitor (DMH1); qPCR was performed on day 3 cell populations. B) WNT inhibits day 3 artery formation; day 2 hPSC-derived dorsal lateral mesoderm was further differentiated with VEGF for 24 hours, in the presence or absence of WNT agonist (CHIR99021) or WNT inhibitor (XAV939); flow cytometry (left) and qPCR (right) was performed on day 3 cell populations. C) TGFβ inhibits day 3 artery formation; day 2 hPSC-derived dorsal lateral mesoderm was further differentiated for 24 hours with VEGF+WNT inhibitor (XAV939), in the presence or absence of TGFβ agonist (Activin, 10 ng/mL) or TGFβ inhibitor (SB-505124, 2 μM); flow cytometry was performed on day 3 cell populations. D) Definition of the complete set of extracellular signals necessary for efficient artery differentiation; day 2 hPSC-derived dorsal lateral mesoderm was further differentiated for 24 hours into artery cells using the complete artery specification media (red; Activin+GDC0941+VEGF+XAV939+AA2P+DMH1) or in conditions in which each factor was individually withheld; flow cytometry was performed on day 3 cell populations. E) qPCR timecourse of hPSCs differentiated towards arteries reveals sequential expression of pluripotency, primitive streak, dorsal lateral mesoderm and finally, pan-endothelial and artery-specific markers; qPCR was performed on day 0 (undifferentiated) and differentiated day 1, 1.5, 2, 2.5 and 3 cell populations, with qPCR data shown normalized to the timepoint with highest expression of each given marker gene.
Figure 8:
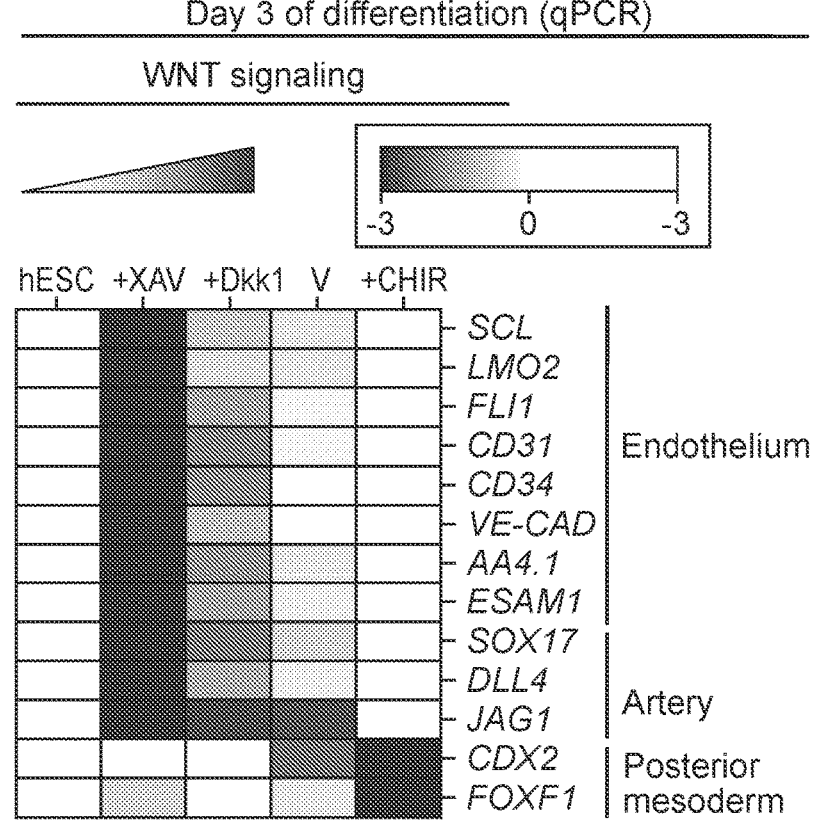
Figure 8:
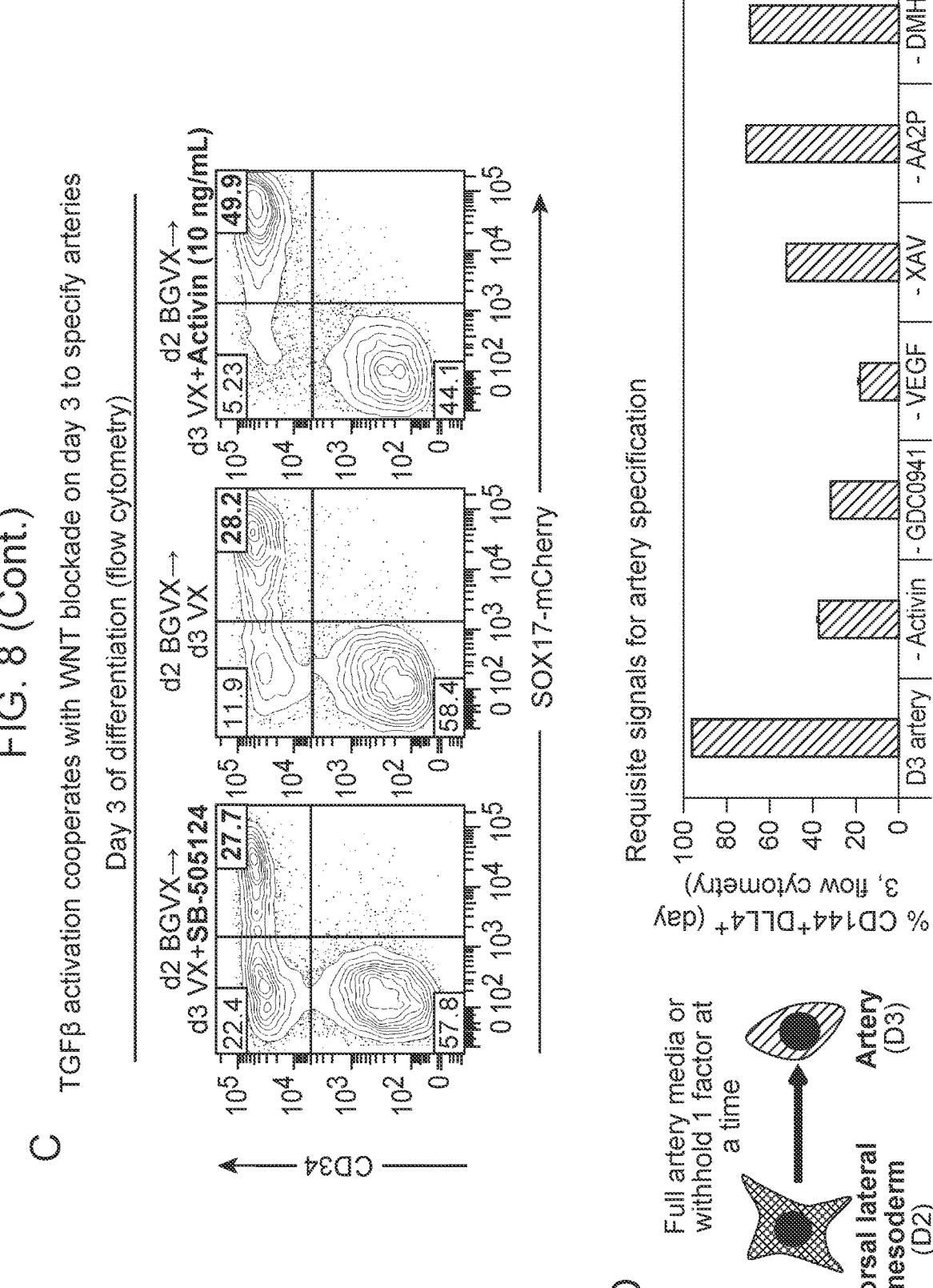
Figure 8:
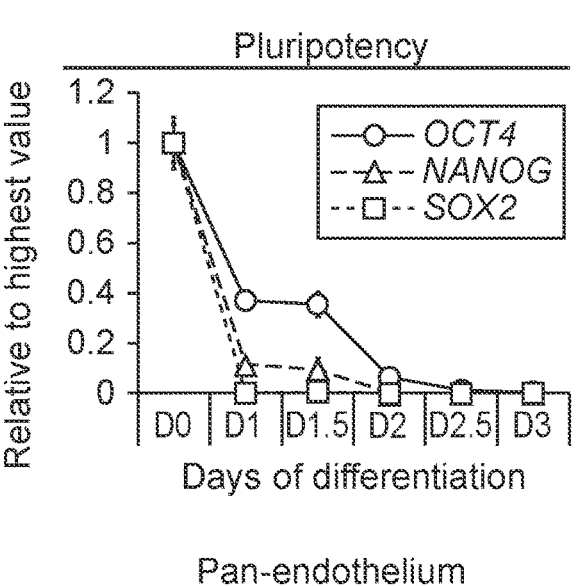
Figure 8:
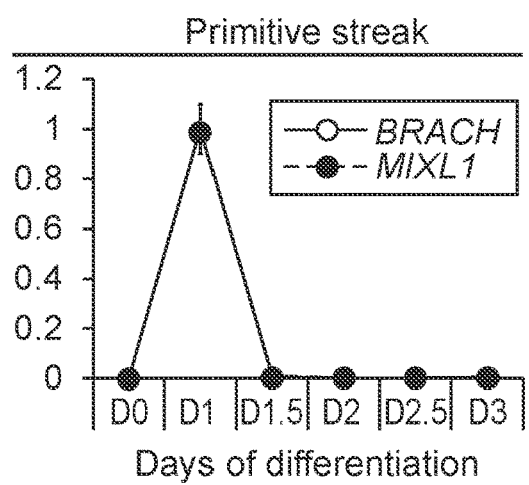
Figure 8:
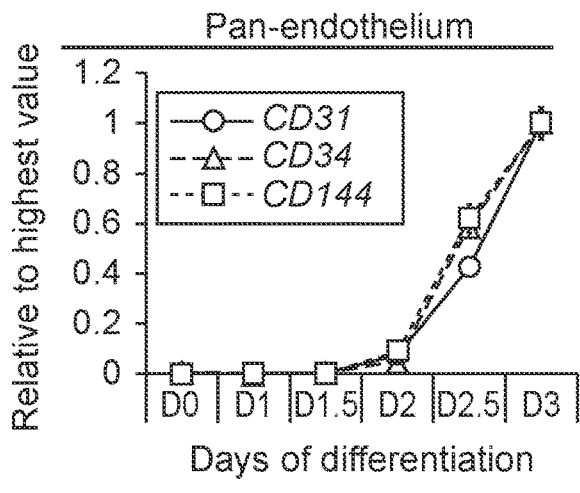
Figure 8:
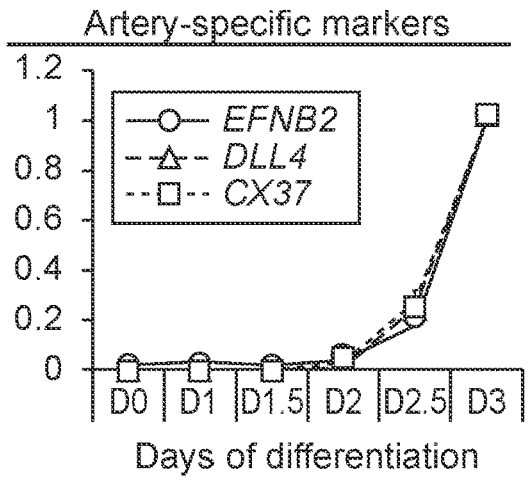
Figure 8:
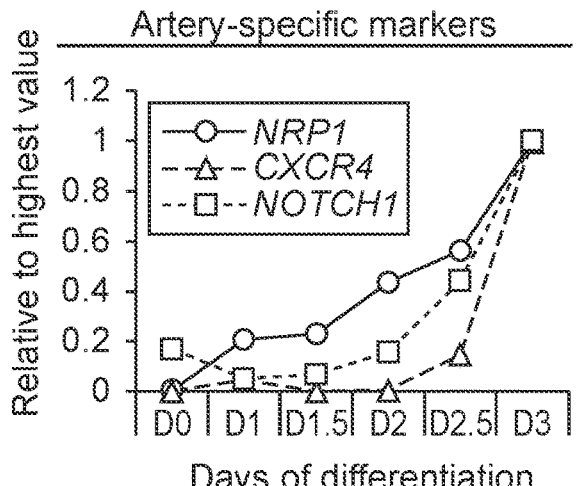
Figure 8:
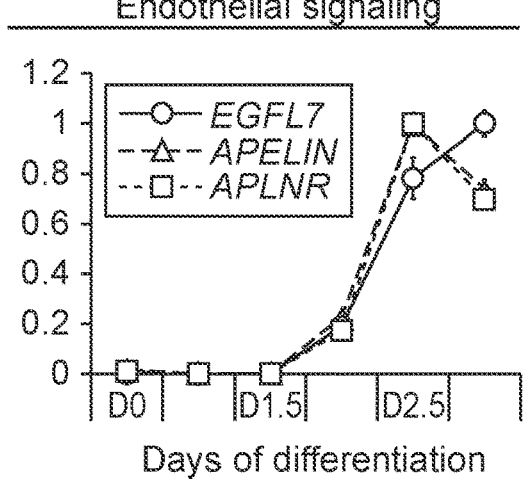
Figure 8:
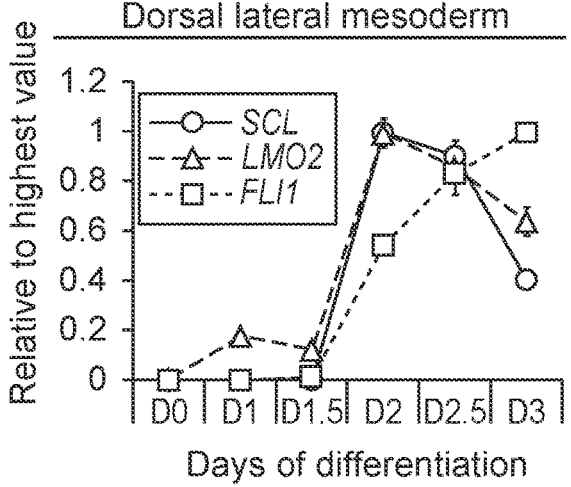
Figure 8:
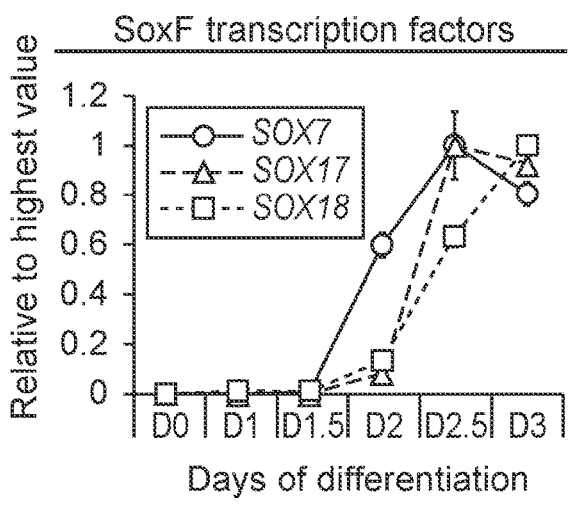
Figure 8:
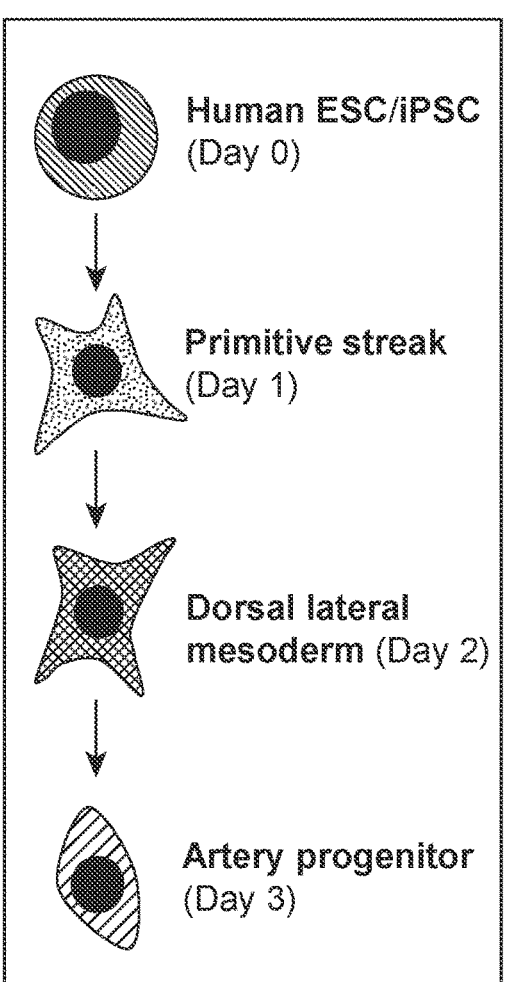
Figure 8:
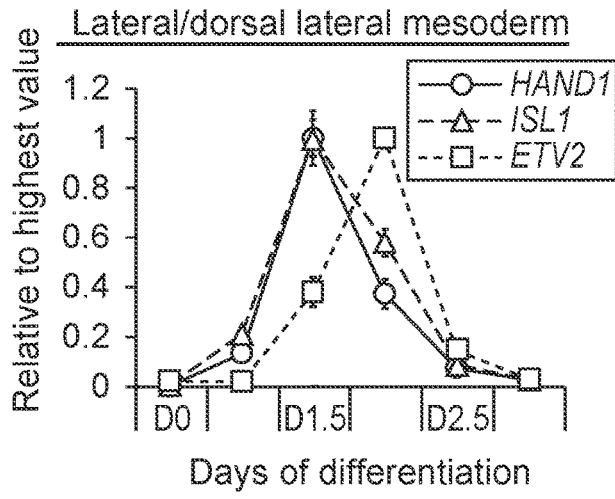
Figure 8:
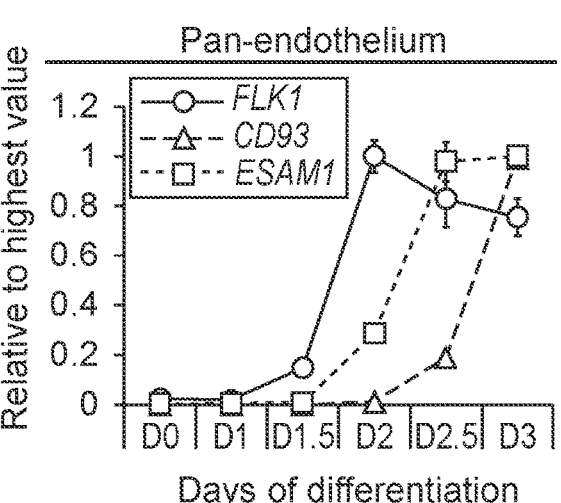
Figure 11:
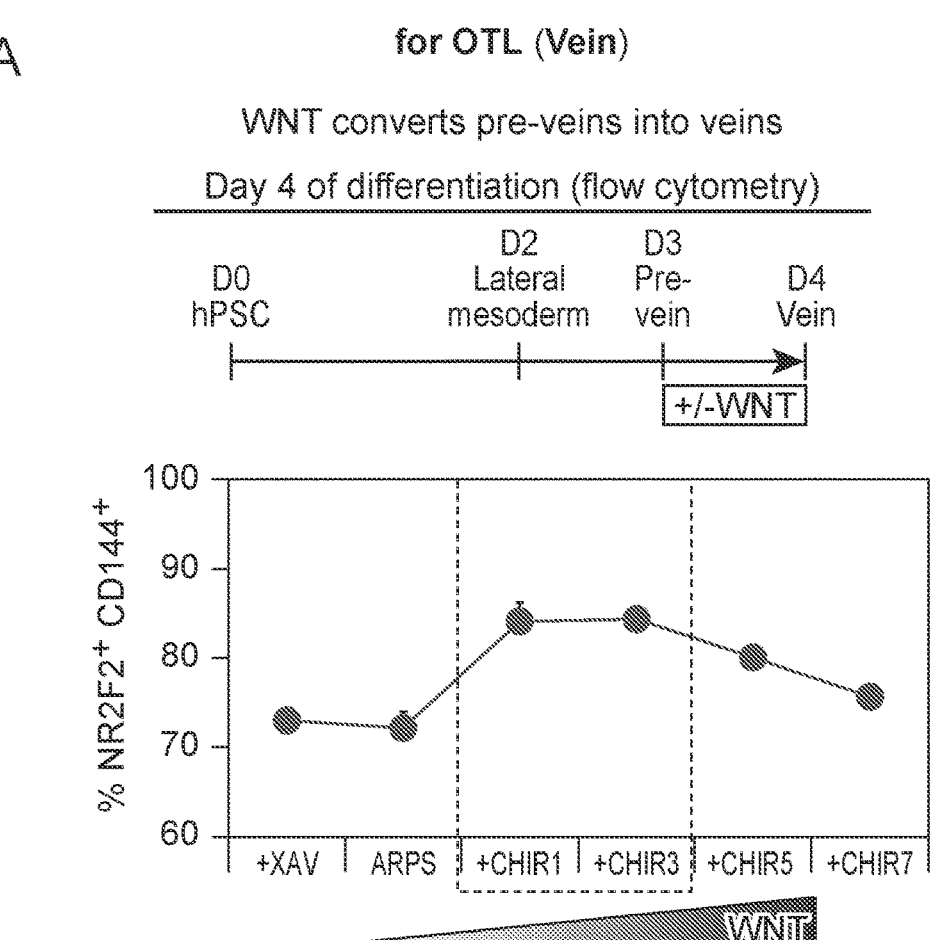
FIG. 11: Optimization of human vein endothelial progenitor generation from hPSCs (related to FIG. 3). A) WNT activation promotes conversion of day 3 pre-vein cells into day 4 vein cells; day 3 hPSC-derived pre-vein population was further differentiated into vein cells (SB505124+ RO4929097+PD0325901+AA2P), in the presence or absence of the WNT agonist for 24 hours; flow cytometry was performed on day 4 vein populations to quantify the purity of NR2F2-GFP$^+$ CD144$^+$ vein cells. B) Strategy to generate a NR2F2-2A-GFP knock-in reporter allele using Cas9/AAV6 genome editing. C) PCR genotyping of individual hESC lines (derived from single colonies) targeted using Cas9/AAV6 genome editing reveals successful integration of the NR2F2-2A-GFP knock-in reporter allele. D) qPCR comparison of undifferentiated hPSCs, day 3 hPSC-derived artery cells and day 4 hPSC-derived vein cells; data are normalized such that for each marker gene, the sample with highest expression is normalized=1.0.
Figure 11:
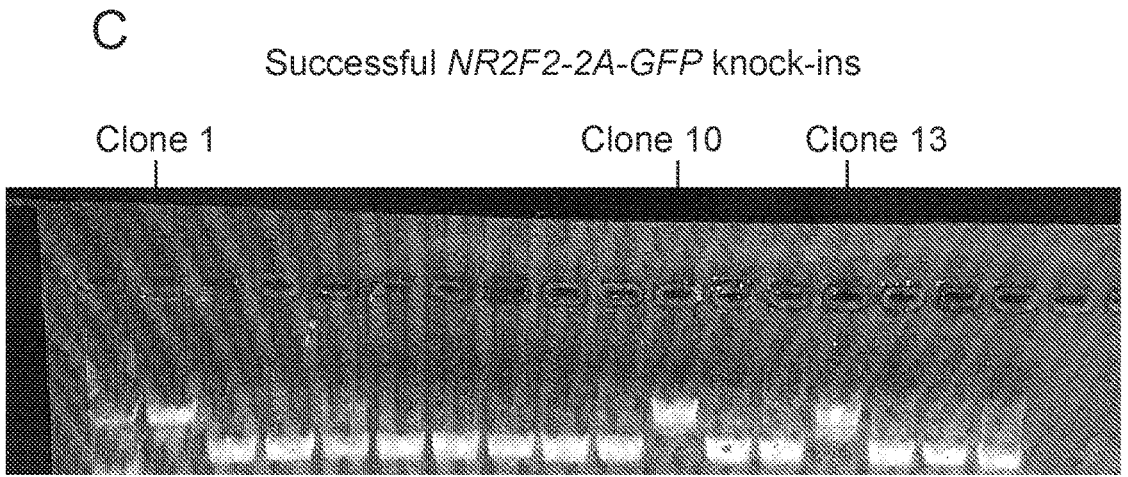
Figure 11:
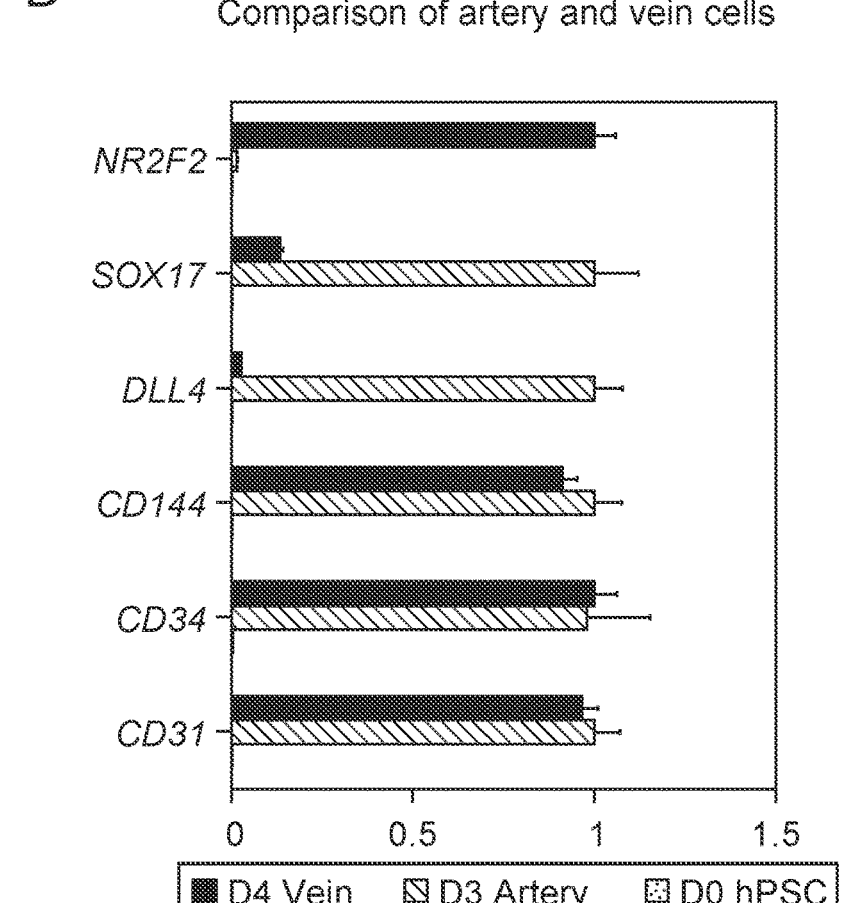

Finally, in addition to manipulation of the aforementioned signals (TGFβ, NOTCH and VEGF/ERK), we found that WNT activation cooperated with ERK inhibition to differentiate day 3 pre-vein cells into day 4 vein cells (FIG. 11a). While the role of WNT signaling in vein development in vivo remains controversial, our data are consistent with the finding that vein endothelial cells in the mouse embryo are actively transducing WNT signals (reviewed by Fish and Wythe, 2015). The efficiency of vein endothelial cells could be further improved by dissociating and re-plating differentiating cells at an intermediate stage of differentiation (FIG. 8).

In order to track and quantify the in vitro specification of vein endothelial cells, we engineered a new fluorescent reporter hPSC line in which we could track the expression of NR2F2, which is the archetypical marker of vein identity in both mouse (Pereira et al., 1999; You et al., 2005) and human (Aranguren et al., 2013). To this end, we exploited Cas9/AAV6 genome editing (Martin et al., 2019) to create a homozygous NR2F2-2A-GFP reporter hPSC line wherein GFP was inserted into the endogenous NR2F2 locus with care to preserve the endogenous NR2F2 coding sequence (FIG. 11b,c), as NR2F2 itself is critical for vein specification (Pereira et al., 1999; You et al., 2005). Using this NR2F2-2A-GFP reporter hPSC line, we found that our vein differentiation protocol generated >80% pure CD144$^+$ NR2F2$^+$ vein cells within 4 days of in vitro differentiation (FIG. 3e). The same differentiation protocol also efficiently differentiated wild-type hESCs into CD144$^+$ NR2F2$^+$ vein endothelial cells, as shown by immunostaining (FIG. 3f). hPSC-derived vein endothelial cells did not express artery markers, and vice versa (FIG. 11d).

Taken together, we propose a 2-step model for vein specification where pre-vein and endothelial identity is first induced by VEGF/ERK, followed by gain of vein identity after ERK inhibition. Therefore while endothelial identity and arterial identity can be simultaneously gained (FIG. 2), it seems that gain of endothelial identity may precede acquisition of vein identity. Hence, in vitro, arteries can be generated earlier (3 days) than veins (5 days) from hPSCs, which may mirror how arterial markers (E8-E8.25) precede venous markers (E8.5) in mouse embryos (Chong et al., 2011). In conclusion, we can rapidly and efficiently generate enriched populations of either human artery-specific endothelial cells (FIG. 2) or vein-specific endothelial cells (FIG. 3) in vitro within 3 or 4 days of hPSC differentiation, respectively.

Cell-surface marker signatures for human artery and vein commitment. Next we sought to identify distinctive cell-surface markers that identify hPSC-derived artery and vein endothelial cells, with the two-fold goals of 1) tracking their developmental bifurcation and 2) to enable their purification for various practical applications. We systematically assessed the expression of 332 unique cell-surface markers on undifferentiated hPSCs (day 0), mid primitive streak (day 1), dorsal lateral mesoderm (day 2), artery endothelial cells (day 3) and vein endothelial cells (day 4) using robotically-enabled, high-throughput flow cytometry (Loh et al., 2016). As expected, pluripotency surface markers SSEA-3 and TRA-1-81 were progressively downregulated during differentiation, and were virtually absent in hPSC-derived artery or vein endothelial cells (FIG. 3g).

A core set of pan-endothelial surface markers were ubiquitously expressed on both hPSC-derived artery and vein endothelial cells, including the widely-accepted endothelial markers CD31 (PECAM1) and CD93 (AA4.1) in addition to underexplored markers such as CD141 and CCR10 (FIG. 3g). CD141—otherwise known as thrombomodulin—is a principal component of the body's anti-clotting pathway; it is expressed on the surface of endothelial cells, where it is the transmembrane receptor for thrombin and switches thrombin from a coagulating factor to an anti-coagulant (Loghmani and Conway, 2018). Another pan-endothelial marker we identified was CCR10, which is the transmembrane receptor for CCL27 and CCL28 and has been reported to mediate the attraction of CCR10$^+$ endothelial cells towards CCL27/CCL28-expressing tumors (Kamezis et al., 2019).

DLL4 (a NOTCH ligand) and NOTCH1 (a NOTCH receptor) were among the most specific surface markers of hPSC-derived artery cells identified by our analysis (FIG. 3g). Indeed D114 and Notch1 are expressed in early artery endothelial cells in the E8.25 mouse embryo (Chong et al., 2011), and both of these genes are crucial for artery specification (Fish and Wythe, 2015).

Conversely, CD73 was the most specific marker of hPSC-derived vein cells (FIG. 3g). CD73—otherwise known as 5' nucleotidase—is a transmembrane enzyme that helps convert extracellular ATP (a danger signal) into adenosine (an anti-inflammatory signal), which in turn restrains T cells and NK cells (Vigano et al., 2019). Consequently CD73 contributes to the immunosuppressive environment of tumors, and CD73 blockade has emerged as a cancer immunotherapy (Vigano et al., 2019).

Taken together, DLL4 and CD73 are mutually-exclusive surface markers that can be used to respectively purify hPSC-derived artery vs. vein endothelial cells. These surface markers reaffirm the efficiency and specificity of our differentiation protocols, which respectively generate >90% pure DLL4$^+$ CD73$^{lo/-}$ artery cells or >80% pure DLL4$^-$ CD73$^{hi}$ vein cells within 3-4 days of hPSC differentiation (FIG. 3h). Notably, our artery differentiation system does not yield contaminating vein cells and vice versa (FIG. 3h). While CD73 expression has been previously reported to be enriched in hPSC-derived vein cells by comparison to artery cells, past differentiation efforts always generated a heterogeneous population comprising only a subpopulation of vein cells (Ditadi et al., 2015).

Efficient differentiation of hPSC-derived "trunk artery" cells expressing HOXA1-HOXA5. Having efficiently generated artery-specific endothelial cells from hPSCs (FIG. 2), we investigated whether these hPSC-derived artery endothelial cells could be used to subsequently generate blood progenitors. While endothelial and blood cells are generally acknowledged to have a close developmental relationship (Clements and Traver, 2013; Ditadi et al., 2017; Dzierzak and Speck, 2008; Ivanovs et al., 2017; Medvinsky et al., 2011), it remains controversial whether endothelial cells generate blood progenitors, and if so, which specific subset of endothelial cells give rise to blood.

By way of background, mesoderm can generate both primitive blood (largely comprising myeloid and erythroid cells) and definitive blood (including HSCs). It is therefore paramount to identify the discover the identity of, and markers of, definitive blood intermediates in order to selectively generate such cells in vitro from hPSCs. We and others have proposed that arteries are the intermediate precursor to definitive blood (FIG. 4a). The arterial origin of HSCs is supported by how deletion of key artery-specifying genes Sox17 and Notch1 does not effect primitive blood but leads to a complete loss of engraftable HSCs (i.e., definitive blood) in vivo (Clarke et al., 2013; Corada et al., 2013; Kim et al., 2007; Kumano et al., 2003). Moreover, these same genetic perturbations generally convert arteries into veins (Clarke et al., 2013; Corada et al., 2013; Kim et al., 2007; Kumano et al. 2003). Conversely, genetic loss of Nr2f2 (otherwise known as COUP-TFII) converts veins into arteries, and hematopoietic-like clusters appear at the supernumerary arteries (You et al., 2005). This suggests, but does not prove, that Sox17$^+$ arteries give rise to HSCs in vivo.

Figure 12:
FIG. 12: Optimizing the generation of trunk artery, hemogenic endothelium and HSC-like cells from hPSCs. A) Retinoic acid (RA) signaling induces HOXA1-5 genes in hPSC-derived trunk artery cells; day 1 hPSC-derived primitive streak cells were differentiated into trunk artery cells over the course of 48 hours, in the presence or absence of RA agonists (ATRA, AM580 or TTNPB) on day 2 alone (for 24 hours), day 3 alone (for 24 hours) or day 2-3 interval (for 48 hours) B) hPSC-derived trunk artery cells can be generated in defined conditions on a defined extracellular matrix (ECM); hPSCs were plated on Geltrex (an undefined ECM matrix); bulk laminin; or recombinant vitronectin or laminin-511. C) hPSCs were differentiated into day-3 artery cells (without RA agonist) or day-3 trunk artery cells (with RA agonist); and then were further differentiated over the course of 6 further days into day-9 HSC-like cells. D) The effectiveness of NOTCH agonist Super-DLL4 (E12) was tested by i) coating plates with Super-DLL4, in the presence or absence of Geltrex or Vitronectin (VTN-N), and then culturing IMCD3 reporter cells carrying a NOTCH-driven luciferase reporter or ii) coating plates with vitronectin (in the presence or absence of Super-DLL4), and then plating hPSC-derived day-3 trunk artery cells; qPCR was then performed every 24 hours, showing that Super-DLL4 upregulated the NOTCH target gene HEY1 E) hPSC-derived day-3 trunk artery cells were dissociated and plated on Vitronectin+Super-DLL4, and then further differentiated into HSC-like cells; i) qPCR was performed every 24 hours and ii) flow cytometry was performed on day 9 F) hPSC-derived day-3 trunk artery cells were dissociated and re-plated at different densities, and then further differentiated into hemogenic endothelium/HSC-like cells (day 7) for 4 further days, which was readout by 1) qPCR or ii) flow cytometry, which indicated that a high cell density (e.g., $1.25 \times 10^6$ cells/cm$^2$ or greater) was critical for efficient differentiation; iii) effect of KnockOut Serum Replacement in the culture medium (i.e., CDM3 basal medium) from days 4-7 of differentiation, compared to no KnockOut Serum Replacement (i.e., CDM2 basal medium), as readout by qPCR on day 7, which indicated that KnockOut Serum Replacement improved differentiation efficiency. G) qPCR of hPSC differentiation into trunk arteries (day 3) and their conversion into hemogenic endothelium (day 6); qPCR data are normalized such that for each gene, expression levels in undifferentiated hPSCs=1.0.
Figure 12:
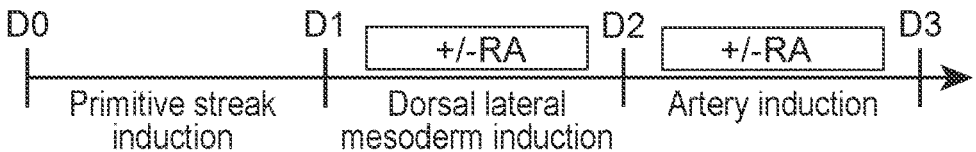
Figure 12:
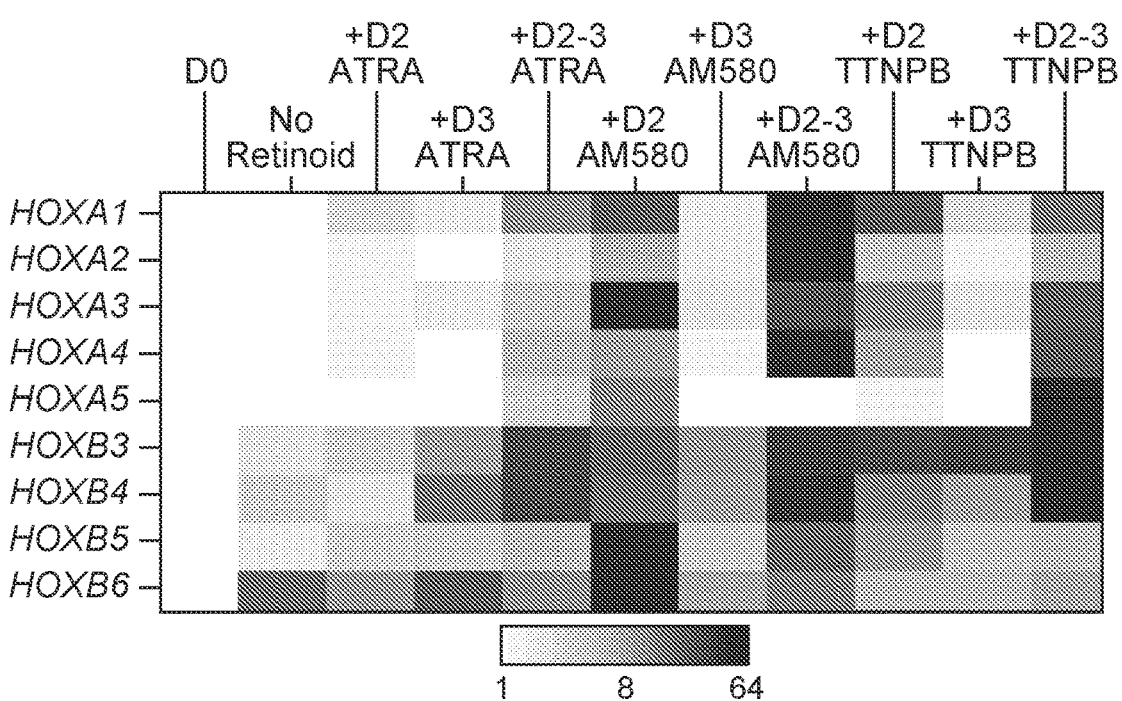
Figure 12:
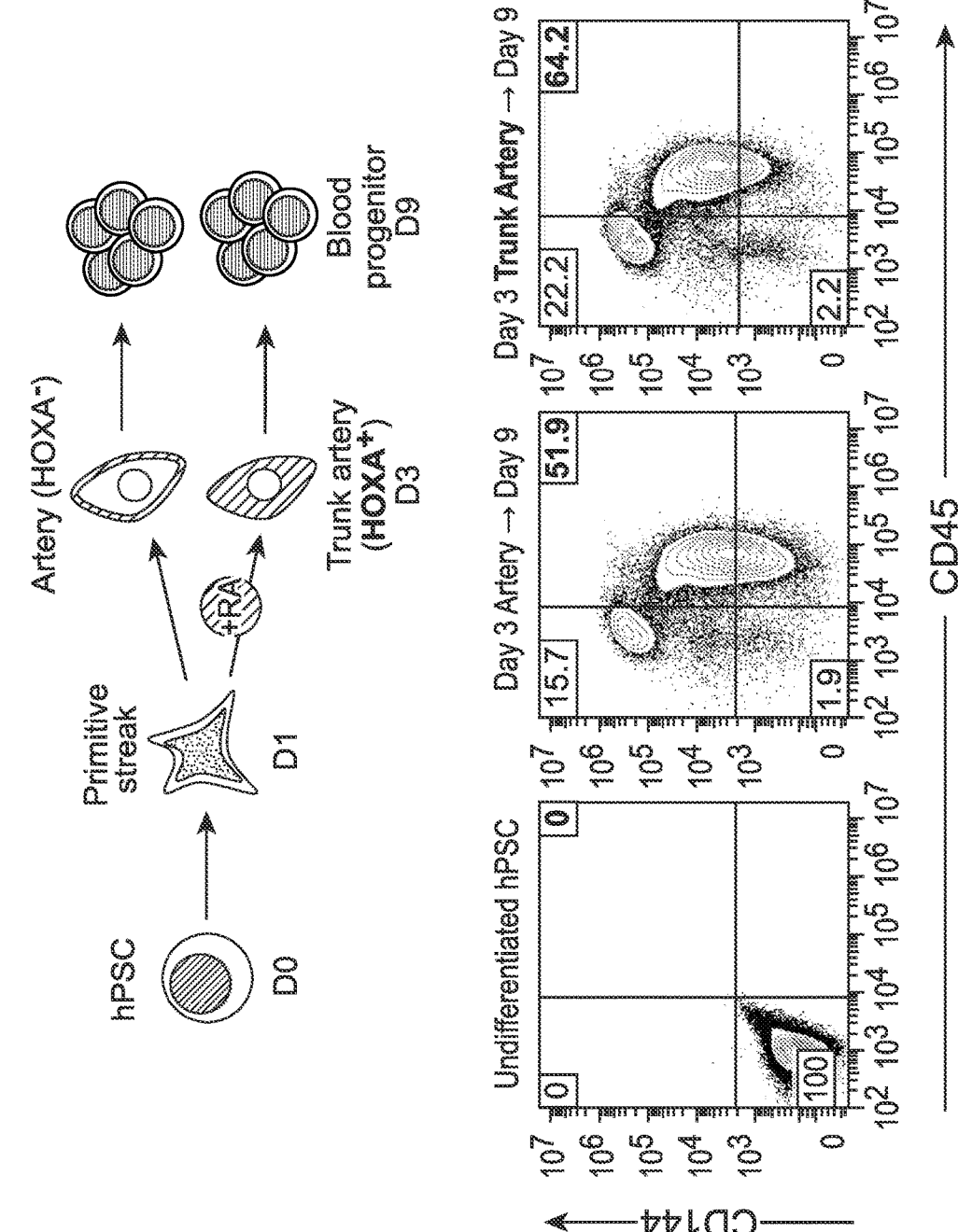
Figure 12:
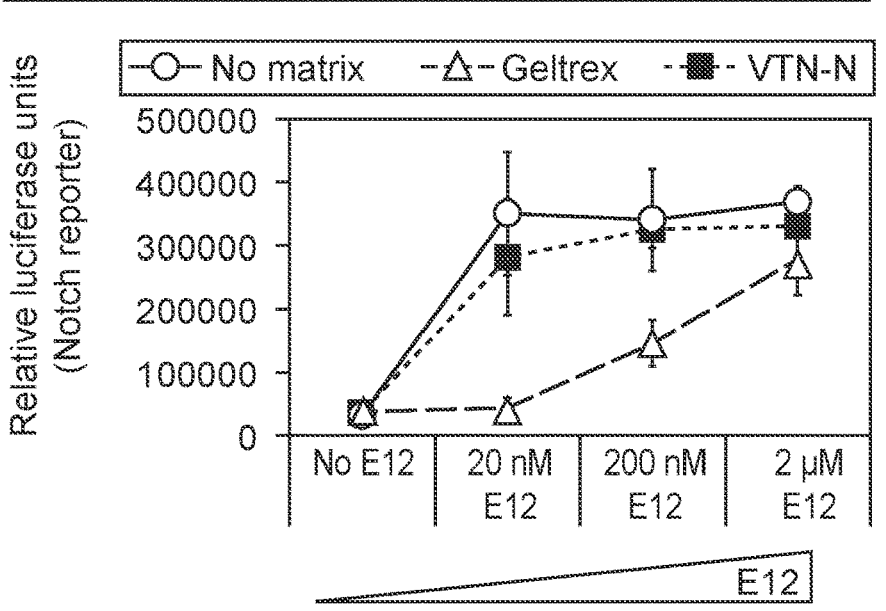
Figure 12:
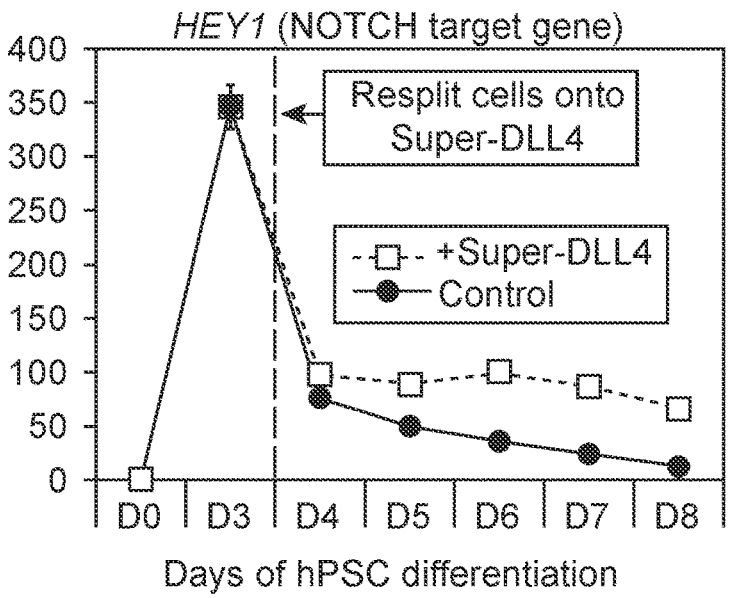
Figure 12:
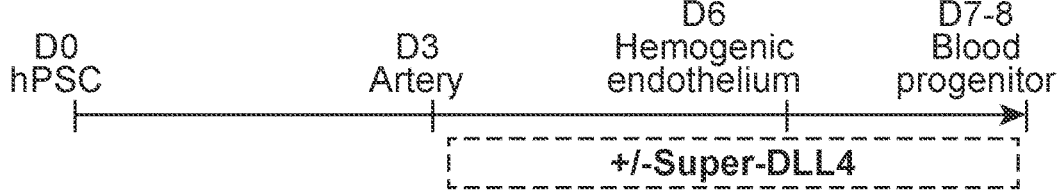
Figure 12:
Figure 12:
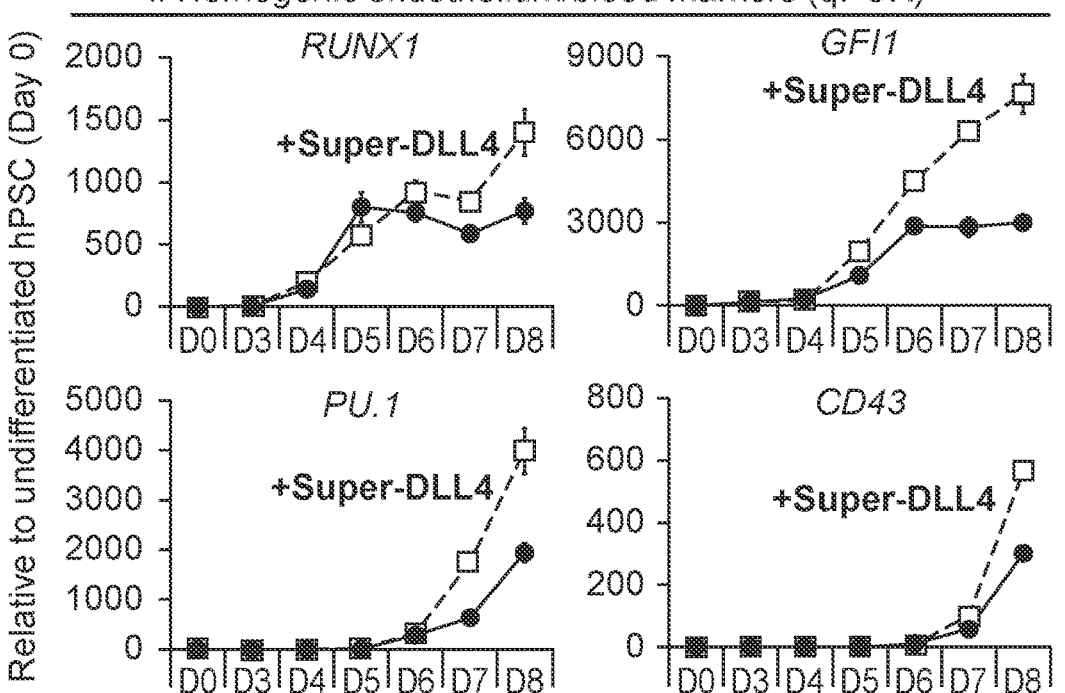
Figure 12:
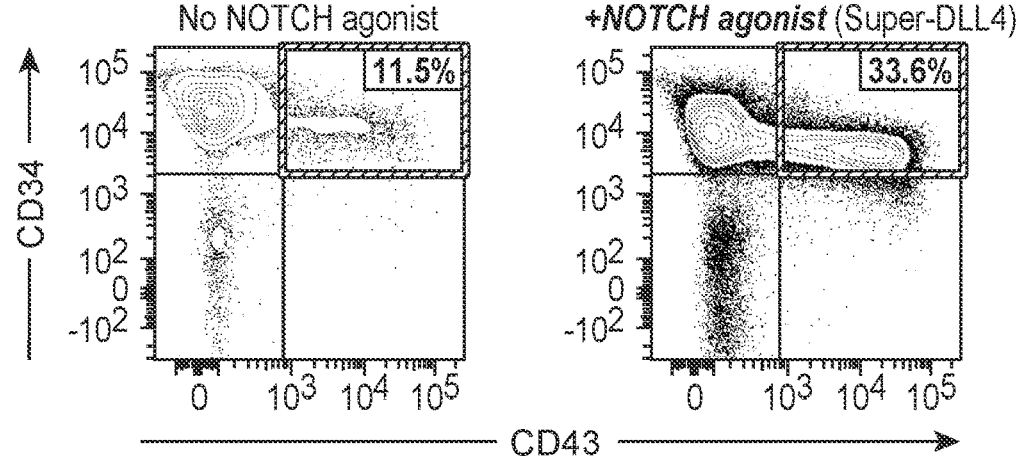
Figure 12:
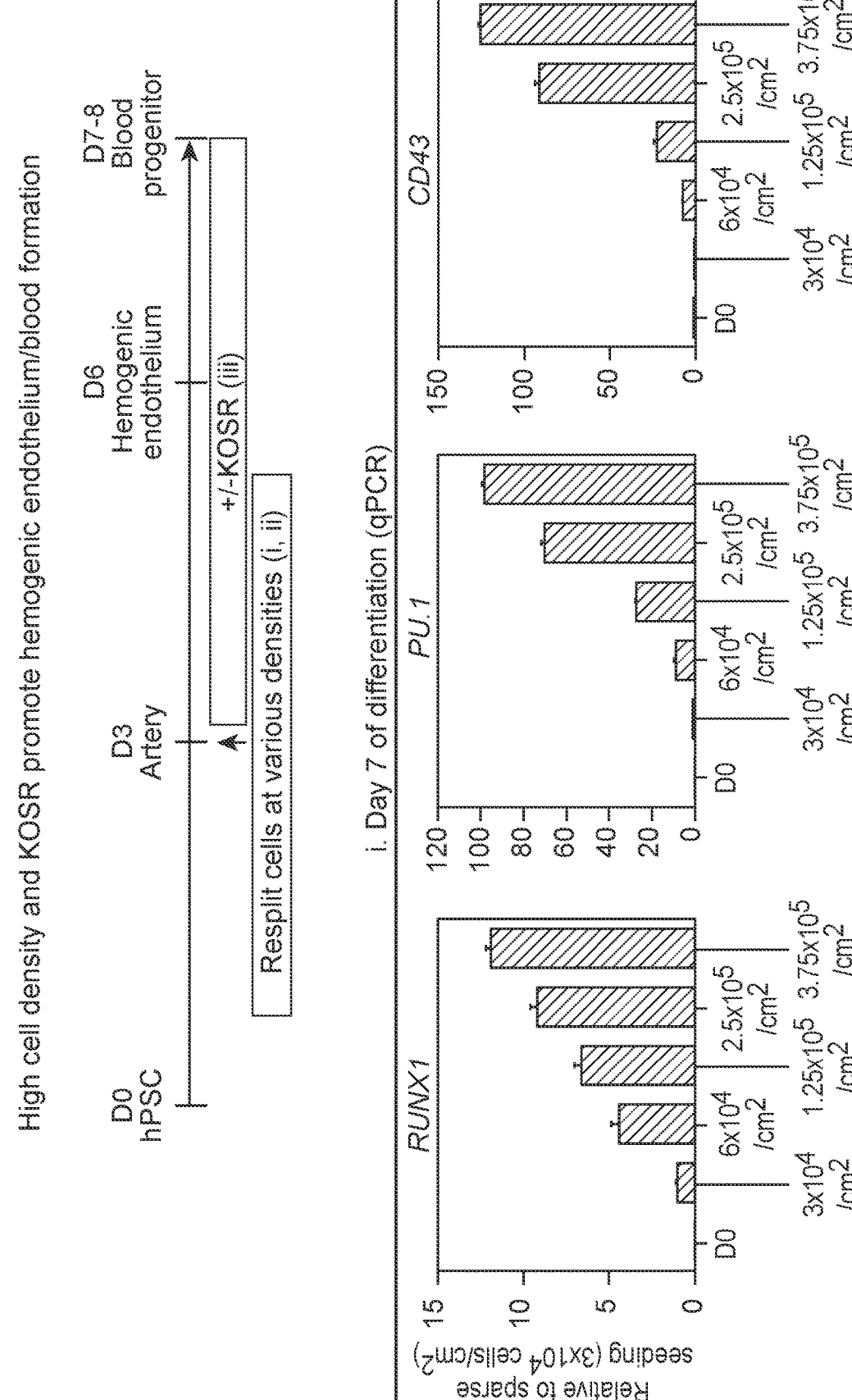
Figure 12:
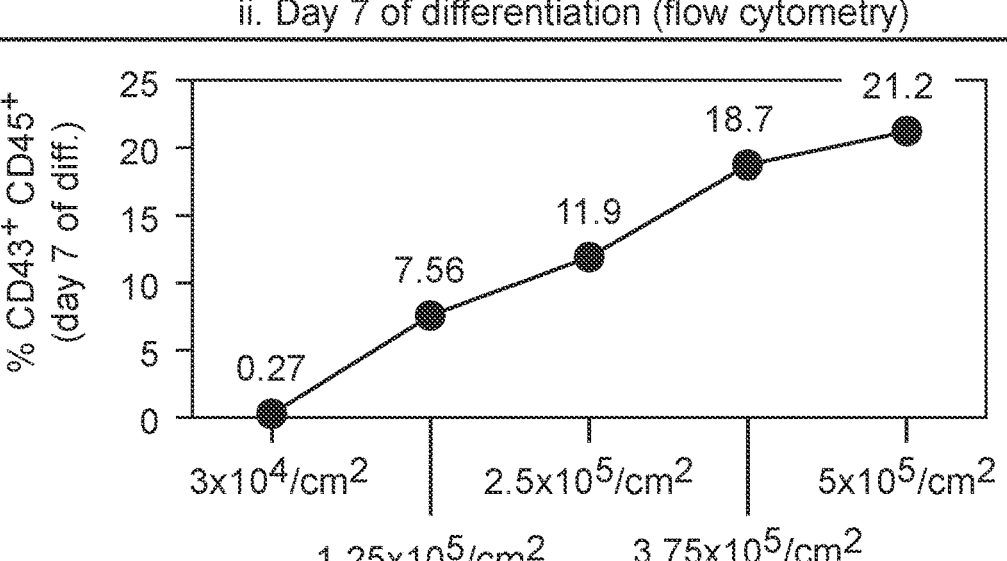
Figure 12:
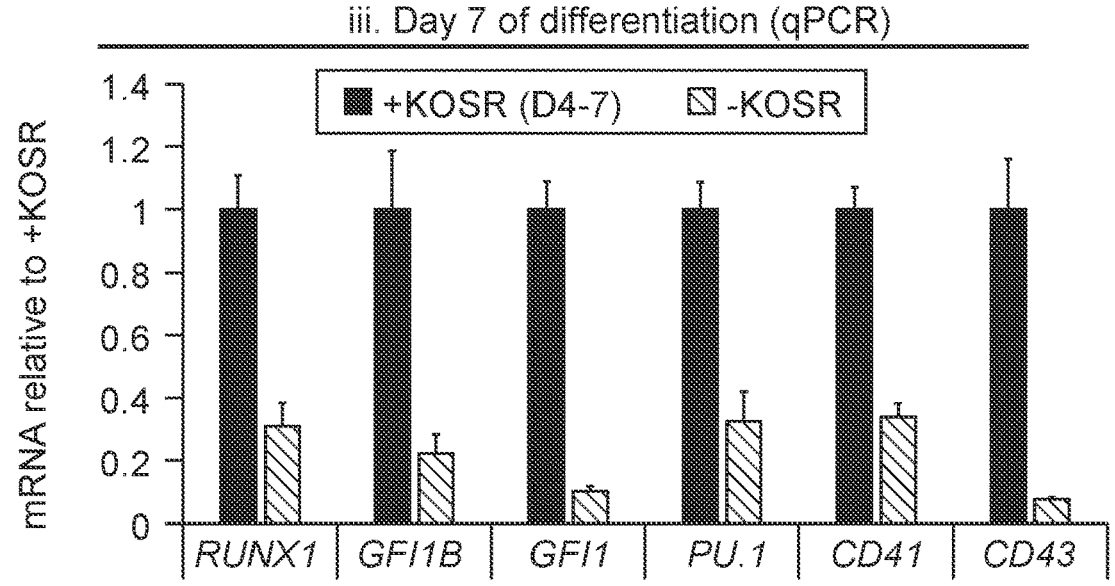
Figure 12:
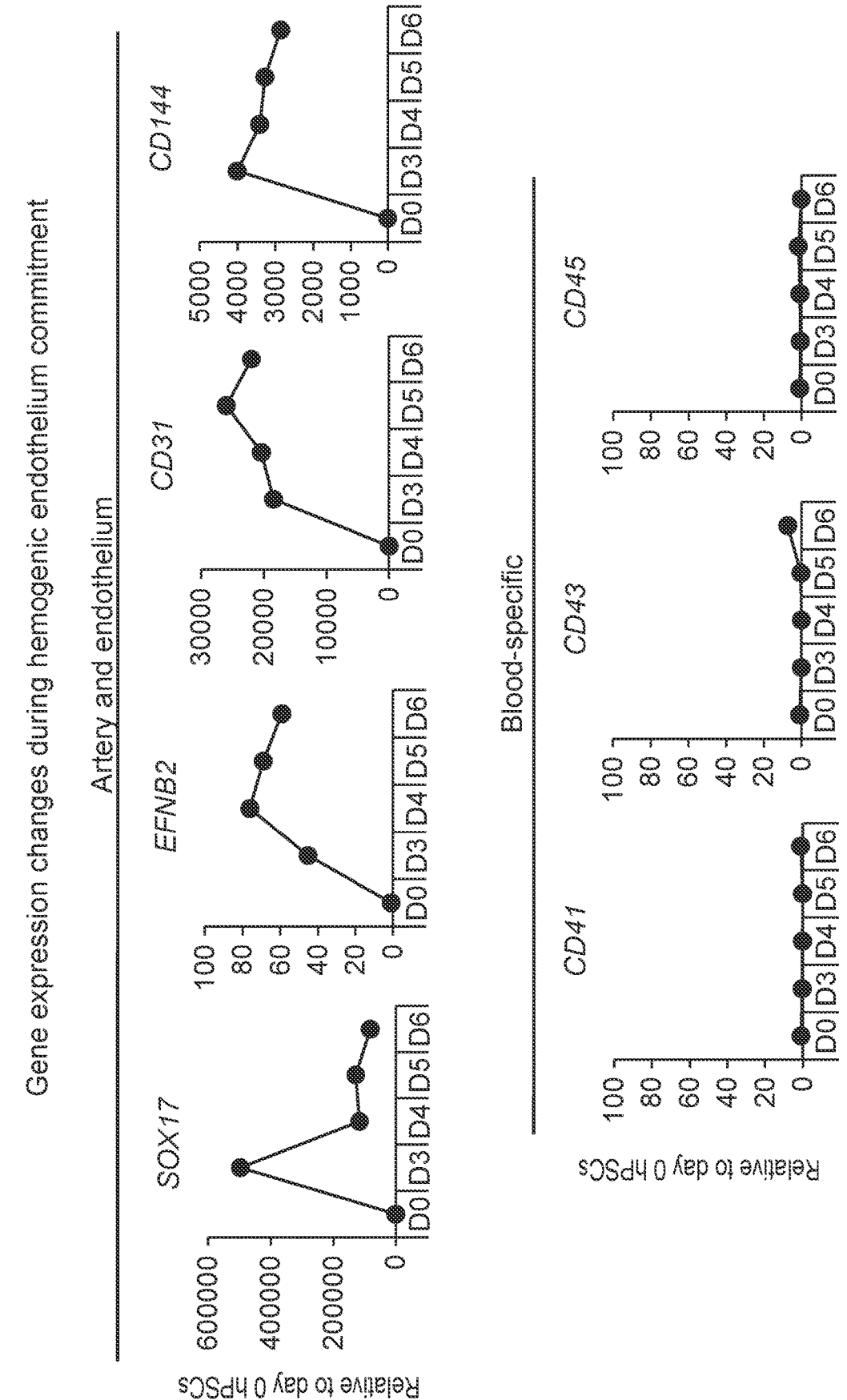

To test whether hPSC-derived arteries can give rise to blood progenitors in vitro, we harnessed our aforementioned system to efficiently differentiate hPSCs into MIXL1$^+$ primitive streak (by day 1 of differentiation), SCL$^+$ LMO2$^+$ dorsal-lateral mesoderm (day 2) and finally, SOX17$^+$ CD34$^+$ DLL4$^+$ arteries (day 3) (FIGS. 1-2). Before testing whether these hPSC-derived artery cells could generate blood progenitors, first we assessed whether they expressed HOXA/HOXB genes, given 1) the expression and functional importance of HOX genes in HSCs (Chen et al., 2016; Dou et al., 2016; Ng et al., 2016) and 2) that HOX genes are normally induced early in mesoderm development in vivo (Iimura and Pourquie, 2006; Ivanovs et al., 2017). Intriguingly, hPSC-derived day 3 artery cells generated using our aforementioned method (FIG. 2) expressed HOXB3-HOXB6 but little to no levels of HOXA1-HOXA5 (FIG. 4*b*, FIG. 12*a*). Hence, the hPSC-derived day 3 artery cells generated using our aforementioned method (FIG. 2) may correspond to the anterior-most endothelial cells in the embryo, where HOXA genes are usually absent (reviewed by Deschamps and Duboule, 2017). By contrast, endothelial cells in the embryonic trunk (e.g., the human dorsal aorta) express HOXA1-HOXA10 (Ng et al., 2016).

We therefore sought to generate hPSC-derived artery endothelial cells that expressed HOXA genes. We found that activation of the retinoic acid (RA) pathway for 48 hours during dorsal-lateral mesoderm (day 2) and artery (day 3) specification enhanced HOXA1-HOXA5 expression by day 3 (FIG. 4*b*, FIG. 12*a*) and had far-reaching effects to subsequently promote the formation of CD144$^+$ CD43$^+$ blood progenitors by day 9 (FIG. 12*c*). These effects were observed using either the pan-retinoic acid receptor (RAR) agonist TTNPB or the RARα agonist AM580 (FIG. 12*a*). These RA-induced day 3 artery populations—which we putatively refer to as "trunk artery" cells, given their HOXA1-HOXA5 expression (FIG. 4*b*, FIG. 12*a*)—expressed endothelial and arterial markers, but not markers of alternate fates such as veins or blood cells (FIG. 4*c*). By day 3 of hPSC differentiation, we could generate a >90% pure CD34$^+$ CD144$^+$ trunk artery population (FIG. 4*c*) in fully-defined conditions which included the use of recombinant vitronectin protein as a basement membrane matrix (FIG. 12*b*).

Intriguingly, the competence of cells to initiate HOXA expression was uniquely restricted to the 24-hour window of dorsal-lateral mesoderm specification; RA activation 1 day later (i.e., during day 3 artery specification) failed to elicit HOXA1-HOXA5 expression (FIG. 12*a*). This is consistent with how Hox genes are typically induced early during mesoderm development in vivo (Iimura and Pourquie, 2006; Ivanovs et al., 2017). Hence while RA is superfluous for efficient generation of SOX17$^+$ CD34$^+$ artery endothelial cells, RA pathway activation immediately after primitive streak formation considerably enhances HOXA gene expression in subsequent mesoderm and endothelial cells.

GP130 and PKA activation and TGFβ blockade differentiates artery progenitors into candidate hemogenic endothelium while suppressing artery fate. After generating SOX17$^+$ CD34$^+$ trunk artery cells by day 3 of hPSC differentiation (FIG. 2*a*), we found that over the next 24 hours, these artery progenitors faced a choice to further differentiate into RUNX1$^+$ candidate hemogenic endothelium (HE) or to remain as arteries by day 4 of differentiation (FIG. 4*d*). Expression of Runx1 in embryonic endothelial cells is thought to signify their future hematopoietic potential, thus delineating candidate HE (Swiers et al., 2013). Over this 24 hour interval, VEGF and TGFβ maintained the expression of arterial genes and suppressed RUNX1 expression.

Conversely, withholding VEGF, suppression of TGFβ and activation of three signaling pathways (GP130, PKA and NOTCH) was critical to allow cells to escape from arterial fate and become candidate HE. Individual withdrawal of GP130 agonists (OSM and LIF), PKA agonist (Forskolin) or the TGFβ inhibitor (SB505124) reduced RUNX1 expression by day 4 of hPSC differentiation, indicating their collective importance (FIG. 4*d*). First, OSM is expressed in the mouse dorsal aorta and enhances formation of Kit$^+$ Sca1$^+$ hematopoietic progenitors in aortic explant cultures (Mukouyama et al., 1998) and mouse embryos lacking gp130 (the OSM coreceptor) have myeloerythroid and lymphoid defects (Yoshida et al., 1996). Second, PKA activation is known to induce runx1 in zebrafish embryos downstream of prostaglandin E2 signaling (Goessling et al., 2009) or potentially, blood-induced shear stress (Diaz et al., 2015). Third, we find that TGFβ inhibits human HE formation, which contrasts with how TGFβ induces zebrafish HE (Monteiro et al., 2016). However, TGFβ has been reported to suppress the conversion of human and mouse cells into hematopoietic cells in vitro (Lis et al., 2017; Vargel et al., 2016; Wang et al., 2012); nonetheless, an in vivo role for TGFβ in mammalian blood development remains to be determined.

Additionally, we found that NOTCH activation and high cell density enhanced HE specification. First, to activate the NOTCH pathway, we dissociated day 3 artery progenitors and cultured them upon an immobilized "Super-DII4" ligand (Luca et al., 2015). Super-DII4 is a variant of the Notch ligand DII4, which was engineered to bind the Notch1 receptor with ~125-fold higher affinity relative to wild-type DII4 (Luca et al., 2015) and which potently induces a transcriptional NOTCH reporter transgene in cultured cells (FIG. 12*di*). While NOTCH signaling typically declined during artery differentiation into hemogenic endothelium (as revealed by declining levels of HEY1, a NOTCH target gene), we found that treatment with Super-DLL4 upregulated HEY1 (FIG. 12*dii*); increased the expression of certain HE markers (GFI1, PU.1; FIG. 12*ei*); and increased the percentage of CD34$^+$ CD43$^+$ blood progenitors (FIG. 12*eii*). This thus demonstrated the importance of NOTCH activation in HE specification. NOTCH is broadly important for HSC development in vivo, as Notch1$^{-/-}$ mice lack HSCs (Kumano et al., 2003), but it was previously unclear at what precise developmental stage NOTCH signaling is critical, as NOTCH activation has been reported to enhance or inhibit blood development in various contexts (Ditadi et al., 2015; Gama-Norton et al., 2015; Uenishi et al., 2018). For instance, previous work suggested that NOTCH activation failed to increase the generation of CD43$^+$ CD144$^+$ blood progenitors during hPSC differentiation (Uenishi et al., 2018). Taken together, we suggest that after the early role of NOTCH signaling in specifying arterial fate (reviewed by Coultas et al., 2005; Fish and Wythe, 2015), it is also persistently required for further progression into HE, thus explaining why HE is diminished in DII4$^{-/-}$ zebrafish (Bonkhofer et al., 2019) and Jag1$^{-/-}$, mouse embryos (Robert-Moreno et al., 2008).

Second, high cell density was paramount for efficient generation of HE, and subsequently blood progenitors. Sparse arterial cells largely failed to generate blood progenitors, whereas dense arterial cultures expressed higher levels of HE markers and differentiated into CD43$^+$ CD45$^+$ blood progenitors>75 times more efficiently (FIG. 12*fi,ii*). Inclusion of KnockOut Serum Replacement in the culture medium at this stage also led to a 3- to 12-fold increase in the expression of HE and blood markers (FIG. 12*fiii*).

Taken together, activation of the GP130, NOTCH and PKA pathways, together with high cell density and the absence of artery-specifying signals TGFβ and VEGF, efficiently converted day 3 hPSC-derived trunk artery cells into day 6 HE. Differentiation of a RUNX1-mOrange knock-in reporter hPSC line (Ikeda et al., 2018) revealed how RUNX1$^-$ CD144$^+$ artery cells (on day 3 of differentiation) transitioned into a >80% pure population of RUNX1$^+$ CD144$^+$ HE cells by day 6 of differentiation (FIG. 4*e*). During the process of HE commitment, distinct hematopoietic transcription factors were progressively upregulated in stepwise fashion. On days 4-5, RUNX1 was upregulated; this was followed by GFI1, GFI1B and PU.1 on day 6 (FIG. 4f). The early upregulation of RUNX1 in hPSC-derived early HE cells is consistent with how, in mouse embryos, Runx1 is among the earliest transcription factors that primes cells with hematopoietic potential (Swiers et al., 2013). Subsequently, Runx1 upregulates transcriptional repressors Gfi1 and Gfi1b, which silence endothelial genes and thereby realize blood identity (Lancrin et al., 2012; Thambyrajah et al., 2016).

We propose that HE cells are heterogeneous, with different HE subtypes marked by different transcription factors, and that such HE subtypes emerge in a temporal sequence. Thus, while HE is sometimes conceptualized as a single cell-type, our findings build upon single-cell profiling studies that suggest heterogeneity in mouse HE in vivo (Swiers et al., 2013). Specifically, we argue that there is a diversity of, and temporal progression of, HE subtypes. During the course of HE commitment, markers of artery (SOX17, EFNB2) and endothelial (CD31, CD144) cells continued to be expressed, and markers of blood cells (CD41, CD43, CD45) were not yet expressed (FIG. 12g) Subsequently, we sought to further differentiate these ~90% pure day-6 hPSC-derived HE cells into blood progenitors.

Generation of $CD34^+$ $CD144^+$ $CD43^+$ $CD45^+$ $KIT^+$ $CD90^+$ HSC-like cells from hPSCs within 9 days of differentiation. We further differentiated day 6 hPSC-derived HE into day 9 HSC-like cells by continuing to apply HE-specifying signals (GP130, NOTCH, PKA and NOTCH agonists together with TGFβ inhibitor), while simultaneously providing the HSC self-renewal agonists UM171 and SR1 and the inflammatory signal IL1β. We applied UM171 (Fares et al., 2014) and SR1 (Boitano et al., 2010) in order to capture any incipiently-arising hPSC-derived HSCs in an undifferentiated state and to prevent them from spontaneously differentiating into downstream progeny. Indeed, we found that SR1 and UM171 stabilized an undifferentiated HSC-like state, and that they decreased the expression of GATA1 and CD45RA (FIG. 13a), which are downstream markers of differentiated, non-self-renewing blood progenitors. We found that inflammatory signal IL1 modestly promoted blood formation in vitro, consistent with how inflammatory signals have been reported to promote HSC development in vivo.

Figure 13:
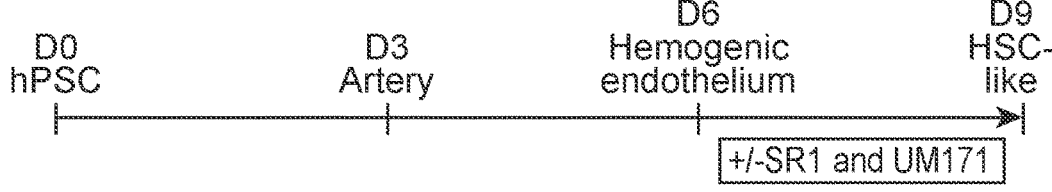
FIG. 13: Optimizing the generation of, and characterizing, hPSC-derived HSC-like cells. A) Formation of hPSC-derived HSC-like cells is enhanced by SR1 and UM171, which collectively inhibit differentiation into GATA1- or CD45RA-expressing downstream progenitors; day 6 hPSC-derived hemogenic endothelium was further differentiated into HSC-like cells over the course of 3 days in the presence or absence of both UM171 and SR1, and i) qPCR was performed every 24 hours and ii) flow cytometry for CD45$^+$ CD45RA$^-$ HSC-like cells was performed on day 9. B) qPCR was performed during hPSC differentiation into HSC-like cells every 24 hours; gene expression was normalized such that undifferentiated hPSCs=1.0. C) RUNX1-mOrange knock-in reporter hPSCs were differentiated into populations containing HSC-like cells in 9 days, which revealed that non-blood cells (CD43$^-$ CD45$^-$) within the population are RUNX1-mOrange$^+$ and hence represent hemogenic endothelium. D) Flow cytometry strategy to purify i) CD144$^+$ CD45$^+$ CD45RA$^-$ hPSC-derived day-9 HSC-like cells and ii) CD34$^+$ CD90$^+$ cord blood HSPCs vs. CD34$^+$ CD90$^-$ cord blood non-HSCs (expanded for 3 days ex vivo prior to FACS sorting) for transcriptional analysis. E) hPSC-derived day-9 HSC-like cells express low levels of the homing receptor CXCR4; i) qPCR every 24 hours of hPSC differentiation shows that CXCR4 mRNA is high in hPSC-derived artery cells, but decreases in hemogenic endothelium and HSC-like cells (qPCR data is normalized, such that undifferentiated hPSCs=1.0; note log$_{10}$ scale); ii) flow cytometry of hPSC-derived day-3 artery cells (subgated for the CD34$^+$ CD144$^+$ population) shows that they highly express CXCR4; iii) flow cytometry of hPSC-derived day-9 HSC-like cells (subgated for the CD45$^+$ CD144$^+$ population) shows that they express low levels of CXCR4. F) qPCR of cord blood HSPCs that were expanded ex vivo for 3 days, and then FACS sorted for CD34$^+$ CD90$^+$ HSPCs, shows that they express HOXA1-10 mRNAs, but not HOXA11 or HOXA13; gene expression is normalized to the expression of YWHAZ (where YWHAZ=100%; note log$_{10}$ scale).
Figure 13:
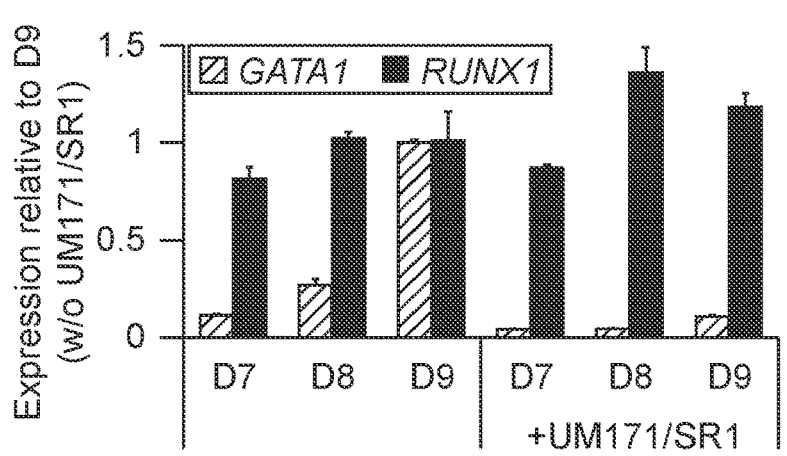
Figure 13:
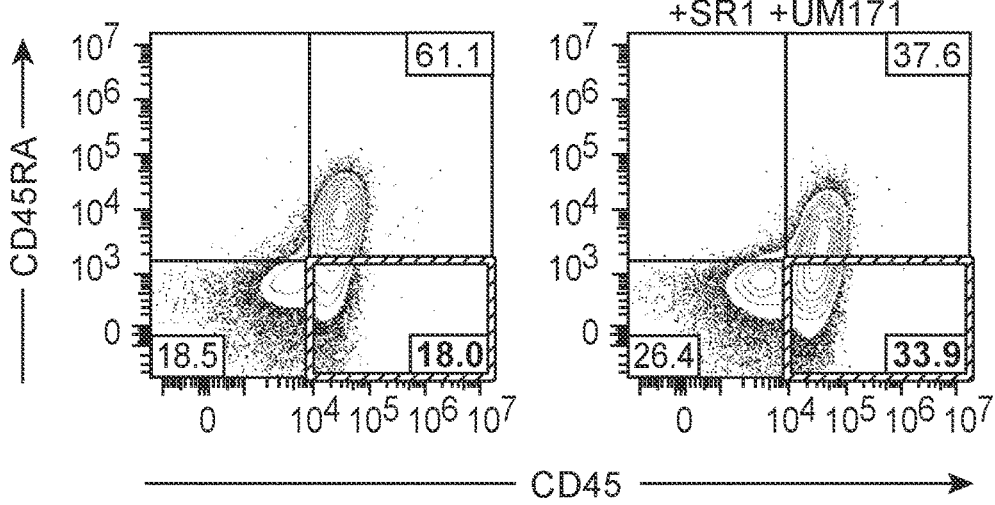
Figure 13:
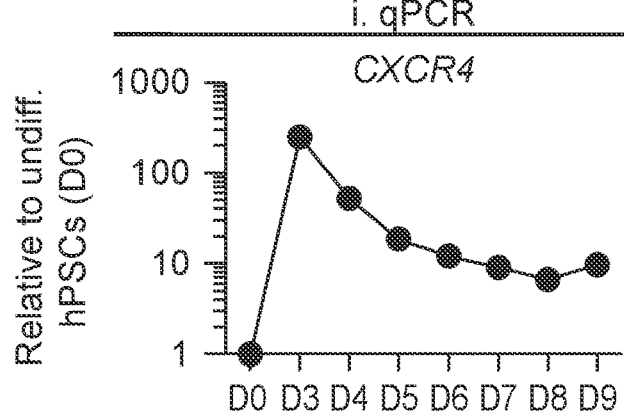
Figure 13:
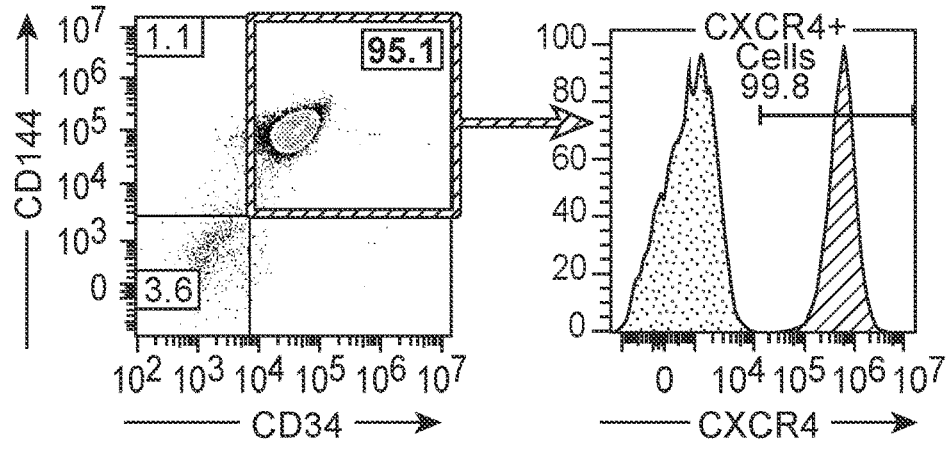
Figure 13:
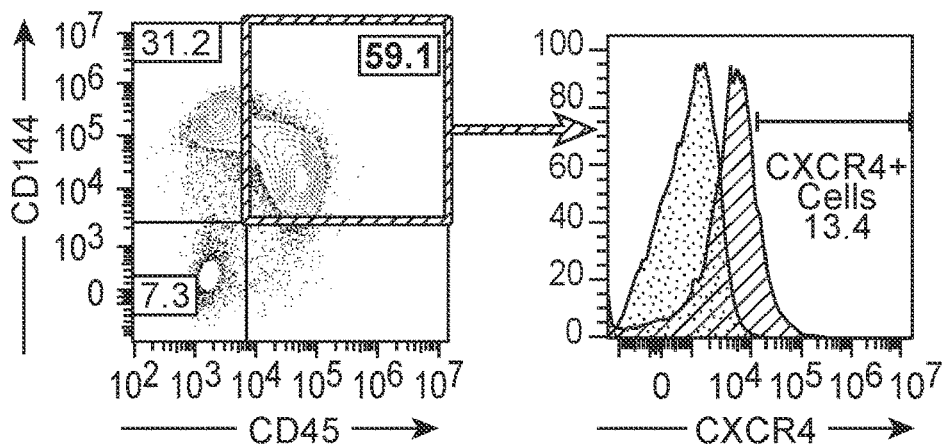
Figures 13, 14:
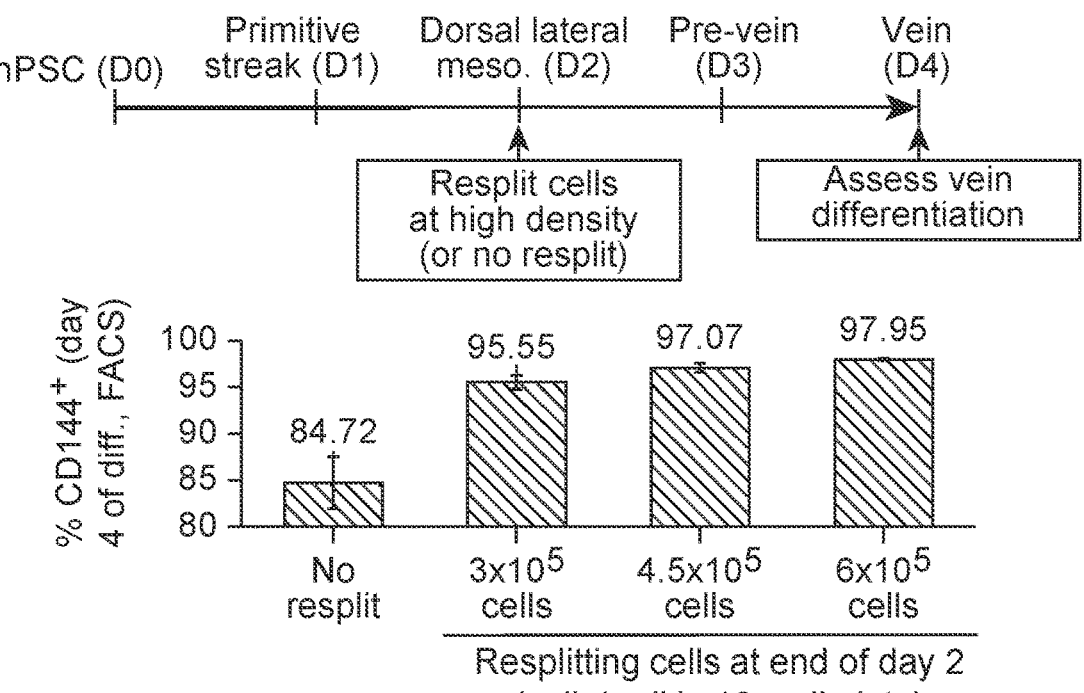
FIG. 14: Optimization of vein differentiation. A) hPSCs were differentiated into vein cells either with or without intermediate re-splitting; for intermediate re-splitting, at the end of day 2 of differentiation, $3\text{-}6\times10^5$ hPSC-derived dorsal lateral mesoderm cells were dissociated and then re-seeded per well in a 12-well plate and after 2 further days of differentiation, flow cytometry revealed that the percentage of CD144$^+$ vein endothelial cells was enhanced by intermediate dissociation and re-plating. B) Comparison of hPSC-derived day-4 vein endothelial cells generated with or without intermediate re-splitting revealed similar expression of venous surface marker CD73 and arterial surface marker DLL4 by flow cytometry (left); qPCR revealed that re-splitting enhanced the expression of pan-endothelial marker CD144/VE-CADHERIN while preserving the expression of arteriovenous markers; qPCR data is shown normalized to undifferentiated day-0 hPSCs (right).
Figure 14:
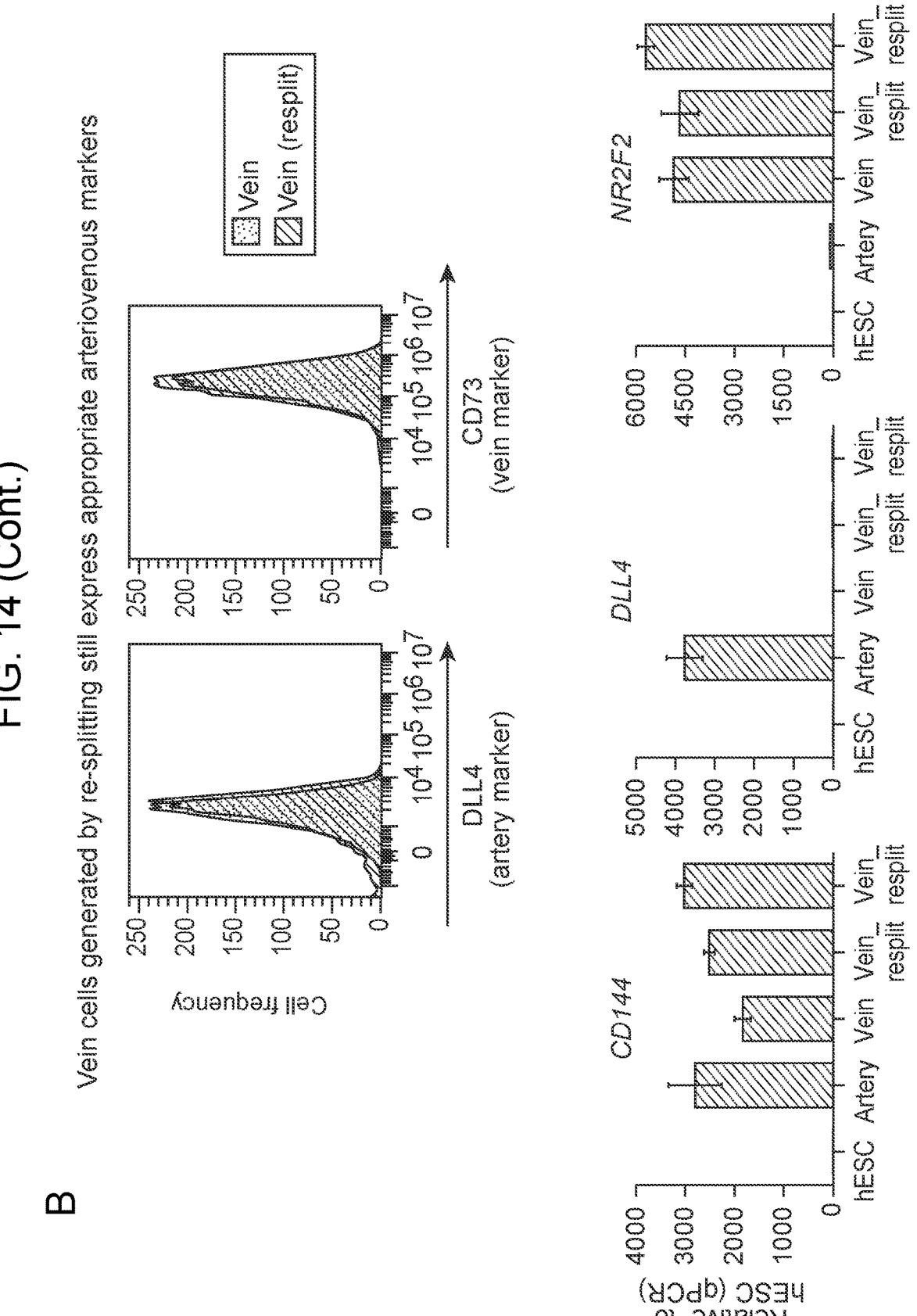

As early as day 7, and peaking at day 9 of hPSC differentiation, HSC-like cells emerged, which were morphologically conspicuous as semiadherent cells located above underlying endothelial-like cells (FIG. 5ai). This was accompanied by the progressive upregulation of various blood surface markers and transcription factors (FIG. 5aii, FIG. 13b). To discriminate blood cells from preceding endothelial or hemogenic endothelial cells, we monitored CD43, the earliest known marker that fully distinguishes endothelial from blood cells (Inlay et al., 2014; Vodyanik et al., 2006) in addition to CD45. By day 9 of differentiation, we generated a >60% pure population of $CD43^+$ $CD45^+$ and $CD34^+$ $CD43^+$ HSC-like cells (FIG. 5aiii). In our differentiation regimen, CD43 expression preceded CD45 (FIG. 5aii), consistent with how E9.5-E10.5 neonate-engrafting HSCs are $CD45^{lo/-}$ (Inlay et al., 2014) but E11.5 adult-engrafting HSCs are $CD45^+$ (Taoudi et al., 2005). Taken together, we can efficiently generate HSC-like cells from hPSCs within 9 days of differentiation.

Day 9 hPSC-derived $CD43^+$ $CD45^+$ HSC-like cells expressed a suite of surface markers associated with human HSCs present in week 4-5 fetal dorsal aorta (Ivanovs et al., 2014) and cord blood (Majeti et al., 2007). The majority (>90%) of the day 9 hPSC-derived $CD43^+$ $CD45^+$ blood progenitor population expressed CD31, CD34, CD90, CD117/KIT and CD144 (FIG. 5a). Our ability to generate hPSC-derived $CD45^+$ $CD144^+$ blood progenitors is striking, as human and mouse embryonic HSCs are $CD45^+$ $CD144^+$ prior to emigration to the fetal liver (Inlay et al., 2014; Ivanovs et al., 2014; Taoudi et al., 2005). CD144 has been proposed as a homing molecule for human embryonic HSCs (Ivanovs et al., 2014) and hPSC-derived $CD34^+$ blood progenitors generated by other differentiation protocols often lack CD144 (Uenishi et al., 2018), suggesting the absence of stem cell-like features. Of note, hPSC-derived blood progenitors continued to express both CD144 and SOX17 (albeit at lower levels than preceding endothelial cells) (FIG. 13b), consistent with how all HSCs in the E11.5 mouse dorsal aorta are $SOX17^+$ $CD144^+$ (Clarke et al., 2013). While Sox17 is silenced in the majority of nascent hematopoietic cells in vivo (Clarke et al., 2013; Lizama et al., 2015), we suggest that early HSCs are still $SOX17^+$ $CD144^+$, and that cells that fully downregulate these markers represent differentiated hematopoietic cell-types.

By day 9, >60% of the entire hPSC-derived culture consisted of $CD45^+$ $CD144^+$ HSC-like cells. ~25% of cells were $CD45^-$ $CD144^+$ hemogenic endothelium cells (which were $RUNX1^+$, but did not express the blood surface markers CD43 and CD45), likely corresponding to recalcitrant hemogenic endothelium cells that failed to progress towards blood (FIG. 13c).

Next, we transcriptionally compared hPSC-derived day-9 blood progenitors with human cord blood HSPCs. To generate the latter cell population, we cultured $CD34^+$ cord blood HSPCs for 3 days ex vivo and then used flow cytometry to isolate $CD34^+$ $CD90^+$ HSPCs (enriched for long-term engrafting HSPCs) and $CD34^+$ $CD90^-$ progenitors (which have minimal long-term engraftment potential) (Zonari et al., 2017) (FIG. 13d). To authenticate the functionality of 3-day-cultured cord blood HSPCs, we demonstrated that the bulk cell population retained the ability to engraft immune-deficient NOD-SCID $Il2rg^{-/-}$ (NSG) mice (FIG. 6e). Transcriptional comparison showed that the hPSC-derived CD45 $CD144^+$ $CD45RA^-$ blood progenitors and cord blood $CD34^+$ $CD90^+$ HSPCs expressed similar levels of 1) pan-blood surface markers (CD31, CD34, CD41, CD43 and CD45), 2) HSC-specific surface markers (CD90, CD201/PROCR), growth factor receptors (MPL, KIT) and 3) core blood transcription factors (RUNX1, GFI1, GFI1B, PU.1, IKZF1/KAROS, IKZF2/HELIOS and MYB) (FIG. 5b,c).

hPSC-derived day-9 HSC-like cells highly expressed ITGA4 (INTEGRIN α4) and ITGB1 (INTEGRIN β1), which are required for the homing of primate and mouse HSC to bone marrow (Papayannopoulou et al., 1995; Papayannopoulou and Nakamoto, 1993) (FIG. 5c,d). These hPSC-derived HSC-like cells also expressed ITGA5 (INTEGRIN α5) and ITGA6 (INTEGRIN α6; a marker of long-term-engrafting HSCs from human cord blood (Notta et al., 2011)) (FIG. 5c,d).

However, hPSC-derived day-9 HSC-like cells expressed specific genes at significantly lower levels than those normally found in human cord blood HSPCs. First, hPSC-derived HSC-like cells expressed low levels of the homing receptor CXCR4/CD184 (Sugiyama et al., 2006) (FIG. 13e), which may suggest defects in their homing upon transplantation, as has been observed with other types of hPSC-derived blood progenitors (Reid et al., 2018). Second, hPSC-derived HSC-like cells expressed low levels of HLF, HOPX and PRDM16 (FIG. 5e). HLF (Gazit et al., 2013; Komorowska et al., 2017; Riddell et al., 2014; Wahlestedt et al., 2017), HOPX (Zhou et al., 2015) and PRDM16 (Aguilo et al., 2011; Chuikov et al., 2010), which are transcription factors/cofactors that have been previously reported to show enriched expression in HSCs and early blood progenitors. Third, consistent with hPSC-derived blood progenitors generated using other differentiation protocols (Dou et al., 2016; Ng et al., 2016), we found that our hPSC-derived HSC-like cells expressed low levels of anterior and medial HOXA genes (FIG. 5e), which have been described as critical for HSC self-renewal and which are expressed in cord blood HSPCs (FIG. 13f). Fourth, hPSC-derived HSC-like cells expressed low levels of other various blood surface markers, including FLT3/CD135, PROM1/CD133 and various class II HLA genes (FIG. 5e). Taken together, though hPSC-derived HSC-like cells share the expression of various markers with cord blood HSPCs, they also lack certain markers.

hPSC-derived HSC-like cells are multipotent in vitro and show limited ability to engraft in vivo. We demonstrated that our day 9 hPSC-derived HSC-like cell population harbored the ability to generate all major types of blood and immune cells in vitro: erythroid, myeloid and lymphoid cells (FIG. 6a). First, in methylcellulose cultures, hPSC-derived HSC-like cells differentiated into a spectrum of myeloid and/or erythroid colonies, indicating the presence of multipotent CFU-GEMM (colony-forming-unit granulocyte, erythroid, macrophage and megakaryocyte) progenitors as well as related types of progenitor (FIG. 6b).

Second, hPSC-derived HSC-like cells could differentiate into red blood cells (erythroid cells) as well as megakaryocytes (the precursors to platelets) in respective in vitro differentiation assays (FIG. 6c). hPSC-derived erythroid cells were $CD34^-$ $CD45^-$ $CD235a^+$ $CD71^+$ and expressed fetal hemoglobin, as shown by HLPC analysis (FIG. 6ci). hPSC-derived megakaryocytes were $CD41a^+$ $CD61^+$ (FIG. 6cii).

Third, hPSC-derived HSC-like cells could differentiate into lymphoid cells (i.e., T cells, FIG. 6d). This was striking, as the ability to generate lymphoid cells is restricted to definitive blood progenitors/HSCs, but not earlier-arising primitive blood lineages (reviewed by Clements and Traver, 2013; Ditadi et al., 2017; Dzierzak and Speck, 2008; Ivanovs et al., 2017; Medvinsky et al., 2011). We tested the ability of hPSC-derived HSC-like cells to differentiate into T cells in 2 separate assays: 1) 2D coculture with 10T1/2 fibroblasts expressing the NOTCH ligands DLL1 and DLL4 (Ando et al. 2015) and 2) 3D coculture with MS5 fibroblasts expressing DLL4 (Montel-Hagen et al., 2019). After 3 weeks of coculture with DLL4-expressing MS5 fibroblasts, hPSC-derived HSC-like cells differentiated into $CD5^+$ $CD7^+$ $CD4^+$ $CD8^+$ T cells that expressed the T-cell receptor (TCRα/β) and the T-cell coreceptor (CD3) (FIG. 6d).

Finally, the sine qua non of authentic HSCs is their ability to engraft and regenerate a new blood and immune system in vivo (Weissman and Shizuru, 2008), and we thus tested whether our hPSC-derived HSC-like cells could engraft immunodeficient NOD-SCID Il2rg$^{-/-}$ (NSG) mice. We used 2 different strategies to transplant hPSC-derived HSC-like cells, and in the same experiments, we separately transplanted ex vivo-expanded human cord blood HSPCs as a positive control (as they are known to engraft NSG mice (Fares et al., 2014)). First, we found that hPSC-derived HSC-like cells failed to robustly engraft neonatal NSG mice upon intrahepatic transplantation (FIG. 6ei). This failure could theoretically be attributable to impaired homing to bone-marrow niches (Reid et al., 2018), as our hPSC-derived HSC-like cells expressed low levels of the key homing receptor CXCR4 (FIG. 13e). Second, in order to overcome these potential homing defects, we directly transplanted hPSC-derived HSC-like cells into the femur of adult NSG mice. Remarkably, we found that 5 months post-transplantation, human blood cells (CD45*) were detectable in vivo, although at low levels (<1% chimerism); most human blood cells were myeloid (CD33*) in lineage (FIG. 6eii). Taken together, hPSC-derived HSC-like cells could engraft in vivo to some extent.

Previous efforts to generate human blood or blood vessel cell-types in vitro from PSCs were often lengthy and stymied by poor differentiation efficiencies. Consequently, these strategies yielded a heterogeneous mixture of miscellaneous cell-types that were poorly suited for regenerative medicine, disease modeling, tissue engineering or basic research. To overcome this limitation, first we systematically mapped the intermediate progenitors through which pluripotent cells differentiate into artery and vein endothelial cells or blood progenitors. Then, we systematically deconvoluted the combinations of inductive and repressive signals that were sufficient to efficiently differentiate pluripotent cells into these various blood and endothelial lineages (summarized in FIG. 1a, FIG. 4a).

Generation of human artery and vein endothelial cells from hPSCs. Endothelial cells—the innermost constituents of blood vessels—pervade all tissues and are far more than simple conduits for oxygen. In health, they are the physical interface between the circulation and tissues and thus control the dynamic entry and exit of immune cells, nutrients and wastes into tissues. Beyond acting as gatekeepers, endothelial cells also constitute signaling centers that provide instructive signals to developing and regenerating tissues as well as self-renewing tissue stem cells. In disease, endothelial cells are the target of atherosclerosis and other widespread pathologies that account for up to two-thirds of human deaths. However, the limited supply of human endothelial cells has remained a fundamental challenge in understanding their basic biology as well as exploiting them for a variety of practical applications. Currently, endothelial cells derived from human patients can only be briefly maintained in vitro, after which they lose expression of endothelial markers and become karyotypically abnormal. This has provided an impetus to generate endothelial cells de novo from hPSCs.

Availing ourselves of a signaling roadmap (FIG. 1a), we generated a >97% pure MIXL1$^+$ primitive streak population in 1 day of hPSC differentiation and then SCL$^+$ HAND1$^+$ dorsal lateral mesoderm in 2 days of hPSC differentiation (FIG. 1). Subsequently, we efficiently differentiated these hPSC-derived dorsal lateral mesoderm progenitors into >90% pure SOX17$^+$ CD144$^+$ artery endothelial cells (FIG. 2) or >80% pure NR2F2$^+$ CD144$^+$ vein endothelial cells (FIG. 3). At the bifurcation point between artery and vein endothelial cells, we find that TGFβ and NOTCH activation (together with PI3K inhibition) specified artery fate, whereas TGFβ and NOTCH inhibition (together with PI3K activation) induced vein fate (FIGS. 2-3). Moreover, VEGF/ERK signaling had a temporally dynamic role in endothelial development; whereas it was initially required for the specification of both artery and pre-vein lineages, subsequently it had to be sharply inhibited to differentiate pre-vein precursors into fully-fledged vein cells (FIG. 3). Our findings thus reveal a more complex signaling code for artery vs. vein specification than previously assumed by the prevailing model, wherein it is generally believed that high VEGF and NOTCH specify arteries, whereas low VEGF specifies veins in vivo.

Our newfound ability to efficiently generate artery and vein endothelial cells provides an ideal source of cells to neovascularize tissues in vivo (for regenerative medicine) and to vascularize engineered tissue grafts of organoids in vitro (for tissue engineering). These hPSC-derived artery and vein endothelial cells should also allow us to build new in vitro models for a variety of human cardiovascular diseases and to screen for new therapeutic interventions. Thus, our ability to create a plentiful supply of human artery and vein endothelial cells from hPSCs should have wide-ranging applications in regenerative medicine, tissue engineering and disease modeling, amongst a number of potential applications.

Generation of human blood progenitors (HSC-like cells) from hPSCs. A major challenge in generating blood progenitors from hPSCs has been that we do not fully understand the developmental intermediates through which they form in vivo, nor do we know the extracellular signals that specify their formation at each step along the way. In developing frog (*Xenopus*) embryos, there is a clearer developmental progression whereby dorsal lateral plate mesoderm (marked by gata2 and fli1) differentiates into endothelial precursors (scl$^+$, lmo2$^+$, vecad$^+$) and subsequently into artery-like cells (dll4$^+$, efnb2$^+$), over stages 20-32 (Ciau-Uitz et al., 2013; Leung et al., 2013). Then, a subset of cells progress into early hemogenic endothelium (runx1$^-$ [stage 36]), which later upregulates gfi1a and spi1/pu.1 (stage 39), prior to budding and forming presumptive blood stem/progenitor cells (stage 43+). However, it remained controversial whether artery cells (or artery-like cells) are the developmental precursor to HSCs in mammalian species, such as mouse and human.

Figure 6:
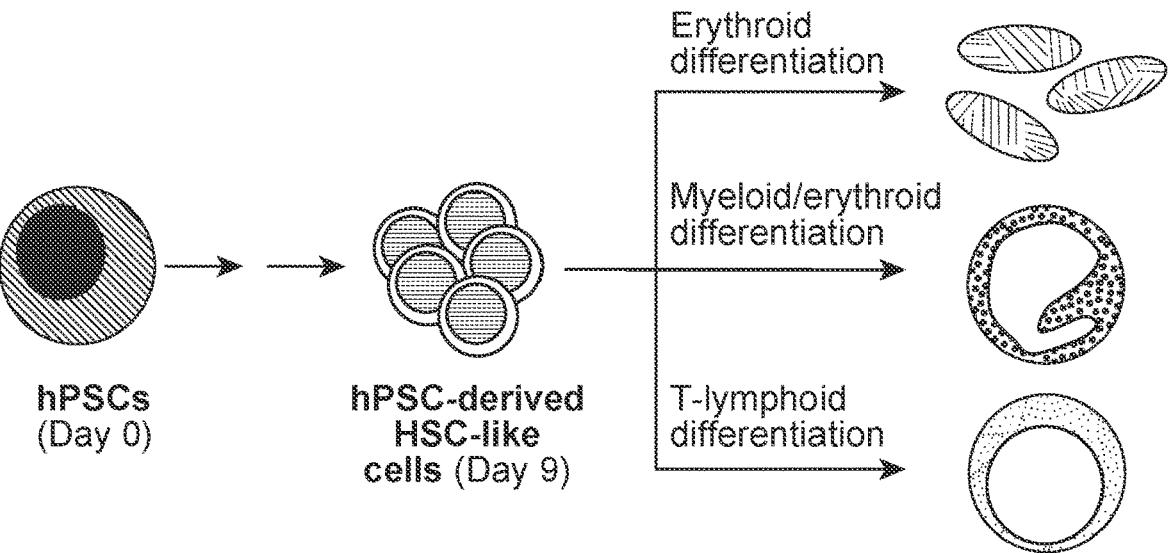
FIG. 6: hPSC-derived HSC-like cells can generate myeloid, erythroid and lymphoid cell-types in vitro. A) Cartoon of strategy to differentiate hPSC-derived day 9 HSC-like cells into multiple types of blood and immune cell in vitro. B) hPSC-derived day 9 HSC-like cells differentiated into multiple types of myeloid and/or erythroid colonies after 10 days of methylcellulose differentiation (CFU=colony-forming unit). C) hPSC-derived day 9 HSC-like cells were differentiated over the course of 14 days into either i) CD34⁺ CD45⁻CD235a⁺ CD71⁺ erythroid cells or ii) CD41a⁺ CD61⁺ megakaryocytes using respective differentiation media; flow cytometry was used to quantify the purity of the respective cell-types, and HPLC was used to assess the type of hemoglobin observed in the hPSC-derived erythroid cells. D) hPSC-derived day 9 HSC-like cells were differentiated over the course of 2-3 weeks into T cells using coculture with two separate types of feeders; flow cytometry was used to quantify the generation of T cells E) hPSC-derived day 9 HSC-like cells were transplanted into immunodeficient NOD-SCID Il2rg⁻/⁻ (NSG) mice, either through i) intrahepatic transplantation into the liver of neonatal NSG mice or it) intrafemoral transplantation into the femur of adult NSG mice; the percentage of human blood cells in transplanted mice was quantified by flow cytometry.
Figure 6:
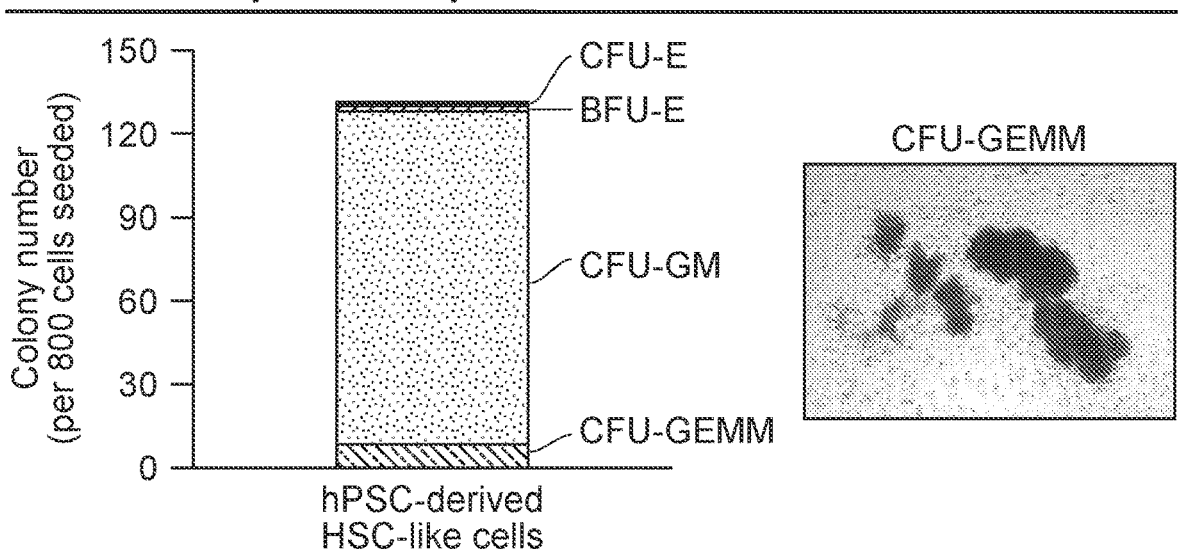
Figure 6:
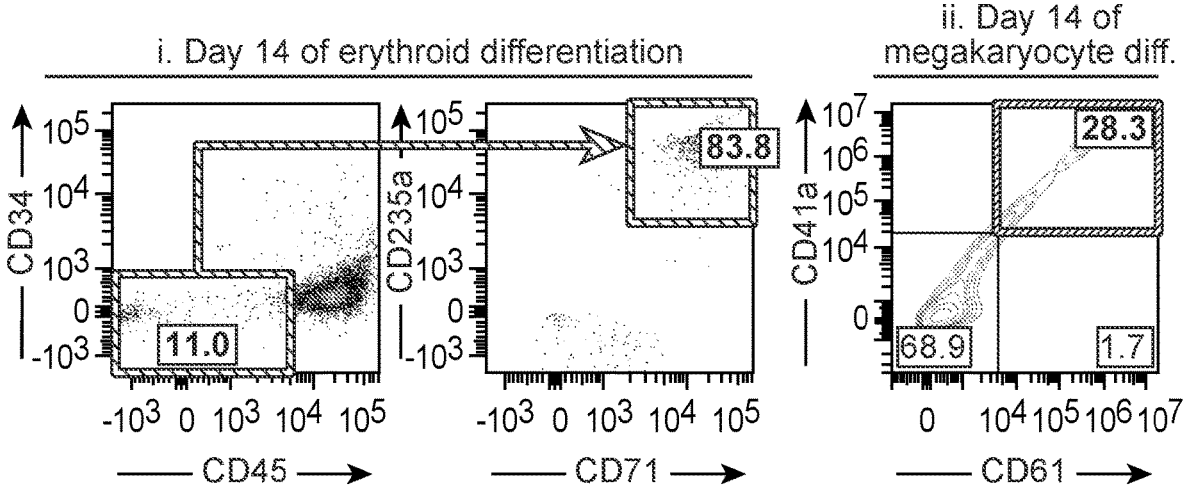
Figure 6:
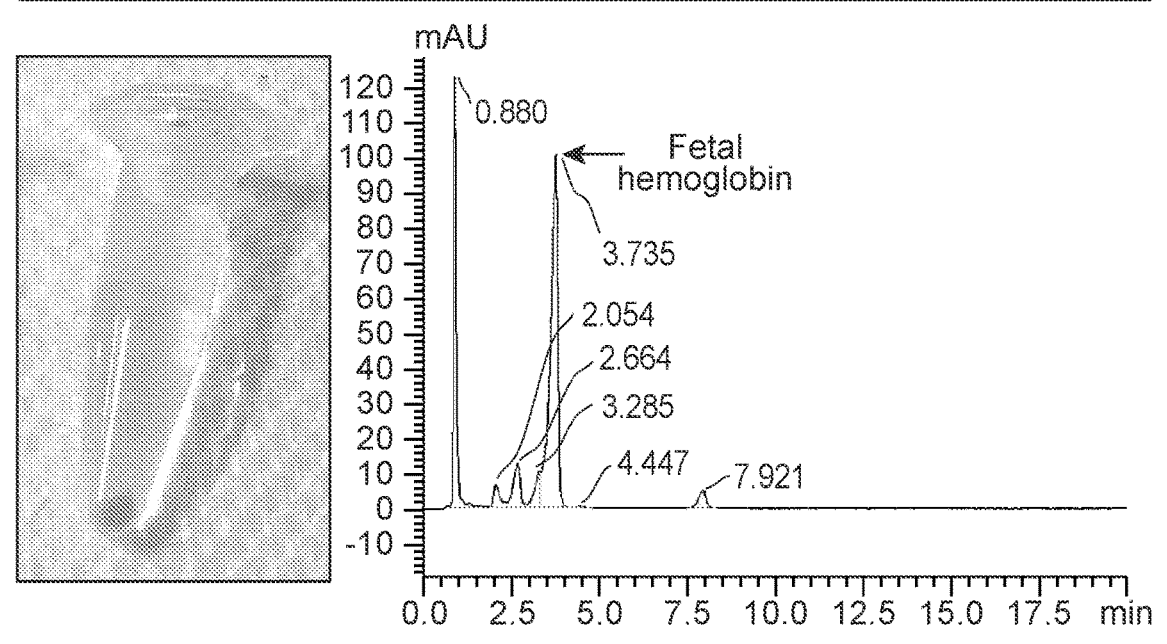
Figure 6:
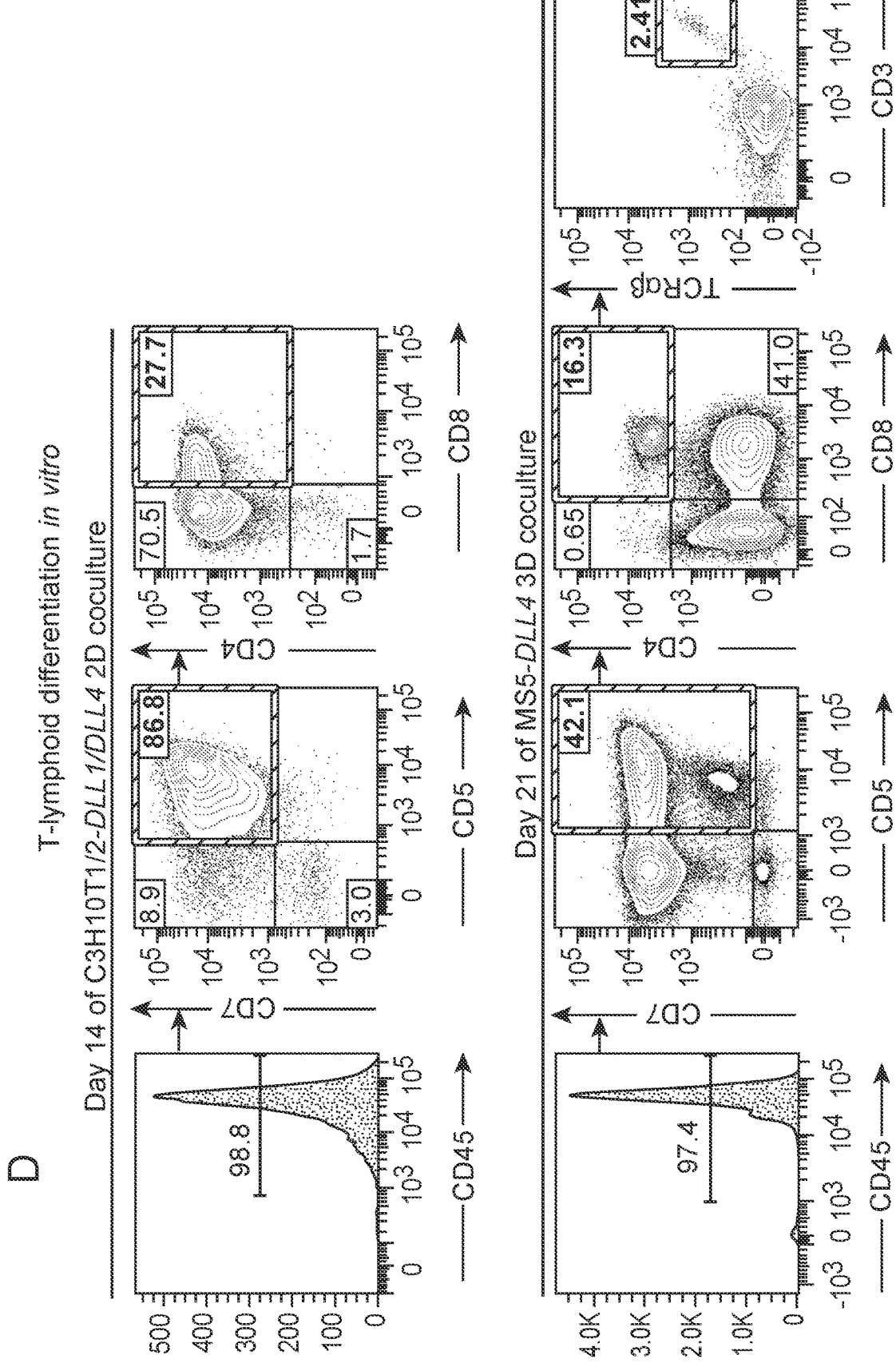
Figure 6:
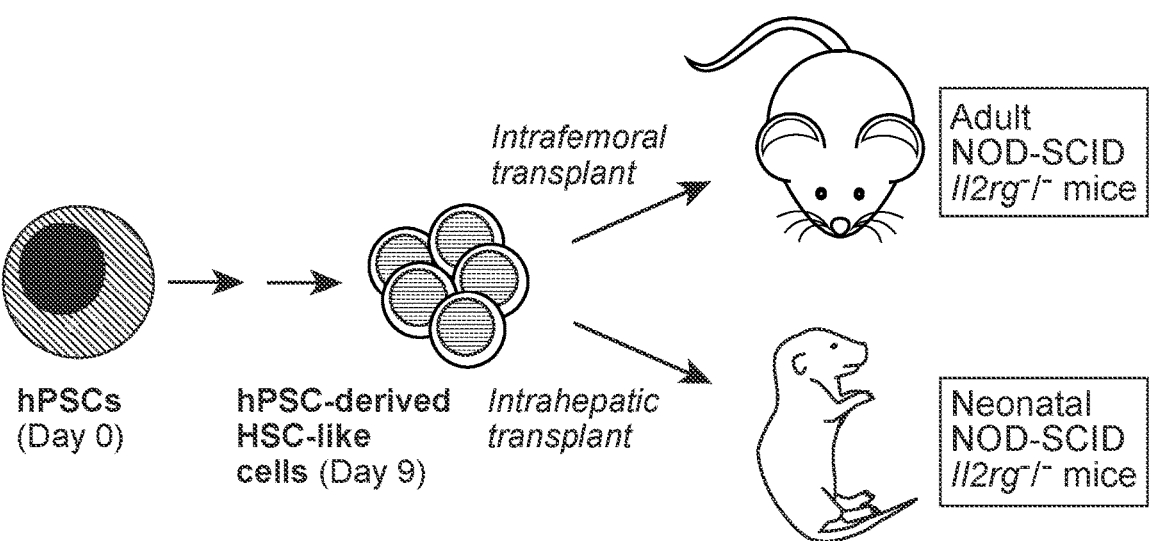
Figure 6:
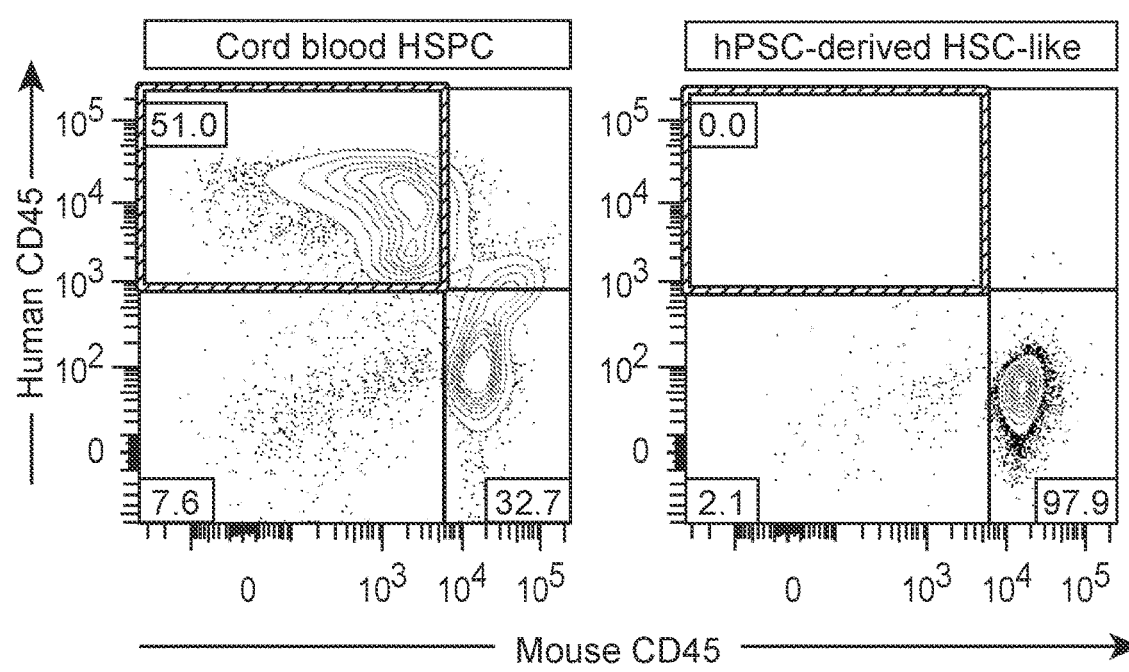
Figure 6:
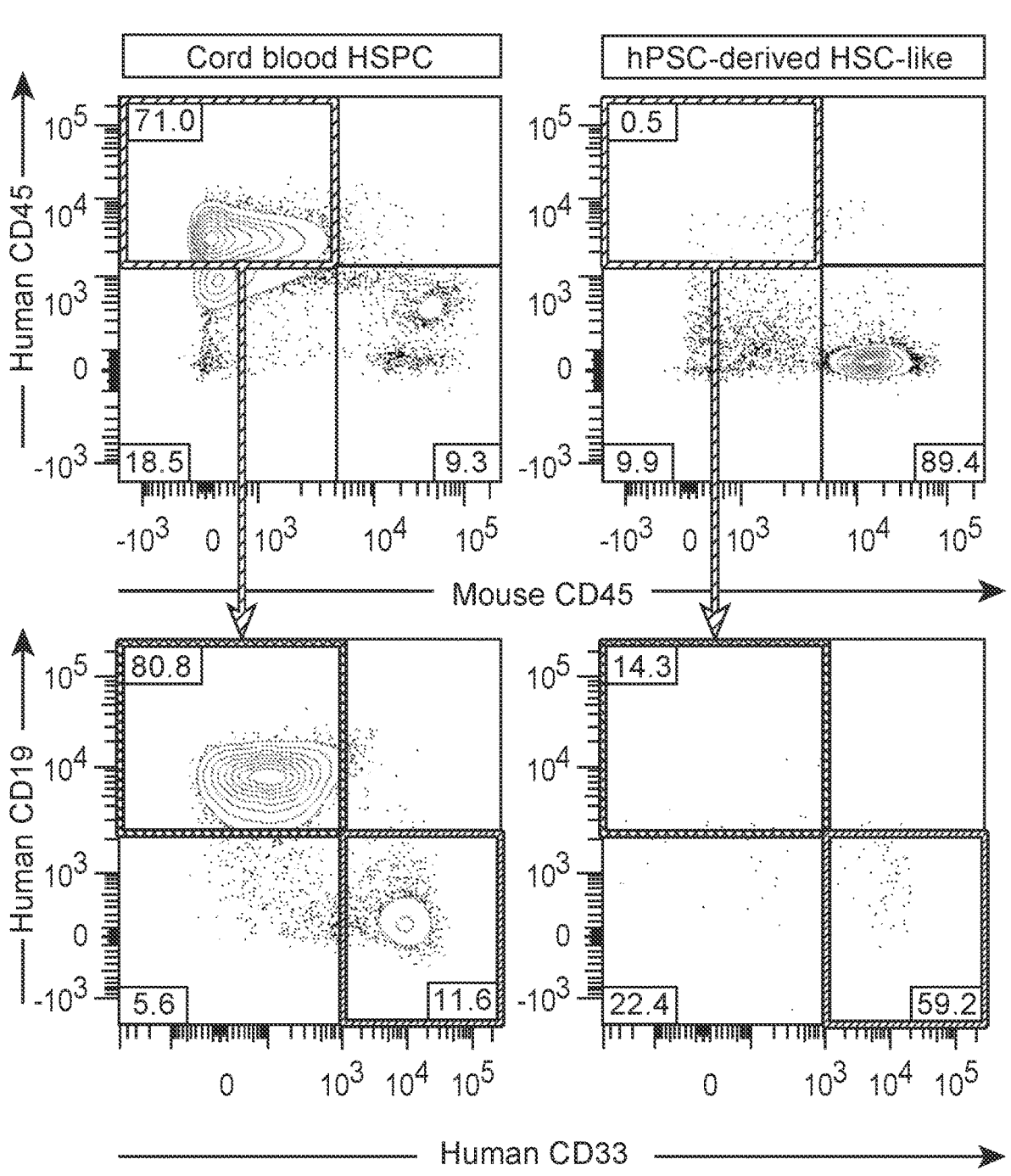

Here we develop a strategy to efficiently differentiate hPSCs into HSC-like cells in defined, monolayer conditions solely using extracellular signals to guide differentiation. We efficiently differentiate hPSCs in stepwise fashion into mid primitive streak (day 1), dorsal lateral mesoderm (day 2), trunk artery cells (day 3, >90% purity), hemogenic endothelium (day 6, >80% purity) and HSC-like cells (day 9, >60% purity). To our knowledge, this is the most rapid and efficient strategy to generate blood progenitors (HSC-like cells) in vitro from hPSCs. The hPSC-derived HSC-like cells express a host of transcription factors and surface markers that mark human HSCs (FIG. 5). Moreover, the hPSC-derived HSC-like cells harbor the ability to differentiate into myeloid, erythroid and lymphoid cells, (including T cells) in vitro and also demonstrate a limited ability to engraft in vivo (FIG. 6). The ability to efficiently and rapidly generate hPSC-derived HSC-like cells provides a gateway to produce a variety of human blood and immune cell-types including T cells and dendritic cells (for cancer immunotherapy), red blood cells (for transfusions) or megakaryocytes/platelets (for blood clotting).

In summary, the newfound capacity to produce fairly homogeneous populations of human blood vessel progenitors (including artery and vein cells) and blood progenitors (namely. HSC-like cells) in culture can serve a broad range of applications including regenerative medicine, tissue engineering and cancer therapy. Finally, this work also provides insight into key lineage intermediates in human blood and blood vessel development and the extracellular signals controlling each step along the way.

Methods

Maintaining undifferentiated hESCs. H1, H7 and H9 hESCs (WiCell) were routinely propagated in mTeSR1 (StemCell Technologies)+1% penicillin/streptomycin (Thermo Fisher) or alternatively, mTeSR Plus (StemCell Technologies)+1% penicillin/streptomycin. For the sake of brevity, we refer to mTeSR1 and mTeSR Plus interchangeably as "mTeSR" for the remainder of these Methods. Undifferentiated hESCs were passaged for maintenance by treating them for 7 minutes with EDTA (Versene, Thermo Fisher) at room temperature, after which EDTA was removed. mTeSR was added, and then hESCs were manually scraped off the plate to generate clumps. hESC clumps were then seeded onto new plates that had been precoated with Geltrex basement membrane matrix (diluted 1:100 in DMEM/F12, Thermo Fisher).

Seeding hESCs for differentiation (Step 0). A different passaging procedure was used to plate hESCs for differentiation; notably, sparse seeding of hESCs as single cells is paramount for efficient differentiation. To seed hESCs for differentiation, largely-confluent hESCs were instead dissociated into single cells (Accutase, Thermo Fisher) and plated into recipient wells in mTeSR supplemented with thiazovivin (1 μM, Tocris; a ROCK inhibitor, to enhance hESC survival after passaging) onto plates precoated with either Geltrex basement membrane matrix (diluted 1:100 in DMEM/F12, Thermo Fisher) or recombinant Vitronectin (10 μg/mL, Thermo Fisher), thus plating 25,000-50,000 hESCs/cm$^2$ (i.e., ~95,000-190,000 hESCs/well of a 12-well plate). Freshly-seeded hESCs were allowed to adhere and recover for 24 hours in mTeSR+1 μM thiazovivin prior to initiating differentiation, during which the hESCs re-formed small clumps. All subsequent differentiation steps were performed in defined, serum-free CDM2 basal media (Loh et al., 2014; Loh et al., 2016). To reiterate, hESCs are maintained by passaging as clumps (to maintain normal karyotype) but are seeded for differentiation as single cells (to enable efficient differentiation).

Day 1 (mid primitive streak induction, 24 hours [Step 1]). Day 0 hESCs were briefly washed (DMEM/F12, Thermo Fisher) to remove all traces of mTeSR+thiazovivin. Then, they were differentiated towards mid primitive streak (MPS) in CDM2 media supplemented with Activin A (30 ng/mL, R&D Systems), BMP4 (40 ng/mL, R&D Systems), CHIR99021 (6 μM, Tocris), and FGF2 (20 ng/mL, Thermo Fisher) for 24 hours, as previously described (Loh et al., 2016) (with the optional addition of PIK90 (100 nM, Calbiochem)).

Day 2 (dorsal lateral mesoderm induction, 24 hours [Step 2a]). Day 1 mid primitive streak cells were briefly washed (DMEM/F12, Thermo Fisher) and then differentiated towards dorsal lateral mesoderm in CDM2 media supplemented with BMP4 (40 ng/mL), GDC-0941 (2.5 μM, Cellagen Technology), Forskolin (10 μM, Tocris), SB-505124 (2 μM, Tocris), VEGF (100 ng/mL, R&D Systems), XAV939 (1 μM, Tocris) and ascorbic acid-2-phosphate (AA2P; 200 μg/mL, Sigma) for 24 hours.

Day 3 (artery progenitor induction, 24 hours [Step 3a]). Day 2 dorsal lateral mesoderm cells were briefly washed (DMEM/F12, Thermo Fisher) and then differentiated towards artery progenitors in CDM2 media supplemented with Activin A (15 ng/mL), DMH1 (250 nM, Tocris), GDC-0941 (2.5 μM), VEGF (100 ng/mL), XAV939 (1 μM) and AA2P (200 μg/mL) for 24 hours.

Day 4-onwards (artery progenitor maintenance [Step 4a]). Day 3 arterial progenitor cells could be maintained in an arterial state for several days by continued treatment with artery progenitor induction media (see above) or EGM2 (Endothelial Cell Growth Medium 2, Lonza), which was refreshed every 24 hours.

Day 2 (trunk dorsal lateral mesoderm induction, 24 hours [Step 2b]). Day 1 mid primitive streak cells were briefly washed (DMEM/F12, Thermo Fisher) and then differentiated towards dorsal lateral mesoderm in CDM2 media supplemented with BMP4 (40 ng/mL), GDC-0941 (2.5 μM, Cellagen Technology), Forskolin (10 μM, Tocris), SB-505124 (2 μM, Tocris), VEGF (100 ng/mL, R&D Systems), XAV939 (1 μM, Tocris), AA2P (200 μg/mL) and TTNPB (0.5 nM) for 24 hours (i.e., the same media as dorsal lateral mesoderm induction, with the addition of TTNPB).

Day 3 (trunk artery progenitor induction, 24 hours [Step 3b]). Day 2 dorsal lateral mesoderm cells were briefly washed (DMEM/F12, Thermo Fisher) and then differentiated towards trunk artery progenitors in CDM2 media supplemented with Activin A (15 ng/mL), DMH1 (250 nM, Tocris), GDC-0941 (2.5 μM), VEGF (100 ng/mL), XAV939 (1 μM), AA2P (200 μg/mL) and TTNPB (0.5 nM, Tocris) for 24 hours (i.e., the same media as artery progenitor induction, with the addition of TTNPB).

Day 4-6 (hemogenic endothelium induction, 72 hours [Step 4b]). Day 3 trunk artery cells were dissociated into a single-cell suspension (Accutase); densely re-seeded at high cell density (500,000 cells/cm$^2$) onto plates precoated with recombinant Vitronectin+Super-DLL4 (20 nM, prepared in-house; otherwise known as E12 (Luca et al., 2015)); and then further differentiated towards hemogenic endothelium in CDM3 media supplemented with Forskolin (10 μM), LIF (20 ng/mL, R&D Systems), OSM (10 ng/mL, R&D Systems) and SB505124 (2 μM) for 24 hours. Hemogenic endothelium induction media was refreshed every 24 hours.

Day 6-9 (HSC-like cell induction, 72 hours [Step 5b]). Day 6 hemogenic endothelium cells were briefly washed (DMEM/F12, Thermo Fisher) and then differentiated towards HSC-like cells in CDM3 media supplemented with Forskolin (10 μM), IL1β (5 ng/mL, R&D Systems), LIF (20 ng/mL), OSM (10 ng/mL), SB505124 (2 μM), SR1 (750 nM, Cellagen Technology) and UM171 (75 nM, ApexBio) for 72 hours. HSC-like cell induction media was refreshed every 24 hours.

Day 3 (pre-vein progenitor induction, 24 hours [Step 3c]). Day 2 dorsal lateral mesoderm cells were briefly washed (DMEM/F12, Thermo Fisher) and then differentiated towards pre-vein progenitors in CDM2 media supplemented with SB505124 (2 μM), DMH1 (250 nM), R04929097 (2 μM, Cellagen Technology), VEGF (100 ng/mL), XAV939 (1 μM) and AA2P (200 μg/mL) for 24 hours.

Day 4 (vein progenitor induction, 24 hours [Step 3d]). Day 3 pre-vein cells were briefly washed (DMEM/F12, Thermo Fisher) and then differentiated towards vein progenitors in CDM2 media supplemented with SB505124 (2 μM), R04929097 (2 μM), PD0325901 (500 nM, Tocris), CHIR99021 (1 μM) and AA2P (200 μg/mL) for 24 hours.

CDM2 basal media composition. The composition of CDM2 has been described previously (Loh et al., 2014; Loh et al., 2016): 50% IMDM+GlutaMAX (Thermo Fisher, 31980-097)+50% F12+GlutaMAX (Thermo Fisher, 31765-092)+1 mg/mL polyvinyl alcohol (Sigma, P8136-250G)+1% v/v chemically defined lipid concentrate (Thermo Fisher, 11905-031)+450 μM 1-thioglycerol (Sigma, M6145-100ML)+0.7 μg/mL recombinant human insulin (Sigma, 11376497001)+15 μg/mL human transferrin (Sigma, 10652202001)+1% v/v penicillin/streptomycin (Thermo Fisher, 15070-063). Polyvinyl alcohol was brought into suspension by gentle warming and magnetic stirring, and the media was sterilely filtered (through a 0.22 μm filter) prior to use.

CDM3 basal media composition. The composition of CDM3 has been described previously (Ang et al., 2018): 45% IMDM+GlutaMAX (Thermo Fisher, 31980-097)+45% F12+GlutaMAX (Thermo Fisher, 31765-092)+10% Knock-Out Serum Replacement (Thermo Fisher, 10828028)+1 mg/mL polyvinyl alcohol (Sigma, P8136-250G)+1% v/v chemically defined lipid concentrate (Thermo Fisher, 11905-031)+1% v/v penicillin/streptomycin (Thermo Fisher, 15070-063). Polyvinyl alcohol was brought into suspension by gentle warming and magnetic stirring, and the media was sterilely filtered (through a 0.22 μm filter) prior to use.

Flow cytometry. Undifferentiated and differentiated hPSCs were dissociated by incubation in TrypLE Express (Gibco) for 5 minutes at 37° C. Subsequently, dissociated cells in TrypLE Express were diluted 1:10 in DMEM/F12 and centrifuged (pelleted) at 500 g for 5 minutes. Each cell pellet was resuspended in FACS buffer (PBS+1 mM EDTA [Invitrogen]+2% v/v FBS [Atlanta Bio]+1% Penicillin/Streptomycin [Gibco]) supplemented with fluorescently-conjugated primary antibodies, and antibody staining occurred for 30 minutes on ice protected from light. After staining, cells were washed twice with FACS buffer and resuspended in 200 μL FACS buffer with DAPI (1:10,000, Biolegend) for live/dead discrimination. Samples were run on a Beckman Coulter CytoFlex analyzer (Stanford Stem Cell Institute FACS Core). For data analysis, cells were gated based on forward and side scatter with height and width used for doublet discrimination. Subsequently, live cells that were negative for DAPI were gated for all marker analyses and calculations of population frequency.

High-throughput flow cytometry. The expression of 332 unique cell-surface markers was assessed across undifferentiated hPSCs (day 0), mid primitive streak (day 1), dorsal lateral mesoderm (day 2), artery progenitors (day 3) and vein progenitors (day 4) through the use of high-throughput flow cytometry as described previously (Loh et al., 2016). In brief, hPSCs or their differentiated mesoderm progeny were dissociated (using TrypLE Express) and plated into individual wells of four 96-well plates, each well containing a distinct antibody against a human cell-surface antigen, altogether totaling 332 unique cell-surface markers across multiple 96-well plates (LEGENDScreen PE-Conjugated Human Antibody Plates; Biolegend, 700001). High-throughput cell-surface marker staining was largely done as per the manufacturer's recommendations, and cells were stained with a viability dye (DAPI, 1.1 μM; Biolegend) prior to robotically-enabled plate-based analysis on an BD FACSCanto (Stanford Stem Cell Institute FACS Core). Stained cells were not fixed prior to FACS analysis. LEGENDScreen data for undifferentiated H7 hPSCs (day 0) and H7-derived mid primitive streak (day 1) was published previously (Loh et al. 2016). LEGENDScreen data for H1-derived dorsal lateral mesoderm (day 2), H1-derived artery progenitors (day 3) and H1-derived vein progenitors (day 4) was generated in this study. Day 3 artery progenitors and day 4 vein progenitors were both co-stained with an anti-CD144 Alexa Fluor 647 antibody (BD, 561567) to identify CD144$^+$ endothelial cells, and surface-marker expression was evaluated specifically in the CD144$^+$ population.

Quantitative PCR. Undifferentiated or differentiated hPSCs were lysed in 350 μL of RLT Plus Buffer and RNA was extracted using the RNeasy Plus Mini Kit (Qiagen) according to the manufacturer's protocol. 300 ng of total RNA was reverse transcribed into cDNA for qPCR using the High-Capacity cDNA Reverse Transcription Kit (Applied Biosystems) according to the manufacturer's protocol. qPCR was performed in 384-well format as previously described (Loh et al., 2016), using gene-specific forward and reverse primers on a QuantStudio 5 qPCR machine (Thermo Fisher). Expression of all genes was normalized to the levels of the reference gene YWHAZ.

Immunostaining. Cells were fixed, permeabilized and immunostained as previously described (Loh et al., 2016). Imaging was conducted using an FV3000 confocal microscope (Olympus).

Basement membrane matrices. First, Geltrex (Gibco) was diluted 1:200 in DMEM/F12 and was used to coat tissue culture plastics for at least 1 hour at 37° C. Second, recombinant human truncated vitronectin (Gibco, A14700; "VTN-N") was diluted to a 10 µg/mL stock in PBS (lacking $Ca^{2+}$ or $Mg^{2+}$) and was used to coat tissue culture plastics for at least 1 hour at 37° C. Third, for NOTCH activation experiments, VTN-N stock was pre-mixed with 200 nM of a high-affinity mutant DLL4 protein (variant E12) overnight and then the VTN-N/E12 mixture was used to coat tissue culture plastics for at least 1 hour at 37° C. to immobilize the E12 ligand on the plate. Subsequently, coated wells were briefly washed with DMEM/F12 to remove any soluble E12 ligand before plating cells.

Genome editing. H1 NR2F2-2A-GFP knock-in hPSCs were genetically engineered as described previously (Martin et al., 2019). In brief, hPSCs were treated with 10 µM ROCK inhibitor (Y-27632) 24 hours prior to editing. Cells at 70-80% confluence were dissociated using Accutase (Life Technologies) followed by neutralization with ROCK inhibitor-supplemented mTeSR1 media. Prior to electroporation, RNP complex was formed by combining 5 µg of HiFi Cas9 (Integrated DNA Technologies) and 1.75 µg of sgRNA for 10 minutes at room temperature, which was then diluted with 20 µL of P3 Primary Cell Solution (Lonza). For each electroporation reaction, 500,000 cells were mixed with the Cas9/sgRNA RNP-containing nucleofection solution. Nucleofection was performed using 16-well Nucleocuvette Strip with 4D Nucleofector system (Lonza) using the CA137 electroporation code. Following electroporation, cells were transferred into one well of a Matrigel-coated 24-well plate containing 500 µL of mTeSR1 media supplemented with 10 µM Y-27632. AAV6 donor vector was added at 100,000 multiplicity of infection (MOI) directly to cells after plating in a 24 well coated with Matrigel. Cells were then incubated at 37° C. for 24 hours. Media was changed 24 hours post-editing and 10 µM Y-27632 was removed 48 hours after. The NR2F2 synthetic sgRNAs were purchased from Synthego with chemically-modified nucleotides at the three terminal positions at both the 5' and 3' ends. Modified nucleotides contained 2'-O-methyl 3'-phosphorothioate.

3D network formation from hPSC-derived endothelial cells. hPSC-derived artery endothelial cells were frozen in 90% FBS+10% DMSO, thawed and cultured in EGM2 medium for 3 days (supplemented with 2 µM Thiazovivin for the first 24 hours). EGM2 media was refreshed every 24 hours for the 3-day period. After 3 days of expansion, hPSC-derived artery endothelial cells were used to produce 3D endothelial networks as described previously (Kurokawa et al., 2017). In brief, hPSC-derived endothelial cells and normal human lung fibroblasts (NHLFs) were respectively dissociated (Trysin-EDTA, 0.05%); mixed at a 1:2 ratio; and resuspended in a 3D fibrin gel for 7 days, during which they were cultured with EGM2 medium. Images were taken after 7 days of network formation.

Endothelial sprouting from hPSC-derived endothelial cells. hPSC-derived artery endothelial cells were dissociated and plated in AggreWell plates to generate spheres that each contained ~1000 cells. Subsequently, they were treated with 25 ng/mL VEGF and FGF2 for 24 hours and images of sprouts that emerges from the spheres were taken.

Shear stress-induced polarization of hPSC-derived endothelial cells. hPSC-derived day-3 artery endothelial cells were cultured with EGM2 medium for 24 hours, either in static culture (standard conditions) or a rotator (shear stress conditions). Shear stress conditions were described previously (Poduri et al., 2017). After 24 hours of static or shear stress conditions, immunostaining for the Golgi body marker GOLPH4 was conducted and the angle of the Golgi relative to the nucleus was quantified.

Subrenal transplantation of hPSC-derived endothelial cells. Day 3 GFP+ hiPSC-derived artery endothelial cells (500,000-550,000 cells, in 2 µL of Matrigel) was injected under the renal capsule of 4-week-old NSG mice. After one month, the mice were sacrificed and the kidneys were collected, and imaged using stereomicroscope and two-photon microscopy.

In utero transplantation of hPSC-derived endothelial cells. Day 3 GFP+ hiPSC-derived artery endothelial cells (10,000 cells, in 2 µL of F12 media) were injected into E11.5 rat embryos via in utero transplantation. After two days, the pregnant dam was sacrificed and the rat embryos were collected for confocal imaging.

Expansion of cord blood HSPCs. Enriched populations of $CD34^+$ cord blood HSPCs (StemExpress) were thawed, counted for live cells, and then plated in HSPC expansion media, which comprised StemSpan II serum-free basal media (StemCell Technologies)+20 ng/mL SCF (R&D Systems)+50 ng/mL TPO (R&D Systems)+20 ng/mL FLT3LG (R&D Systems)+20 ng/mL IL6 (R&D Systems)+75 nM UM171 (ApexBio)+750 nM SR1 (Cellagen Technologies). Immediately after thawing, cell concentration in expansion media was adjusted to ~250,000 viable cells/mL and then 200 µL of the cell suspension was deposited into each well of an untreated 96-well U-bottom plate (i.e., ~50,000 cells were plated per individual well). Human cord blood HSPC populations were cultured for 3 days in HSPC expansion media before FACS purification to isolate the $CD34^+$ $CD90^+$ and $CD34'CD90^-$ subpopulations for qPCR comparisons with hESC-derived HSC-like cells.

Methylcellulose differentiation of hPSC-derived HSC-like cells. Cultures of hPSC-derived day 9 HSC-like cells were dissociated using TrypLE Express (Thermo Fisher), triturated and then diluted 1:10 with DMEM/F12 before pelleting by centrifugation (500 g for 5 minutes). Cells were resuspended in IMDM+20% FBS at a concentration of 8,000 cells/mL. 400 µL of cell suspension (~3,200 cells) was added to 4 mL of MethoCult Enriched (StemCell Technologies, 04445). The tube of MethoCult was vortexed thoroughly (in order to evenly resuspend the cells) and incubated at room temperature for 5 minutes to allow bubbles to rise to the top. Using a blunt end needle attached to a syringe, 1 mL of the resultant mixture (~800 cells) was pipetted into three separate 35 mm dishes (StemCell Technologies, 27100). These smaller dishes were placed in a 15-cm dish containing a 10-cm dish with 25 mL of water to prevent MethoCult medium from drying out. After 10 days of culture, colonies were counted and scored according to manufacturers' guidelines (StemCell Technologies).

Erythroid differentiation of hPSC-derived HSC-like cells. hPSC-derived day 9 HSC-like cells were differentiated into erythroid cells largely as previously described (Dulmovits et al., 2016). In brief, erythroid differentiation was conducted in StemSpan SFEM II base medium was supplemented with 100 U/mL penicillin-streptomycin, 10 ng/mL SCF, 1 ng/mL IL-3 (PeproTech, Rocky Hill, NJ, USA), 3 U/mL erythropoietin (eBiosciences, San Diego, CA, USA), 200 µg/mL transferrin (Sigma-Aldrich, St. Louis, MO, USA), 3% human serum type AB (heat-inactivated from Atlanta Biologicals, Flowery Branch, GA, USA), 2% human plasma (umbilical cord blood), 10 µg/mL insulin (Sigma-Aldrich, St. Louis, MO, USA), and 3 U/mL heparin (Sigma-Aldrich, St. Louis, MO, USA). In the first phase of erythroid differentiation (day 0-7), cells were cultured at $1\times10^5$ cells/mL. In the second phase, d7-10, cells were maintained at $1\times10^5$ cells/mL, and IL-3 was removed from the culture. In the third phase, day 11-14, cells were cultured at $1\times10^6$ cells/mL, and transferrin was increased to 1 mg/mL within the culture medium.

Megakaryocyte differentiation of hPSC-derived HSC-like cells. hPSC-derived day 9 HSC-like cells were differentiated into megakaryocytes. 10,000 cells were seeded in one well of a 96-well U-bottom plate in StemSpan II basal media (StemCell Technologies)+1% megakaryocyte expansion supplement (StemCell Technologies). Half the media was changed every 3 days, and megakaryocyte differentiation was conducted for 2 weeks.

T-cell differentiation of hPSC-derived HSC-like cells. hPSC-derived day 9 HSC-like cells were differentiated into T cells using two separate systems. First, they were cocultured as monolayers with DLL1/DLL4-expressing 10T1/2 fibroblasts for 2 weeks, as previously described (Ando et al., 2015). Second, they were cocultured as 3D aggregates with DLL4-expressing MS5 fibroblasts for 3 weeks, as previously described (Montel-Hagen et al., 2019).

Preparation of hPSC-derived HSC-like cells for transplantation. Cultures of day 9 HSC-like cells were dissociated using either TrypLE Express or Accutase (both from Thermo Fisher), triturated and diluted 1:10 in DMEM/F12 before pelleting by centrifugation (5 mins). Subsequently, cells were resuspended in a small volume of IMDM with 20% FBS and then counted by hemocytometer. After counting, cells were adjusted to a concentration of ~105-10 cells/30 µL for intrahepatic or intrafemoral transplantation (see below).

Intrahepatic transplantation of hPSC-derived HSC-like cells. Immunodeficient NOD-SCID Ilr2g$^{-/-}$ mice (hereafter referred to as NSG mice; obtained from The Jackson Laboratory) were used as recipients for human HSPC intrahepatic transplants. 2- to 4-day-old NSG neonates were irradiated (100 rads) and then were intrahepatically transplanted with 30 µL of HSPCs in IMDM+20% FBS media using a 27-gauge syringe (BD Tuberculin Syringe, catalog no. 305620). During intrahepatic transplantation, care was taken to inject mice directly into the liver lobule (between the lungs and the milk spot). Subsequently, transplanted neonates were rubbed in cage bedding and then returned to their cages.

Intrafemoral transplantation of hPSC-derived HSC-like cells. Immunodeficient adult NOD-C57BL/6 SCID Il2rg$^{-/-}$ Kit$^{W41/W41}$ mice (NBSGW, obtained from The Jackson Laboratory) (McIntosh et al., 2015) were used as recipients for human HSPC intrafemoral transplants. Non-irradiated, 6-10 week old NBSGW mice were anesthetized with isoflurane. A 27-gauge syringe was used to drill into the right femur starting at the knee-cap and moving proximal into the bone marrow parallel with the femur. The needle was removed and another 27-gauge syringe with 30 µL of HSPCs (in IMDM+20% FBS media) was inserted into the previously drilled hole, and the cells were slowly injected directly into the femur's bone marrow cavity. Subsequently, transplanted mice were returned to their cages where they were monitored as they recovered under a heat lamp.

REFERENCES

Aguilo, F., Avagyan, S., Labar, A., Sevilla, A., Lee, D.-F., Kumar, P., Lemischka, I. R., Zhou, B. Y., and Snoeck, H.-W. (2011). Prdm16 is a physiologic regulator of hematopoietic stem cells. Blood 117, 5057-5066.

Ando, M., Nishimura. T., Yamazaki. S., Yamaguchi, T., Kawana-Tachikawa, A., Hayama, T., Nakauchi, Y., Ando, J., Ota, Y., Takahashi, S., et al. (2015). A Safeguard System for Induced Pluripotent Stem Cell-Derived Rejuvenated T Cell Therapy. Stem Cell Reports.

Ang, L., Tan, A., Autio, M., Goh, S., Choo, S., Lee, K., Tan, J., Pan, B., Lee, J., Lum, J., et al. (2018). A roadmap for human liver differentiation from pluripotent stem cells. Cell Reports 22, 2190-2205.

Aranguren, X. L., Agirre, X., Beerens, M., Coppiello, G., Uriz, M., Vandersmissen, I., Benkheil, M., Panadero, J., Aguado, N., Pascual-Montano, A., et al. (2013). Unraveling a novel transcription factor code determining the human arterial-specific endothelial cell signature. Blood 122, 3982-3992.

Auger. F. A., Gibot, L., and Lacroix, D. (2013). The pivotal role of vascularization in tissue engineering. Annual review of biomedical engineering 15, 177-200.

Augustin, H. G., and Koh, G. Y. (2017). Organotypic vasculature: From descriptive heterogeneity to functional pathophysiology. Science 357.

Baratchi, S., Khoshmanesh, K., Woodman, O. L., Potocnik, S., Peter, K., and McIntyre, P. (2017). Molecular Sensors of Blood Flow in Endothelial Cells. Trends in Molecular Medicine 23, 850-868. Behrens, K., Maul, K., Tekin, N., Kriebitzsch, N., Indenbirken, D., Prassolov, V., Müller, U., Serve, H., Cammenga, J., and Stocking, C. (2017). RUNX1 cooperates with FLT3-ITD to induce leukemia. The Journal of experimental medicine 214, 737-752.

Bertrand, J. Y., Chi, N. C., Santoso, B., Teng, S., Stainier, D. Y. R., and Traver, D. (2010). Haematopoietic stem cells derive directly from aortic endothelium during development. Nature.

Boisset, J.-C., Clapes, T., Klaus, A., Papazian, N., Onderwater, J., Mommaas-Kienhuis, M., Cupedo, T., and Robin, C. (2015). Progressive maturation toward hematopoietic stem cells in the mouse embryo aorta. Blood 125, 465-469.

Boisset, J.-C., van Cappellen, W., Andrieu-Soler, C., Galjart, N., Dzierzak, E., and Robin, C. (2010). In vivo imaging of haematopoietic cells emerging from the mouse aortic endothelium. Nature 464, 116-120.

Boitano, A. E., Wang, J., Romeo, R., Bouchez, L. C., Parker. A. E., Sutton. S. E., Walker, J. R., Flaveny, C. A., Perdew, G. H., Denison, M. S., et al. (2010). Aryl hydrocarbon receptor antagonists promote the expansion of human hematopoietic stem cells. Science 329, 1345-1348.

Bonkhofer, F., Rispoli, R., Pinheiro, P., Krecsmarik, M., Schneider-Swales, J., Tsang, I. H. C., de Bruijn, M., Monteiro, R., Peterkin, T., and Patient, R. (2019). Blood stem cell-forming haemogenic endothelium in zebrafish derives from arterial endothelium. Nature Communications, 1-14.

Chen, J. Y., Miyanishi, M., Wang, S. K., Yamazaki, S., Sinha, R., Kao, K. S., Seita, J., Sahoo, D., Nakauchi, H., and Weissman, I. L. (2016). Hoxb5 marks long-term haematopoietic stem cells and reveals a homogenous perivascular niche. Nature 530, 223-227.

Cheung, C., Bernardo, A. S., Trotter, M. W. B., Pedersen, R. A., and Sinha, S. (2012). Generation of human vascular smooth muscle subtypes provides insight into embryological origin-dependent disease susceptibility. Nat Biotechnol.

Choi, K., Kennedy, M., Kazarov, A., Papadimitriou, J. C., and Keller, G. (1998). A common precursor for hematopoietic and endothelial cells. Development 125, 725-732.

Chong, D. C., Koo, Y., Xu, K., Fu, S., and Cleaver, O. (2011). Stepwise arteriovenous fate acquisition during mammalian vasculogenesis. Developmental Dynamics 240, 2153-2165.

Christensen, J. L., Wright, D. E., Wagers, A. J., and Weissman, I. L. (2004). Circulation and chemotaxis of fetal hematopoietic stem cells. PLoS Biol 2, E75.

Chuikov, S., Levi, B. P., Smith, M. L., and Morrison, S. J. (2010). Prdm16 promotes stem cell maintenance in multiple tissues, partly by regulating oxidative stress. Nature Cell Biology 12, 999-1006.

Ciau-Uitz, A., Pinheiro, P., Kirmizitas, A., Zuo, J., and Patient, R. (2013). VEGFA-dependent and -independent pathways synergise to drive Scl expression and initiate programming of the blood stem cell lineage in Xenopus. Development 140, 2632-2642.

Clarke, R. L., Yzaguirre, A. D., Yashiro-Ohtani, Y., Bondue, A., Blanpain, C., Pear, W. S., Speck, N. A., and Keller, G. (2013). The expression of Sox17 identifies and regulates haemogenic endothelium. Nature Cell Biology 15, 502-510.

Clements. W. K., and Traver, D. (2013). Signalling pathways that control vertebrate haematopoietic stem cell specification. Nat Rev Immunol 13, 336-348.

Corada, M., Orsenigo, F., Morini. M. F., Pitulescu, M. E., Bhat, G., Nyqvist, D., Breviario, F., Conti, V., Briot, A., Iruela-Arispe, M. L., et al. (2013). Sox17 is indispensable for acquisition and maintenance of arterial identity. Nature Communications 4, 2609.

Coultas, L., Chawengsaksophak, K., and Rossant, J. (2005). Endothelial cells and VEGF in vascular development. Nature 438, 937-945.

Davis, R. P., Ng, E. S., Costa, M., Mossman, A. K., Sourris, K., Elefanty, A. G., and Stanley, E. G. (2008). Targeting a GFP reporter gene to the MIXL1 locus of human embryonic stem cells identifies human primitive streak-like cells and enables isolation of primitive hematopoietic precursors. Blood 111, 1876-1884.

de Bruijn, M. F., Speck, N. A., Peeters, M. C., and Dzierzak, E. (2000). Definitive hematopoietic stem cells first develop within the major arterial regions of the mouse embryo. EMBO J 19, 2465-2474.

Deschamps, J., and Duboule, D. (2017). Embryonic timing, axial stem cells, chromatin dynamics, and the Hox clock. Genes & Development 31, 1406-1416.

Diaz, M. F., Li, N., Lee, H. J., Adamo, L., Evans, S. M., Willey, H. E., Arora, N., Torisawa, Y.-s., Vickers, D. A., Morris, S. A., et al. (2015). Biomechanical forces promote blood development through prostaglandin E2 and the cAMP-PKA signaling axis. The Journal of experimental medicine 212, 665-680.

Ditadi, A., Sturgeon, C. M., and Keller, G. (2017). A view of human haematopoietic development from the Petri dish. Nature Reviews Molecular Cell Biology 18, 56-67.

Ditadi, A., Sturgeon. C. M., Tober, J., Awong, G., Kennedy, M., Yzaguirre, A. D., Azzola, L., Ng, E. S., Stanley, E. G., French, D. L., et al. (2015). Human definitive haemogenic endothelium and arterial vascular endothelium represent distinct lineages. Nature Cell Biology 17, 580-591.

Dou, D. R., Calvanese, V., Sierra, M. I., Nguyen, A. T., Minasian, A., Saarikoski, P., Sasidharan, R., Ramirez, C. M., Zack, J. A., Crooks, G. M., et al. (2016). Medial HOXA genes demarcate haematopoietic stem cell fate during human development. Nature Cell Biology 18, 595-606.

Duarte, A., Hirashima, M., Benedito, R., Trindade, A., Diniz, P., Bekman, E., Costa, L., Henrique, D., and Rossant, J. (2004). Dosage-sensitive requirement for mouse DlI4 in artery development. Genes & Development 18, 2474-2478.

Dulmovits, B. M., Appiah-Kubi, A. O., Papoin, J., Hale, J., He, M., Al-Abed, Y., Didier, S., Gould, M., Husain-Krautter, S., Singh, S. A., et al. (2016). Pomalidomide reverses γ-globin silencing through the transcriptional reprogramming of adult hematopoietic progenitors. Blood 127, 1481-1492.

Dzierzak, E., and Speck, N. A. (2008). Of lineage and legacy: the development of mammalian hematopoietic stem cells. Nat Immunol 9, 129-136.

Eilken, H. M., Nishikawa, S.-I., and Schroeder, T. (2009). Continuous single-cell imaging of blood generation from haemogenic endothelium. Nature 457, 896-900.

Ema, H., and Nakauchi, H. (2000). Expansion of hematopoietic stem cells in the developing liver of a mouse embryo. Blood 95, 2284-2288.

Fares. I., Chagraoui, J., Gareau, Y., Gingras, S., Ruel, R., Mayotte. N., Csaszar, E., Knapp, D. J. H. F., Miller, P., Ngom, M., et al. (2014). Pyrimidoindole derivatives are agonists of human hematopoietic stem cell self-renewal. Science 345, 1509-1512.

Fish, J. E., and Wythe, J. D. (2015). The molecular regulation of arteriovenous specification and maintenance. Developmental Dynamics 244, 391-409.

Gale, N. W., Dominguez, M. G., Noguera, I., Pan, L., Hughes, V., Valenzuela, D. M., Murphy, A. J., Adams, N. C., Lin, H. C., Holash, J., et al. (2004). Haploinsufficiency of delta-like 4 ligand results in embryonic lethality due to major defects in arterial and vascular development. Proceedings of the National Academy of Sciences of the United States of America 101, 15949-15954.

Gale, R. P., and Armitage, J. O. (2018). Are We Prepared for Nuclear Terrorism? New England Journal of Medicine 378, 1246-1254.

Gama-Norton, L., Ferrando, E., Ruiz-Herguido, C., Liu, Z., Liu, Z., Guiu, J., Islam, A. B. M. M. K., Lee, S.-U., Yan, M., Guidos, C. J., et al. (2015). Notch signal strength controls cell fate in the haemogenic endothelium. Nature Communications 6, 8510.

Gaspar, H. B., Qasim, W., Davies, E. G., Rao, K., Amrolia, P. J., and Veys, P. (2013). How I treat severe combined immunodeficiency. Blood 122, 3749-3758.

Gazit, R., Garrison, B. S., Rao, T. N., Shay, T., Costello, J., Ericson, J., Kim, F., Collins, J. J., Regev, A., Wagers, A. J., et al. (2013). Transcriptome analysis identifies regulators of hematopoietic stem and progenitor cells. Stem Cell Reports 1, 266-280.

Gekas, C., Dieterlen-Lièvre, F., Orkin, S. H., and Mikkola, H. K. A. (2005). The placenta is a niche for hematopoietic stem cells. Developmental Cell 8, 365-375.

Goessling, W., North, T. E., Loewer, S., Lord, A. M., Lee, S., Stoick-Cooper, C. L., Weidinger, G., Puder, M., Daley, G. Q., Moon, R. T., et al. (2009). Genetic interaction of PGE2 and Wnt signaling regulates developmental specification of stem cells and regeneration. Cell 136, 1136-1147.

Graf, T., and Enver, T. (2009). Forcing cells to change lineages. Nature 462, 587-594.

Herzog, Y., Kalcheim, C., Kahane, N., Reshef, R., and Neufeld, G. (2001). Differential expression of neuropilin-1 and neuropilin-2 in arteries and veins. Mech Dev 109, 115-119.

His, W. (1900). Lecitoblast und Angioblast der Wirbefthiere: Histogenetische Studien (Leipzig, Germany: B. G. Teubner).

Hong, C. C., Peterson, Q. P., Hong, J.-Y., and Peterson, R. T. (2006). Artery/vein specification is governed by opposing phosphatidylinositol-3 kinase and MAP kinase/ERK signaling. Curr Biol 16, 1366-1372.

Huber, T. L., Kouskoff, V., Fehling, H. J., Palis, J., and Keller, G. (2004). Haemangioblast commitment is initiated in the primitive streak of the mouse embryo. Nature 432, 625-630.

Hügle, T., and Daikeler, T. (2010). Stem cell transplantation for autoimmune diseases. Haematologica 95, 185-188.

Iimura, T., and Pourquie, O. (2006). Collinear activation of Hoxb genes during gastrulation is linked to mesoderm cell ingression. Nature 442, 568-571.

Ikeda, K., Uchida, N., Nishimura, T., White, J., Martin, R. M., Nakauchi, H., Sebastiano, V., Weinberg, K. I., and Porteus, M. H. (2018). Efficient scarless genome editing in human pluripotent stem cells. Nature Methods 15, 1045-1047.

Inlay, M. A., Serwold, T., Mosley, A., Fathman, J. W., Dimov, I. K., Seita, J., and Weissman, I. L.

(2014). Identification of Multipotent Progenitors that Emerge Prior to Hematopoietic Stem Cells in Embryonic Development. Stem Cell Reports 2, 457-472.

Ivanovs, A., Rybtsov, S., Anderson. R. A., Turner, M. L., and Medvinsky, A. (2014). Identification of the niche and phenotype of the first human hematopoietic stem cells. Stem Cell Reports 2, 449-456.

Ivanovs, A., Rybtsov, S., Ng, E. S., Stanley, E. G., Elefanty, A. G., and Medvinsky, A. (2017). Human haematopoietic stem cell development: from the embryo to the dish. Development 144, 2323-2337.

Johnson, T. E., Umbenhauer, D. R., Hill, R., Bradt, C., Mueller, S. N., Levine, E. M., and Nichols, W. W. (1992). Karyotypic and phenotypic changes during in vitro aging of human endothelial cells. Journal of Cellular Physiology 150, 17-27.

Karnezis, T., Farnsworth. R. H., Harris, N. C., Williams, S. P., Caesar, C., Byrne, D. J., Herle, P., Macheda, M. L., Shayan, R., Zhang, Y.-F., et al. (2019). CCL27/CCL28-CCR10 Chemokine Signaling Mediates Migration of Lymphatic Endothelial Cells. Cancer Research 79, 1558-1572.

Kiefer, F., and Siekmann, A. F. (2011). The role of chemokines and their receptors in angiogenesis. Cellular and Molecular Life Sciences 68, 2811-2830.

Kieusseian, A., Brunet de la Grange, P., Burlen-Defranoux, O., Godin, I., and Cumano, A. (2012). Immature hematopoietic stem cells undergo maturation in the fetal liver. Development 139, 3521-3530.

Kim, I., Saunders. T. L., and Morrison. S. J. (2007). Sox17 dependence distinguishes the transcriptional regulation of fetal from adult hematopoietic stem cells. Cell 130, 470-483.

Kirmizitas, A., Meiklejohn, S., Ciau-Uitz, A., Stephenson, R., and Patient, R. (2017). Dissecting BMP signaling input into the gene regulatory networks driving specification of the blood stem cell lineage. Proceedings of the National Academy of Sciences of the United States of America 114, 5814-5821.

Kissa, K., and Herbomel, P. (2010). Blood stem cells emerge from aortic endothelium by a novel type of cell transition. Nature.

Komorowska, K., Doyle, A., Wahlestedt, M., Subramaniam, A., Debnath, S., Chen, J., Soneji, S., Van Handel, B., Mikkola, H. K. A., Miharada, K., et al. (2017). Hepatic Leukemia Factor Maintains Quiescence of Hematopoietic Stem Cells and Protects the Stem Cell Pool during Regeneration. Cell Reports 21, 3514-3523.

Krebs, L. T., Shutter, J. R., Tanigaki, K., Honjo, T., Stark, K. L., and Gridley, T. (2004). Haploinsufficient lethality and formation of arterovenous malformations in Notch pathway mutants. Genes & Development 18, 2469-2473.

Kumano, K., Chiba, S., Kunisato, A., Sata, M., Saito, T., Nakagami-Yamaguchi, E., Yamaguchi, T., Masuda, S., Shimizu, K., Takahashi, T., et al. (2003). Notch1 but not Notch2 is essential for generating hematopoietic stem cells from endothelial cells. Immunity 18, 699-711.

Kumaravelu, P., Hook, L., Morrison, A. M., Ure, J., Zhao, S., Zuyev, S., Ansell, J., and Medvinsky, A. (2002). Quantitative developmental anatomy of definitive haematopoietic stem cells/long-term repopulating units (HSC/RUs): role of the aorta-gonad-mesonephros (AGM) region and the yolk sac in colonisation of the mouse embryonic liver. Development 129, 4891-4899.

Kurokawa, Y. K., Yin, R. T., Shang, M. R., Shirure, V. S., Moya. M. L., and George, S. C. (2017). Human Induced Pluripotent Stem Cell-Derived Endothelial Cells for Three-Dimensional Microphysiological Systems. Tissue engineering Part C, Methods 23, 474-484.

Lancrin, C., Mazan, M., Stefanska, M., Patel, R., Lichtinger, M., Costa, G., Vargel, O., Wilson, N. K., Möröy, T., Bonifer, C., et al. (2012). GFI1 and GFI1B control the loss of endothelial identity of hemogenic endothelium during hematopoietic commitment. Blood 120, 314-322.

Lancrin, C., Sroczynska, P., Stephenson, C., Allen, T., Kouskoff, V., and Lacaud, G. (2009). The haemangioblast generates haematopoietic cells through a haemogenic endothelium stage. Nature 457, 892-895.

Lawson, K. A., Meneses, J. J., and Pedersen, R. A. (1991). Clonal analysis of epiblast fate during germ layer formation in the mouse embryo. Development 113, 891-911.

Lawson, N. D., Scheer, N., Pham, V. N., Kim, C. H., Chitnis, A. B., Campos-Ortega, J. A., and Weinstein, B. M. (2001). Notch signaling is required for arterial-venous differentiation during embryonic vascular development. Development 128, 3675-3683.

Lawson, N. D., Vogel, A. M., and Weinstein, B. M. (2002). sonic hedgehog and vascular endothelial growth factor act upstream of the Notch pathway during arterial endothelial differentiation. Developmental Cell 3, 127-136.

Leung, A., Ciau-Uitz, A., Pinheiro, P., Monteiro, R., Zuo, J., Vyas, P., Patient, R., and Porcher, C. (2013). Uncoupling VEGFA Functions in Arteriogenesis and Hematopoietic Stem Cell Specification. Developmental Cell 24, 144-158.

Lian, X., Bao, X., Al-Ahmad, A., Liu, J., Wu, Y., Dong, W., Dunn, K. K., Shusta, E. V., and Palecek, S. P. (2014). Efficient Differentiation of Human Pluripotent Stem Cells to Endothelial Progenitors via Small-Molecule Activation of WNT Signaling. Stem Cell Reports 3, 804-816.

Lim, W. A., and June, C. H. (2017). The Principles of Engineering Immune Cells to Treat Cancer. Cell 168, 724-740.

US 12,680,077 B2

71

72

Lis. R., Karrasch, C. C., Poulos, M. G., Kunar, B., Redmond, D., Duran, J. G. B., Badwe, C. R., Schachterle, W., Ginsberg, M., Xiang, J., et al. (2017). Conversion of adult endothelium to immunocompetent haematopoietic stem cells. Nature 18, 1111.

Lizama, C. O., Hawkins, J. S., Schmitt, C. E., Bos, F. L., Zape, J. P., Cautivo, K. M., Borges Pinto, H., Rhyner, A. M., Yu, H., Donohoe, M. E., et al. (2015). Repression of arterial genes in hemogenic endothelium is sufficient for haematopoietic fate acquisition. Nature Communications 6, 7739.

Loghmani, H., and Conway, E. M. (2018). Exploring traditional and nontraditional roles for thrombomodulin. Blood 132, 148-158.

Loh, K. M., Ang, L. T., Zhang, J., Kumar, V., Ang, J., Auyeong, J. Q., Lee, K. L., Choo, S. H., Lim, C Y. Y., Nichane, M., et al. (2014). Efficient Endoderm Induction from Human Pluripotent Stem Cells by Logically Directing Signals Controlling Lineage Bifurcations. Cell Stem Cell 14, 237-252.

Loh, K. M., Chen. A., Koh, P. W., Deng, T. Z., Sinha, R., Tsai, J. M., Barkal, A. A., Shen, K. Y., Jain, R., Morganti, R. M., et al. (2016). Mapping the Pairwise Choices Leading from Pluripotency to Human Bone, Heart, and Other Mesoderm Cell Types. Cell 166, 451-467.

Luca, V. C., Jude, K. M., Pierce, N. W., Nachury, M. V., Fischer, S., and Garcia, K. C. (2015). Structural biology. Structural basis for Notch1 engagement of Delta-like 4. Science 347, 847-853.

Majeti, R., Park, C. Y., and Weissman, I. L. (2007). Identification of a hierarchy of multipotent hematopoietic progenitors in human cord blood. Cell Stem Cell 1, 635-645.

Martin, R. M., Ikeda. K., Cromer, M. K., Uchida, N., Nishimura, T., Romano, R., Tong, A. J., Lemgart, V. T., Camarena, J., Pavel-Dinu, M., et al. (2019). Highly Efficient and Marker-free Genome Editing of Human Pluripotent Stem Cells by CRISPR-Cas9 RNP and AAV6 Donor-Mediated Homologous Recombination. Cell Stem Cell 24, 821-828.e825.

McIntosh, B. E., Brown, M. E., Duffin, B. M., Maufort, J. P., Vereide, D. T., Slukvin, I. I., and Thomson, J. A. (2015). Nonirradiated NOD,B6.SCID Il2rγ−/− KitW41/W41 (NBSGW) Mice Support Multilineage Engraftment of Human Hematopoietic Cells. Stem Cell Reports 4, 171-180.

Medvinsky, A., Rybtsov, S., and Taoudi, S. (2011). Embryonic origin of the adult hematopoietic system: advances and questions. Development 138, 1017-1031.

Monteiro, R., Pinheiro, P., Joseph, N., Peterkin, T., Koth, J., Repapi, E., Bonkhofer, F., Kirmizitas, A., and Patient, R. (2016). Transforming Growth Factor β Drives Hemogenic Endothelium Programming and the Transition to Hematopoietic Stem Cells. Developmental Cell 38, 358-370.

Montel-Hagen, A., Seet, C. S., Li, S., Chick, B., Zhu, Y., Chang, P., Tsai, S., Sun, V., Lopez, S., Chen, H.-C., et al. (2019). Organoid-Induced Differentiation of Conventional T Cells from Human Pluripotent Stem Cells. Cell Stem Cell, 1-23.

Mukouyama, Y.-s., Hara, T., Xu, M.-j., Tamura, K., Donovan, P. J., Kim, H.-j., Kogo, H., Tsuji, K., Nakahata, T., and Miyajima, A. (1998). In Vitro Expansion of Murine Multipotential Hematopoietic Progenitors from the Embryonic Aorta-Gonad-Mesonephros Region. Immunity 8, 105-114.

Murray, P. D. F. (1932). The development in vitro of the blood of the early chick embryo. Philosophical transactions of the Royal Society of London Series B, Biological sciences 111, 497-521.

Ng, E. S., Azzola, L., Bruveris, F. F., Calvanese, V., Phipson, B., Vlahos, K., Hirst, C., Jokubaitis, V. J., Yu, Q. C., Maksimovic, J., et al. (2016). Differentiation of human embryonic stem cells to HOXA+ hemogenic vasculature that resembles the aorta-gonad-mesonephros. Nature Biotechnology, 1-47.

Nishikawa, S. (2012). Hemangioblast: an in vitro phantom. Wiley Interdiscip Rev Dev Biol 1, 603-608.

Notta, F., Doulatov, S., Laurenti, E., Poeppi, A., Jurisica, I., and Dick, J. E. (2011). Isolation of single human hematopoietic stem cells capable of long-term multilineage engraftment. Science 333, 218-221.

Novosel, E. C., Kleinhans, C., and Kluger, P. J. (2011). Vascularization is the key challenge in tissue engineering. Advanced Drug Delivery Reviews 63, 300-311.

Olmer, R., Engels, L., Usman, A., Menke, S., Malik, M. N. H., Pessler, F., GShring, G., Bornhorst, D., Bolten, S., Abdelilah-Seyfried. S., et al. (2018). Differentiation of Human Pluripotent Stem Cells into Functional Endothelial Cells in Scalable Suspension Culture. Stem Cell Reports 10, 1657-1672.

Papayannopoulou, T., Craddock, C., Nakamoto, B., Priestley, G. V., and Wolf, N. S. (1995). The VLA4/VCAM-1 adhesion pathway defines contrasting mechanisms of lodgement of transplanted murine hemopoietic progenitors between bone marrow and spleen. Proc Natl Acad Sci USA 92, 9647-9651.

Papayannopoulou, T., and Nakamoto, B. (1993). Peripheralization of hemopoietic progenitors in primates treated with anti-VLA4 integrin. Proceedings of the National Academy of Sciences 90, 9374-9378.

Park, M. A., Kumar, A., Jung, H. S., Uenishi, G., Moskvin, O. V., Thomson, J. A., and Slukvin, I. I. (2018). Activation of the Arterial Program Drives Development of Definitive Hemogenic Endothelium with Lymphoid Potential. Cell Reports 23, 2467-2481.

Passweg, J. R., Baldomero, H., Bader, P., Bonini, C., Duarte, R. F., Dufour, C., Gennery, A., Kröger, N., Kuball, J., Lanza, F., et al. (2017). Use of haploidentical stem cell transplantation continues to increase: the 2015 European Society for Blood and Marrow Transplant activity survey report. Bone Marrow Transplantation 52, 811-817.

Patsch, C., Challet-Meylan, L., Thoma, E. C., Urich, E., Heckel, T., O' Sullivan, J. F., Grainger, S. J., Kapp, F. G., Sun, L., Christensen, K., et al. (2015). Generation of vascular endothelial and smooth muscle cells from human pluripotent stem cells. Nature Cell Biology 17, 994-1003.

Pereira, F. A., Qiu, Y., Zhou, G., Tsai, M. J., and Tsai, S. Y. (1999). The orphan nuclear receptor COUP-TFII is required for angiogenesis and heart development. Genes & Development 13, 1037-1049.

Pijuan Sala, B., Griffiths, J. A., Guibentif, C., Hiscock, T. W., Jawaid, W., Calero-Nieto, F. J., Mulas, C., Ibarra-Soria, X., Tyser, R. C. V., Ho, D. L. L., et al. (2019). A single-cell molecular map of mouse gastrulation and early organogenesis. Nature, 1-25.

Poduri, A., Chang, A. H., Raftrey, B., Rhee, S., Van, M., and Red-Horse, K. (2017). Endothelial cells respond to the direction of mechanical stimuli through SMAD signaling to regulate coronary artery size. Development 144, 3241-3252.

Potente, M., and Mäkinen, T. (2017). Vascular heterogeneity and specialization in development and disease. Nature Reviews Molecular Cell Biology 18, 477-494.

Rafii, S., Butler, J. M., and Ding, B.-S. (2016). Angiocrine functions of organ-specific endothelial cells. Nature 529, 316-325.

Reid, J. C., Tanasijevic, B., Golubeva, D., Boyd, A. L., Porras, D. P., Collins, T. J., and Bhatia, M. (2018). CXCL12/CXCR4 Signaling Enhances Human PSC-Derived Hematopoietic Progenitor&nbsp; Function and Overcomes Early In&nbsp;Vivo Transplantation Failure. Stem Cell Reports 10, 1625-1641.

Riddell, J., Gazit, R., Garrison, B. S., Guo, G., Saadatpour, A., Mandal, P. K., Ebina, W., Volchkov, P., Yuan, G.-C., Orkin, S. H., et al. (2014). Reprogramming committed murine blood cells to induced hematopoietic stem cells with defined factors. Cell 157, 549-564.

Robert-Moreno, A., Guiu, J., Ruiz-Herguido, C., López, M. E., Inglés-Esteve, J., Riera, L., Tipping, A., Enver. T., Dzierzak. E., Gridley, T., et al. (2008). Impaired embryonic haematopoiesis yet normal arterial development in the absence of the Notch ligand Jagged1. The EMBO Journal 27, 1886-1895.

Sabin, F. R. (1917). Preliminary note on the differentiation of angioblasts and the method by which they produce blood-vessels, blood-plasma and red blood-cells as seen in the living chick. The Anatomical Record 13, 199-204.

Sakamoto, Y., Hara, K., Kanai-Azuma, M., Matsui, T., Miura, Y., Tsunekawa, N., Kurohmaru, M., Saijoh, Y., Koopman, P., and Kanai, Y. (2007). Redundant roles of Sox17 and Sox18 in early cardiovascular development of mouse embryos. Biochem Biophys Res Commun 360, 539-544.

Seo, S., Fujita, H., Nakano, A., Kang, M., Duarte, A., and Kume, T. (2006). The forkhead transcription factors, Foxc1 and Foxc2, are required for arterial specification and lymphatic sprouting during vascular development. Developmental Biology 294, 458-470.

Shalaby, F., Rossant, J., Yamaguchi, T. P., Gertsenstein, M., Wu, X. F., Breitman, M. L., and Schuh, A. C. (1995). Failure of blood-island formation and vasculogenesis in Flk-1-deficient mice. Nature 376, 62-66.

Shutter, J. R., Scully. S., Fan, W., Richards, W. G., Kitajewski, J., Deblandre, G. A., Kintner, C. R., and Stark, K. L. (2000). Dll4, a novel Notch ligand expressed in arterial endothelium. Genes & Development 14, 1313-1318.

Slukvin, I. I., and Uenishi, G. I. (2018). Arterial Identity Of Hemogenic Endothelium: A Key To Unlock Definitive Hematopoietic Commitment In hPSC Cultures. Experimental Hematology.

Sriram. G., Tan, J. Y., Islam. I., Rufaihah. A. J., and Cao, T. (2015). Efficient differentiation of human embryonic stem cells to arterial and venous endothelial cells under feeder- and serum-free conditions. Stem Cell Research & Therapy. 1-17.

Sugimura, R., Jha, D. K., Han, A., Soria-Valles, C., da Rocha, E. L., Lu, Y.-F., Goettel, J. A., Serrao, E., Rowe, R. G., Malleshaiah, M., et al. (2017). Haematopoietic stem and progenitor cells from human pluripotent stem cells. Nature 545, 432-438.

Sugiyama, T., Kohara, H., Noda, M., and Nagasawa, T. (2006). Maintenance of the hematopoietic stem cell pool by CXCL12-CXCR4 chemokine signaling in bone marrow stromal cell niches. Immunity 25, 977-988.

Swiers, G., Baumann, C., O' Rourke, J., Giannoulatou, E., Taylor, S., Joshi, A., Moignard, V., Pina, C., Bee, T., Kokkaliaris, K. D., et al. (2013). Early dynamic fate changes in haemogenic endothelium characterized at the single-cell level. Nature Communications 4, 2924.

Tam, P. P., and Beddington, R. S. (1987). The formation of mesodermal tissues in the mouse embryo during gastrulation and early organogenesis. Development 99, 109-126.

Taoudi, S., Morrison, A. M., Inoue, H., Gribi, R., Ure, J., and Medvinsky, A. (2005). Progressive divergence of definitive haematopoietic stem cells from the endothelial compartment does not depend on contact with the foetal liver. Development 132, 4179-4191.

Thambyrajah, R., Mazan, M., Patel, R., Moignard, V., Stefanska, M., Marinopoulou, E., Li, Y., Lancrin, C., Clapes, T., Möröy, T., et al. (2016). GFI1 proteins orchestrate the emergence of haematopoietic stem cells through recruitment of LSD1. Nature Cell Biology 18, 21-32.

Themeli, M., Riviere, I., and Sadelain, M. (2015). New cell sources for T cell engineering and adoptive immunotherapy. Cell Stem Cell 16, 357-366.

Thorsteinsdottir, U., Mamo, A., Kroon, E., Jerome, L., Bijl, J., Lawrence, H. J., Humphries, K., and Sauvageau. G. (2002). Overexpression of the myeloid leukemia-associated Hoxa9 gene in bone marrow cells induces stem cell expansion. Blood 99, 121-129.

Thorsteinsdottir, U., Sauvageau, G., Hough, M. R., Dragowska, W., Lansdorp, P. M., Lawrence, H. J., Largman, C., and Humphries, R. K. (1997). Overexpression of HOXA10 in murine hematopoietic cells perturbs both myeloid and lymphoid differentiation and leads to acute myeloid leukemia. Molecular and Cellular Biology 17, 495-505.

Uenishi, G. I., Jung, H. S., Kumar, A., Park, M. A., Hadland, B. K., McLeod, E., Raymond, M., Moskvin, O., Zimmerman, C. E., Theisen, D. J., et al. (2018). NOTCH signaling specifies arterial-type definitive hemogenic endothelium from human pluripotent stem cells. Nature Communications, 1-14.

Ueno, H., and Weissman, I. L. (2006). Clonal analysis of mouse development reveals a polyclonal origin for yolk sac blood islands. Developmental Cell 11, 519-533.

Vargel, O., Zhang, Y., Kosim, K., Ganter, K., Foehr, S., Mardenborough, Y., Shvartsman, M., Enright, A. J., Krijgsveld, J., and Lancrin, C. (2016). Activation of the TGFβ pathway impairs endothelial to haematopoietic transition. Scientific Reports 6, 21518.

Vigano, S., Alatzoglou. D., Irving, M., Ménétrier-Caux, C., Caux. C., Romero, P., and Coukos, G. (2019). Targeting Adenosine in Cancer Immunotherapy to Enhance T-Cell Function. Frontiers in immunology 10, 925.

Vodyanik, M. A., Thomson, J. A., and Slukvin, I. I. (2006). Leukosialin (CD43) defines hematopoietic progenitors in human embryonic stem cell differentiation cultures. Blood 108, 2095-2105.

Vogeli, K. M., Jin, S.-W., Martin, G. R., and Stainier, D. Y. R. (2006). A common progenitor for haematopoietic and endothelial lineages in the zebrafish gastrula. Nature 443, 337-339.

Wahlestedt, M., Ladopoulos, V., Hidalgo, I., Sánchez Castillo, M., Hannah, R., Säwén, P., Wan, H., Dudenhöffer-Pfeifer, M., Magnusson, M., Norddahl, G. L., et al. (2017). Critical Modulation of Hematopoietic Lineage Fate by Hepatic Leukemia Factor. Cell Reports 21, 2251-2263.

Wahlster, L., and Daley. G. Q. (2016). Progress towards generation of human haematopoietic stem cells. Nature Cell Biology.

Wang, C., Tang, X., Sun, X., Miao, Z., Lv, Y., Yang, Y., Zhang, H., Zhang, P., Liu, Y., Du, L., et al. (2012). TGFβ inhibition enhances the generation of hematopoietic progenitors from human ES cell-derived hemogenic endothelial cells using a stepwise strategy. Cell Research 22, 194-207.

Wang, H. U., Chen, Z. F., and Anderson, D. J. (1998). Molecular distinction and angiogenic interaction between embryonic arteries and veins revealed by ephrin-B2 and its receptor Eph-B4. Cell 93, 741-753.

Wang, P., Rodriguez, R. T., Wang, J., Ghodasara, A., and Kim, S. K. (2011). Targeting SOX17 in human embryonic stem cells creates unique strategies for isolating and analyzing developing endoderm. Cell Stem Cell 8, 335-346.

Weissman, I. L., and Shizuru, J. A. (2008). The origins of the identification and isolation of hematopoietic stem cells, and their capability to induce donor-specific transplantation tolerance and treat autoimmune diseases. Blood 112, 3543-3553.

Weng, W., Sukowati, E. W., and Sheng, G. (2007). On hemangioblasts in chicken. PLoS ONE 2, e1228.

Wilkinson, A. C., Ishida, R., Kikuchi, M., Sudo, K., Morita, M., Crisostomo, R. V., Yamamoto, R., Loh, K. M., Nakamura, Y., Watanabe, M., et al. (2019). Long-term ex vivo haematopoietic-stem-cell expansion allows nonconditioned transplantation. Nature, 1.

Xiong, J.-W. (2008). Molecular and developmental biology of the hemangioblast. Developmental Dynamics 237, 1218-1231.

Yoder, M. C., Hiatt, K., Dutt, P., Mukherjee, P., Bodine, D. M., and Orlic, D. (1997a). Characterization of definitive lymphohematopoietic stem cells in the day 9 murine yolk sac. Immunity 7, 335-344.

Yoder, M. C., Hiatt, K., and Mukherjee, P. (1997b). In vivo repopulating hematopoietic stem cells are present in the murine yolk sac at day 9.0 postcoitus. Proc Natl Acad Sci USA 94, 6776-6780.

Yoshida, K., Taga, T., Saito, M., Suematsu, S., Kumanogoh, A., Tanaka, T., Fujiwara, H., Hirata, M., Yamagami, T., Nakahata, T., et al. (1996). Targeted disruption of gp130, a common signal transducer for the interleukin 6 family of cytokines, leads to myocardial and hematological disorders. Proceedings of the National Academy of Sciences 93, 407-411.

You, L.-R., Lin, F.-J., Lee, C. T., DeMayo, F. J., Tsai, M.-J., and Tsai, S. Y. (2005). Suppression of Notch signalling by the COUP-TFII transcription factor regulates vein identity. Nature 435, 98-104.

Zhang, J., Chu, L.-F., Hou, Z., Schwartz, M. P., Hacker, T., Vickerman, V., Swanson, S., Leng, N., Nguyen, B. K., Elwell, A., et al. (2017). Functional characterization of human pluripotent stem cell-derived arterial endothelial cells. Proceedings of the National Academy of Sciences of the United States of America, 201702295.

Zhou, X., Crow, A. L., Hartiala, J., Spindler, T. J., Ghazalpour, A., Barsky, L. W., Bennett, B. B., Parks, B. W., Eskin, E., Jain. R., et al. (2015). The Genetic Landscape of Hematopoietic Stem Cell Frequency in Mice. Stem Cell Reports, 1-14.

Zonari, E., Desantis, G., Petrillo, C., Boccalatte, F. E., Lidonnici, M. R., Kajaste-Rudnitski, A., Aiuti, A., Ferrari, G., Naldini, L., and Gentner, B. (2017). Efficient Ex Vivo Engineering and Expansion of Highly Purified Human Hematopoietic Stem and Progenitor Cell Populations for Gene Therapy. Stem Cell Reports, 1-14.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A method of producing a substantially pure population of hematopoietic stem cells (HSC) in defined monolayer conditions in media comprising extracellular signaling agents to guide differentiation, the method comprising:

(a) differentiating human pluripotent stem cells by culture in media comprising a BMP agonist, an FGF agonist, a WNT agonist, and TGFβ agonist for a period of about 1 day to generate a population of primitive streak cells;

(b) differentiating the primitive streak cells by culture in media comprising a WNT inhibitor, BMP agonist, VEGF agonist, PI3K inhibitor, CAMP agonist, TGFβ inhibitor, and Vitamin C for a period of about 1 day to 36 hours or longer to generate a population of dorsal lateral mesoderm;

(c) differentiating the dorsal lateral mesoderm cells by culture in media comprising: (i) a VEGF agonist, TGFβ agonist, WNT inhibitor, PI3K inhibitor, BMP inhibitor, and Vitamin C; or (ii) a VEGF agonist, TGFβ agonist, WNT inhibitor, PI3K inhibitor, BMP inhibitor, and Vitamin C for a period of about 1 day to produce a population of artery progenitor cells;

(d) differentiating the artery progenitor cells by culture at high density in media comprising an OSM agonist, LIF agonist, CAMP agonist, TGFβ inhibitor, Notch agonist, and serum replacement for about 2 to about 3 days to produce a population of hemogenic endothelium cells; and (e) differentiating the hemogenic endothelium in media comprising an OSM agonist, LIF agonist, CAMP agonist, IL-1 agonist, aryl hydrocarbon receptor inhibitor, TGFβ inhibitor, UM171, Notch agonist, and serum replacement for a period of from about 2 to about 3 days to generate a population of HSC.

2. The method of claim 1, wherein the method further comprises contacting the artery progenitor cells in step (c) with a DLL4 binding agent and isolating the artery progenitor cells by binding of the DLL4 binding agent to the artery progenitor cells and selecting for DLL4 binding cells to produce a purified population of artery progenitor cells.

3. A substantially pure population of hematopoietic stem cells produced by the method according to claim 1.

4. A method of treatment, comprising administering to an individual the population of cells according to claim 3.

5. A method of screening a substantially pure population of hematopoietic stem cells for a cellular response, comprising contacting a population of substantially pure population of hematopoietic stem cells of claim 3 with a pharmacological agent and evaluating the population of cells for a cellular response induced by the pharmacological agent.

6. The method of claim 1, wherein the media in step (b) comprises a retinoic acid agonist.

7. The method of claim 1, wherein the media in step (c) comprises a retinoic acid agonist.

8. The method of claim 1, wherein the substantially pure population of hematopoietic stem cells (HSC) comprises greater than 90% HSC.

9. The method of claim 1, wherein the HSC express core HSC markers HLF and HOXA5-10.

\* \* \* \* \*